(12) United States Patent
Herdewijn et al.

(10) Patent No.: US 8,901,132 B2
(45) Date of Patent: Dec. 2, 2014

(54) THIAZOLOPYRIMIDINE MODULATORS AS IMMUNOSUPPRESSIVE AGENTS

(75) Inventors: Piet Herdewijn, Wezemaal (BE); Steven De Jonghe, Tervuren (BE); Ling-Jie Gao, Bierbeek (BE); Mi-Yeon Jang, Leuven (BE); Bart Vanderhoydonck, Diest (BE); Mark Jozef Albert Waer, Heverlee (BE); Yuan Lin, Arlington, MA (US); Jean Ferdinand Herman, Heverlee (BE); Thierry Andre Michel Louat, Saint Chamond (FR)

(73) Assignee: Katholieke Universiteit Leuven, K.U. Leuven R&D, Leuven (BE)

( * ) Notice: Subject to any disclaimer, the term of this patent is extended or adjusted under 35 U.S.C. 154(b) by 434 days.

(21) Appl. No.: 13/255,429

(22) PCT Filed: Mar. 15, 2010

(86) PCT No.: PCT/EP2010/053318
§ 371 (c)(1),
(2), (4) Date: Nov. 14, 2011

(87) PCT Pub. No.: WO2010/103130
PCT Pub. Date: Sep. 16, 2010

(65) Prior Publication Data
US 2012/0046278 A1  Feb. 23, 2012

(30) Foreign Application Priority Data

Mar. 13, 2009 (GB) .................................. 0904353.0
Mar. 13, 2009 (GB) .................................. 0904373.8
Jun. 26, 2009 (GB) .................................. 0911022.2

(51) Int. Cl.
*A61K 31/519* (2006.01)
*C07D 495/02* (2006.01)
*C07D 513/22* (2006.01)
*C07D 513/04* (2006.01)

(52) U.S. Cl.
CPC ............ *C07D 513/04* (2013.01); *A61K 31/519* (2013.01)
USPC ........ 514/258.1; 544/242; 544/253; 544/280; 514/247; 514/256

(58) Field of Classification Search
CPC ... A61K 31/519; C07D 495/02; C07D 513/22
USPC ........ 544/242, 253, 280; 514/247, 256, 258.1
See application file for complete search history.

(56) References Cited

U.S. PATENT DOCUMENTS 8,158,626 B2 * 4/2012 Castanedo et al. ......... 514/234.2
8,168,633 B2 * 5/2012 Hancox et al. ............. 514/234.2

FOREIGN PATENT DOCUMENTS

| WO | 01/58906 A1 | 8/2001 |
| WO | 2007/134958 A1 | 11/2007 |
| WO | 2008/005303 A2 | 1/2008 |
| WO | 2008/057402 A2 | 5/2008 |
| WO | 2008/059368 A2 | 5/2008 |
| WO | 2008/152390 A1 | 12/2008 |
| WO | 2009/013545 A2 | 1/2009 |

* cited by examiner

*Primary Examiner* — Golam M M Shameem
(74) *Attorney, Agent, or Firm* — McDonnell Boehnen Hulbert & Berghoff LLP

(57) ABSTRACT

The present invention relates to compound of formula I, II, III, or IV, and/or a pharmaceutical acceptable addition salt thereof and/or a stereoisomer thereof and/or a solvate thereof, wherein $R^1$, $R^2$, $R^3$, $R^4$, $R^5$, $R^6$, $R^7$, $R^8$, $R^9$, $R^{11}$, and $R^{12}$ are as defined in the claim 1. The present invention also relates to a method for their preparation, as well as to pharmaceutical compositions thereof. The present invention further relates to the use of said compounds as biologically active ingredients, more specifically as medicaments for the treatment of disorders and pathologic conditions such as, but not limited to, immune and auto-immune disorders, organ and cells transplant rejections.

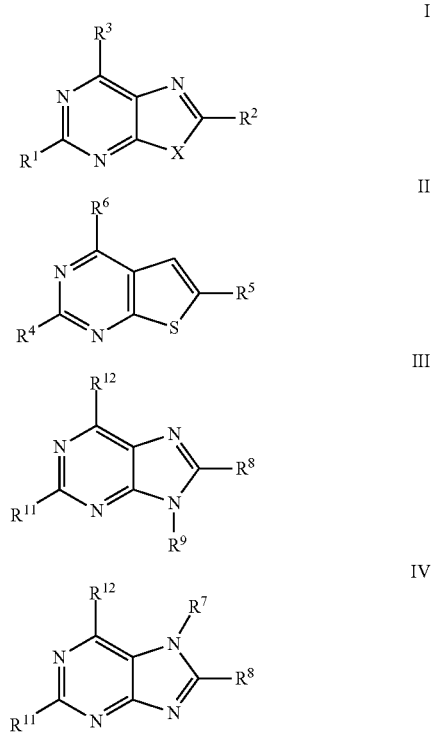

16 Claims, No Drawings

THIAZOLOPYRIMIDINE MODULATORS AS IMMUNOSUPPRESSIVE AGENTS

This application is a US national phase of International Application No. PCT/EP2010/053318 filed on Mar. 15, 2010, which claims the benefit of Great Britain patent application 0904353.0, filed Mar. 13, 2009, Great Britain patent application 0904373.8, filed Mar. 13, 2009 and Great Britain application 0911022.2, filed Jun. 26, 2009, the disclosures of which are incorporated herein by reference in their entirety.

FIELD OF THE INVENTION

The present invention relates to a class of novel thiazolo[5,4-d]pyrimidine, oxazolo[5,4-d]pyrimidine, thieno[2,3-d]pyrimidine and purine derivatives and a method for their preparation, as well as to pharmaceutical compositions comprising one or more of said thiazolo[5,4-d]pyrimidine, oxazolo[5,4-d]pyrimidine, thieno[2,3-d]pyrimidine and purine derivatives and one or more pharmaceutically acceptable excipients. The present invention further relates to the use of said novel thiazolo[5,4-d]pyrimidine, oxazolo[5,4-d]pyrimidine, thieno[2,3-d]pyrimidine and purine derivatives as biologically active ingredients, more specifically as medicaments for the treatment of disorders and pathologic conditions such as, but not limited to, immune and auto-immune disorders, organ and cells transplant rejections.

BACKGROUND OF THE INVENTION

Thiazolo[5,4-d]pyrimidines and oxazolo[5,4-d]pyrimidines can be considered as structural analogues of purines, in which the imidazole moiety is replaced by a 1,3-thiazole or 1,3-oxazole ring system. Although purine chemistry is extensively described in literature, the number of medicinal chemistry papers that describe the synthesis and biological evaluation of oxazolopyrimidines and thiazolopyrimidines is limited. Apparently, the oxazolopyrimidine and thiazolopyrimidine scaffold is not very frequently used in drug discovery programs.

However, biological activities of certain thiazolo[5,4-d]pyrimidines and oxazolo[5,4-d]pyrimidines have been reported. 2,5-Diaminothiazolo[5,4-d]pyrimidin-7(6H)-one, a thio-isostere of 8-amino-guanine, was found to be a weak inhibitor of purine nucleoside phosphorylase (J. C. Sircar et al. *J. Med. Chem.* 1986, 29, 1804-1806). Thiazolo[5,4-d]pyrimidines were covered by several patent applications as activators of caspases and inducers of apoptosis (WO2008/057402), anti-angiogenic agents (WO2004/01314), growth factor receptor inhibitors (EP1731523), heat shock protein 90 inhibitors (WO2008/059368) and xanthine oxidase inhibitors (WO2007/004688). WO2008/152390 discloses thiazolo[5,4-d]pyrimidines and their use as inhibitors of phosphatidylinositol-3 kinase. WO 2008/005303 discloses vanilloid receptor 1 (TRPV1) modulating thiazolo[5,4-d]pyrimidine analogues and their use for the treatment of diseases, such as pain, arthritis, itch, cough, asthma, or inflammatory bowel disease.

2-Aryloxazolo[5,4-d]pyrimidines have been described as adenosine kinase inhibitors (M. Bauser; et al. *Bioorg. Med. Chem. Lett.* 2004, 14, 1997-2000). 7-Amino-5-phenylethylamino-2-furyl-oxazolo[5,4-d]pyrimidines act as brain $A_{2A}$ adenosine receptor ($A_{2A}AR$) antagonists (M. H. Holschbach, et al. *Eur. J. Med. Chem.* 2006, 41, 7-15). 7-(Substituted-cyclopentyl)aminooxazolo[5,4-d]pyrimidines have been reported to possess tumor growth inhibitory activity (WO/2008/019124). However none of these documents teaches or suggests thiazolo[5,4-d]pyrimidine or oxazolo[5,4-d]pyrimidine derivatives having the substitution pattern disclosed by the present invention.

A huge number of thieno[2,3-d]pyrimidines is already known in the art. WO 2007/102679 discloses thienopyrimidines with at position 4 a pyrrole-2,5-dione substituent which strongly inhibits IKB kinase-β (IKK-β) involved in the activation of a transcriptional factor, NF-κB, which is associated with inducing various immune and inflammatory diseases, whereby a composition comprising the compound is a useful therapeutic agent against inflammatory diseases, in particular, arthritis and cancer. WO 2007/084815 discloses 2-carboxamide substituted thieno(2,3-d)pyrimidines inhibitors of one or more of the EGFR, HER-2, c-Src, Lyn, c-Abl, Aurora-A or VEGF kinase proteins and the like possessing anti-tumor cell proliferation activity, and as such are useful in treating or ameliorating a EGFR, HER-2, c-Src, Lyn, c-Abl, Aurora-A or VEGF kinase receptor mediated, angiogenesis-mediated or hyperproliferative disorder.

WO 2006/071988 discloses certain 4,5-disubstituted thienopyrimidine derivatives which are useful for the inhibition of PDE10 enzymes, and thus are useful for treating psychiatric or neurological syndromes, such as psychoses, obsessive-compulsive disorder and/or Parkinson's disease. WO 2004/111057 discloses compounds which are particularly useful for inhibiting potassium channels Kv1. 5), which are known targets for the treatment of cardiac arrhythmia in the atria such as atrial fibrillation. However, none of these documents teaches or suggests thieno(2,3-d)pyrimidine derivatives having the substitution pattern disclosed by the present invention.

Marketed drugs with a purine based skeleton are known. Examples include theophylline (drug for the treatment of asthma) and azathioprine (drug for the treatment of transplant rejection). Anti-cancer drugs with a purine scaffold include 6-mercaptoguanine and thioguanine. Purines are also an important constituent of antiviral nucleosides such as acyclovir (used for the treatment of herpes virus infections) and ganciclovir (medication used for treatment of cytomegalovirus infections). Abacavir and dideoxyadenosine (ddA) are both purine nucleosides acting as reverse transcriptase inhibitors and both compounds are licensed as anti-HIV agents.

Purines display a broad range of biological activities and as a result a huge number of purine analogues is already known in the art. WO 2009/005687 discloses purine derivatives and their use as modulators of Toll-like receptor 7. Compounds and pharmaceutical compositions which selectively activate toll-like receptor 7 are useful for treating viral infections in patients. WO 2008/135232 relates to substituted purines and purine derivatives as inhibitors of Aurora A, Aurora B, Aurora C, CHK2, JNK1 α1, JNK3 and abl kinase. These compounds possess antiproliferative properties and are useful in the treatment of proliferative disorders such as cancer, leukemia, psoriasis and the like. WO 2008/094737 discloses purine derivatives as inhibitors of calcium dependent protein kinase 1 (PfCDPKI). These purines are useful for treating malaria. WO 2008/090181 relates to a new series of purine derivatives as inhibitors of Janus kinases. JAK3 kinase inhibitors have been recognized as a new class of effective immunosuppressive agents useful for transplant rejection prevention and in the prevention or treatment of immune, autoimmune, inflammatory and proliferative diseases such as psoriasis, psoriatic arthritis, rheumatoid arthritis, multiple sclerosis, inflammatory bowel diseases, systemic lupus erythematosus, type I diabetes and complications from diabetes, allergic reactions and leukemia. WO 2008/060301 also discloses 7-substituted purine derivatives as immunosuppressive drugs useful for treatment of an autoimmune disease, an inflammatory disease, a mast cell mediated disease, hematological malignancy and organ transplant rejection. However none of these documents teaches or suggests purine derivatives having the substitution pattern disclosed by the present invention.

However there is a continuous need in the art for specific and highly therapeutically active compounds, such as, but not limited to, drugs for treating immune and autoimmune disorders, organ and cells transplant rejections. In particular, there is a need in the art to provide immunosuppressive compounds, which are active in a minor dose in order to replace existing drugs having significant side effects and to decrease treatment costs.

Currently used immunosuppressive drugs include antiproliferative agents, such as methotrexate (a 2,4-diaminopyrido (3,2-d)pyrimidine derivative disclosed by U.S. Pat. No. 2,512,572), azathioprine, and cyclophosphamide. Since these drugs affect mitosis and cell division, they have severe toxic effects on normal cells with high turn-over rate such as bone marrow cells and the gastrointestinal tract lining. Accordingly, marrow depression and liver damage are common side effects of these antiproliferative drugs.

Anti-inflammatory compounds used to induce immunosuppression include adrenocortical steroids such as dexamethasone and prednisolone. The common side effects observed with the use of these compounds are frequent infections, abnormal metabolism, hypertension, and diabetes.

Other immunosuppressive compounds currently used to inhibit lymphocyte activation and subsequent proliferation include cyclosporine, tacrolimus and rapamycin. Cyclosporine and its relatives are among the most commonly used immunosuppressant drugs. Cyclosporine is typically used for preventing or treating organ rejection in kidney, liver, heart, pancreas, bone marrow, and heart-lung transplants, as well as for the treatment of autoimmune and inflammatory diseases such as Crohn's disease, aplastic anemia, multiple-sclerosis, myasthenia gravis, uveitis, biliary cirrhosis, etc. However, cyclosporines suffer from a small therapeutic dose window and severe toxic effects including nephrotoxicity, hepatotoxicity, hypertension, hirsutism, cancer, and neurotoxicity.

Additionally, monoclonal antibodies with immunosuppressant properties, such as OKT3, have been used to prevent and/or treat graft rejection. Introduction of such monoclonal antibodies into a patient, as with many biological materials, induces several side-effects, such as dyspnea. Within the context of many life-threatening diseases, organ transplantation is considered a standard treatment and, in many cases, the only alternative to death. The immune response to foreign cell surface antigens on the graft, encoded by the major histocompatibility complex (hereinafter referred as MHC) and present on all cells, generally precludes successful transplantation of tissues and organs unless the transplant tissues come from a compatible donor and the normal immune response is suppressed. Other than identical twins, the best compatibility and thus, long term rates of engraftment, are achieved using MHC identical sibling donors or MHC identical unrelated cadaver donors. However, such ideal matches are difficult to achieve. Further, with the increasing need of donor organs an increasing shortage of transplanted organs currently exists. Accordingly, xenotransplantation has emerged as an area of intensive study, but faces many hurdles with regard to rejection within the recipient organism.

The host response to an organ allograft involves a complex series of cellular interactions among T and B lymphocytes as well as macrophages or dendritic cells that recognize and are activated by foreign antigen. Co-stimulatory factors, primarily cytokines, and specific cell-cell interactions, provided by activated accessory cells such as macrophages or dendritic cells are essential for T-cell proliferation. These macrophages and dendritic cells either directly adhere to T-cells through specific adhesion proteins or secrete cytokines that stimulate T-cells, such as IL-12 and IL-15. Accessory cell-derived co-stimulatory signals stimulate activation of interleukin-2 (IL-2) gene transcription and expression of high affinity IL-2 receptors in T-cells. IL-2 is secreted by T lymphocytes upon antigen stimulation and is required for normal immune responsiveness. IL-2 stimulates lymphoid cells to proliferate and differentiate by binding to IL-2 specific cell surface receptors (IL-2R). IL-2 also initiates helper T-cell activation of cytotoxic T-cells and stimulates secretion of interferon-γ which in turn activates cytodestructive properties of macrophages. Furthermore, IFN-γ and IL-4 are also important activators of MHC class II expression in the transplanted organ, thereby further expanding the rejection cascade by enhancing the immunogenicity of the grafted organ. The current model of a T-cell mediated response suggests that T-cells are primed in the T-cell zone of secondary lymphoid organs, primarily by dendritic cells. The initial interaction requires cell to cell contact between antigen-loaded MHC molecules on antigen-presenting cells (hereinafter referred as APC) and the T-cell receptor/CD3 complex on T-cells. Engagement of the TCR/CD3 complex induces CD154 expression predominantly on CD4 T-cells that in turn activate the APC through CD40 engagement, leading to improved antigen presentation. This is caused partly by upregulation of CD80 and CD86 expression on the APC, both of which are ligands for the important CD28 co-stimulatory molecule on T-cells. However, engagement of CD40 also leads to prolonged surface expression of MHC-antigen complexes, expression of ligands for 4-1BB and OX-40 (potent co-stimulatory molecules expressed on activated T-cells). Furthermore, CD40 engagement leads to secretion of various cytokines (e.g., IL-12, IL-15, TNF-α, IL-1, IL-6, and IL-8) and chemokines, all of which have important effects on both APC and T-cell activation and maturation. Similar mechanisms are involved in the development of auto-immune disease, such as type I diabetes. In humans and non-obese diabetic mice, insulin-dependent diabetes mellitus results from a spontaneous T-cell dependent autoimmune destruction of insulin-producing pancreatic beta, cells that intensifies with age. The process is preceded by infiltration of the islets with mononuclear cells (insulitis), primarily composed of T lymphocytes. A delicate balance between auto-aggressive T-cells and suppressor-type immune phenomena determines whether expression of auto-immunity is limited to insulitis or not. Therapeutic strategies that target T-cells have been successful in preventing further progress of the autoimmune disease. These include neonatal thymectomy, administration of cyclosporine, and infusion of anti-pan T-cell, anti-CD4, or anti-CD25 (IL-2R) monoclonal antibodies. The aim of all rejection prevention and auto-immunity reversal strategies is to suppress the patient's immune reactivity to the antigenic tissue or agent, with a minimum of morbidity and mortality. Accordingly, a number of drugs are currently being used or investigated for their immunosuppressive properties. As discussed above, the most commonly used immunosuppressant is cyclosporine, which however has numerous side effects. Accordingly, in view of the relatively few choices for agents effective at immunosuppression with low toxicity profiles and manageable side effects, there exists a need in the art for identification of alternative immunosuppressive agents and for agents acting as complement to calcineurin inhibition.

SUMMARY OF THE INVENTION

The present invention is based on the unexpected finding that certain combinations of substituents at different positions of the thiazolo[5,4-d]pyrimidine, oxazolo[5,4-d]pyrimidine, thieno[2,3-d]pyrimidine and purine ring system, said combinations not being suggested by the prior art, are able to meet one or more of the medical needs recited herein above and to show unexpected biological properties, in particular have significant immunosuppressive activity.

The present invention concerns a compound of I, II, III or IV:

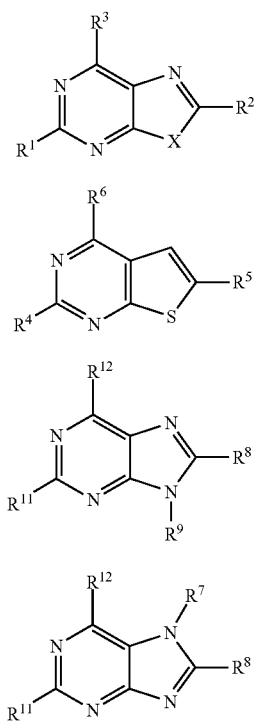

wherein
X is S or O;
R$^1$ is selected from the group consisting of halogen, cyano, carboxylic acid, acyl, thioacyl, alkoxycarbonyl, acyloxy, carbonate, carbamate, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, $C_{1-7}$ alkyloxy;
R$^3$ is selected from the group consisting of (mono- or di-) $C_{1-12}$ alkylamino; monoarylamino; diarylamino; (mono- or di-) $C_{3-10}$ cycloalkylamino; (mono- or di-) hydroxy $C_{1-7}$ alkylamino; (mono- or di-) $C_{1-4}$ alkylarylamino; (mono- or di-) aryl$C_{1-4}$ alkylamino; morpholinyl; mercapto $C_{1-7}$ alkyl; $C_{1-7}$ alkoxy, aralkylthio, piperidinyl, pyrrolidinyl, homopiperazinyl and piperazinyl, wherein said piperidinyl, pyrrolidinyl, homopiperazinyl or piperazinyl is optionally N-substituted with a substituent R$^{20}$ selected from the group consisting of formyl, acyl, thioacyl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl, wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thioureido, sulfonamido, hydroxylamino, alkoxyamino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino; and
R$^2$ is selected from the group consisting of heteroaryl and aryl groups; halogen; $C_{1-7}$ alkyl; $C_{2-7}$ alkenyl; $C_{2-7}$ alkynyl; halo $C_{1-7}$ alkyl; $C_{3-10}$ cycloalkyl; carboxy $C_{1-7}$ alkyl; carboxyaryl; $C_{1-7}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; thio-acylamino; alkoxyamino; thioalkyl-amino; acetal; thio-acetal; carboxylic acid; carboxylic acid esters, thiocarboxylic acid; thiocarboxylic acid esters, thioesters, halides, anhydrides, amides and thioamides; hydroxyl; sulfhydryl; nitro; cyano; carbamoyl; thiocarbamoyl; ureido; thioureido; amino; alkylamino; cycloalkylamino; alkenylamino; cyclo-alkenylamino; alkynylamino; arylamino; arylalkylamino; hydroxyalkylamino; mercaptoalkylamino; heterocyclic amino; heterocyclic substituted arylamino; heterocyclic-substituted alkyl-amino; oximino; alkyloximino; hydrazino; alkylhydrazino; phenylhydrazino; esters, thioesters, halides, anhydrides, amides and thioamides thereof; aromatic or heterocyclic substituents substituted with an aliphatic spacer between the thiazolo(5,4-d)pyrimidine or oxazolo(5,4-d)pyrimidine ring and the aromatic or heterocyclic substituent, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, carbamoyl, thiocarbamoyl, ureido, thioureido, sulfonamido, hydroxylamino, alkoxyamino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino; wherein said aliphatic spacer is a branched or straight, saturated or unsaturated aliphatic chains of 1 to 7 carbon atoms optionally containing one or more functions, atoms or radicals independently selected from the group consisting of halogen, carbonyl, thiocarbonyl, hydroxyl, thiol, ether, thio-ether, acetal, thio-acetal, amino, imino, oximino, alkyloximino, aminoacid, cyano, acylamino, thioacylamino, carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkyl-amino, cycloalkylamino, alkenylamino, cycloalkenyl-amino, alkynylamino, arylamino, arylalkyl-amino, hydroxyalkylamino, mercaptoalkylamino, heterocyclic-substituted alkylamino, hetero-cyclic amino, heterocyclic-substituted arylamino, hydrazino, alkylhydrazino, phenylhydrazino, sulfonyl, sulfinyl and sulfonamido;

$R^4$ is selected from the group consisting of halogen, cyano, carboxylic acid, acyl, thioacyl, alkoxycarbonyl, acyloxy, carbonate, carbamate, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, $C_{1-7}$ alkyloxy;

$R^6$ is selected from the group consisting of (mono- or di-) $C_{1-12}$ alkylamino, monoarylamino, diarylamino, (mono- or di-) $C_{3-10}$ cycloalkylamino, (mono- or di-) hydroxy $C_{1-7}$ alkylamino, (mono- or di-) $C_{1-4}$ alkylarylamino, (mono- or di-) aryl$C_{1-4}$ alkylamino, morpholinyl, mercapto $C_{1-7}$ alkyl, $C_{1-7}$ alkoxy, homopiperazinyl and piperazinyl, wherein said homopiperazinyl or piperazinyl is optionally N-substituted with a substituent $R^{21}$ selected from the group consisting of formyl, acyl, thioacyl, amide, thioamide, sulfonyl, sulfinyl, carboxylate, thio-carboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl; wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino;

$R^5$ is selected from the group consisting of heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino; wherein $R^{12}$ is represented by the general formula V:

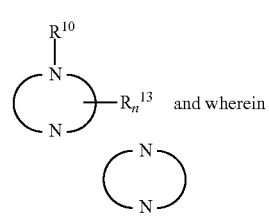

schematically represents a saturated or partly unsaturated heterocyclic ring with at least two nitrogen atoms in the said heterocyclic ring and with a total of 5 to 7 atoms in the said heterocyclic ring, and optionally with one or more other heteroatoms in the said heterocyclic ring or attached to one or more carbon atoms of said heterocyclic ring, wherein one of said at least two nitrogen atoms in the heterocyclic ring is attached to a carbon atom 6 of the purine ring;

each substituent $R^{13}$ of the heterocyclic ring is a group independently selected from the group consisting of halogen, nitro, $C_{1-7}$ alkyl (optionally containing one or more functions or radicals selected from the group consisting of halogen, carbonyl, thiocarbonyl, hydroxyl, sulfhydryl, $C_{1-7}$ alkoxy, thio $C_{1-7}$ alkyl, thio $C_{3-10}$ cycloalkyl, acetal, thioacetal, imino, oximino, alkyloximino, amino-acid, cyano, (thio)carboxylic acid, (thio) carboxylic acid ester or amide, nitro, amino, $C_{1-7}$ alkylamino, cycloalkylamino, alkenylamino, cycloalkenyl-amino, alkynylamino, arylamino, arylalkylamino, hydroxyalkylamino, mercapto-alkylamino, heterocyclic-substituted alkylamino, heterocyclic amino, heterocyclic-substituted arylamino, hydrazino, alkylhydrazino, phenylhydrazino, sulfonyl and sulfonamido), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, sulfhydryl, amino, $C_{1-7}$ alkylamino, cycloalkylamino, alkenylamino, cycloalkenylamino, alkynylamino, arylamino, arylalkyl-amino, hydroxyalkylamino, mercaptoalkylamino, heterocyclic-substituted alkylamino, heterocyclic amino, heterocyclic-substituted arylamino, hydrazino, alkylhydrazino, phenylhydrazino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, (thio)carboxylic acid or esters or thioesters or amides or thioamides thereof;

n is an integer from 0 to 6; for example n is an integer selected from 0, 1, 3, 4 or 5, preferably, n is 0, 1, 2, or 3, more preferably, n is 0 or 1, yet more preferably n is 0;

$R^{10}$ is selected from the group consisting of formyl, acyl, thioacyl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, aralkenyl, aryloxyalkyl, arylalkyl and aryl; wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino; and $R^{11}$ is selected from the group consisting of halogen, cyano, carboxylic acid, acyl, thioacyl, alkoxycarbonyl, acyloxy, carbonate, carbamate, $C_{1-7}$ alkyl, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, $C_{1-7}$ alkyloxy;

$R^{8}$ is selected from the group consisting of heteroaryl and aryl groups; halogen; $C_{1-7}$ alkyl; $C_{2-7}$ alkenyl; $C_{2-7}$ alkynyl; halo $C_{1-7}$ alkyl; carboxy $C_{1-7}$ alkyl; carboxyaryl; $C_{1-7}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acylamino; thio-acylamino; alkoxyamino; thioalkyl-amino; acetal; thio-acetal; carboxylic acid; carboxylic acid esters, thioesters, halides, anhydrides, amides and thioamides; thiocarboxylic acid; thiocarboxylic acid esters, thioesters, halides, anhydrides, amides and thioamides; hydroxyl; sulfhydryl; nitro; cyano; carbamoyl; thiocarbamoyl; ureido; thioureido; amino; alkylamino; cycloalkylamino; alkenylamino; cyclo-alkenylamino; alkynylamino; arylamino; arylalkylamino; hydroxyalkylamino; mercaptoalkyl-amino; heterocyclic amino; heterocyclic substituted arylamino; heterocyclic-substituted alkyl-amino; oximino; alkyloximino; hydrazino; alkylhydrazino; phenylhydrazino; esters, thioesters, halides, anhydrides, amides and thioamides thereof; aromatic or heterocyclic substituents substituted with an aliphatic spacer between the purine ring and the aromatic or heterocyclic substituent; wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino; and wherein said aliphatic spacer is a branched or straight, saturated or unsaturated aliphatic chain of 1 to 7 carbon atoms optionally containing one or more functions, atoms or radicals independently selected from the group consisting of halogen, carbonyl, thiocarbonyl, hydroxyl, thiol, ether, thio-ether, acetal, thio-acetal, amino, imino, oximino, alkyloximino, aminoacid, cyano, acylamino, thioacylamino, carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkyl-amino, cycloalkylamino, alkenylamino, cycloalkenylamino, alkynylamino, arylamino, arylalkyl-amino, hydroxyalkylamino, mercaptoalkylamino, heterocyclic-substituted alkylamino, hetero-cyclic amino, heterocyclic-substituted arylamino, hydrazino, alkylhydrazino, phenylhydrazino, sulfonyl, sulfinyl and sulfonamido;

$R^{7}$ and $R^{9}$ are selected from the group consisting of hydrogen, $C_{3-7}$ alkenyl, $C_{2-7}$ alkynyl, halo $C_{1-7}$ alkyl, $C_{3-10}$ cycloalkyl, aryl, arylalkyl, alkylaryl, acyl sulfonyl and $C_{1-7}$ alkyl, wherein said $C_{1-7}$ alkyl is optionally containing one or more functions or radicals selected from the group consisting of halogen, carbonyl, thiocarbonyl, hydroxyl, sulfhydryl, $C_{1-7}$ alkoxy, thio $C_{1-7}$ alkyl, thio $C_{3-10}$ cycloalkyl, acetal, thioacetal, imino, oximino, alkyloximino, amino-acid, cyano, (thio)carboxylic acid, (thio)carboxylic acid ester or amide, nitro, amino, $C_{1-7}$ alkylamino, cycloalkylamino, alkenylamino, cycloalkenyl-amino, alkynylamino, arylamino, arylalkylamino, hydroxyalkylamino, mercapto-alkylamino, heterocyclic-substituted alkylamino, heterocyclic amino, heterocyclic-substituted arylamino, hydrazino, alkylhydrazino, phenylhydrazino, sulfonyl and sulfonamido), wherein acyl group refers to a carbonyl group adjacent to a $C_{1-7}$ alkyl, a $C_{3-10}$ cycloalkyl, an aryl, an arylalkyl or a heterocyclic group, or is selected from the group comprising alkanoyl, cycloalkanoyl, cycloalkyl-alkanoyl, alkenoyl, alkylthioalkanoyl, alkanesulfonyl, alkoxycarbonyl, alkylcarbamoyl, alkylcarbamidoyl, alkoxalyl, aroyl, aralkanoyl, aralkenoyl, aryloxyalkanoyl, arylthioalkanoyl, arylaminoalkanoyl, aryloxycarbonyl, aralkoxycarbonyl, arylcarbamoyl, arylglyoxyloyl, arylthiocarbamoyl, arylcarbamidoyl, heterocyclic-carbonyl, heterocyclicalkanoyl, wherein said heterocyclic group is an aromatic or non-aromatic 5- to 7-membered heterocyclic ring with one or more heteroatoms selected from the group consisting of nitrogen, oxygen and sulfur in said ring;

and/or a pharmaceutical acceptable addition salt thereof and/or a stereoisomer thereof and/or a solvate thereof.

The present invention also concerns a compound having formula I, II, III or IV, for use as a medicine.

The present invention also concerns a compound having formula I, II, III or IV, for use as a medicine for the prevention or treatment of immune disorders in an animal, preferably in a mammal. In an embodiment, said immune disorder is an autoimmune disorder or an immune disorder as a result from an organ or cells transplantation. In an embodiment, said mammal is a human being.

The present invention also concerns a pharmaceutical composition comprising a therapeutically effective amount of a compound having formula I, II, III or IV, and one or more pharmaceutically acceptable excipients. Said composition may further comprise one or more biologically active drugs being selected from the group consisting of immunosuppressant and/or immunomodulator drugs, and antineoplastic drugs.

The present invention also concerns a method of prevention or treatment of an immune disorder in an animal, comprising the administration of a therapeutically effective amount of a compound having formula I, II, III or IV, optionally in combination with one or more pharmaceutically acceptable excipients.

The present invention also concerns a process for preparation of the thiazolo(5,4-d)pyrimidine derivatives of formula I, wherein X=S, and comprising the steps of: (a) acylation of 2,5-diamino-4,6-dihydroxypyrimidine; (b) treatment with a thionation reagent; (c) treatment with iodomethane; (d) oxidation reaction by adding an oxidating agent; and (e) a nucleophilic aromatic substitution reaction. In an embodiment, in step (a) said acylation is performed with a carboxylic acid ($R^2COOH$) or an acid chloride ($R^2C(O)Cl$). In an embodiment, step (a) further comprises the addition of a coupling reagent. In an embodiment, said coupling reagent is N,N'-dicyclohexylcarbodiimide (DCC) or N,N'-diisopropylcarbodiimide (DIC) or 1-(3-dimethylaminopropyl)-3-ethylcarbodiimide hydrochloride (EDCl). In another embodiment, step (a) further comprises the addition of additives such as 1-hydroxybenzotriazole (HOBt) and 1-hydroxy-7-azabenzotriazole (HOAt). In an embodiment, in step (b) said thionation reagent is phosphorus pentasulfide or a Lawesson's reagent. In an embodiment, in step (b) said treatment with a thionation reagent is performed in high-boiling solvents such as pyridine, toluene or xylene. In an embodiment, step (c) is performed in alkaline conditions. In an embodiment, in step (d) said oxidating agent is m-chloro-peroxybenzoic acid or hydrogen peroxide. In an embodiment, in step (e) a piperazine is introduced at position 7. In an embodiment, the thiazolo(5,4-d)pyrimidine derivatives of formula I are $R^2$-substituted 5-amino-7-N-piperazino thiazolo(5,4-d)pyrimidine derivatives.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

One embodiment of the present invention concerns a compound according to the invention wherein, $R^3$ and $R^2$ have any of the values as described herein and $R^1$ is selected from the group comprising aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino; preferably, said $R^1$ is selected from the group comprising amino, N-protected amino, (mono- or di) $C_{1-7}$ alkylamino, (mono- or di) arylamino, (mono- or di) $C_{3-10}$ cycloalkylamino, (mono- or di) $C_{1-4}$ alkyl-arylamino; preferably, said $R^1$ is selected from the group comprising amino, (mono- or di) $C_{1-7}$ alkylamino, (mono- or di) arylamino; preferably, said $R^1$ is selected from the group comprising amino, and (mono- or di) $C_{1-7}$ alkylamino; more preferably $R^1$ is amino.

In an embodiment, the present invention concern a compound of formula I, II, III or IV, a pharmaceutical acceptable addition salt thereof and/or a stereoisomer thereof and/or a solvate thereof, wherein $R^1$, $R^4$, and $R^{11}$ are each independently selected from the group consisting of amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino.

One embodiment of the present invention concerns a compound according to the invention wherein X is S. Another embodiment of the present invention concerns a compound according to the invention wherein X is O.

One embodiment of the present invention concerns a compound according to the invention wherein $R^1$ and $R^2$ have any of the values as described herein and $R^3$ is selected from the group consisting of monoarylamino; diarylamino; (mono- or di-) aryl$C_{1-4}$ alkylamino; morpholinyl; $C_{1-7}$ alkoxy, aralkylthio, piperidinyl, pyrrolidinyl, homopiperazinyl and piperazinyl, wherein said piperidinyl, pyrrolidinyl, homopiperazinyl or piperazinyl is optionally N-substituted with a substituent $R^{20}$, wherein $R^{20}$ has the same meaning as defined herein.

One embodiment of the present invention concerns a compound according to the invention wherein $R^4$ and $R^5$ have any of the values as described herein and $R^6$ is selected from the group consisting of (mono- or di-) $C_{1-12}$ alkylamino, monoarylamino, diarylamino, (mono- or di-) $C_{3-10}$ cycloalkylamino, (mono- or di-) aryl$C_{1-4}$ alkylamino, morpholinyl, $C_{1-7}$ alkoxy, homopiperazinyl and piperazinyl, wherein said homopiperazinyl or piperazinyl is optionally N-substituted with a substituent $R^{21}$, wherein $R^{21}$ has the same meaning as that defined in herein.

One embodiment of the present invention concerns a compound according to the invention wherein $R^{11}$, $R^7$, $R^8$ and $R^9$ have any of the values as described herein and n is 0 and $R^{19}$ is selected from the group consisting of formyl, acyl, thioacyl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-carboxylic ester-alkyl, aryloxyalkyl, arylalkyl and aryl; wherein the aryl moiety of each of said aryloxyalkyl, arylalkyl and aryl radicals is optionally substituted with one or more substituents independently selected from the group consisting of halogen, $C_{1-7}$ alkyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, formyl, carbamoyl, thiocarbamoyl, sulfonamido, hydroxylamino, alkoxy-amino, mercaptoamino, thioalkylamino, cyano, alkylamino, cycloalkylamino.

One embodiment of the present invention concerns a compound according to the invention wherein $R^1$ and $R^3$ have any of the values as described herein $R^2$ is selected from the group consisting of heteroaryl and aryl groups; $C_{1-7}$ alkyl; $C_{3-10}$ cycloalkyl; halo $C_{1-7}$ alkyl; carboxy $C_{1-7}$ alkyl; carboxyaryl; $C_{1-7}$ alkoxy; $C_{3-10}$ cycloalkoxy; aryloxy; arylalkyloxy; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acylamino; thio-acylamino; alkoxyamino; carbamoyl; thiocarbamoyl; aromatic or heterocyclic substituents substituted with an aliphatic spacer between the thiazolo(5,4-d)pyrimidine or oxazolo(5,4-d)pyrimidine ring and the aromatic or heterocyclic substituent, wherein said heteroaryl or aryl groups are optionally substituted with one or more substituents selected from the group consisting of halogen, $C_{1-7}$ alkyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, thio $C_{1-7}$ alkyl, thio $C_{3-10}$ cycloalkyl, thioaryl, thio-heterocyclic, arylalkylthio, heterocyclic-substituted alkylthio, carbamoyl, thiocarbamoyl, sulfonamido, hydroxylamino, alkoxy-amino, acylamino, thioacylamino, cyano, wherein said aliphatic spacer is a branched or straight, saturated or unsaturated aliphatic chains of 1 to 7 carbon atoms optionally containing one or more functions, atoms or radicals independently selected from the group consisting of halogen, thiol, ether, thio-ether, amino, cyano, acylamino, nitro, thio $C_{1-7}$ alkyl.

One embodiment of the present invention concerns a compound according to the invention wherein $R^4$ and $R^6$ have any of the values as described herein and $R^5$ is an aryl group, wherein said aryl group is optionally substituted with one or more substituents selected from the group consisting of halogen, $C_{1-7}$ alkyl, halo $C_{1-7}$ alkyl, nitro, hydroxyl, sulfhydryl, $C_{1-7}$ alkoxy, thio $C_{1-7}$ alkyl, cyano.

One embodiment of the present invention concerns a compound according to the invention wherein $R^{11}$, $R^7$, $R^{12}$ and $R^9$ have any of the values as described herein, and $R^8$ is selected from the group consisting of heteroaryl and aryl groups; $C_{1-7}$ alkyl; halo $C_{1-7}$ alkyl; $C_{1-7}$ alkoxy; $C_{3-10}$ cycloalkoxy; aryloxy; arylalkyloxy; thio $C_{1-7}$ alkyl; thio $C_{3-10}$ cycloalkyl; thioaryl; thioheterocyclic; arylalkylthio; heterocyclic-substituted alkylthio; aromatic or heterocyclic substituents substituted with an aliphatic spacer between the purine ring and the aromatic or heterocyclic substituent; wherein said heteroaryl or aryl groups are optionally substituted with one or more substituents selected from the group consisting of halogen, $C_{1-7}$ alkyl, halo $C_{1-7}$ alkyl, nitro, hydroxyl, sulfhydryl, amino, $C_{1-7}$ alkoxy, $C_{3-10}$ cycloalkoxy, thio $C_{1-7}$ alkyl, and wherein said aliphatic spacer is a branched or straight, saturated or unsaturated aliphatic chain of 1 to 7 carbon atoms optionally containing one or more functions, atoms or radicals independently selected from the group consisting of halogen, carbonyl, hydroxyl, thiol, cyano, nitro, thio $C_{1-7}$ alkyl, thio $C_{3-10}$ cycloalkyl.

One embodiment of the present invention concerns a compound according to the invention wherein $R^3$, $R^6$ are each independently homopiperazinyl or piperazinyl, wherein said homopiperazinyl or piperazinyl is each respectively optionally N-substituted with a substituent $R^{20}$, $R^{21}$, wherein $R^{20}$ and $R^{21}$ have the same meaning as that defined herein.

One embodiment of the present invention concerns a compound according to the invention wherein $R^1$, $R^4$ and $R^{11}$ are each independently amino.

One embodiment of the present invention concerns a compound according to the invention wherein $R^1$ and $R^3$ have any of the values as described herein and $R^2$ is selected from the group consisting of phenyl; pyridin-3-yl; pyridin-2-yl; pyridin-4-yl; 4-fluorophenethyl; 4-fluorophenyl; 4-bromophenethyl; pentyl; tolyl; (4-fluorophenyl)butyl; (4-fluorophenyl)propyl; 4-chlorophenyl; 4-methylphenethyl; 3,4-dimethoxyphenethyl; 3-methoxyphenethyl; furan-2-yl; 2-phenylethyl; cyclohexyl; methoxyl methyl; cyclopropyl; 2-thiophen-2-ylethyl; cyclopentyl-(4-fluorophenyl)methyl; 1-(4-fluorophenyl)propyl; 4-fluorophenylamino; methylsulfinyl; 1-(4-chlorophenyl)ethyl; 3-methoxyphenyl; 4-chlorophenyl; 4-chlorophenylmethyl; N-oxopyridine-3-yl; 1-(4-chlorophenyl)cyclopropyl; 3,4-dichlorophenyl; methylthio; 1-phenylcyclopropyl; 1-(4-fluorophenyl)ethyl; 1-(4-fluorophenyl)-2-phenylethyl; 2-(4-fluorophenoxy)ethyl; morpholino; preferably 4-fluorophenyl, 4-fluorobenzyl, 4-fluorophenethyl, 2-(4-fluorophenoxy)ethyl, 1-(4-fluorophenyl)ethyl, 1-(4-fluorophenyl)-2-phenylethyl, 3-pyridyl, 3-methoxyphenyl, cyclopropyl, cyclohexyl, 3,4-dichlorophenyl, 1-phenylcyclopropyl, 1-(4-chlorophenyl)cyclopropyl, 2-thiophen-2-ylethyl, pentyl, and 2-phenylethyl.

One embodiment of the present invention concerns a compound according to the invention wherein $R^4$ and $R^6$ have any of the values as described herein and $R^5$ is phenyl or 4-fluorophenyl.

One embodiment of the present invention concerns a compound according to the invention wherein $R^1$ and $R^2$ have any of the values as described herein and $R^3$ is selected from the group consisting of p-tolyl piperazinyl-1-carboxylate; N-methyl-N-p-tolylpiperazinyl-1-carboxamide; N-p-tolylpiperazinyl-1-carbothioamide; —N-hexylpiperazinyl-1-carboxamide; 4-(N-4-fluorophenylcarboxamide)piperazin-1-yl; N-cyclohexylpiperazinyl-1-carboxamide; N-phenylpiperazinyl-1-carboxamide; N-(4-(trifluoromethyl)phenyl)piperazinyl-1-carboxamide, piperazin-1-yl-2-(4-chlorophenoxy)ethanone; piperazin-1-yl-2-(4-methoxyphenoxy)ethanone; benzylsulfonylpiperazin-1-yl; N-(4-cyanophenyl)piperazinyl-1-carboxamide; N-(4-methoxybenzyl)piperazinyl-1-carboxamide; N-(4-chlorophenyl)piperazinyl-1-carboxamide; N-m-tolylpiperazinyl-1-carboxamide; piperazin-1-yl-2-(m-tolyloxy)ethanone; piperazin-1-yl-2-(4-chlorophenoxy)-2-methylpropan-1-one; piperazin-1-yl-2-(4-trifluoromethoxyphenoxy)ethanone; piperazin-1-yl-2-(4-fluorophenoxy)ethanone; piperazin-1-yl-2-(4-bromophenoxy)ethanone; piperazin-1-yl-3-(4-fluorophenyl)propan-1-one; piperazin-1-yl-2-(3-chlorophenoxy)ethanone; 4-acetylphenoxy-piperazin-1-yl-ethanone; piperazin-1-yl-2-oxoethoxy)benzoate; piperazin-1-yl-2-(4-hydroxyphenoxy)ethanone; piperazin-1-yl-3-(4-bromophenyl)propan-1-one; N-(2-methoxyphenyl)piperazinyl-carboxamide; N-(4-bromophenyl)piperazinyl-carboxamide; N-(2,4-difluorophenyl)piperazinyl-carboxamide; piperazin-1-yl-2-(4-chloro-2-methylphenoxy)ethanone; piperazin-1-yl-2-(2,4-dichlorophenoxy)ethanone; (methylphenyl-carbamoyl)methyl]piperazin-1-yl; phenoxyethyl)piperazin-1-yl; (4-chlorophenyl)acetyl]-piperazin-1-yl; (4-chlorophenyl)acetyl]-piperazin-1-yl; [2-(3-nitrophenoxy)acetyl]-piperazin-1-yl; 4-(2-methoxyethyl)-piperazin-1-yl; 4-acetylpiperazin-1-yl; 4-isobutylpiperazin-1-yl; 3-chloro-4-fluorophenyl-amino; 4-(2-phenoxyethyl)piperazin-1-yl; 4-benzoylpiperidine-1-yl; 4-chlorophenoxyacetyl) pyrrolidin-3-(S)-ylamino; 1-tert-butoxycarbonylpyrrolidin-3-(S)-ylamino; 1-benzyloxycarbonylpiperidin-3-ylamino; 3-(R)-(4-chlorobenzoylamino)-pyrrolidin-1-yl; 3-(R)-[2-(4-chlorophenoxy)-acetylamino]pyrrolidin-1-yl; 3-(R)-tert-butoxycarbonylamino; 4-(phenethylcarbamoyl-methyl)piperazin-1-yl; 4-thiazol-2-yl-piperazine-1-yl;

4-[(methylphenylcarbamoyl)-methyl]piperazin-1-yl; 4-chlorophenoxy)acetyl]homopiperazin-1-yl; 4-phenylmethanesulfonylpiperazin-1-yl; 4-(3-phenylpropionyl)piperazin-1-yl; 4-[2-phenoxyacetyl]piperazin-1-yl; 4-[2-(4-chlorophenyl)acetyl]piperazin-1-yl; 4-[2-(3-nitrophenoxy)acetyl]piperazin-1-yl; 4-(phenylsulfonyl)piperazin-1-yl; pyrimidin-7-yl-piperazinyl-1-carboxylate; 4-benzylpiperazin-1-yl; piperazin-1-yl-1-morpholinoethanone; 4-pentylpiperazin-1-yl; 4-(thiazol-2-yl)piperazin-1-yl; 4-m-tolylpiperazin-1-yl; 3-methoxypropylamino; ethoxy; 2-methoxyethoxy; benzylthio; benzyl amino; preferably methylthio, piperazin-1-yl, ethoxy, morpholino, 4-m-tolyl-carbamoyl-piperazin-1-yl, 4-(4-chlorophenoxyacetyl)piperazin-1-yl, 4-[2-(4-bromophenoxy)acetyl]-piperazin-1-yl, 4-[2-(3-nitrophenoxy)acetyl]-piperazin-1-yl, and 4-(2-phenoxyacetyl)-piperazin-1-yl.

One embodiment of the present invention concerns a compound according to the invention wherein $R^2$ is selected from the group consisting of 4-fluorophenyl, 4-fluorobenzyl, 4-fluorophenethyl, 2-(4-fluorophenoxy)ethyl, 1-(4-fluorophenyl)ethyl, 1-(4-fluorophenyl)-2-phenylethyl, 3-pyridyl, 3-methoxyphenyl, cyclopropyl, cyclohexyl, 3,4-dichlorophenyl, 1-phenylcyclopropyl, 1-(4-chlorophenyl)cyclopropyl, 2-thiophen-2-ylethyl, pentyl, and 2-phenylethyl; $R^1$ and is amino; and $R^3$ is selected from the group consisting of methylthio, piperazin-1-yl, ethoxy, morpholino, 4-m-tolyl-carbamoyl-piperazin-1-yl, 4-(4-chlorophenoxyacetyl)piperazin-1-yl, 4-[2-(4-bromophenoxy)acetyl]-piperazin-1-yl, 4-[2-(3-nitrophenoxy)acetyl]-piperazin-1-yl, and 4-(2-phenoxyacetyl)-piperazin-1-yl.

One embodiment of the present invention concerns a compound according to the invention wherein, $R^4$ and $R^6$ have any of the values as described herein and $R^5$ is phenyl or 4-fluorophenyl.

One embodiment of the present invention concerns a compound according to the invention wherein, $R^4$ and $R^5$ have any of the values as described herein and $R^6$ is 4(m-tolylcarbamoyl)piperazin-1-yl or 4-(2-(4-chlorophenoxy)acetyl)piperazin-1-yl.

One embodiment of the present invention concerns a compound according to the invention wherein $R^7$, $R^8$, $R^9$, and $R^{11}$ have any of the values as described herein and $R^{12}$ is 4-(4-chlorophenoxy)acetylpiperazin-1-yl or 4-(phenoxyacetyl)piperazin-1-yl.

One embodiment of the present invention concerns a compound according to the invention wherein, $R^5$ is phenyl or 4-fluorophenyl; $R^4$ is amino; and $R^6$ is (4(m-tolylcarbamoyl)piperazin-1-yl or (4-(2-(4-chlorophenoxy)acetyl)piperazin-1-yl).

One embodiment of the present invention concerns a compound according to the invention wherein, $R^7$, $R^{12}$, $R^9$, and $R^{11}$ have any of the values as described herein and $R^8$ is 4-fluorophenyl or methylthio.

One embodiment of the present invention concerns a compound according to the invention wherein $R^{12}$, $R^8$, and $R^{11}$ have any of the values as described herein $R^9$ is hydrogen or methyl.

One embodiment of the present invention concerns a compound according to the invention wherein $R^8$, $R^{12}$, and $R^{11}$ have any of the values as described herein $R^7$ is hydrogen or methyl.

One embodiment of the present invention concerns a compound according to the invention wherein $R^{11}$ is amino, $R^{12}$ is 4-(4-chlorophenoxy)acetylpiperazin-1-yl or (4-phenoxyacetyl)piperazin-1-yl, $R^8$ is 4-fluorophenyl or methylthio, and $R^9$ is hydrogen or methyl.

One embodiment of the present invention concerns a compound according to the invention wherein $R^{11}$ is amino, $R^{12}$ is 4-(4-chlorophenoxy)acetylpiperazin-1-yl or 4-(phenoxyacetyl)piperazin-1-yl, $R^8$ is 4-fluorophenyl or methylthio, and $R^7$ is hydrogen or methyl.

In an embodiment, the present invention encompasses a thiazolo(5,4-d)pyrimidine or oxazolo(5,4-d)pyrimidine derivative having the general formula I: wherein —X is S or O;

$R^1$ is selected from the group consisting of hydrogen, halogen, cyano, carboxylic acid, acyl, thioacyl, alkoxycarbonyl, acyloxy, carbonate, carbamate, $C_{1-7}$ alkyl, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, $C_{1-7}$ alkyloxy;

$R^3$ is selected from the group consisting of (mono- or di-) $C_{1-12}$ alkylamino; monoarylamino; diarylamino; (mono- or di-) $C_{3-10}$ cycloalkylamino; (mono- or di-) hydroxy $C_{1-7}$ alkylamino; (mono- or di-) $C_{1-4}$ alkylarylamino; (mono- or di-) aryl$C_{1-4}$ alkylamino; morpholinyl; mercapto $C_{1-7}$ alkyl; $C_{1-7}$ alkoxy, homopiperazinyl and piperazinyl, wherein said homopiperazinyl or piperazinyl is optionally N-substituted with a substituent $R^{29}$ selected from the group consisting of formyl, acyl, thioacyl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl, wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino; and $R^2$ is selected from the group consisting of heteroaryl and aryl groups; hydrogen; halogen; $C_{1-7}$ alkyl; $C_{2-7}$ alkenyl; $C_{2-7}$ alkynyl; halo $C_{1-7}$ alkyl; carboxy $C_{1-7}$ alkyl; carboxyaryl; $C_{1-7}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl;

thioheterocyclic; arylalkylthio; heterocyclic-substituted alkylthio; hydroxylamino; acylamino; thio-acylamino; alkoxyamino; thioalkyl-amino; acetal; thio-acetal; carboxylic acid; carboxylic acid esters, thioesters, halides, anhydrides, amides and thioamides; thiocarboxylic acid; thiocarboxylic acid esters, thioesters, halides, anhydrides, amides and thioamides; hydroxyl; sulfhydryl; nitro; cyano; carbamoyl; thiocarbamoyl; ureido; thioureido; amino; alkylamino; cycloalkylamino; alkenylamino; cyclo-alkenylamino; alkynylamino; arylamino; arylalkylamino; hydroxyalkylamino; mercaptoalkyl-amino; heterocyclic amino; heterocyclic substituted arylamino; heterocyclic-substituted alkylamino; oximino; alkyloximino; hydrazino; alkylhydrazino; phenylhydrazino; esters, thioesters, halides, anhydrides, amides and thioamides thereof; aromatic or heterocyclic substituents substituted with an aliphatic spacer between the thiazolo(5,4-d)pyrimidine or oxazolo(5,4-d)pyrimidine ring and the aromatic or heterocyclic substituent, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino; and wherein said aliphatic spacer is a branched or straight, saturated or unsaturated aliphatic chains of 1 to 7 carbon atoms optionally containing one or more functions, atoms or radicals independently selected from the group consisting of halogen, carbonyl, thiocarbonyl, hydroxyl, thiol, ether, thio-ether, acetal, thio-acetal, amino, imino, oximino, alkyloximino, aminoacid, cyano, acylamino, thioacylamino, carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkyl-amino, cycloalkylamino, alkenylamino, cycloalkenylamino, alkynylamino, arylamino, arylalkyl-amino, hydroxyalkylamino, mercaptoalkylamino, heterocyclic-substituted alkylamino, hetero-cyclic amino, heterocyclic-substituted arylamino, hydrazino, alkylhydrazino, phenylhydrazino, sulfonyl, sulfinyl and sulfonamido; and/or a pharmaceutical acceptable addition salt thereof and/or a stereoisomer thereof and/or a solvate thereof.

One embodiment of the present invention concerns thiazolo(5,4-d)pyrimidine or oxazolo(5,4-d)pyrimidine of formula I, any subgroup thereof, or stereoisomeric forms thereof, wherein $R^2$ and $R^3$ have any of the values as described herein and $R^1$ is selected from the group consisting of amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino.

One embodiment of the present invention concerns thiazolo(5,4-d)pyrimidine or oxazolo(5,4-d)pyrimidine of formula I, any subgroup thereof, or stereoisomeric forms thereof, wherein $R^2$ and $R^1$ have any of the values as described herein and $R^3$ is homopiperazinyl or piperazinyl. One embodiment of the present invention concerns thiazolo(5,4-d)pyrimidine or oxazolo(5,4-d)pyrimidine of formula I, any subgroup thereof, or stereoisomeric forms thereof, wherein $R^1$ and $R^3$ have any of the values as described herein and $R^2$ is selected from the group consisting of 4-fluorophenyl, 4-fluorobenzyl, 4-fluorophenethyl, 2-(4-fluorophenoxy)ethyl, 1-(4-fluorophenyl)ethyl, 1-(4-fluorophenyl)-2-phenylethyl, 3-pyridyl, 3-methoxyphenyl, cyclopropyl, cyclohexyl, 3,4-dichlorophenyl, 1-phenylcyclopropyl, 1-(4-chlorophenyl)cyclopropyl, 2-thiophen-2-ylethyl, pentyl, and 2-phenylethyl.

One embodiment of the present invention concerns thiazolo(5,4-d)pyrimidine or oxazolo(5,4-d)pyrimidine of formula I, any subgroup thereof, or stereoisomeric forms thereof, wherein $R^2$ and $R^3$ have any of the values as described herein and $R^1$ is selected from the group consisting of amino, methyl, and hydrogen.

One embodiment of the present invention concerns thiazolo(5,4-d)pyrimidine or oxazolo(5,4-d)pyrimidine of formula I, any subgroup thereof, or stereoisomeric forms thereof, wherein $R^2$ and $R^1$ have any of the values as described herein and $R^3$ is selected from the group consisting of methylthio, piperazin-1-yl, ethoxy, morpholino, 4-m-tolylcarbamoyl-piperazin-1-yl, 4-(4-chlorophenoxyacetyl)piperazin-1-yl, 4-[2-(4-bromophenoxy)acetyl]-piperazin-1-yl, 4-[2-(3-nitrophenoxy)acetyl]-piperazin-1-yl, and 4-(2-phenoxyacetyl)-piperazin-1-yl.

One embodiment of the present invention concerns thiazolo(5,4-d)pyrimidine or oxazolo(5,4-d)pyrimidine of formula I, any subgroup thereof, or stereoisomeric forms thereof, wherein $R^2$ is selected from the group consisting of 4-fluorophenyl, 4-fluorobenzyl, 4-fluorophenethyl, 2-(4-fluorophenoxy)ethyl, 1-(4-fluorophenyl)ethyl, 1-(4-fluorophenyl)-2-phenylethyl, 3-pyridyl, 3-methoxyphenyl, cyclopropyl, cyclohexyl, 3,4-dichlorophenyl, 1-phenylcyclopropyl, 1-(4-chlorophenyl)cyclopropyl, 2-thiophen-2-ylethyl, pentyl, and 2-phenylethyl; $R^5$ is selected from the group consisting of amino, methyl, and hydrogen; and $R^7$ is selected from the group consisting of methylthio, piperazin-1-yl, ethoxy, morpholino, 4-m-tolylcarbamoyl-piperazin-1-yl, 4-(4-chlorophenoxyacetyl)piperazin-1-yl, 4-[2-(4-bromophenoxy)acetyl]-piperazin-1-yl, 4-[2-(3-nitrophenoxy)acetyl]-piperazin-1-yl, and 4-(2-phenoxyacetyl)-piperazin-1-yl.

One embodiment of the present invention concerns thiazolo(5,4-d)pyrimidine or oxazolo(5,4-d)pyrimidine of formula I, any subgroup thereof, or stereoisomeric forms thereof, wherein X is S. One embodiment of the present invention concerns thiazolo(5,4-d)pyrimidine or oxazolo(5,4-d)pyrimidine of formula I, any subgroup thereof, or stereoisomeric forms thereof, wherein X is O.

One embodiment of the present invention concerns thiazolo(5,4-d)pyrimidine or oxazolo(5,4-d)pyrimidine of formula I, any subgroup thereof, or stereoisomeric forms thereof, being selected from the group consisting of: 2-(4-fluorophenyl)-7-(methylthio)thiazolo[5,4-d]pyrimidin-5-amine; 2-(4-fluorobenzyl)-7-(methylthio)thiazolo[5,4-d]pyrimidin-5-amine; 2-(4-fluorophenethyl)-7-methylthio-thiazolo[5,4-d]pyrimidin-5-amine; 2-(2-(4-fluorophenoxy)ethyl)-7-(methylthio)thiazolo[5,4-d]pyrimidin-5-amine;

2-(4-fluorophenyl)-5-methyl-7-methylthio-thiazolo[5,4-d]
pyrimidine; 2-(4-fluorophenyl)-7-(piperazin-1-yl)-thiazolo
[5,4-d]pyrimidin-5-amine; 2-(4-fluorobenzyl)-7-(piperazin-
1-yl)-thiazolo[5,4-d]pyrimidin-5-amine; 2-(4-
fluorophenethyl)-7-(piperazin-1-yl)thiazolo[5,4-d]
pyrimidin-5-amine; 7-(benzylthio)-2-(4-fluorophenyl)
thiazolo[5,4-d]pyrimidin-5-amine; 2-(4-fluorophenyl)-7-(2-
methoxyethoxy)-thiazolo[5,4-d]pyrimidin-5-amine;
7-ethoxy-2-(4-fluorophenyl)thiazolo[5,4-d]pyrimidin-5-
amine; 7-ethoxy-2-(4-fluorobenzyl)thiazolo[5,4-d]pyrimi-
din-5-amine; 2-(4-fluorophenyl)-N-7-(3-methoxypropyl)
thiazolo[5,4-d]pyrimidine-5,7-diamine; 2-(4-fluorophenyl)-
7-morpholino-thiazolo[5,4-d]pyrimidin-5-amine; 2-(4-
fluorobenzyl)-7-morpholino-thiazolo[5,4-d]pyrimidin-5-
amine; 2-(4-fluorophenyl)-7-(4-m-tolylpiperazin-1-yl)-
thiazolo[5,4-d]pyrimidin-5-amine; 2-(4-fluorophenyl)-7-(4-
(thiazol-2-yl)piperazin-1-yl)thiazolo[5,4-d]pyrimidin-5-
amine; 2-(4-fluorophenyl)-7-(4-pentylpiperazin-1-yl)
thiazolo[5,4-d]pyrimidin-5-amine; 2-(4-(5-amino-2-(4-
fluorophenyl)thiazolo[5,4-d]pyrimidin-7-yl)piperazin-1-yl)-
1-morpholinoethanone; 7-(4-benzylpiperazin-1-yl)-2-(4-
fluorophenyl)thiazolo[5,4-d]pyrimidin-5-amine; benzyl-4-
(5-amino-2-(4-fluorophenyl)thiazolo[5,4-d]pyrimidin-7-yl)
piperazine-1-carboxylate; 2-(4-fluorophenyl)-7-(4-
(phenylsulfonyl)piperazin-1-yl)thiazolo[5,4-d]pyrimidin-5-
amine; 4-(5-amino-2-(4-fluorophenyl)-thiazolo[5,4-d]
pyrimidin-7-yl)-N-p-tolylpiperazine-1-carboxamide; 4-(5-
amino-2-(4-fluorophenyl)thiazolo[5,4-d]pyrimidin-7-yl)-N-
m-tolylpiperazine-1-carboxamide; 4-(5-amino-2-(4-
fluorobenzyl)thiazolo[5,4-d]pyrimidin-7-yl)-N-m-
tolylpiperazine-1-carboxamide; 1-(4-(5-amino-2-(4-
fluorophenyl)thiazolo[5,4-d]pyrimidin-7-yl)piperazin-1-yl)-
2-(4-chlorophenoxy)ethanone; 1-(4-(5-amino-2-(4-
fluorobenzyl)thiazolo[5,4-d]pyrimidin-7-yl)piperazin-1-yl)-
2-(4-chlorophenoxy)ethanone; 2-(4-chlorophenoxy)-1-(4-
(2-(4-fluorophenyl)-5-methylthiazolo[5,4-d]pyrimidin-7-yl)
piperazin-1-yl)ethanone; 1-(4-(5-amino-2-(2-(4-
fluorophenoxy)ethyl)thiazolo[5,4-d]pyrimidin-7-yl)
piperazin-1-yl)-2-(4-chlorophenoxy)ethanone; 1-(4-(5-
amino-2-(4-fluorophenethyl)-thiazolo[5,4-d]pyrimidin-7-
yl)piperazin-1-yl)-2-(4-chlorophenoxy)ethanone; 1-(4-(5-
amino-2-(4-fluorophenethyl)thiazolo[5,4-d]pyrimidin-7-yl)
piperazin-1-yl)-2-(4-methoxyphenoxy)ethanone; 1-(4-(5-
amino-2-(4-fluorophenethyl)thiazolo[5,4-d]pyrimidin-7-yl)
piperazin-1-yl)-2-(4-fluorophenoxy)ethanone; 1-(4-(5-
amino-2-(4-fluorophenethyl)thiazolo[5,4-d]pyrimidin-7-yl)
piperazin-1-yl)-2-(4-bromophenoxy)ethanone; 1-(4-(5-
amino-2-(4-fluorophenethyl)thiazolo[5,4-d]pyrimidin-7-yl)
piperazin-1-yl)-2-(m-tolyloxy)ethanone; 1-(4-(5-amino-2-
(4-fluorophenethyl)thiazolo[5,4-d]pyrimidin-7-yl)
piperazin-1-yl)-2-(2,4-dichlorophenoxy)ethanone; 1-(4-(5-
amino-2-(4-fluorophenethyl)thiazolo[5,4-d]pyrimidin-7-yl)
piperazin-1-yl)-3-(4-fluorophenoxy)propan-1-one; 2-(1-(4-
fluorophenyl)ethyl)-7-methylthio-thiazolo[5,4-d]pyrimidin-
5-amine; 2-(1-(4-fluorophenyl)-2-phenylethyl)-7-
(methylthio)thiazolo[5,4-d]pyrimidin-5-amine; 1-(4-(5-
amino-2-(1-(4-fluorophenyl)ethyl)thiazolo[5,4-d]
pyrimidin-7-yl)piperazin-1-yl)-2-(4-chlorophenoxy)
ethanone; 1-(4-(5-amino-2-(1-(4-fluorophenyl)-2-
phenylethyl)thiazolo[5,4-d]pyrimidin-7-yl)piperazin-1-yl)-
2-(4-chlorophenoxy)ethanone; 4-(5-amino-2-(1-(4-
fluorophenyl)ethyl)thiazolo[5,4-d]pyrimidin-7-yl)-N-m-
tolylpiperazine-1-carboxamide; 2-(4-fluorophenyl)-5,7-bis
(methylthio)-thiazolo[5,4-d]pyrimidine; 5,7-bis(butylthio)-2-
(4-fluorophenyl)thiazolo[5,4-d]pyrimidine; 5,7-bis
(benzylthio)-2-(4-fluorophenyl)thiazolo[5,4-d]pyrimidine;
7-ethoxy-2-(4-fluorophenyl)-5-(methylthio)thiazolo[5,4-d]
pyrimidine; 5-amino-2-cyclopropyl-7-methylthio-thiazolo
[5,4-d]pyrimidine; 5-amino-2-(2-phenylethyl)-7-methylth-
iothiazolo[5,4-d]pyrimidine; 5-amino-2-cyclohexyl-7-
methylthiothiazolo[5,4-d]pyrimidine; 5-amino-2-(3-
pyridinyl)-7-methylthiothiazolo[5,4-d]pyrimidine; 5-amino-
2-(4-chlorobenzyl)-7-methylthiothiazolo[5,4-d]pyrimidine;
5-amino-2-(3-methoxyphenyl)-7-methylthiothiazolo[5,4-d]
pyrimidine; 5-amino-2-(4-chlorophenyl)-7-(methylthio)
thiazolo[5,4-d]pyrimidine; 5-amino-2-cyclopropyl-7-meth-
oxythiazolo[5,4-d]pyrimidine; 5-amino-2-cyclopropyl-7-N-
piperazino-thiazolo[5,4-d]pyrimidine; 5-amino-2-(3,4-
dichlorophenyl)-7-(N-piperazino)thiazolo[5,4-d]
pyrimidine; 5-amino-2-(1-phenylcyclopropyl)-7-(N-
piperazino)thiazolo[5,4-d]pyrimidine; 5-amino-2-(1-(4-
chlorophenyl)cyclopropyl)-7-(N-piperazino)thiazolo[5,4-d]
pyrimidine; 5-amino-7-N-piperazino-2-methylthio-thiazolo
[5,4-d]pyrimidine; 5-amino-7-[4-(4-chlorophenoxyacetyl)
piperazin-1-yl]-2-(1-phenylcyclopropyl)thiazolo[5,4-d]
pyrimidine; 5-amino-7-[4-(4-chlorophenoxyacetyl)
piperazin-1-yl]-2-methylthio-thiazolo[5,4-d]pyrimidine;
5-amino-7-[4-(4-chlorophenoxyacetyl)piperazin-1-yl]-2-(3,
4-dichlorophenyl)thiazolo[5,4-d]pyrimidine; 5-amino-7-[4-
(4-chlorophenoxyacetyl)piperazin-1-yl]-2-(1-(4-chlorophe-
nyl)cyclopropyl)thiazolo[5,4-d]pyrimidine; 5-amino-7-[4-
(4-chlorophenoxyacetyl)piperazin-1-yl]-2-(2-phenylethyl)
thiazolo[5,4-d]pyrimidine; 5-amino-2-cyclopropyl-7-[4-(4-
chlorophenoxyacetyl)piperazin-1-yl]-thiazolo[5,4-d]
pyrimidine; 5-amino-7-[4-(4-chlorophenoxyacetyl)
piperazin-1-yl]-2-cyclohexylthiazolo[5,4-d]pyrimidine;
5-amino-7-[4-(4-chlorophenoxyacetyl)piperazin-1-yl]-2-
(pyridine-3-yl)thiazolo[5,4-d]pyrimidine; 5-amino-7-[4-(4-
chlorophenoxyacetyl)piperazin-1-yl]-2-(N-oxopyridine-3-
yl)thiazolo[5,4-d]pyrimidine; 5-amino-7-[4-(4-
chlorophenoxyacetyl)piperazin-1-yl]-2-(4-
chlorophenylmethyl)thiazolo[5,4-d]pyrimidine; 5-amino-7-
[4-(4-chlorophenoxyacetyl)piperazin-1-yl]-2-(4-
chlorophenyl)thiazolo[5,4-d]pyrimidine; 5-amino-7-[4-(4-
chlorophenoxyacetyl)piperazin-1-yl]-2-(3-methoxyphenyl)
thiazolo[5,4-d]pyrimidine; 5-amino-7-[4-(4-
chlorophenoxyacetyl)piperazin-1-yl]-2-(1-(4-chlorophenyl)
ethyl)thiazolo[5,4-d]pyrimidine; 5-amino-7-[4-(4-
chlorophenoxyacetyl)piperazin-1-yl]-2-(4-
fluorophenylamino)-thiazolo[5,4-d]pyrimidine; 5-amino-2-
(4-fluorophenyl)-7-(4-[2-(4-bromophenoxy)acetyl]-
piperazin-1-yl)-thiazolo[5,4-d]pyrimidine; 5-amino-2-(4-
fluorophenyl)-7-(4-[2-(3-nitrophenoxy)acetyl]-piperazin-1-
yl)-thiazolo[5,4-d]pyrimidine; 5-amino-2-(4-fluorophenyl)-
7-(4-(2-phenoxyacetyl)-piperazin-1-yl)-thiazolo[5,4-d]
pyrimidine; 5-amino-2-[2-(4-fluorophenyl)ethyl]-7-(4-[2-
(3-nitrophenoxy)acetyl]piperazin-1-yl)-thiazolo[5,4-d]
pyrimidine; 5-amino-2-[2-(4-fluorophenyl)ethyl]-7-(4-[2-
(4-chlorophenyl)acetyl]piperazin-1-yl)-thiazolo[5,4-d]
pyrimidine; 5-amino-2-[2-(4-fluorophenyl)ethyl]-7-(4-m-
tolylcarbamoylpiperazin-1-yl)-thiazolo[5,4-d]pyrimidine;
5-amino-2-[2-(4-fluorophenyl)ethyl]-7-(4-[2-phenoxy-
acetyl]piperazin-1-yl)-thiazolo[5,4-d]pyrimidine; 5-amino-
2-[2-(4-fluorophenyl)ethyl]-7-[4-(4-chlorobenzoyl)piper-
azin-1-yl]-thiazolo[5,4-d]pyrimidine; 5-amino-2-[2-(4-
fluorophenyl)ethyl]-7-[4-(3-phenylpropionyl)piperazin-1-
yl]-thiazolo[5,4-d]pyrimidine; 5-amino-2-[2-(4-
fluorophenyl)ethyl]-7-[4-phenylmethanesulfonylpiperazin-
1-yl]-thiazolo[5,4-d]pyrimidine; 5-amino-2-[2-(4-
fluorophenyl)ethyl]-7-(4-[2-(4-chlorophenoxy)acetyl]
homopiperazin-1-yl)-thiazolo[5,4-d]pyrimidine; 5-amino-
2-[2-(4-fluorophenyl)ethyl]-7-(4-[(methylphenylcarbamoyl)-
methyl]piperazin-1-yl)-thiazolo[5,4-d]pyrimidine; 5-amino-
2-[2-(4-fluorophenyl)ethyl]-7-(4-thiazol-2-yl-piperazine-1- yl)-thiazolo[5,4-d]pyrimidine; 5-amino-2-[2-(4-fluorophenyl)ethyl]-7-(4-(phenethylcarbamoyl-methyl)piperazin-1-yl)-thiazolo[5,4-d]pyrimidine; 5-amino-2-[2-(4-fluorophenyl)ethyl]-7-((3-(R)-tert-butoxycarbonylamino)pyrrolidin-1-yl)-thiazolo[5,4-d]pyrimidine; 5-amino-2-[2-(4-fluorophenyl)ethyl]-7-(3-(R)-[2-(4-chlorophenoxy)-acetylamino]pyrrolidin-1-yl)-thiazolo[5,4-d]pyrimidine; 5-amino-2-[2-(4-fluorophenyl)ethyl]-7-(3-(R)-(4-chlorobenzoylamino)-pyrrolidin-1-yl)-thiazolo[5,4-d]pyrimidine; 5-amino-2-[2-(4-fluorophenyl)ethyl]-7-(1-benzyloxycarbonylpiperidin-3-ylamino)-thiazolo[5,4-d]pyrimidine; 5-amino-2-[2-(4-fluorophenyl)ethyl]-7-(1-tert-butoxycarbonylpyrrolidin-3-(S)-ylamino)-thiazolo[5,4-d]pyrimidine; 5-amino-2-[2-(4-fluorophenyl)ethyl]-7-(1-(4-chlorophenoxyacetyl)pyrrolidin-3-(S)-ylamino)-thiazolo[5,4-d]pyrimidine; 5-amino-2-[2-(4-fluorophenyl)ethyl]-7-(4-benzoylpiperidine-1-yl)-thiazolo[5,4-d]pyrimidine; 5-amino-2-[2-(4-fluorophenyl)ethyl]-7-(4-(2-phenoxyethyl)piperazin-1-yl)-thiazolo[5,4-d]pyrimidine; 5-amino-2-[1-(4-fluorophenyl)propyl]-7-(4-[2-(4-chlorophenoxy)acetyl]piperazin-1-yl)thiazolo[5,4-d]pyrimidine; 5-amino-2-[cyclopentyl-(4-fluorophenyl)methyl]-7-(4-[2-(4-chlorophenoxy)acetyl]piperazin-1-yl)thiazolo[5,4-d]pyrimidine; 5-amine-7-piperazin-1-yl-2-(2-thiophen-2-ylethyl)thiazolo[5,4-d]pyrimidine; 5-amino-2-(2-thiophen-2-ylethyl)-7-(4-[2-(4-chloro-phenoxy)acetyl]piperazin-1-yl)thiazolo[5,4-d]pyrimidine; 5-amino-2-(2-thiophen-2-ylethyl)-7-(4-[2-(4-chloro-phenyl)acetyl]piperazin-1-yl)thiazolo[5,4-d]pyrimidine; 5-amino-2-(2-thiophen-2-ylethyl)-7-(4-(4-chloro-benzoyl)piperazin-1-yl)thiazolo[5,4-d]pyrimidine; 5-amino-2-(2-thiophen-2-ylethyl)-7-(4-m-tolylcarbamoylpiperazin-1-yl)thiazolo[5,4-d]pyrimidine; 2-(4-chlorophenoxy)-1-(4-(2-(4-fluorophenyl)oxazolo[5,4-d]pyrimidin-7-yl)piperazin-1-yl)ethanone; 2-(4-chlorophenoxy)-1-(4-(2-(4-fluorophenyl)-5-methyl-oxazolo[5,4-d]pyrimidin-7-yl)piperazin-1-yl)ethanone; 1-(4-(5-amino-2-(4-fluorophenyl)oxazolo[5,4-d]pyrimidin-7-yl)piperazin-1-yl)-2-(4-chlorophenoxy)ethanone; 2-(4-chlorophenoxy)-1-(4-(2-(4-fluorobenzyl)oxazolo[5,4-d]pyrimidin-7-yl)piperazin-1-yl)ethanone; 2-(4-chlorophenoxy)-1-(4-(2-(4-fluorobenzyl)-5-methyloxazolo[5,4-d]pyrimidin-7-yl)piperazin-1-yl)ethanone; 1-(4-(5-amino-2-(4-fluorophenethyl)oxazolo[5,4-d]pyrimidin-7-yl)piperazin-1-yl)-2-(4-chlorophenoxy)ethanone; N-(3-chloro-4-fluorophenyl)-2-(4-fluorophenyl)-oxazolo[5,4-d]pyrimidin-7-amine; N-7-(3-chloro-4-fluorophenyl)-2-(4-fluorophenyl)-oxazolo[5,4-d]pyrimidine-5,7-diamine; 5-amino-2-cyclopropyl-7-N-piperazino-oxazolo[5,4-d]pyrimidine; 5-amino-2-methoxymethyl-7-N-piperazino-oxazolo[5,4-d]pyrimidine; 5-amino-2-cyclohexyl-7-N-piperazino-oxazolo[5,4-d]pyrimidine; 5-amino-2-pentyl-7-N-piperazino-oxazolo[5,4-d]pyrimidine; 5-amino-2-(2-phenylethyl)-7-N-piperazino-oxazolo[5,4-d]pyrimidine; 5-amino-2-cyclopropyl-7-[4-(4-chlorophenoxyacetyl)piperazin-1-yl]-oxazolo[5,4-d]pyrimidine; 5-amino-7-[4-(4-chlorophenoxyacetyl)piperazin-1-yl]-2-methoxylmethyloxazolo[5,4-d]pyrimidine; 5-amino-2-cyclohexyl-7-[4-(4-chlorophenoxyacetyl)piperazin-1-yl]oxazolo[5,4-d]pyrimidine; 5-amino-7-[4-(4-chlorophenoxyacetyl)piperazin-1-yl]-2-pentyloxazolo[5,4-d]pyrimidine; 5-amino-2-(2-phenylethyl)-7-[4-(4-chlorophenoxyacetyl)piperazin-1-yl]oxazolo[5,4-d]pyrimidine; 5-amino-2-(4-fluorophenyl)-7-(4-isobutylpiperazin-1-yl)-oxazolo[5,4-d]pyrimidine; 5-amino-2-(4-fluorophenyl)-7-(4-acetylpiperazin-1-yl)-oxazolo[5,4-d]pyrimidine; 5-amino-2-(4-fluorophenyl)-7-[4-(2-methoxyethyl)-piperazin-1-yl]-oxazolo[5,4-d]pyrimidine; 5-amino-2-(4-fluorophenyl)-7-(4-[2-(3-nitrophenoxy)acetyl]-piperazin-1-yl)-oxazolo[5,4-d]pyrimidine; 5-amino-2-[2-(4-fluorophenyl)ethyl]-7-(4-[2-(4-chlorophenyl)acetyl]-piperazin-1-yl)-oxazolo[5,4-d]pyrimidine; 5-amino-2-[2-(4-fluorophenyl)ethyl]-7-(4-[4-chlorobenzoyl]piperazin-1-yl)-oxazolo[5,4-d]pyrimidine; 5-amino-2-[2-(4-fluorophenyl)ethyl]-7-(4-m-tolylcarbamoylpiperazin-1-yl)-oxazolo[5,4-d]pyrimidine; 5-amino-2-[2-(4-fluorophenyl)ethyl]-7-(4-(2-phenoxyethyl)piperazin-1-yl)-oxazolo[5,4-d]pyrimidine; and 5-amino-2-[2-(4-fluorophenyl)ethyl]-7-(4-[(methylphenyl-carbamoyl)methyl]piperazin-1-yl)-oxazolo[5,4-d]pyrimidine.

The present invention also concerns thiazolo(5,4-d)pyrimidine or oxazolo(5,4-d)pyrimidine of formula I, any subgroup thereof, or stereoisomeric forms thereof, for use as a medicine.

The present invention also concerns thiazolo(5,4-d)pyrimidine or oxazolo(5,4-d)pyrimidine of formula I, any subgroup thereof, or stereoisomeric forms thereof, for use as a medicine for the prevention or treatment of immune disorders in an animal.

The present invention also concerns the use of the thiazolo(5,4-d)pyrimidine or oxazolo(5,4-d)pyrimidine of formula I, any subgroup thereof, or stereoisomeric forms thereof, for the manufacture of a medicament for the prevention or treatment of an immune disorder in an animal. In an embodiment, said immune disorder is an autoimmune disorder or an immune disorder as a result from an organ or a cells transplantation. In an embodiment, said animal is a mammal, preferably said mammal is a human being. In an embodiment, said immune disorder is an autoimmune disorder or an immune disorder as a result from an organ or cells transplantation.

The present invention also concerns a pharmaceutical composition comprising a therapeutically effective amount of a thiazolo(5,4-d)pyrimidine or oxazolo(5,4-d)pyrimidine of formula I, any subgroup thereof, or stereoisomeric forms thereof, and one or more pharmaceutically acceptable excipients. In an embodiment, said pharmaceutical composition further comprises one or more biologically active drugs being selected from the group consisting of immunosuppressant and/or immunomodulator drugs, and antineoplastic drugs.

The present invention also concerns a method of prevention or treatment of an immune disorder in an animal, comprising the administration of a therapeutically effective amount of a thiazolo(5,4-d)pyrimidine or oxazolo(5,4-d)pyrimidine derivative or formula I, optionally in combination with one or more pharmaceutically acceptable excipients. In an embodiment, said immune disorder is an autoimmune disorder or an immune disorder as a result from an organ or cells transplantation. In an embodiment, said animal is a mammal, preferably said mammal is a human being.

The present invention also concerns a process for preparation of the thiazolo(5,4-d)pyrimidine derivatives of formula I, wherein X=S, and comprising the steps of: (a) acylation of 2,5-diamino-4,6-dihydroxypyrimidine; (b) treatment with a thionation reagent; (c) treatment with iodomethane; (d) oxidation reaction by adding an oxidating agent; and (e) a nucleophilic aromatic substitution reaction. In an embodiment, in step (a) said acylation is performed with a carboxylic acid ($R^2COOH$) or an acid chloride ($R^2C(O)Cl$). In an embodiment, step (a) further comprises the addition of a coupling reagent. In an embodiment, said coupling reagent is N,N'-dicyclohexylcarbodiimide (DCC) or N,N'-diisopropylcarbodiimide (DIC) or 1-(3-dimethylaminopropyl)-3-ethylcarbodiimide hydrochloride (EDCl). In another embodiment, step (a) further comprises the addition of additives such as 1-hydroxybenzotriazole (HOBt) and 1-hydroxy-7-azabenzotriazole (HOAt). In an embodiment, in step (b) said thionation reagent is phosphorus pentasulfide or a Lawesson's reagent. In an embodiment, in step (b) said treatment with a thionation reagent is performed in high-boiling solvents such as pyridine, toluene or xylene. In an embodiment, step (c) is performed in alkaline conditions. In an embodiment, in step (d) said oxidating agent is m-chloro-peroxybenzoic acid or hydrogen peroxide. In an embodiment, in step (e) a piperazine is introduced at position 7. In an embodiment, the thiazolo(5,4-d)pyrimidine derivatives of formula I are $R^2$-substituted 5-amino-7-N-piperazino thiazolo(5,4-d)pyrimidine derivatives.

In an embodiment, the present invention encompasses a thieno(2,3-d)pyrimidine derivative having the general formula II: wherein $R^4$ is selected from the group consisting of halogen, cyano, carboxylic acid, acyl, thioacyl, alkoxycarbonyl, acyloxy, carbonate, carbamate, $C_{1-7}$ alkyl, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, $C_{1-7}$ alkyloxy;

$R^6$ is selected from the group consisting of (mono- or di-) $C_{1-12}$ alkylamino, monoarylamino, diarylamino, (mono- or di-) $C_{3-10}$ cycloalkylamino, (mono- or di-) hydroxy $C_{1-7}$ alkylamino, (mono- or di-) $C_{1-4}$ alkylarylamino, (mono- or di-) aryl$C_{1-4}$ alkylamino, morpholinyl, mercapto $C_{1-7}$ alkyl, $C_{1-7}$ alkoxy, homopiperazinyl and piperazinyl, wherein said homopiperazinyl or piperazinyl is optionally N-substituted with a substituent $R^{21}$ selected from the group consisting of formyl, acyl, thioacyl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl, wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino; and $R^5$ is selected from the group consisting of heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, or a pharmaceutical acceptable addition salt thereof, or a stereoisomer thereof, or a solvate thereof.

One embodiment of the present invention concerns thieno (2,3-d)pyrimidine derivative of formula II, any subgroup thereof, or stereoisomeric forms thereof, wherein $R^5$ and $R^6$ have any of the values as described herein, and wherein $R^4$ is selected from the group consisting of amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino.

One embodiment of the present invention concerns thieno (2,3-d)pyrimidine derivative of formula II, any subgroup thereof, or stereoisomeric forms thereof, wherein $R^4$ and $R^5$ have any of the values as described herein and wherein $R^6$ is homopiperazinyl or piperazinyl.

One embodiment of the present invention concerns thieno (2,3-d)pyrimidine derivative of formula II, any subgroup thereof, or stereoisomeric forms thereof, wherein $R^4$ and $R^6$ have any of the values as described herein and wherein $R^5$ is phenyl or 4-fluorophenyl.

5One embodiment of the present invention concerns thieno (2,3-d)pyrimidine derivative of formula II, any subgroup thereof, or stereoisomeric forms thereof, wherein $R^5$ and $R^6$ have any of the values as described herein and wherein $R^4$ is butyl, methyl, or amino.

One embodiment of the present invention concerns thieno (2,3-d)pyrimidine derivative of formula II, any subgroup thereof, or stereoisomeric forms thereof, wherein $R^4$ and $R^5$ have any of the values as described herein and wherein $R^6$ is 4(m-tolylcarbamoyl)piperazin-1-yl or 4-(2-(4-chlorophenoxy)acetyl)piperazin-1-yl.

One embodiment of the present invention concerns thieno (2,3-d)pyrimidine derivative of formula II, any subgroup thereof, or stereoisomeric forms thereof, wherein $R^5$ is phenyl or 4-fluorophenyl; $R^4$ is butyl, methyl, or amino; and $R^6$ is (4(m-tolylcarbamoyl)piperazin-1-yl or (4-(2-(4-chlorophenoxy)acetyl)piperazin-1-yl).

One embodiment of the present invention concerns thieno (2,3-d)pyrimidine derivative of formula II, any subgroup thereof, or stereoisomeric forms thereof, being selected from the group consisting of: 1-(4-(2-butyl-6-(4-fluorophenyl) thieno[2,3-d]pyrimidin-4-yl)piperazin-1-yl)-2-(4-chlorophenoxy)ethanone; 2-butyl-N-(3-chloro-4-fluorophenyl)-6-(4-fluorophenyl)thieno[2,3-d]pyrimidin-4-amine; 2-(4-chlorophenoxy)-1-(4-(6-(4-fluorophenyl)-2-methylthieno[2,3-d]pyrimidin-4-yl)piperazin-1-yl)ethanone; 1-(4-(2-amino-6-(4-fluorophenyl)thieno[2,3-d]pyrimidin-4-yl)piperazin-1- yl)-2-(4-chlorophenoxy)ethanone; 2-amino-4-N-benzylamino-6-(4-fluorophenyl)-thieno[2,3-d]pyrimidine; 2-amino-4-N-piperazinyl-6-phenyl-thieno[2,3-d]pyrimidine; 2-amino-4-(4-m-tolylcarbamoylpiperazin-1-yl)-6-phenyl-thieno[2,3-d]pyrimidine; 2-amino-4-(4-m-tolylcarbamoylpiperazin-1-yl)-6-phenyl-thieno[2,3-d]pyrimidine; 2-amino-4-(4-p-chlorophenylcarbamoylpiperazin-1-yl)-6-phenyl-thieno[2,3-d]pyrimidine; 2-amino-4-4-[2-phenoxy)acetyl]piperazin-1-yl)-6-phenyl-thieno[2,3-d]pyrimidine; 2-amino-4-N-homopiperazinyl-6-phenyl-thieno[2,3-d]pyrimidine; 2-amino-4-(4-[2-(4-chlorophenoxy)acetyl]homopiperazin-1-yl)-6-phenyl-thieno[2,3-d]pyrimidine; 2-amino-4-(4-[4-chlorobenzoyl]homopiperazin-1-yl)-6-phenyl-thieno[2,3-d]pyrimidine; 2-amino-4-(4-[(methylphenyl-carbamoyl)methyl]piperazin-1-yl)-6-phenyl-thieno[2,3-d]pyrimidine; 2-amino-4-(4-(2-phenoxyethyl)piperazin-1-yl)-6-phenyl-thieno[2,3-d]pyrimidine; 2-amino-4-(3-(R)-tert-butoxycarbonylamino)pyrrolidin-1-yl)-6-phenyl-thieno[2,3-d]pyrimidine; 2-amino-4-(3-(R)-amino)pyrrolidin-1-yl)-6-phenyl-thieno[2,3-d]pyrimidine; 2-amino-4-(3-(R)-[2-(4-chlorophenoxy)-acetylamino]pyrrolidin-1-yl)-6-phenyl-thieno[2,3-d]pyrimidine; 2-amino-4-(3-(R)-(4-chlorobenzoylamino)-pyrrolidin-1-yl)-6-phenyl-thieno[2,3-d]pyrimidine; 2-amino-4-N-piperazinyl-6-(4-fluorophenyl)-thieno[2,3-d]pyrimidine; 2-amino-4-[N-(hydrocinnamoyl)-piperazin-1-yl]-6-(4-fluorophenyl)-thieno[2,3-d]pyrimidine; 2-amino-4-[4-phenylmethanesulfonylpiperazin-1-yl]-6-(4-fluorophenyl)-thieno[2,3-d]pyrimidine; 2-amino-4-[N-(cyclohexanoyl)-piperazinyl]-6-(4-fluorophenyl)-thieno[2,3-d]pyrimidine; 2-amino-4-[N-(isonicotinoyl)-piperazinyl]-6-(4-fluorophenyl)-thieno[2,3-d]pyrimidine; 2-amino-4-[N-(diisopropylcarbamoyl)-piperazinyl-6-(4-fluorophenyl)-thieno[2,3-d]pyrimidine; 2-amino-4-(4-benzoylpiperidine-1-yl)-6-(4-fluorophenyl)-thieno[2,3-d]pyrimidine; 2-amino-4-N-piperazino-thieno[2,3-d]pyrimidine; 2-amino-4-(4-[2-(4-chlorophenoxy)acetyl]piperazin-1-yl)-thieno[2,3-d]pyrimidin-4-(3H)-one; 2-(4-chlorophenoxy)-1-(4-(6-(4-fluorophenyl)-2-phenylthieno[2,3-d]pyrimidin-4-yl)piperazin-1-yl)ethanone; 4-(4-(2-(4-chlorophenoxy)acetyl)piperazin-1-yl)-6-(4-fluorophenyl)thieno[2,3-d]pyrimidine-2-carboxylate; ethyl 2-(4-(4-(2-(4-chlorophenoxy)acetyl)piperazin-1-yl)-6-(4-fluorophenyl)thieno[2,3-d]pyrimidin-2-yl)acetate; 4-(4-(2-(4-chlorophenoxy)acetyl)piperazin-1-yl)-6-(4-fluorophenyl)thieno[2,3-d]pyrimidine-2-carboxamide; 4-(4-(2-(4-chlorophenoxy)acetyl)piperazin-1-yl)-6-(4-fluorophenyl)-N-(2-methoxyethyl)thieno[2,3-d]pyrimidine-2-carboxamide; 4-(4-(2-(4-chlorophenoxy)acetyl)piperazin-1-yl)-6-(4-fluorophenyl)thieno[2,3-d]pyrimidine-2-carboxylic acid; 2-(4-(4-(2-(4-chlorophenoxy)acetyl)piperazin-1-yl)-6-(4-fluorophenyl)thieno[2,3-d]pyrimidin-2-yl)acetamide; 4-(2-amino-6-(4-fluorophenyl)thieno[2,3-d]pyrimidin-4-yl)-N-m-tolylpiperazine-1-carboxamide; 4-(6-(4-fluorophenyl)-2-phenylthieno[2,3-d]pyrimidin-4-yl)-N-m-tolylpiperazine-1-carboxamide; ethyl 6-(4-fluorophenyl)-4-(4-(m-tolylcarbamoyl)piperazin-1-yl)thieno[2,3-d]pyrimidine-2-carboxylate; 6-(4-fluorophenyl)-4-(4-(m-tolylcarbamoyl)piperazin-1-yl)thieno[2,3-d]pyrimidine-2-carboxamide; 4-ethoxy-6-(4-fluorophenyl)thieno[2,3-d]pyrimidin-2-amine; 6-(4-fluorophenyl)-4-morpholinothieno[2,3-d]pyrimidin-2-amine; N-(3-chloro-4-fluorophenyl)-6-(4-fluorophenyl)-2-methylthieno[2,3-d]pyrimidin-4-amine; and 4-(3-chloro-4-fluorophenylamino)-6-(4-fluorophenyl)thieno[2,3-d]pyrimidine-2-carboxylate.

The present invention also concerns thieno(2,3-d)pyrimidine derivative of formula II, any subgroup thereof, or stereoisomeric forms thereof, for use as a medicine.

The present invention also concerns thieno(2,3-d)pyrimidine derivative of formula II, any subgroup thereof, or stereoisomeric forms thereof, for use as a medicine for the prevention or treatment of immune disorders in an animal.

The present invention also concerns the use of the thieno (2,3-d)pyrimidine derivative of formula II, any subgroup thereof, or stereoisomeric forms thereof, for the manufacture of a medicament for the prevention or treatment of an immune disorder in an animal. In an embodiment, said immune disorder is an autoimmune disorder or an immune disorder as a result from an organ or a cells transplantation. In an embodiment, said animal is a mammal, preferably said mammal is a human being. In an embodiment, said immune disorder is an autoimmune disorder or an immune disorder as a result from an organ or cells transplantation.

The present invention also concerns a pharmaceutical composition comprising a therapeutically effective amount of a thieno(2,3-d)pyrimidine derivative of formula II, any subgroup thereof, or stereoisomeric forms thereof, and one or more pharmaceutically acceptable excipients. In an embodiment, said pharmaceutical composition further comprises one or more biologically active drugs being selected from the group consisting of immunosuppressant and/or immunomodulator drugs, and antineoplastic drugs.

The present invention also concerns a method of prevention or treatment of an immune disorder in a mammal, comprising the administration of a therapeutically effective amount of a thieno(2,3-d)pyrimidine derivative of formula II, any subgroup thereof, or stereoisomeric forms thereof, optionally in combination with one or more pharmaceutically acceptable excipients. In an embodiment, said immune disorder is an autoimmune disorder or an immune disorder as a result from an organ or cells transplantation. In an embodiment, said animal is a mammal, preferably said mammal is a human being.

In an embodiment, the present invention also concerns a process for preparation of the thieno(2,3-d)pyrimidine derivative of formula II, any subgroup thereof, or stereoisomeric forms thereof, comprising the steps of: a ring closure reaction on methyl 2-aminothiophene-3-carboxylate; activation of carbonyl group by halogenation; a nucleophilic aromatic substitution reaction; introduction of a halogen at position 5; and introduction of $R^5$ by a palladium-catalyzed cross-coupling reaction.

In another embodiment, the present invention also concerns a process for preparation of the thieno(2,3-d)pyrimidine derivative of formula II, any subgroup thereof, or stereoisomeric forms thereof, comprising the steps of: a ring closure reaction on methyl 2-aminothiophene-3-carboxylate; treatment with a thionation reagent; an alkylation reaction; conversion of the thiomethyl group to sulfon by oxidation; introduction of the piperazine; introduction of a halogen at position 5; and introduction of $R^5$ by a palladium-catalyzed cross-coupling reaction.

In another embodiment, the present invention also concerns a process for preparation of the thieno(2,3-d)pyrimidine derivative of formula II, any subgroup thereof, or stereoisomeric forms thereof, comprising the steps of: a ring closure reaction on methyl 2-aminothiophene-3-carboxylate; treatment with benzotriazol-1-yloxytris(dimethylamino)phosphonium hexafluorophosphate (BOP), a base, and piperazine leading to the formation of 2-amino-4-N-piperazinyl-thieno[2,3-d]pyrimidine; introduction of a halogen at position 5; and introduction of $R^5$ by a palladium-catalyzed cross-coupling reaction.

In other specific embodiments, said ring closure reaction is effected by treatment with chloroformamidine hydrochloride. In other specific embodiments, said introduction of a halogen at position 5 is effected by treatment with n-BuLi and carbon tetrahalide as halogen source, preferably said halogen is bromide. In other specific embodiments, said introduction of a halogen at position 5 is effected by reaction with N-halosuccinimide (NhS) in $CCl_4$. In other specific embodiments, said halogen is bromide and said N-halosuccinimide (NhS) is N-bromosuccinimide (NBS). Preferably, said palladium-catalyzed cross-coupling reaction is a Suzuki coupling which include reactions with aryl boronic acids or aryl boronic acid pinacol esters; a Heck reaction which include reactions with terminal alkenes; a Sonogashira reaction which includes reactions with terminal alkynes and a Buchwald-Hartwig reaction which include reactions with arylamines; a Negishi reaction which includes the nickel- or palladium-catalyzed coupling of organozinc compounds with various halides; or a Kumada coupling which includes coupling of Grignard reagents with aryl halides. In an embodiment, said activation of carbonyl group by halogenation is performed in acidic conditions. Preferably, said activation of carbonyl group by halogenation is performed by using phosphorus oxychloride or thionylchloride. In other specific embodiments, said nucleophilic aromatic substitution reaction introduces a piperazine moiety at position 4. In other specific embodiments, said treatment with a thionation reagent is performed by heating with phosphorus pentasulfide or Lawesson's reagent in pyridine or toluene. In other specific embodiments, said alkylation reaction is performed by treatment with an alkylhalide, such as methyliodide or benzylbromide; under alkaline conditions such as NaOH or triethylamine conditions; in a polar solvent, such as water, DMF or DMSO. In other specific embodiments, said oxidation is performed by treatment with m-chloro-peroxybenzoic acid or hydrogen peroxide. In other specific embodiments, said introduction of the piperazine is performed by a nucleophilic aromatic substitution reaction. In other specific embodiments, said base is triethylamine, diisopropylethylamine, or DBU. In other specific embodiments, the thieno(2,3-d)pyrimidine derivatives are $R^5$-substituted 2-amino-4-N-piperazino-thieno[2,3-d]pyrimidine derivatives.

In an embodiment, the present invention encompasses a purine derivative having the general formula III or IV: wherein substituent $R^{12}$ is represented by the general formula V:

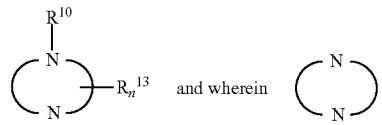

schematically represents a saturated or partly unsaturated heterocyclic ring with at least two nitrogen atoms in the said heterocyclic ring and with a total of 5 to 7 atoms in the said heterocyclic ring, and optionally with one or more other heteroatoms in the said heterocyclic ring or attached to one or more carbon atoms of said heterocyclic ring (for instance in the form of a carbonyl or thiocarbonyl group), wherein one of said at least two nitrogen atoms in the heterocyclic ring is attached to a carbon atom 6 of the purine ring;

each substituent $R^{13}$ of the heterocyclic ring is a group independently selected from the group consisting of halogen, nitro, $C_{1-7}$ alkyl (optionally containing one or more functions or radicals selected from the group consisting of halogen, carbonyl, thiocarbonyl, hydroxyl, sulfhydryl, $C_{1-7}$ alkoxy, thio $C_{1-7}$ alkyl, thio $C_{3-10}$ cycloalkyl, acetal, thioacetal, imino, oximino, alkyloximino, amino-acid, cyano, (thio)carboxylic acid, (thio)carboxylic acid ester or amide, nitro, amino, $C_{1-7}$ alkylamino, cycloalkylamino, alkenylamino, cycloalkenylamino, alkynylamino, arylamino, arylalkylamino, hydroxyalkylamino, mercapto-alkylamino, heterocyclic-substituted alkylamino, heterocyclic amino, heterocyclic-substituted arylamino, hydrazino, alkylhydrazino, phenylhydrazino, sulfonyl and sulfonamido), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, sulfhydryl, amino, $C_{1-7}$ alkylamino, cycloalkylamino, alkenylamino, cycloalkenylamino, alkynylamino, arylamino, arylalkyl-amino, hydroxyalkylamino, mercaptoalkylamino, heterocyclic-substituted alkylamino, heterocyclic amino, heterocyclic-substituted arylamino, hydrazino, alkylhydrazino, phenylhydrazino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, (thio)carboxylic acid or esters or thioesters or amides or thioamides thereof;

n is an integer from 0 to 6;

$R^{10}$ is selected from the group consisting of formyl, acyl, thioacyl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl, wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino; and $R^{11}$ is selected from the group consisting of halogen, cyano, carboxylic acid, acyl, thioacyl, alkoxycarbonyl, acyloxy, carbonate, carbamate, $C_{1-7}$ alkyl, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, $C_{1-7}$ alkyloxy;

R$^8$ is selected from the group consisting of heteroaryl and aryl groups; halogen; C$_{1-7}$ alkyl; C$_{2-7}$ alkenyl; C$_{2-7}$ alkynyl; halo C$_{1-7}$ alkyl; carboxy C$_{1-7}$ alkyl; carboxyaryl; C$_{1-7}$ alkoxy; C$_{3-10}$ cycloalkoxy; aryloxy; arylalkyloxy; oxyheterocyclic; heterocyclic-substituted alkyloxy; thio C$_{1-7}$ alkyl; thio C$_{3-10}$ cycloalkyl; thioaryl; thioheterocyclic; arylalkylthio; heterocyclic-substituted alkylthio; hydroxylamino; acylamino; thio-acylamino; alkoxyamino; thioalkyl-amino; acetal; thio-acetal; carboxylic acid; carboxylic acid esters, thioesters, halides, anhydrides, amides and thioamides; thiocarboxylic acid; thiocarboxylic acid esters, thioesters, halides, anhydrides, amides and thioamides; hydroxyl; sulfhydryl; nitro; cyano; carbamoyl; thiocarbamoyl; ureido; thioureido; amino; alkylamino; cycloalkylamino; alkenylamino; cyclo-alkenylamino; alkynylamino; arylamino; arylalkylamino; hydroxyalkylamino; mercaptoalkyl-amino; heterocyclic amino; heterocyclic substituted arylamino; heterocyclic-substituted alkylamino; oximino; alkyloximino; hydrazino; alkylhydrazino; phenylhydrazino; esters, thioesters, halides, anhydrides, amides and thioamides thereof; aromatic or heterocyclic substituents substituted with an aliphatic spacer between the purine ring and the aromatic or heterocyclic substituent,
  wherein said heteroaryl or aryl groups are optionally substituted with one or more substituents selected from the group consisting of halogen, C$_{1-7}$ alkyl, C$_{2-7}$ alkenyl, C$_{2-7}$ alkynyl, halo C$_{1-7}$ alkyl, nitro, hydroxyl, sulfhydryl, amino, C$_{1-7}$ alkoxy, C$_{3-10}$ cycloalkoxy, aryloxy, arylalkyloxy, oxyheterocyclic, heterocyclic-substituted alkyloxy, thio C$_{1-7}$ alkyl, thio C$_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thio-alkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino; and
  wherein said aliphatic spacer is a branched or straight, saturated or unsaturated aliphatic chain of 1 to 7 carbon atoms optionally containing one or more functions, atoms or radicals independently selected from the group consisting of halogen, carbonyl, thiocarbonyl, hydroxyl, thiol, ether, thio-ether, acetal, thio-acetal, amino, imino, oximino, alkyloximino, aminoacid, cyano, acylamino, thioacylamino, carbamoyl, thiocarbamoyl, ureido, thio-ureido, carboxylic acid ester or halide or anhydride or amide, thiocarboxylic acid or ester or thioester or halide or anhydride or amide, nitro, thio C$_{1-7}$ alkyl, thio C$_{3-10}$ cycloalkyl, hydroxylamino, mercaptoamino, alkyl-amino, cycloalkylamino, alkenylamino, cycloalkenylamino, alkynylamino, arylamino, arylalkyl-amino, hydroxyalkylamino, mercaptoalkylamino, heterocyclic-substituted alkylamino, hetero-cyclic amino, heterocyclic-substituted arylamino, hydrazino, alkylhydrazino, phenylhydrazino, sulfonyl, sulfinyl and sulfonamido;

R$^7$ and R$^9$ are selected from the group consisting of hydrogen, C$_{1-7}$ alkyl (optionally containing one or more functions or radicals selected from the group consisting of halogen, carbonyl, thiocarbonyl, hydroxyl, sulfhydryl, C$_{1-7}$ alkoxy, thio C$_{1-7}$ alkyl, thio C$_{3-10}$ cycloalkyl, acetal, thioacetal, imino, oximino, alkyloximino, amino-acid, cyano, (thio)carboxylic acid, (thio)carboxylic acid ester or amide, nitro, amino, C$_{1-7}$ alkylamino, cycloalkylamino, alkenylamino, cycloalkenyl-amino, alkynylamino, arylamino, arylalkylamino, hydroxyalkylamino, mercapto-alkylamino, heterocyclic-substituted alkylamino, heterocyclic amino, heterocyclic-substituted arylamino, hydrazino, alkylhydrazino, phenylhydrazino, sulfonyl and sulfonamido), C$_{3-7}$ alkenyl, C$_{2-7}$ alkynyl, halo C$_{1-7}$ alkyl, C$_{3-10}$ cycloalkyl, aryl, arylalkyl, alkylaryl, acyl and sulfonyl;

or a pharmaceutical acceptable addition salt thereof, or a stereoisomer thereof, or a solvate thereof.

One embodiment of the present invention concerns purine derivative of formula III or IV, any subgroup thereof, or stereoisomeric forms thereof, wherein R$^7$, R$^8$, R$^9$, R$^{12}$ have any of the values as described herein and wherein R$^{11}$ is amino.

One embodiment of the present invention concerns purine derivative of formula III or IV, any subgroup thereof, or stereoisomeric forms thereof, wherein R$^7$, R$^8$, R$^9$, R$^{11}$ have any of the values as described herein and wherein R$^{12}$ is 4-(4-chlorophenoxy)acetylpiperazin-1-yl or 4-(phenoxyacetyl)piperazin-1-yl.

One embodiment of the present invention concerns purine derivative of formula III or IV, any subgroup thereof, or stereoisomeric forms thereof, wherein R$^7$, R$^{11}$, R$^9$, R$^{12}$ have any of the values as described herein and wherein R$^8$ is 4-fluorophenyl or methylthio.

One embodiment of the present invention concerns purine derivative of formula III or IV, any subgroup thereof, or stereoisomeric forms thereof, wherein R$^7$, R$^8$, R$^{11}$, R$^{12}$ have any of the values as described herein and wherein R$^9$ is hydrogen or methyl.

One embodiment of the present invention concerns purine derivative of formula III or IV, any subgroup thereof, or stereoisomeric forms thereof, wherein R$^{11}$, R$^8$, R$^9$, R$^{12}$ have any of the values as described herein and wherein R$^7$ is hydrogen or methyl.

One embodiment of the present invention concerns purine derivative of formula III or IV, any subgroup thereof, or stereoisomeric forms thereof, wherein R$^{11}$ is amino, R$^{12}$ is 4-(4-chlorophenoxy)acetylpiperazin-1-yl or (4-phenoxyacetyl)piperazin-1-yl, R$^8$ is 4-fluorophenyl or methylthio, and R$^9$ is hydrogen or methyl.

One embodiment of the present invention concerns purine derivative of formula III or IV, any subgroup thereof, or stereoisomeric forms thereof, wherein R$^{11}$ is amino, R$^{12}$ is 4-(4-chlorophenoxy)acetylpiperazin-1-yl or 4-(phenoxyacetyl)piperazin-1-yl, R$^8$ is 4-fluorophenyl or methylthio, and R$^7$ is hydrogen or methyl.

One embodiment of the present invention concerns purine derivative of formula III or IV, any subgroup thereof, or stereoisomeric forms thereof, being selected from the group consisting of: 2-amino-6-[4-(4-chlorophenoxyacetyl)piperazin-1-yl]-8-(4-fluorophenyl)-9H-purine; 2-amino-6-[4-(4-chlorophenoxyacetyl)piperazin-1-yl]-8-(3,4-dimethoxyphenyl)-9H-purine; 2-amino-6-[4-(4-chlorophenoxyacetyl)piperazin-1-yl]-8-(4-bromophenyl)-9H-purine; 2-amino-6-[4-(4-chlorophenoxyacetyl)piperazin-1-yl]-8-(4-chlorophenyl)-9H-purine; 2-amino-6-[4-(4-chlorophenoxyacetyl)piperazin-1-yl]-8-(3-chlorophenyl)-9H-purine; 2-amino-6-[4-(4-chlorophenoxyacetyl)piperazin-1-yl]-8-(4-trifluoromethylphenyl)-9H-purine; 2-amino-6-[4-(4-chlorophenoxyacetyl)piperazin-1-yl]-8-(4- trifluoromethoxyphenyl)-9H-purine; 2-amino-6-[4-(4-chlorophenoxyacetyl)piperazin-1-yl]-8-(4-methylphenyl)-9H-purine; 2-amino-6-[4-(4-chlorophenoxyacetyl)piperazin-1-yl]-8-propyl-9H-purine; 2-amino-6-[4-(4-chlorophenoxyacetyl)piperazin-1-yl]-8-(cyclopropyl)-9H-purine; 2-amino-6-[4-(4-chlorophenoxyacetyl)piperazin-1-yl]-8-(t-butyl)-9H-purine; 2-amino-6-[4-(4-chlorophenoxyacetyl)piperazin-1-yl]-8-methyl-9H-purine; 2-amino-6-[4-(phenoxyacetyl)piperazin-1-yl]-8-(4-fluorophenyl)-9H-purine; 2-amino-6-[4-(3-methoxy-benzoyl)piperazin-1-yl]-8-(4-fluorophenyl)-9H-purine; 2-amino-6-[4-(2-thiophene-acetyl)piperazin-1-yl]-8-(4-fluorophenyl)-9H-purine; 2-amino-6-[4-(4-chloro-benzoyl)piperazin-1-yl]-8-(4-fluorophenyl)-9H-purine; 2-amino-6-[(4-α-toluenesulfonyl)piperazin-1-yl]-8-(4-fluorophenyl)-9H-purine; 2-amino-6-[4-(1-naphthoyl)piperazin-1-yl]-8-(4-fluorophenyl)-9H-purine; 2-amino-6-[4-acetylpiperazin-1-yl]-8-(4-fluorophenyl)-9H-purine; 2-amino-6-[4-(thiazol-2-yl)piperazin-1-yl]-8-(4-fluorophenyl)-9H-purine; 2-(4-(2-amino-8-(4-fluorophenyl)-9H-purin-6-yl)piperazin-1-yl)-1-(pyrrolidin-1-yl)ethanone; 2-(4-(2-amino-8-(4-fluorophenyl)-9H-purin-6-yl)piperazin-1-yl)-1-morpholinoethanone; 2-(4-(2-amino-8-(4-fluorophenyl)-9H-purin-6-yl)piperazin-1-yl)-N-(pyridin-3-yl)acetamide; 2-(4-(2-amino-8-(4-fluorophenyl)-9H-purin-6-yl)piperazin-1-yl)-N-methyl-N-phenylacetamide; 2-amino-6-[4-(4-chlorophenyl)piperazin-1-yl]-8-(4-fluorophenyl)-9H-purine; 2-amino-6-[4-(4-fluorophenyl)piperazin-1-yl]-8-(4-fluorophenyl)-9H-purine; 2-(4-(2-amino-8-(4-fluorophenyl)-9H-purin-6-yl)piperazin-1-yl)-N-(pyridin-2-yl)acetamide; 2-(4-(2-amino-8-(4-fluorophenyl)-9H-purin-6-yl)piperazin-1-yl)-N-(thiazol-2-yl)acetamide; 2-amino-6-[4-(4-fluorobenzyl)piperazin-1-yl]-8-(4-fluorophenyl)-9H-purine; 2-amino-6-[4-(4-pyridinyl)piperazin-1-yl]-8-(4-fluorophenyl)-9H-purine; 2-amino-6-(homopiperazin-1-yl)-8-(4-fluorophenyl)-9H-purine; 2-amino-6-[4-(4-chlorophenoxyacetyl)homopiperazin-1-yl]-8-(4-fluorophenyl)-9H-purine; 2-amino-6-[4-(N-3-tolylcarbamoyl)-homopiperazin-1-yl]-8-(4-fluorophenyl)-9H-purine; 2-amino-6-[4-(4-chlorophenoxyacetyl)piperazin-1-yl]-8-methylthio-9H-purine; 2-amino-6-[4-(4-chlorophenoxyacetyl)piperazin-1-yl]-8-propylthio-9H-purine; 2-amino-6-[4-(4-chlorophenoxyacetyl)piperazin-1-yl]-8-benzylthio-9H-purine; 2-amino-6-[4-(4-chlorophenoxyacetyl)piperazin-1-yl]-8-(2-phenylethylthio)-9H-purine; 2-amino-6-[4-(4-chlorophenoxyacetyl)piperazin-1-yl]-9-methyl-8-methylthio-purine; 2-amino-6-[4-(4-chlorophenoxyacetyl)piperazin-1-yl]-8-(cyclopentylthio)-9H-purine; 2-amino-6-[4-(4-chlorophenoxyacetyl)piperazin-1-yl]-8-(4-fluorophenyl)-9-methylpurine; 2-amino-6-[4-(4-chlorophenoxyacetyl)piperazin-1-yl]-8-(4-fluorophenyl)-9-benzylpurine; 2-amino-6-(piperazin-1-yl)-8-(4-fluorophenyl)-9H-purine; 2-amino-6-[4-(hydrocinnamoyl)-piperazin-1-yl]-8-(4-fluorophenyl)-9H-purine.

The present invention also concerns purine derivatives of formula III or IV, any subgroup thereof, or stereoisomeric forms thereof, for use as a medicine.

The present invention also concerns purine derivatives of formula III or IV, any subgroup thereof, or stereoisomeric forms thereof, for use as a medicine for the prevention or treatment of immune disorders in an animal. In an embodiment, said immune disorder is an autoimmune disorder or an immune disorder as a result from an organ or cells transplantation. In an embodiment, said animal is a mammal. In an embodiment, said mammal is a human being.

The present invention also concerns the use of a purine derivative of formula III or IV, any subgroup thereof, or stereoisomeric forms thereof, for the manufacture of a medicament for the prevention or treatment of an immune disorder in an animal. In an embodiment, said immune disorder is an autoimmune disorder or an immune disorder as a result from an organ or cells transplantation. In an embodiment, said animal is a mammal. In an embodiment, said mammal is a human being.

The present invention also concerns a pharmaceutical composition comprising a therapeutically effective amount of a purine derivative of formula III or IV, any subgroup thereof, or stereoisomeric forms thereof, and one or more pharmaceutically acceptable excipients. In an embodiment, said pharmaceutical composition further comprises one or more biologically active drugs being selected from the group consisting of immunosuppressant and/or immunomodulator drugs, and antineoplastic drugs.

The present invention also concerns a method of prevention or treatment of an immune disorder in a mammal, comprising the administration of a therapeutically effective amount of a purine derivative of formula III or IV, any subgroup thereof, or stereoisomeric forms thereof, optionally in combination with one or more pharmaceutically acceptable excipients. In an embodiment, said immune disorder is an autoimmune disorder or an immune disorder as a result from an organ or cells transplantation. In an embodiment, said mammal is a human being.

The present invention also encompasses processes for the preparation of compounds of Formula (I), (II), (III), (IV) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) (II), (III), (IV) and the subgroups thereof can be prepared by a succession of steps as described herein. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below: 2,5,7-tri-substituted thiazolo[5,4-d]pyrimidine derivatives of formula Ia can be prepared as shown hereunder in Scheme 1.

Scheme 1

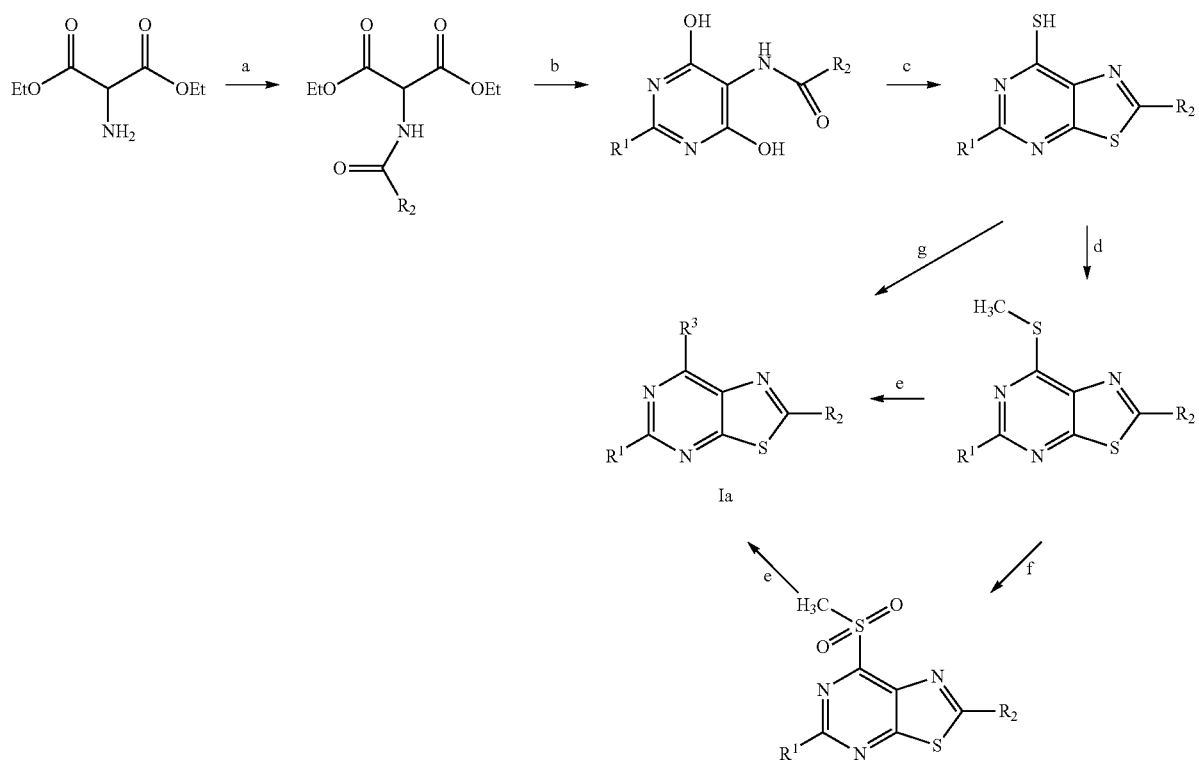

The synthesis starts from commercially available diethyl aminomalonate hydrochloride or dimethyl aminomalonate hydrochloride (not shown in Scheme 1). Conversion into the corresponding amides in step (a) can achieved by acylation with commercially available acid chlorides, bearing the general formula $R^2C(O)Cl$ (such as for example, but not limited to acetyl chloride, benzoyl chloride, phenoxyacetyl chloride). The amino group can also be coupled with commercially available carboxylic acids, using standard peptide coupling procedures, using a carboxylic acid, bearing the general formula $R^2C(O)OH$ and a coupling reagent such as dicyclohexylcarbodiimide (DCC), diisopropylcarbodiimide (DIC) or 1-(3-dimethylaminopropyl)-3-ethylcarbodiimide hydrochloride (EDCl). Additives such as 1-hydroxybenzotriazole (HOBt) and 1-hydroxy-7-azabenzotriazole (HOAt) can be added to increase the reaction rate. In order to construct the pyrimidine scaffold, the dialkyl acylaminomalonate formed in step (a) can be treated with guanidine, acetamidine or thiourea in an ethanolic sodium ethoxide solution yielding 2-$R^1$-substituted pyrimidines in step (b). By the judicious choices of the carboxylic acid (or acid chloride) and the coupling partner, different substituents can be introduced at positions 2 and 5 of the thiazolo[5,4-d]pyrimidine scaffold. Conversion of the lactam functionalities of 5-acylaminopyrimidine-4,6-diol into thiolactam groups and a concomitant ring closure reaction affording the thiazolo[5,4-d]pyrimidine scaffold can be achieved in step (c), by heating the compound with thionation reagents such as for example phosphorus pentasulfide or Lawesson's reagent in high-boiling solvents such as pyridine, toluene or xylene. In order to introduce a high degree of molecular diversity at position 7, alkylation of the thio group to the corresponding thioethers is effected in step (d). Therefore, the 7-thio-compounds are treated with an alkylhalide (preferably iodomethane as shown in Scheme 1) in the presence of a base (such as for example triethylamine or NaOH) in an appropriate polar solvent (such as for example DMSO, DMF or water) to afford the corresponding alkylsulfanyl analogues. In step (e), the thiomethyl group can be exchanged for a nucleophile bearing the general formula $R^7H$. Nucleophiles can be primary or secondary amines (such as for example, but not limited to, isopropylamine, morpholine and piperazine) or alcoxides. In case of less reactive nucleophiles, it might be necessary to increase the reactivity of thioether group by oxidation to the corresponding sulfones with m-chloroperoxybenzoic acid (mCPBA) in dichloromethane (step (f)). The reaction of sulfone derivatives with a range of primary and secondary amines affords the 2-$R^2$,5-$R^1$,7-$R^3$ trisubstituted thiazolo[5,4-d]pyrimidines. In case a piperazine substituent is introduced at position 7 of the scaffold ($R^3$=N-piperazinyl; structure not shown in Scheme 1), the second nitrogen can be further derivatised by reaction with chloroformates, isocyanates, acid chlorides (or carboxylic acids) and sulfonyl chlorides yielding carbamates, urea, amides and sulfonamides, respectively.

A one step procedure in order to introduce an amine at position 7 starting from the 7-thio-thiazolo[5,4-d]pyrimidine derivative is possible using 1,1,1,3,3,3-hexamethyldisilazane (HMDS) in a high boiling solvents such as toluene, xylene or pyridine (step (g)).

2,5,7-tri-substituted thiazolo[5,4-d]pyrimidine derivatives of formula Ia can also be prepared as shown hereunder in Scheme 2.

Scheme 2

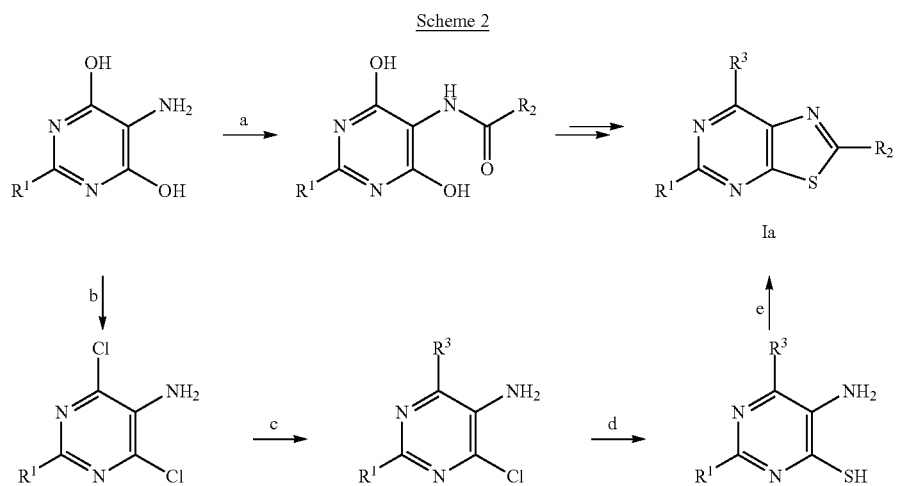

Scheme 2 depicts an alternative scheme for the synthesis of 2,5,7-trisubstituted thiazolo[5,4-d]pyrimidines, starting from a commercially available 2-$R^1$-substituted-5-amino-4,6-dihydroxypyrimidine analogue, from which the amino group can be converted to an amide analogue in step (a) using the methods described before, yielding a 2-$R^1$-substituted-5-acylamino-4,6-dihydroxypyrimidine derivative. Alternatively, this dihydroxy pyrimidine analogue can also be converted to its dichloro analogue in step (b) using chlorinating agents (such as for example thionyl chloride or phosphorus oxychloride). In step (c), a nucleophilic aromatic substitution with one equivalent of an appropriate nucleophile, bearing the general formula $R^3H$, yields the 2-$R^1$,4-$R^3$,5-amino-6-chloro-pyrimidine analogue. Introduction of a sulfhydryl group by reaction with sodium sulfide yields the 2-$R^1$,4-$R^3$-5-amino-6-sulfhydryl-pyrimidine analogue in step (d). A ring closure reaction with commercially available acid chlorides or aldehydes, bearing the general formula $R^2C(O)Cl$ or $R^2CHO$, yields then the 2-$R^2$-5-$R^1$-7-$R^3$ trisubstituted thiazolo[5,4-d]pyrimidines in step (e).

2,5,7-trisubstituted oxazolo[5,4-d]pyrimidines of formula Ib can be prepared as shown in Scheme 3.

Scheme 3

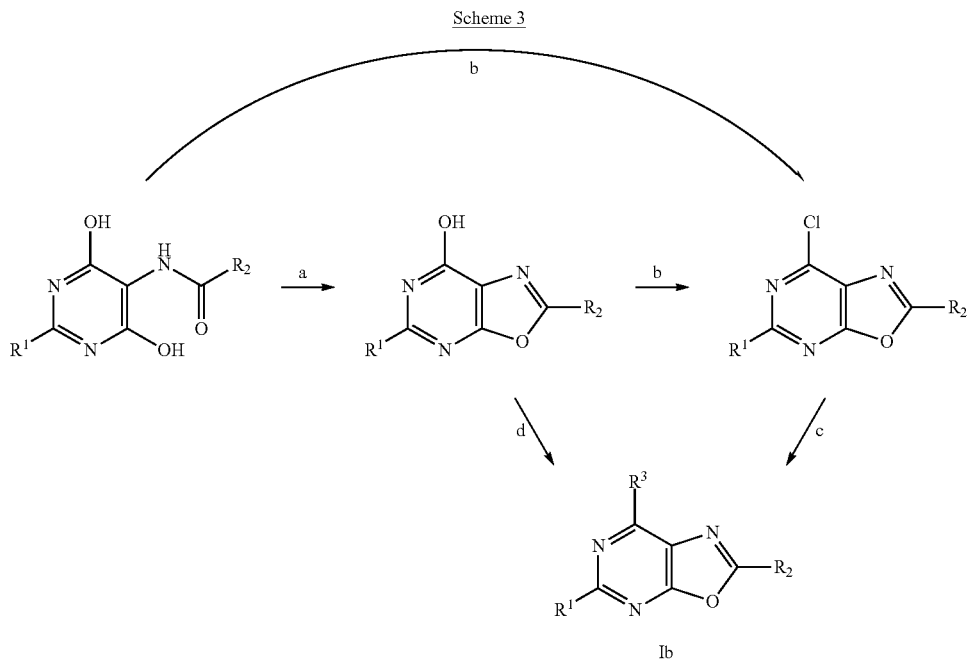

The synthesis starts from intermediates that have been generated using synthetic schemes described in Schemes 1 and 2. Treatment of the 4,6-dihydroxy-pyrimidine analogue in steps (a) and step (b) with a chlorinating agent (such as for example $POCl_3$, $SOCl_2$, $PCl_5$) yields the 7-hydroxy- (step a) or 7-chloro derivative (step b), depending on the reaction time. The chlorine can be exchanged for a wide variety of oxygen, nitrogen or sulphur containing nucleophiles, bearing the general formula $R^3H$ in step (c). Treatment of the lactam with benzotriazol-1-yloxytris(dimethylamino)phosphonium hexafluorophosphate (BOP), a base (such as for example triethylamine, diisopropylethylamine, DBU) and a nitrogen or oxygen nucleophile also leads to the formation of the corresponding 7-substituted oxazolo[5,4-d]pyrimidine analogues in step (d).

2-R$^2$-substituted 5-amino-7-N-piperazino thiazolo(5,4-d) pyrimidine derivatives of formula Ic can also be prepared as shown hereunder in Scheme 4.

such as 1-hydroxybenzotriazole (HOBt) and 1-hydroxy-7-azabenzotriazole (HOAt) can be added. In order to construct the thiazole moiety in step (b), the acylaminopyrimidine analogue is heated with thionation reagents such as for example phosphorus pentasulfide or Lawesson's reagents in high-boiling solvents such as pyridine, toluene or xylene. The thio group is then converted to its thiomethyl derivative in step (c) by treatment with iodomethane under alkaline conditions.

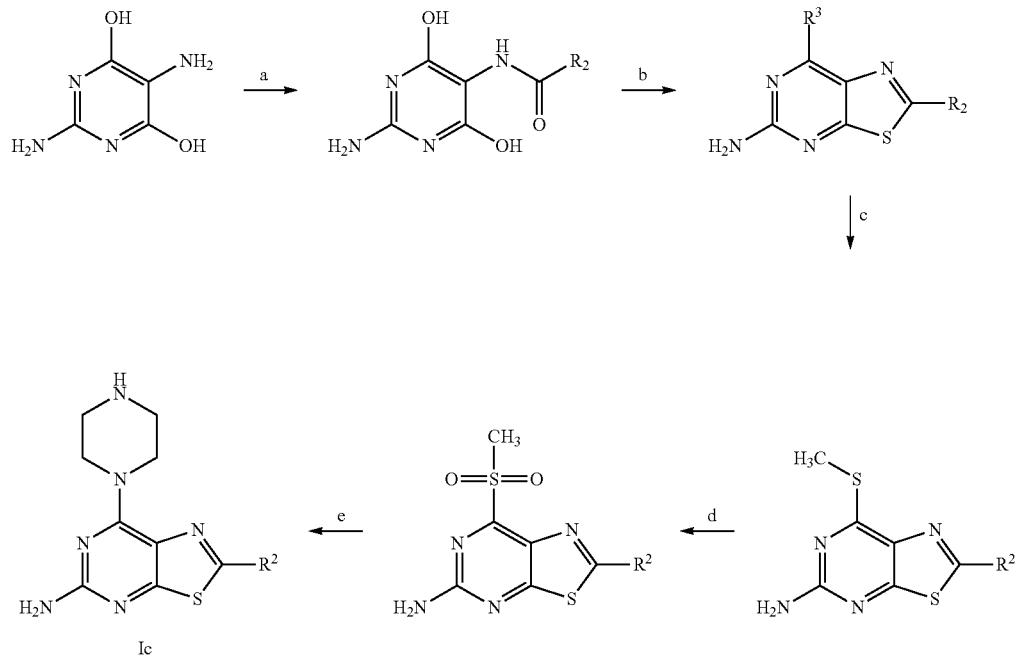

Scheme 4

The synthesis of a 2-R$^2$-substituted 5-amino-7-N-piperazino thiazolo(5,4-d)pyrimidine of formula Ic can starts from commercially available 2,5-diamino-4,6-dihydroxypyrimidine hydrochloride. Acylation of one of the amino group yielding the amide derivative is achieved in step (a) by reaction with an appropriate acid chloride (bearing the general formula R$^2$C(O)Cl) or with an appropriate acid (bearing the general formula R$^2$COOH) and a coupling reagent, such as for example N,N'-dicyclohexylcarbodiimide (DCC) or N,N'-diisopropylcarbodiimide (DIC) or 1-(3-dimethylaminopropyl)-3-ethylcarbodiimide hydrochloride (EDCl). Additives Further oxidation of the thiomethyl group with an oxidating agent (for example m-chloro-peroxybenzoic acid or hydrogen peroxide) affords the sulfoxide or sulfon derivative. In the final step (e), piperazine is introduced at position 7 of the scaffold by a nucleophilic aromatic substitution.

2,4,6-trisubstituted thieno[2,3-d]pyrimidine of formula II can be prepared as shown hereunder in Scheme 5.

Scheme 5

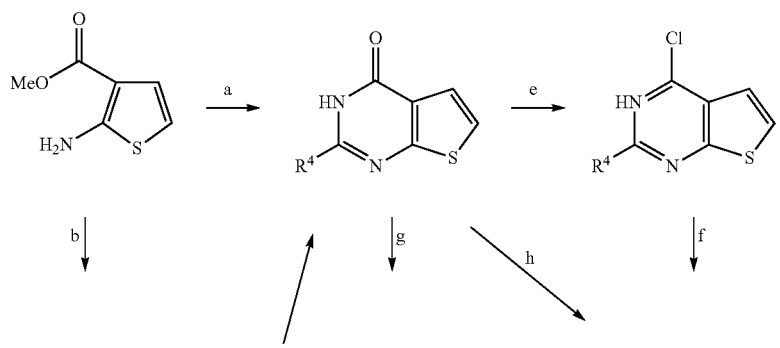

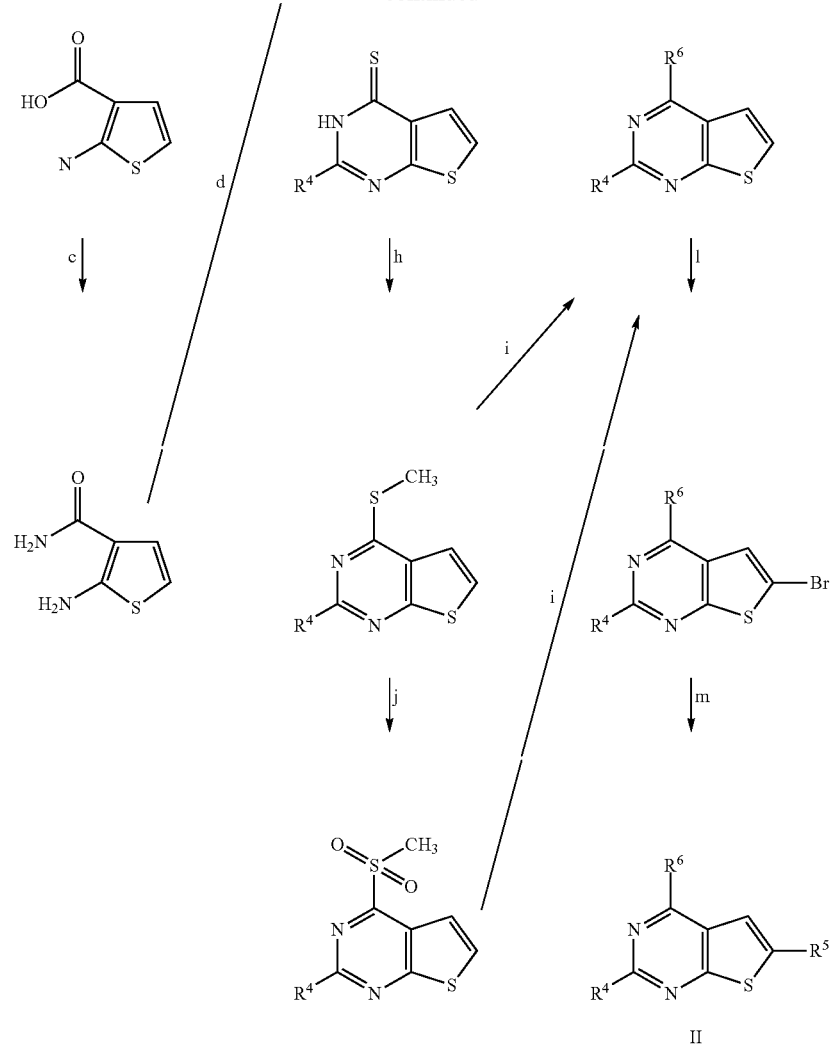

Scheme 5 schematically depicts the synthesis of 2,4,6-trisubstituted thieno[2,3-d]pyrimidine of formula II starting from the commercially available methyl 2-aminothiophene-3-carboxylate or ethyl 2-aminothiophene-3-carboxylate (structure not shown). In order to construct the thieno[2,3-d]pyrimidine scaffold, a ring closure reaction can be effected in step (a) with formamide (yielding a hydrogen at position 2) or with chloroformamidine hydrochloride (furnishing an amino group at position 2). In order to build up alkyl and aryl groups at position 2 of the scaffold, reactions with commercially available nitriles (such as for example, but not limited to, acetonitrile and benzonitrile) under acidic conditions gives access to 2-substituted thieno[2,3-d]pyrimidine analogues. Examples of substituents that can be introduced that way are methyl (by reaction with acetonitrile) and phenyl (by reaction with benzonitrile). Alternatively, the methyl- or ethylester can be hydrolyzed under basic aqueous conditions (e.g. using sodium hydroxide or lithium hydroxide) in step (b) yielding the free carboxylic acid. By using standard peptide coupling procedures in step (c) the corresponding carboxamide is obtained. This might also be achieved by treatment of the carboxylic acid with thionyl chloride or oxalylchloride affording the acid chloride which can be easily converted to an amide by treatment with ammonia. Reaction of 2-amino-3-carboxamido-thiophene with a wide range of orthoesters (e.g. triethylorthoformate and triethylorthoacetate) yields a 2-substituted-thieno[2,3-d]pyrimidin-4(3H)one analogue in step (d). Alternatively, 2-amino-3-carboxamido-thiophene can also be reacted in step (d) with a wide range of commercially available acid chlorides in order to construct the thieno[2,3-d]pyrimidine scaffold. Once the thieno[2,3-d]pyrimidine scaffold is formed in step (a) or step (d), different substituents at various positions can be introduced. In order to make variations at position 4, the oxo group of the lactam functionality can be converted into a good leaving group such as a halogen yielding an aryl chloride. This activation of carbonyl group by halogenation in step (e) is usually performed under harsh and acidic conditions using phosphorus oxychloride or thionylchloride. It might be that additional steps of protection of labile functional groups are needed before halogenation. The 4-chloro-thieno[2,3-d]pyrimidine analogue can be further derivatised either by a nucleophilic aromatic substitution reaction ($S_NAr$) or by palladium-catalyzed cross-coupling reactions in step (f). As an alternative method the lactam group can be converted into a thiolactam group in step (g), by reaction with a thionation reagent such as for example by heating with phosphorus pentasulfide or Lawesson's reagent in pyridine or toluene. The thio group is then alkylated in step (h) by treatment with an alkylhalide (such as for example methyliodide, benzylbromide) under alkaline conditions (e.g. NaOH, triethylamine) in a polar solvent (such as water, DMF or DMSO). The thiomethyl group can then be displaced by a suitable nucleophile bearing the general formula $R^6H$ (an amine or an alkoxide) yielding a 4-substituted thieno[2,3-d]pyrimidine analogue in step (i). In case of less reactive nucleophiles (such as for example aniline), it might be that the thiomethyl group first needs to be oxidized to its corresponding sulfoxide or sulfon by treatment with m-chloro-peroxybenzoic acid or hydrogen peroxide in step (j). Recently, phosphonium-mediated $S_NAr$ reactions for the derivatisation of heterocyclic amides have been reported (Z. K. Wan et al. *J. Org. Chem.* 2007, 72, 10194-10210; Z. K. Wan et al. *Org. Lett.* 2006, 2425-2428). Treatment of the lactam with benzotriazol-1-yloxytris(dimethylamino)phosphonium hexafluorophosphate (BOP), a base (such as for example triethylamine, diisopropylethylamine, DBU) and a nitrogen or oxygen nucleophile leads to the formation of the corresponding 4-substituted thieno[2,3-d]pyrimidine in step (k). In order to introduce structural variety at position 6 of the scaffold, a halogen is introduced in step (l). The regioselective introduction of a bromine at position 6 can be performed with n-BuLi and carbon tetrabromide as bromine source at low temperature (−78° C.). Alternatively, reaction with N-bromosuccinimide (NBS) in $CCl_4$ is also feasible. The 6-bromo-thieno[2,3-d]pyrimidine is an ideal starting material for further derivatisation (step (m)) at position 6 by palladium-catalyzed cross-coupling reactions, such as for example Suzuki couplings (reactions with aryl boronic acids or aryl boronic acid pinacol esters), Heck reactions (reactions with terminal alkenes), Sonogashira (reaction with terminal alkynes) and Buchwald-Hartwig reactions (reaction with arylamines), Negishi reaction (the nickel- or palladium-catalyzed coupling of organozinc compounds with various halides), Kumada coupling (coupling of Grignard reagents with aryl halides).

Scheme 6

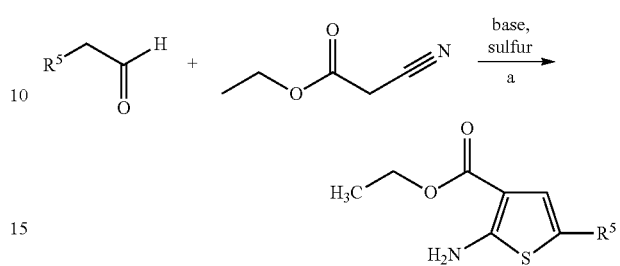

In Scheme 6, an alternative synthesis of 2,4,6-trisubstituted thieno[2,3-d]pyrimidine analogues is depicted, in which a 5-substituted ethyl 2-aminothiophene-3-carboxylate is used as a starting material. This compound can be easily generated using the multicomponent Gewald reaction in step (a), in which an aldehyde (with the general formula $R^5CH_2CHO$) is condensed with ethyl cyanoacetate in the presence of a base (e.g. triethylamine, morpholine) and elemental sulfur. Depending on the nature of the substituent $R^5$ in the starting aldehyde, a broad structural variety can be introduced at position 6 of the thieno[2,3-d]pyrimidine scaffold. The compound obtained in this way is very similar to the starting material in Scheme 5 and therefore similar reaction sequences can be followed, as explained already in Scheme 5.

2-amino-4-N-piperazino-6-substituted thieno[2,3-d]pyrimidine of formula IIa can also be prepared as shown hereunder in Scheme 7.

Scheme 7

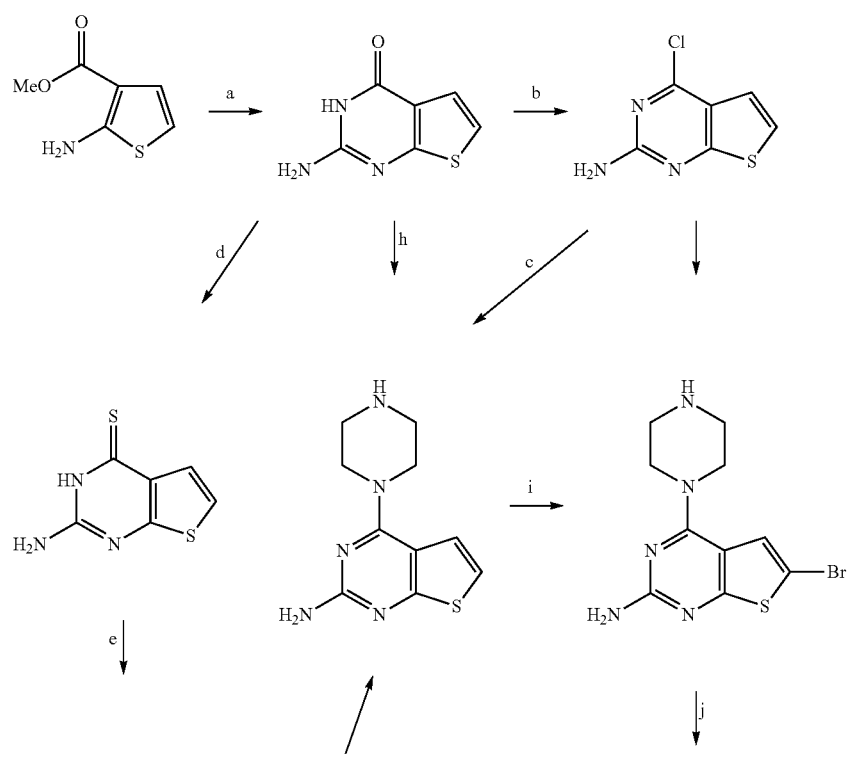

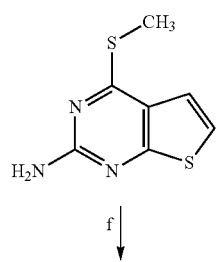

-continued

The synthesis of 2-amino-4-N-piperazino-6-substituted thieno[2,3-d]pyrimidine of formula IIa starts from commercially available methyl 2-aminothiophene-3-carboxylate. In step (a), a ring closure reaction is effected by treatment with chloroformamidine hydrochloride. The oxo group of the lactam functionality can be converted into a good leaving group such as halogens yielding an aryl chloride. This activation of carbonyl group by halogenation in step (b) is usually performed under harsh and acidic conditions using phosphorus oxychloride or thionylchloride. An additional step of protection of the amino group is needed before halogenation. Introduction of the piperazine moiety at position 4 of the scaffold happens in step (c) by a nucleophilic aromatic substitution reaction. As an alternative method the lactam group can be converted into a thiolactam group in step (d), by reaction with a thionation reagent such as for example by heating with phosphorus pentasulfide or Lawesson's reagent in pyridine or toluene. The thio group is then alkylated in step (e) by treatment with an alkylhalide (such as for example methyliodide, benzylbromide) under alkaline conditions (e.g. NaOH, triethylamine) in a polar solvent (such as water, DMF or DMSO). The thiomethyl group can be oxidized to its corresponding sulfon by treatment with m-chloro-peroxybenzoic acid or hydrogen peroxide in step (f). In step (g), the piperazine is then introduced.

Alternatively, treatment of the lactam with benzotriazol-1-yloxytris(dimethylamino)phosphonium hexafluorophosphate (BOP), a base (such as for example triethylamine, diisopropylethylamine, DBU) and piperazine as nucleophile leads to the formation of the corresponding 2-amino-4-N-piperazinyl-thieno[2,3-d]pyrimidine analogue in step (h).

A halogen at position 5 is introduced in step (i). The regioselective introduction of a bromine at position 5 can be performed with n-BuLi and carbon tetrabromide as bromine source at low temperature (−78° C.). Alternatively, reaction with N-bromosuccinimide (NBS) in $CCl_4$ is also feasible. The 5-bromo-thieno[2,3-d]pyrimidine is an ideal starting material for further derivatisation at position 5 by palladium-catalyzed cross-coupling reactions (in step (j)), such as for example Suzuki couplings (reactions with aryl boronic acids or aryl boronic acid pinacol esters), Heck reactions (reactions with terminal alkenes), Sonogashira (reaction with terminal alkynes) and Buchwald-Hartwig reactions (reaction with arylamines), Negishi reaction (the nickel- or palladium-catalyzed coupling of organozinc compounds with various halides), Kumada coupling (coupling of Grignard reagents with aryl halides).

6,8-trisubstituted purine analogues of formula IIIa can be prepared as shown hereunder in Scheme 8.

Scheme 8

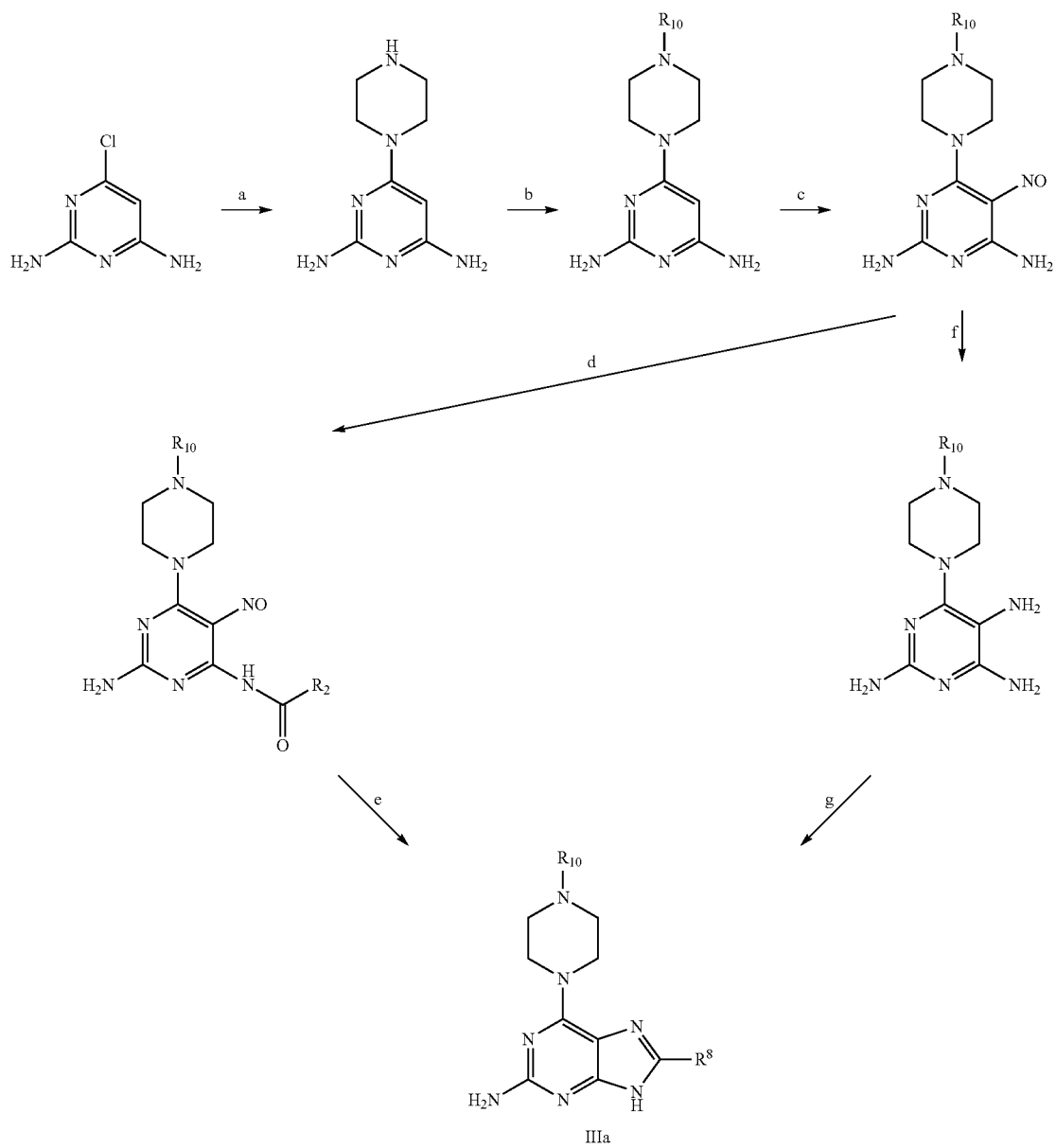

In a first step (a), commercially available 2,6-di-amino-4-chloro-pyrimidine is treated with a nucleophile such as for example piperazine (as shown in Scheme 8). However, this reaction is not limited to piperazine, but can be expanded to other types of nitrogen-containing nucleophiles such as, but not limited to, morpholine, pyrrolidine, methoxyethylamine and piperidine. Also oxygen-containing nucleophiles, such as sodium ethoxide and sodium isopropoxide can be introduced. In the second step (b), the piperazine moiety at position 4 of the pyrimidine ring is further derivatised. This can be achieved by coupling with appropriate acid chlorides (affording amide derivatives), by coupling with sulfonylchlorides (yielding sulfonamides), by reaction with isocyanates (yielding urea), by reaction with isothiocyanates (furnishing thiourea) and by reaction with chloroformates (yielding carbamates). In step (c), a nitroso substituent is introduced at position 5 of the pyrimidine scaffold, by reaction with sodium nitrite in water under acidic conditions (by use of acetic acid or hydrochloric acid). In step (d), the exocyclic amino group at position 6 is acylated in THF in the presence of a base such as for example potassium carbonate or triethylamine. The reductive cyclization in order to construct the purine scaffold in step (e) is achieved by treatment of the acylamino intermediate with triphenylphosphine in toluene or xylene as solvent. Alternatively, the nitroso group can be reduced to the corresponding amino group in step (f). This can be done with, for example, sodium dithionite in water, or catalytically (using hydrogen gas and a catalyst such as Raney Nickel). In step (g), the 5,6-di-amino-pyrimidine intermediate can then be ring closed in order to construct the purine scaffold. This can be done by reaction with carboxylic acids (bearing the general formula $R^8COOH$), in which first a 5-acylaminopyrimidne is formed, followed by an acid-catalyzed ring closure. Alternatively, an aldehyde (bearing the general formula $R^8$CHO) can be used as coupling partner, in which first a Schiff base is formed between the 5-amino-moiety and the aldehyde, followed by oxidative cyclization in the presence of ferric chloride or copper acetate.

2,6,8-trisubstituted purine analogues of formula IIIa can be prepared as shown in Scheme 9, using 2,6-diamino-4-mercaptopyrimidine as starting material.

directly from the nitroso intermediate or via the amino intermediate), affording a 2-amino-6-thiomethyl-8-substituted purine analogue in step (c). The thiomethyl group can directly be displaced by a suitable nucleophile (such as piperazine, as shown in Scheme 9) in step (d). Alternatively, the thiomethyl group can be oxidized in step (e) using an oxidizing agent, such as m-chloro-peroxybenzoic acid, affording the corresponding sulfone derivative, which can be displaced by an appropriate nucleophile in step (f) (such as, but not limited to, Scheme 9

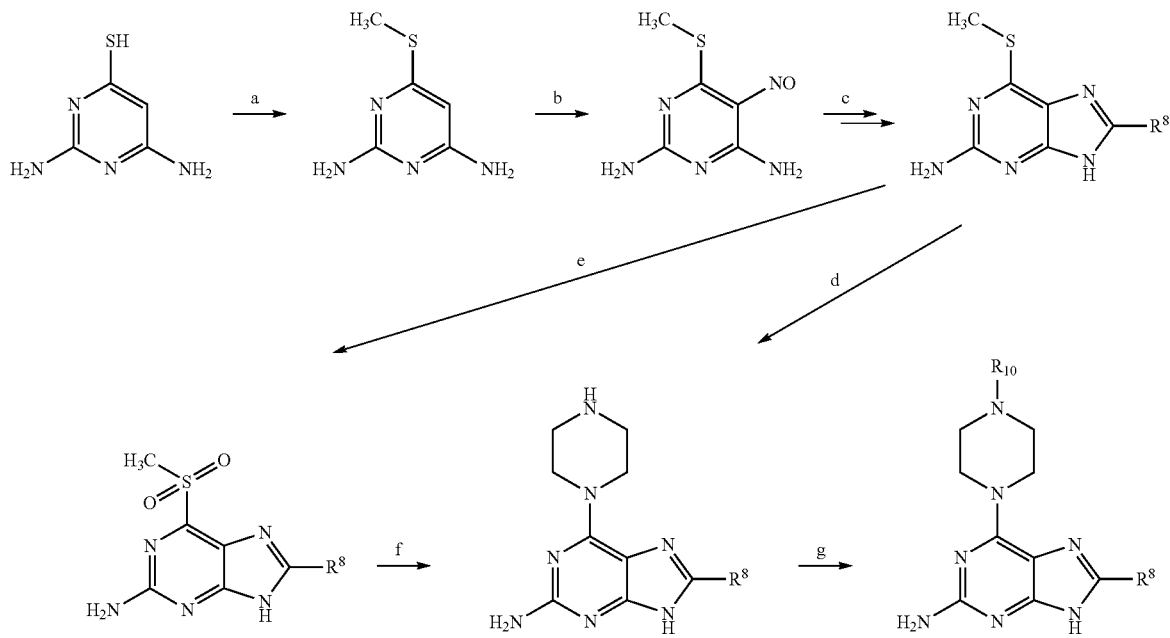

In the first step (a), the thiol group is selectively alkylated (for example methylated, as shown in Scheme 9), by treatment with an appropriate alkylhalide under alkaline conditions (using for example potassium carbonate or sodium hydroxide as a base). In step (b), the nitroso group is introduced at position 5 of the pyrimidine scaffold, using similar reaction circumstances as explained in Scheme 8. This 5-nitroso pyrimidine derivative can then be used to construct the purine scaffold, as already mentioned in Scheme 8 (either piperazine, as shown in Scheme 9). The piperazine moiety can be further derivatised in step (g), as explained in step (b) from Scheme 8.

2,6,8-trisubstituted purine analogues of formula IIIb can be prepared as shown in Scheme 10, using 2-mercapto-4-hydroxy-6-amino-pyrimidine as starting material.

Scheme 10

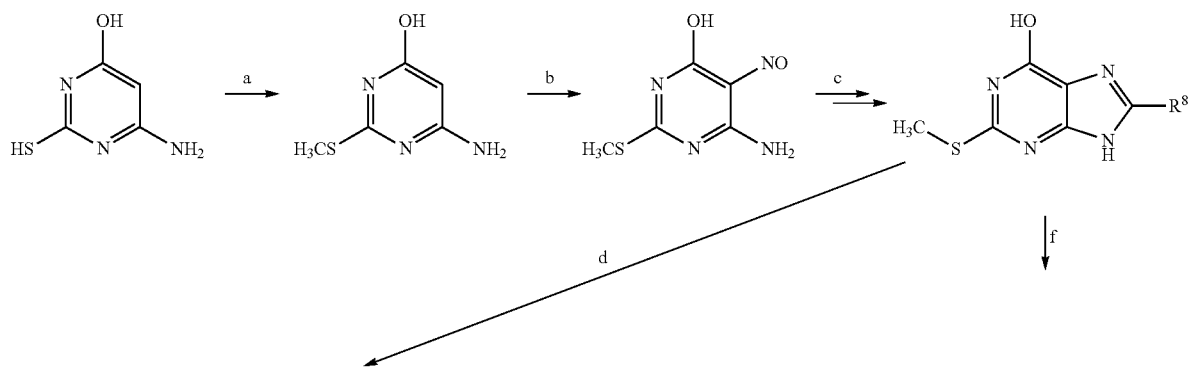

-continued

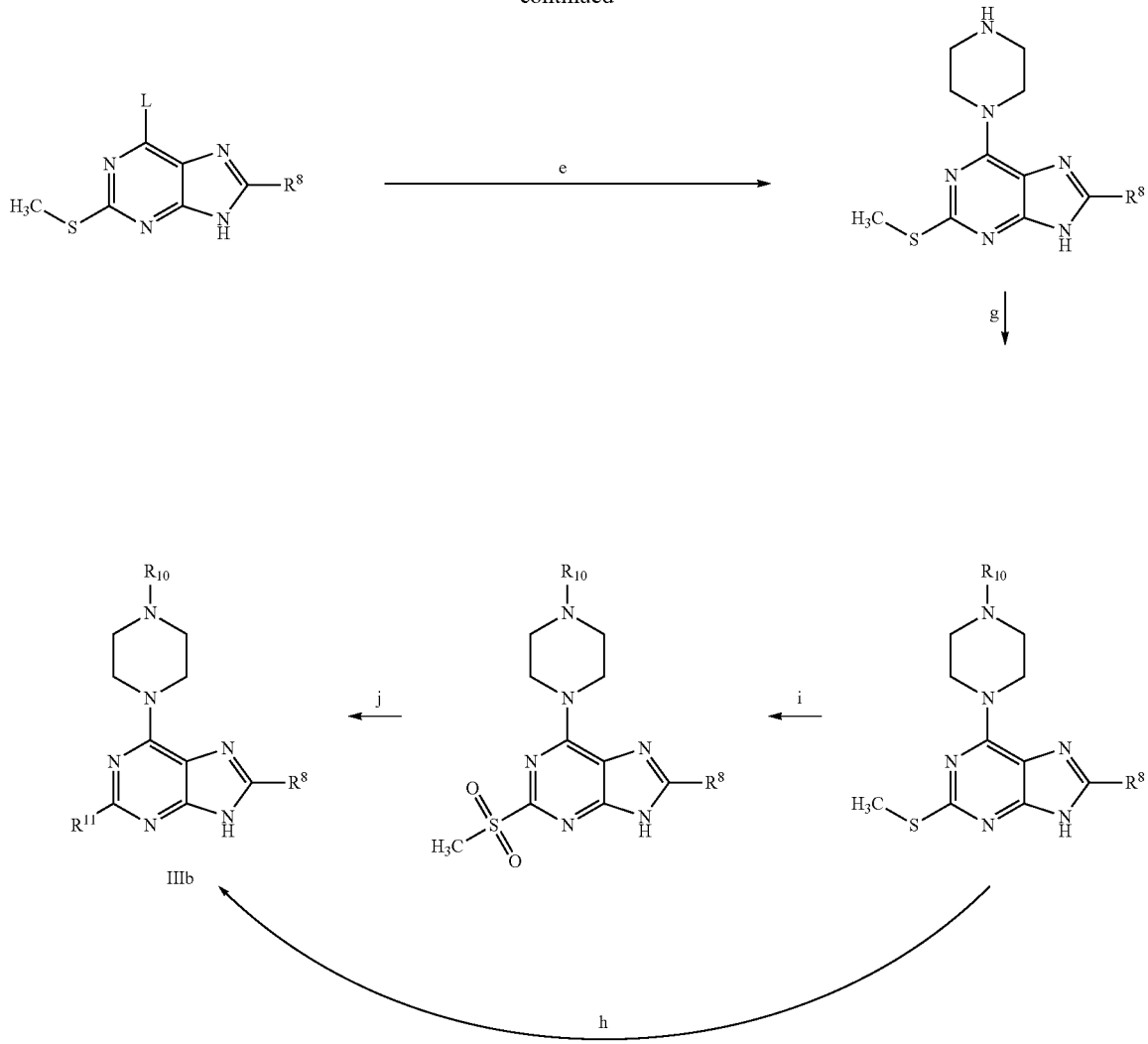

This method allows to introduce structural variety at position 2 of the purine scaffold. In the first step (a), the thiol group is selectively alkylated (for example methylated, as shown in Scheme 10), by treatment with an appropriate alkylhalide under alkaline conditions (using for example potassium carbonate or sodium hydroxide as a base). In step (b), the nitroso group is introduced at position 5 of the pyrimidine scaffold, using similar reaction circumstances as explained in Scheme 8. This nitroso intermediate can then be used to construct the purine scaffold, as already mentioned in Scheme 6 (either directly from the nitroso derivative or via the 5,6-di-amino analogue), affording a 2-thiomethyl-6-hydroxy-8-substituted purine analogue in step (c). Activation of the tautomeric hydroxyl group at position 6 of the purine scaffold for the subsequent nucleophilic displacement reaction occurs in step (d) by preparing the corresponding 6-(1, 2,4-triazolyl)-purine derivative or 6-chloro-purine derivative. The 6-triazolyl derivative can be obtained by treating the 6-oxo-purine derivative with POCl₃ or 4-chlorophenyl phosphorodichloridate and 1,2,4-triazole in an appropriate solvent such as, but not limited to, pyridine or acetonitrile. The 4-chloro derivative can be obtained by treating the 6-oxo-purine derivative with thionyl chloride or POCl₃. The chlorine atom or thiazolyl group is designated as L in Scheme 10.

Nucleophilic displacement of the triazolyl group or chlorine atom occurs in step (e) by reaction with an appropriate nucleophile, such as, but not limited to, piperazine, as shown in Scheme 10. Recently, phosphonium-mediated $S_NAr$ reactions for the derivatisation of heterocyclic amides have been reported (Z. K. Wan et al. *J. Org. Chem.* 2007, 72, 10194-10210; Z. K. Wan et al. *Org. Lett.* 2006, 2425-2428). Treatment of the lactam with benzotriazol-1-yloxytris(dimethylamino)phosphonium hexafluorophosphate (BOP), a base (such as for example triethylamine, diisopropylethylamine, DBU) and a nucleophile (such as, but not limited to, piperazine) leads to the formation of the corresponding 6-N-piperazino-substituted purine analogue in step (f). The piperazine moiety can be further derivatised in step (g) as explained earlier in step (b) of Scheme 8. The thiomethyl group can directly be displaced by suitable nitrogen-, oxygen- or sulfur-containing nucleophiles in step (h). Alternatively, it might be necessary to oxidize the thiomethyl group to its corresponding sulfoxide using hydrogen peroxide or m-chloro-peroxybenzoic acid in step (i). In the last step (j), the sulfoxide group can be exchanged by a suitable nucleophile affording the desired 2,6,8-trisubstituted purine analogue.

2,6,8,9-tetrasubstituted or 2,6,7,8,-tetrasubstituted purine analogues of formula III and/or IV can be prepared as shown in Scheme 11.

Scheme 11

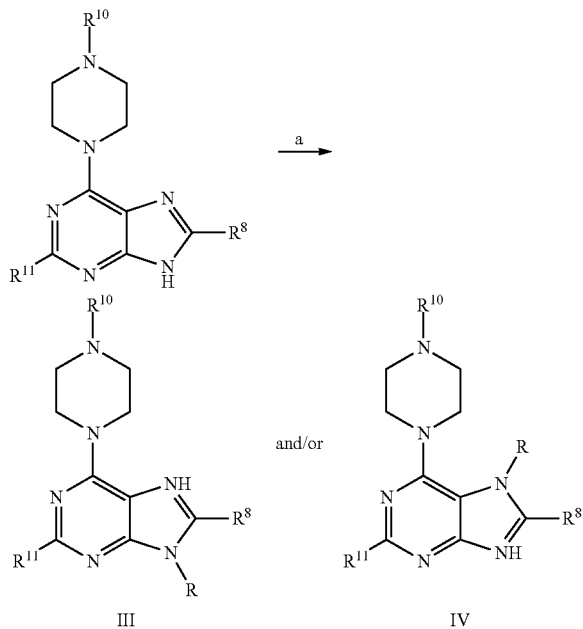

In step (a), a purine analogue (synthesized according to one of the synthetic pathways explained in Schemes 8-10), is alkylated with an appropriate alkylhalide bearing the general formula RX (such as for example iodomethane, ethylbromide, benzylbromide), and a base (such as for example sodium hydride or potassium carbonate) in a polar aprotic solvent (such as for example DMF). This reaction can lead to two regio-isomers, depending on the site of alkylation. Both compounds can be separated through techniques known to the person skilled in the art, such as flash chromatography and HPLC.

In a particular embodiment, the present invention also relates to the thiazolo(5,4-d)pyrimidine, oxazolo(5,4-d)pyrimidine, thieno[2,3-d]pyrimidine and purine derivatives of formula I, II, III or IV, being selected from the group consisting of:

2-(4-fluorophenyl)-7-(piperazin-1-yl)-thiazolo[5,4-d]pyrimidin-5-amine
2-(4-fluorobenzyl)-7-(piperazin-1-yl)-thiazolo[5,4-d]pyrimidin-5-amine
2-(4-fluorophenethyl)-7-(piperazin-1-yl)thiazolo[5,4-d]pyrimidin-5-amine
2-(4-fluorophenyl)-7-(2-methoxyethoxy)-thiazolo[5,4-d]pyrimidin-5-amine
7-ethoxy-2-(4-fluorophenyl)thiazolo[5,4-d]pyrimidin-5-amine
7-ethoxy-2-(4-fluorobenzyl)thiazolo[5,4-d]pyrimidin-5-amine
2-(4-fluorophenyl)-N-7-(3-methoxypropyl)thiazolo[5,4-d]pyrimidine-5,7-diamine
2-(4-fluorophenyl)-7-morpholino-thiazolo[5,4-d]pyrimidin-5-amine
2-(4-fluorobenzyl)-7-morpholino-thiazolo[5,4-d]pyrimidin-5-amine
2-(4-fluorophenyl)-7-(4-m-tolylpiperazin-1-yl)-thiazolo[5,4-d]pyrimidin-5-amine
2-(4-fluorophenyl)-7-(4-(thiazol-2-yl)piperazin-1-yl)thiazolo[5,4-d]pyrimidin-5-amine
2-(4-fluorophenyl)-7-(4-pentylpiperazin-1-yl)thiazolo[5,4-d]pyrimidin-5-amine
2-(4-(5-amino-2-(4-fluorophenyl)thiazolo[5,4-d]pyrimidin-7-yl)piperazin-1-yl)-1-morpholinoethanone
7-(4-benzylpiperazin-1-yl)-2-(4-fluorophenyl)thiazolo[5,4-d]pyrimidin-5-amine
benzyl-4-(5-amino-2-(4-fluorophenyl)thiazolo[5,4-d]pyrimidin-7-yl)piperazine-1-carboxylate
2-(4-fluorophenyl)-7-(4-(phenylsulfonyl)piperazin-1-yl)thiazolo[5,4-d]pyrimidin-5-amine
4-(5-amino-2-(4-fluorophenyl)-thiazolo[5,4-d]pyrimidin-7-yl)-N-p-tolylpiperazine-1-carboxamide
4-(5-amino-2-(4-fluorophenyl)thiazolo[5,4-d]pyrimidin-7-yl)-N-m-tolylpiperazine-1-carboxamide
4-(5-amino-2-(4-fluorobenzyl)thiazolo[5,4-d]pyrimidin-7-yl)-N-m-tolylpiperazine-1-carboxamide
1-(4-(5-amino-2-(4-fluorophenyl)thiazolo[5,4-d]pyrimidin-7-yl)piperazin-1-yl)-2-(4-chlorophenoxy)ethanone
1-(4-(5-amino-2-(4-fluorobenzyl)thiazolo[5,4-d]pyrimidin-7-yl)piperazin-1-yl)-2-(4-chlorophenoxy)ethanone
2-(4-chlorophenoxy)-1-(4-(2-(4-fluorophenyl)-5-methylthiazolo[5,4-d]pyrimidin-7-yl)piperazin-1-yl)ethanone
1-(4-(5-amino-2-(2-(4-fluorophenoxy)ethyl)thiazolo[5,4-d]pyrimidin-7-yl)piperazin-1-yl)-2-(4-chlorophenoxy)ethanone
1-(4-(5-amino-2-(4-fluorophenethyl)-thiazolo[5,4-d]pyrimidin-7-yl)piperazin-1-yl)-2-(4-chlorophenoxy)ethanone
1-(4-(5-amino-2-(4-fluorophenethyl)thiazolo[5,4-d]pyrimidin-7-yl)piperazin-1-yl)-2-(4-methoxyphenoxy)ethanone
1-(4-(5-amino-2-(4-fluorophenethyl)thiazolo[5,4-d]pyrimidin-7-yl)piperazin-1-yl)-2-(4-fluorophenoxy)ethanone
1-(4-(5-amino-2-(4-fluorophenethyl)thiazolo[5,4-d]pyrimidin-7-yl)piperazin-1-yl)-2-(4-bromophenoxy)ethanone
1-(4-(5-amino-2-(4-fluorophenethyl)thiazolo[5,4-d]pyrimidin-7-yl)piperazin-1-yl)-2-(m-tolyloxy)ethanone
1-(4-(5-amino-2-(4-fluorophenethyl)thiazolo[5,4-d]pyrimidin-7-yl)piperazin-1-yl)-2-(2,4-dichlorophenoxy)ethanone
1-(4-(5-amino-2-(4-fluorophenethyl)thiazolo[5,4-d]pyrimidin-7-yl)piperazin-1-yl)-3-(4-fluorophenoxy)propan-1-one
1-(4-(5-amino-2-(1-(4-fluorophenyl)ethyl)thiazolo[5,4-d]pyrimidin-7-yl)piperazin-1-yl)-2-(4-chlorophenoxy)ethanone
1-(4-(5-amino-2-(1-(4-fluorophenyl)-2-phenylethyl)thiazolo[5,4-d]pyrimidin-7-yl)piperazin-1-yl)-2-(4-chlorophenoxy)ethanone
4-(5-amino-2-(1-(4-fluorophenyl)ethyl)thiazolo[5,4-d]pyrimidin-7-yl)-N-m-tolylpiperazine-1-carboxamide
5-amino-2-cyclopropyl-7-methoxythiazolo[5,4-d]pyrimidine
5-amino-2-cyclopropyl-7-N-piperazino-thiazolo[5,4-d]pyrimidine
5-amino-2-(3,4-dichlorophenyl)-7-(N-piperazino)thiazolo[5,4-d]pyrimidine
5-amino-2-(1-phenylcyclopropyl)-7-(N-piperazino)thiazolo[5,4-d]pyrimidine
5-amino-2-(1-(4-chlorophenyl)cyclopropyl)-7-(N-piperazino)thiazolo[5,4-d]pyrimidine
5-amino-7-N-piperazino-2-methylthio-thiazolo[5,4-d]pyrimidine 5-amino-7-[4-(4-chlorophenoxyacetyl)piperazin-1-yl]-2-(1-phenylcyclopropyl)thiazolo[5,4-d]pyrimidine
5-amino-7-[4-(4-chlorophenoxyacetyl)piperazin-1-yl]-2-methylthio-thiazolo[5,4-d]pyrimidine
5-amino-7-[4-(4-chlorophenoxyacetyl)piperazin-1-yl]-2-(3,4-dichlorophenyl)thiazolo[5,4-d]pyrimidine
5-amino-7-[4-(4-chlorophenoxyacetyl)piperazin-1-yl]-2-(1-(4-chlorophenyl)cyclopropyl)thiazolo[5,4-d]pyrimidine
5-amino-7-[4-(4-chlorophenoxyacetyl)piperazin-1-yl]-2-(2-phenylethyl)thiazolo[5,4-d]pyrimidine
5-amino-2-cyclopropyl-7-[4-(4-chlorophenoxyacetyl)piperazin-1-yl]-thiazolo[5,4-d]pyrimidine
5-amino-7-[4-(4-chlorophenoxyacetyl)piperazin-1-yl]-2-cyclohexylthiazolo[5,4-d]pyrimidine
5-amino-7-[4-(4-chlorophenoxyacetyl)piperazin-1-yl]-2-(pyridine-3-yl)thiazolo[5,4-d]pyrimidine
5-amino-7-[4-(4-chlorophenoxyacetyl)piperazin-1-yl]-2-(N-oxopyridine-3-yl)thiazolo[5,4-d]pyrimidine
5-amino-7-[4-(4-chlorophenoxyacetyl)piperazin-1-yl]-2-(4-chlorophenylmethyl)thiazolo[5,4-d]pyrimidine
5-amino-7-[4-(4-chlorophenoxyacetyl)piperazin-1-yl]-2-(4-chlorophenyl)thiazolo[5,4-d]pyrimidine
5-amino-7-[4-(4-chlorophenoxyacetyl)piperazin-1-yl]-2-(3-methoxyphenyl)thiazolo[5,4-d]pyrimidine
5-amino-7-[4-(4-chlorophenoxyacetyl)piperazin-1-yl]-2-(1-(4-chlorophenyl)ethyl)thiazolo[5,4-d]pyrimidine
5-amino-7-[4-(4-chlorophenoxyacetyl)piperazin-1-yl]-2-(4-fluorophenylamino)-thiazolo[5,4-d]pyrimidine
5-amino-2-(4-fluorophenyl)-7-(4-[2-(4-bromophenoxy)acetyl]-piperazin-1-yl)-thiazolo[5,4-d]pyrimidine
5-amino-2-(4-fluorophenyl)-7-(4-[2-(3-nitrophenoxy)acetyl]-piperazin-1-yl)-thiazolo[5,4-d]pyrimidine
5-amino-2-(4-fluorophenyl)-7-(4-(2-phenoxyacetyl)-piperazin-1-yl)-thiazolo[5,4-d]pyrimidine
5-amino-2-[2-(4-fluorophenyl)ethyl]-7-(4-[2-(3-nitrophenoxy)acetyl]piperazin-1-yl)-thiazolo[5,4-d]pyrimidine
5-amino-2-[2-(4-fluorophenyl)ethyl]-7-(4-[2-(4-chlorophenyl)acetyl]piperazin-1-yl)-thiazolo[5,4-d]pyrimidine
5-amino-2-[2-(4-fluorophenyl)ethyl]-7-(4-m-tolylcarbamoylpiperazin-1-yl)-thiazolo[5,4-d]pyrimidine
5-amino-2-[2-(4-fluorophenyl)ethyl]-7-(4-[2-phenoxyacetyl]piperazin-1-yl)-thiazolo[5,4-d]pyrimidine
5-amino-2-[2-(4-fluorophenyl)ethyl]-7-[4-(4-chlorobenzoyl)piperazin-1-yl]-thiazolo[5,4-d]pyrimidine
5-amino-2-[2-(4-fluorophenyl)ethyl]-7-[4-(3-phenylpropionyl)piperazin-1-yl]-thiazolo[5,4-d]pyrimidine
5-amino-2-[2-(4-fluorophenyl)ethyl]-7-[4-phenylmethanesulfonylpiperazin-1-yl]-thiazolo[5,4-d]pyrimidine
5-amino-2-[2-(4-fluorophenyl)ethyl]-7-(4-[2-(4-chlorophenoxy)acetyl]homopiperazin-1-yl)-thiazolo[5,4-d]pyrimidine
5-amino-2-[2-(4-fluorophenyl)ethyl]-7-(4-[(methylphenylcarbamoyl)-methyl]piperazin-1-yl)-thiazolo[5,4-d]pyrimidine
5-amino-2-[2-(4-fluorophenyl)ethyl]-7-(4-thiazol-2-yl-piperazine-1-yl)-thiazolo[5,4-d]pyrimidine
5-amino-2-[2-(4-fluorophenyl)ethyl]-7-(4-(phenethylcarbamoyl-methyl)piperazin-1-yl)-thiazolo[5,4-d]pyrimidine
5-amino-2-[2-(4-fluorophenyl)ethyl]-7-((3-(R)-tert-butoxycarbonylamino)pyrrolidin-1-yl)-thiazolo[5,4-d]pyrimidine
5-amino-2-[2-(4-fluorophenyl)ethyl]-7-(3-(R)-[2-(4-chlorophenoxy)-acetylamino]pyrrolidin-1-yl)-thiazolo[5,4-d]pyrimidine
5-amino-2-[2-(4-fluorophenyl)ethyl]-7-(3-(R)-(4-chlorobenzoylamino)-pyrrolidin-1-yl)-thiazolo[5,4-d]pyrimidine
5-amino-2-[2-(4-fluorophenyl)ethyl]-7-(1-benzyloxycarbonylpiperidin-3-ylamino)-thiazolo[5,4-d]pyrimidine
5-amino-2-[2-(4-fluorophenyl)ethyl]-7-(1-tert-butoxycarbonylpyrrolidin-3-(S)-ylamino)-thiazolo[5,4-d]pyrimidine
5-amino-2-[2-(4-fluorophenyl)ethyl]-7-(1-(4-chlorophenoxyacetyl)pyrrolidin-3-(S)-ylamino)-thiazolo[5,4-d]pyrimidine
5-amino-2-[2-(4-fluorophenyl)ethyl]-7-(4-benzoylpiperidine-1-yl)-thiazolo[5,4-d]pyrimidine
5-amino-2-[2-(4-fluorophenyl)ethyl]-7-(4-(2-phenoxyethyl)piperazin-1-yl)-thiazolo[5,4-d]pyrimidine
5-amino-2-[1-(4-fluorophenyl)propyl]-7-(4-[2-(4-chlorophenoxy)acetyl]piperazin-1-yl)thiazolo[5,4-d]pyrimidine
5-amino-2-[cyclopentyl-(4-fluorophenyl)methyl]-7-(4-[2-(4-chlorophenoxy)acetyl]piperazin-1-yl)thiazolo[5,4-d]pyrimidine
5-amino-7-piperazin-1-yl-2-(2-thiophen-2-yl-ethyl)-thiazolo[5,4-d]pyrimidine
5-amino-2-(2-thiophen-2-ylethyl)-7-(4-[2-(4-chloro-phenoxy)acetyl]piperazin-1-yl)thiazolo[5,4-d]pyrimidine
5-amino-2-(2-thiophen-2-ylethyl)-7-(4-[2-(4-chloro-phenyl)acetyl]piperazin-1-yl)thiazolo[5,4-d]pyrimidine
5-amino-2-(2-thiophen-2-ylethyl)-7-(4-(4-chloro-benzoyl)piperazin-1-yl)thiazolo[5,4-d]pyrimidine
5-amino-2-(2-thiophen-2-ylethyl)-7-(4-m-tolylcarbamoylpiperazin-1-yl)thiazolo[5,4-d]pyrimidine
2-(4-chlorophenoxy)-1-(4-(2-(4-fluorophenyl)oxazolo[5,4-d]pyrimidin-7-yl)piperazin-1-yl)ethanone
2-(4-chlorophenoxy)-1-(4-(2-(4-fluorophenyl)-5-methyl-oxazolo[5,4-d]pyrimidin-7-yl)piperazin-1-yl)ethanone
1-(4-(5-amino-2-(4-fluorophenyl)oxazolo[5,4-d]pyrimidin-7-yl)piperazin-1-yl)-2-(4-chlorophenoxy)ethanone
2-(4-chlorophenoxy)-1-(4-(2-(4-fluorobenzyl)oxazolo[5,4-d]pyrimidin-7-yl)piperazin-1-yl)ethanone
2-(4-chlorophenoxy)-1-(4-(2-(4-fluorobenzyl)-5-methyloxazolo[5,4-d]pyrimidin-7-yl)piperazin-1-yl)ethanone
1-(4-(5-amino-2-(4-fluorophenethyl)oxazolo[5,4-d]pyrimidin-7-yl)piperazin-1-yl)-2-(4-chlorophenoxy)ethanone
N-(3-chloro-4-fluorophenyl)-2-(4-fluorophenyl)-oxazolo[5,4-d]pyrimidin-7-amine
N-7-(3-chloro-4-fluorophenyl)-2-(4-fluorophenyl)-oxazolo[5,4-d]pyrimidine-5,7-diamine
5-amino-2-cyclopropyl-7-N-piperazino-oxazolo[5,4-d]pyrimidine
5-amino-2-methoxymethyl-7-N-piperazino-oxazolo[5,4-d]pyrimidine
5-amino-2-cyclohexyl-7-N-piperazino-oxazolo[5,4-d]pyrimidine
5-amino-2-pentyl-7-N-piperazino-oxazolo[5,4-d]pyrimidine
5-amino-2-(2-phenylethyl)-7-N-piperazino-oxazolo[5,4-d]pyrimidine
5-amino-2-cyclopropyl-7-[4-(4-chlorophenoxyacetyl)piperazin-1-yl]-oxazolo[5,4-d]pyrimidine
5-amino-7-[4-(4-chlorophenoxyacetyl)piperazin-1-yl]-2-methoxymethyloxazolo[5,4-d]pyrimidine 5-amino-2-cyclohexyl-7-[4-(4-chlorophenoxyacetyl)piperazin-1-yl]oxazolo[5,4-d]pyrimidine
5-amino-7-[4-(4-chlorophenoxyacetyl)piperazin-1-yl]-2-pentyloxazolo[5,4-d]pyrimidine
5-amino-2-(2-phenylethyl)-7-[4-(4-chlorophenoxyacetyl)piperazin-1-yl]oxazolo[5,4-d]pyrimidine
5-amino-2-(4-fluorophenyl)-7-(4-isobutylpiperazin-1-yl)-oxazolo[5,4-d]pyrimidine
5-amino-2-(4-fluorophenyl)-7-(4-acetylpiperazin-1-yl)-oxazolo[5,4-d]pyrimidine
5-amino-2-(4-fluorophenyl)-7-[4-(2-methoxyethyl)-piperazin-1-yl]-oxazolo[5,4-d]pyrimidine
5-amino-2-(4-fluorophenyl)-7-(4-[2-(3-nitrophenoxy)acetyl]-piperazin-1-yl)-oxazolo[5,4-d]pyrimidine
5-amino-2-[2-(4-fluorophenyl)ethyl]-7-(4-[2-(4-chlorophenyl)acetyl]-piperazin-1-yl)-oxazolo[5,4-d]pyrimidine
5-amino-2-[2-(4-fluorophenyl)ethyl]-7-(4-[4-chlorobenzoyl]piperazin-1-yl)-oxazolo[5,4-d]pyrimidine
5-amino-2-[2-(4-fluorophenyl)ethyl]-7-(4-m-tolylcarbamoylpiperazin-1-yl)-oxazolo[5,4-d]pyrimidine
5-amino-2-[2-(4-fluorophenyl)ethyl]-7-(4-(2-phenoxyethyl)piperazin-1-yl)-oxazolo[5,4-d]pyrimidine
5-amino-2-[2-(4-fluorophenyl)ethyl]-7-(4-[(methylphenyl-carbamoyl)methyl]piperazin-1-yl)-oxazolo[5,4-d]pyrimidine
5-amino-2-phenyl-7-N-piperazinyl-thiazolo[5,4-d]pyrimidine
5-amino-2-(2-furyl)-7-N-piperazinyl-thiazolo[5,4-d]pyrimidine
5-amino-2-(4-fluoro-phenyl)-7-N-piperazinyl-thiazolo[5,4-d]pyrimidine
1-(4-(5-amino-2-phenylthiazolo[5,4-d]pyrimidin-7-yl)piperazin-1-yl)-2-(4-methoxyphenoxy)ethanone
1-(4-(5-amino-2-(furan-2-yl)thiazolo[5,4-d]pyrimidin-7-yl)piperazin-1-yl)-2-(4-fluorophenoxy)ethanone
1-(4-(5-amino-2-(furan-2-yl)thiazolo[5,4-d]pyrimidin-7-yl)piperazin-1-yl)-2-(m-tolyloxy)ethanone
1-(4-(5-amino-2-(4-fluorophenyl)thiazolo[5,4-d]pyrimidin-7-yl)piperazin-1-yl)-2-(m-tolyloxy)ethanone
1-(4-(5-amino-2-(4-fluorophenyl)thiazolo[5,4-d]pyrimidin-7-yl)piperazin-1-yl)-2-(2,4-dichlorophenoxy)ethanone
1-(4-(5-amino-2-(4-fluorophenyl)thiazolo[5,4-d]pyrimidin-7-yl)piperazin-1-yl)-2-(4-chloro-2-methylphenoxy)ethanone
1-(4-(5-amino-2-(4-fluorophenyl)thiazolo[5,4-d]pyrimidin-7-yl)piperazin-1-yl)-2-(3-chlorophenoxy)ethanone
1-(4-(5-amino-2-phenylthiazolo[5,4-d]pyrimidin-7-yl)piperazin-1-yl)-2-(4-chlorophenoxy)ethanone
4-(5-amino-2-(4-fluorophenyl)thiazolo[5,4-d]pyrimidin-7-yl)-N-(4-cyanophenyl)piperazine-1-carboxamide
4-(5-amino-2-(4-fluorophenyl)thiazolo[5,4-d]pyrimidin-7-yl)-N-(2,4-difluorophenyl)piperazine-1-carboxamide
4-(5-amino-2-(4-fluorophenyl)thiazolo[5,4-d]pyrimidin-7-yl)-N-(4-bromophenyl)piperazine-1-carboxamide
4-(5-amino-2-(4-fluorophenyl)thiazolo[5,4-d]pyrimidin-7-yl)-N-(2-methoxyphenyl)piperazine-1-carboxamide
4-(5-amino-2-phenylthiazolo[5,4-d]pyrimidin-7-yl)-N-m-tolylpiperazine-1-carboxamide
5-amino-7-(N-piperazin-1-yl)-2-(pyridin-3-yl)thiazolo[5,4-d]pyrimidine
4-(5-amino-2-(pyridin-3-yl)thiazolo[5,4-d]pyrimidin-7-yl)-N-p-tolylpiperazine-1-carboxamide
1-(4-(5-amino-2-(4-fluorophenethyl)thiazolo[5,4-d]pyrimidin-7-yl)piperazin-1-yl)-3-(4-bromophenyl)propan-1-one
1-(4-(5-amino-2-(4-fluorophenethyl)thiazolo[5,4-d]pyrimidin-7-yl)piperazin-1-yl)-2-(4-hydroxyphenoxy)ethanone
methyl 4-(2-(4-(5-amino-2-(4-fluorophenethyl)thiazolo[5,4-d]pyrimidin-7-yl)piperazin-1-yl)-2-oxoethoxy)benzoate
1-(4-(5-amino-2-(4-fluorophenethyl)thiazolo[5,4-d]pyrimidin-7-yl)piperazin-1-yl)-2-(4-(trifluoromethoxy)phenoxy)ethanone
2-(4-acetylphenoxy)-1-(4-(5-amino-2-(4-fluorophenethyl)thiazolo[5,4-d]pyrimidin-7-yl)piperazin-1-yl)ethanone
1-(4-(5-amino-2-(4-fluorophenethyl)thiazolo[5,4-d]pyrimidin-7-yl)piperazin-1-yl)-2-(3-chlorophenoxy)ethanone
4-(5-amino-2-(4-fluorophenethyl)thiazolo[5,4-d]pyrimidin-7-yl)-N-(4-cyanophenyl)piperazine-1-carboxamide
1-(4-(5-amino-2-(4-fluorobenzyl)thiazolo[5,4-d]pyrimidin-7-yl)piperazin-1-yl)-2-(4-methoxyphenoxy)ethanone
1-(4-(5-amino-2-(4-fluorobenzyl)thiazolo[5,4-d]pyrimidin-7-yl)piperazin-1-yl)-2-(4-bromophenoxy)ethanone
4-(5-amino-2-(4-fluorobenzyl)thiazolo[5,4-d]pyrimidin-7-yl)-N-(4-cyanophenyl)piperazine-1-carboxamide
1-(4-(5-amino-2-(4-fluorophenyl)thiazolo[5,4-d]pyrimidin-7-yl)piperazin-1-yl)-2-(4-fluorophenoxy)ethanone
1-(4-(5-amino-2-(4-fluorophenyl)thiazolo[5,4-d]pyrimidin-7-yl)piperazin-1-yl)-2-(4-methoxyphenoxy)ethanone
1-(4-(5-amino-2-(4-fluorophenyl)thiazolo[5,4-d]pyrimidin-7-yl)piperazin-1-yl)-2-(4-bromophenoxy)ethanone
1-(4-(5-amino-2-(4-fluorophenyl)thiazolo[5,4-d]pyrimidin-7-yl)piperazin-1-yl)-3-(4-fluorophenyl)propan-1-one
1-(4-(5-amino-2-(4-fluorophenyl)thiazolo[5,4-d]pyrimidin-7-yl)piperazin-1-yl)-2-(4-chlorophenoxy)-2-methylpropan-1-one
2-(3-methoxyphenethyl)-7-(piperazin-1-yl)thiazolo[5,4-d]pyrimidin-5-amine
2-(3,4-dimethoxyphenethyl)-7-(piperazin-1-yl)thiazolo[5,4-d]pyrimidin-5-amine
2-(4-methylphenethyl)-7-(piperazin-1-yl)thiazolo[5,4-d]pyrimidin-5-amine
1-(4-(5-amino-2-(3-methoxyphenethyl)thiazolo[5,4-d]pyrimidin-7-yl)piperazin-1-yl)-2-(4-methoxyphenoxy)ethanone
1-(4-(5-amino-2-(3-methoxyphenethyl)thiazolo[5,4-d]pyrimidin-7-yl)piperazin-1-yl)-2-(4-bromophenoxy)ethanone
1-(4-(5-amino-2-(3-methoxyphenethyl)thiazolo[5,4-d]pyrimidin-7-yl)piperazin-1-yl)-2-(4-chlorophenoxy)ethanone
1-(4-(5-amino-2-(3,4-dimethoxyphenethyl)thiazolo[5,4-d]pyrimidin-7-yl)piperazin-1-yl)-2-(4-bromophenoxy)ethanone
1-(4-(5-amino-2-(3,4-dimethoxyphenethyl)thiazolo[5,4-d]pyrimidin-7-yl)piperazin-1-yl)-2-(4-methoxyphenoxy)ethanone
1-(4-(5-amino-2-(4-methylphenethyl)thiazolo[5,4-d]pyrimidin-7-yl)piperazin-1-yl)-2-(4-bromophenoxy)ethanone
1-(4-(5-amino-2-(4-methylphenethyl)thiazolo[5,4-d]pyrimidin-7-yl)piperazin-1-yl)-2-(4-methoxyphenoxy)ethanone 1-(4-(5-amino-2-(4-methylphenethyl)thiazolo[5,4-d]pyrimidin-7-yl)piperazin-1-yl)-2-(4-chlorophenoxy)ethanone
7-(piperazin-1-yl)-2-(pyridin-3-yl)thiazolo[5,4-d]pyrimidin-5-amine
7-(piperazin-1-yl)-2-(pyridin-2-yl)thiazolo[5,4-d]pyrimidin-5-amine
7-(piperazin-1-yl)-2-(pyridin-4-yl)thiazolo[5,4-d]pyrimidin-5-amine
2-(4-chlorophenyl)-7-(piperazin-1-yl)thiazolo[5,4-d]pyrimidin-5-amine
1-(4-(5-amino-2-(4-chlorophenyl)thiazolo[5,4-d]pyrimidin-7-yl)piperazin-1-yl)-2-(4-methoxyphenoxy)ethanone
1-(4-(5-amino-2-(pyridin-3-yl)thiazolo[5,4-d]pyrimidin-7-yl)piperazin-1-yl)-2-(4-methoxyphenoxy)ethanone
1-(4-(5-amino-2-(pyridin-3-yl)thiazolo[5,4-d]pyrimidin-7-yl)piperazin-1-yl)-2-(4-fluorophenoxy)ethanone
1-(4-(5-amino-2-(pyridin-3-yl)thiazolo[5,4-d]pyrimidin-7-yl)piperazin-1-yl)-2-(4-trifluoromethoxyphenoxy)ethanone
1-(4-(5-amino-2-(pyridin-3-yl)thiazolo[5,4-d]pyrimidin-7-yl)piperazin-1-yl)-2-(4-chlorophenoxy)-2-methylpropan-1-one
1-(4-(5-amino-2-(pyridin-3-yl)thiazolo[5,4-d]pyrimidin-7-yl)piperazin-1-yl)-2-(m-tolyloxy)ethanone
4-(5-amino-2-(pyridin-3-yl)thiazolo[5,4-d]pyrimidin-7-yl)-N-m-tolylpiperazine-1-carboxamide
4-(5-amino-2-(pyridin-3-yl)thiazolo[5,4-d]pyrimidin-7-yl)-N-(4-chlorophenyl)piperazine-1-carboxamide
4-(5-amino-2-(pyridin-3-yl)thiazolo[5,4-d]pyrimidin-7-yl)-N-(4-methoxybenzyl)piperazine-1-carboxamide
4-(5-amino-2-(pyridin-3-yl)thiazolo[5,4-d]pyrimidin-7-yl)-N-(4-cyanophenyl)piperazine-1-carboxamide
1-(4-(5-amino-2-(4-chlorophenyl)thiazolo[5,4-d]pyrimidin-7-yl)piperazin-1-yl)-2-(4-methoxyphenoxy)ethanone
1-(4-(5-amino-2-(pyridin-4-yl)thiazolo[5,4-d]pyrimidin-7-yl)piperazin-1-yl)-2-(4-chlorophenoxy)ethanone
1-(4-(5-amino-2-(pyridin-2-yl)thiazolo[5,4-d]pyrimidin-7-yl)piperazin-1-yl)-2-(4-chlorophenoxy)ethanone
2-(4-fluorophenethyl)-7-(piperazin-1-yl)thiazolo[5,4-d]pyrimidine
2-(4-fluorophenyl)-7-(piperazin-1-yl)thiazolo[5,4-d]pyrimidine
2-(3-(4-fluorophenyl)propyl)-7-(piperazin-1-yl)thiazolo[5,4-d]pyrimidin-5-amine
2-(4-(4-fluorophenyl)butyl)-7-(piperazin-1-yl)thiazolo[5,4-d]pyrimidin-5-amine
2-(4-bromophenethyl)-7-(piperazin-1-yl)thiazolo[5,4-d]pyrimidin-5-amine
2-pentyl-7-(piperazin-1-yl)thiazolo[5,4-d]pyrimidin-5-amine
7-(piperazin-1-yl)-2-p-tolylthiazolo[5,4-d]pyrimidin-5-amine
1-(4-(5-amino-2-(3-(4-fluorophenyl)propyl)thiazolo[5,4-d]pyrimidin-7-yl)piperazin-1-yl)-2-(4-chlorophenoxy)ethanone
1-(4-(5-amino-2-(3-(4-fluorophenyl)propyl)thiazolo[5,4-d]pyrimidin-7-yl)piperazin-1-yl)-2-(4-methoxyphenoxy)ethanone
1-(4-(5-amino-2-(4-(4-fluorophenyl)butyl)thiazolo[5,4-d]pyrimidin-7-yl)piperazin-1-yl)-2-(4-chlorophenoxy)ethanone
1-(4-(5-amino-2-(4-(4-fluorophenyl)butyl)thiazolo[5,4-d]pyrimidin-7-yl)piperazin-1-yl)-2-(4-methoxyphenoxy)ethanone
1-(4-(5-amino-2-p-tolylthiazolo[5,4-d]pyrimidin-7-yl)piperazin-1-yl)-2-(4-methoxyphenoxy)ethanone
1-(4-(5-amino-2-p-tolylthiazolo[5,4-d]pyrimidin-7-yl)piperazin-1-yl)-2-(4-chlorophenoxy)ethanone
1-(4-(5-amino-2-pentylthiazolo[5,4-d]pyrimidin-7-yl)piperazin-1-yl)-2-(4-methoxyphenoxy)ethanone
1-(4-(5-amino-2-pentylthiazolo[5,4-d]pyrimidin-7-yl)piperazin-1-yl)-2-(4-chlorophenoxy)ethanone
1-(4-(5-amino-2-(4-bromophenethyl)thiazolo[5,4-d]pyrimidin-7-yl)piperazin-1-yl)-2-(4-methoxyphenoxy)ethanone
1-(4-(5-amino-2-(4-bromophenethyl)thiazolo[5,4-d]pyrimidin-7-yl)piperazin-1-yl)-2-(4-chlorophenoxy)ethanone
1-(4-(2-(4-fluorophenyl)thiazolo[5,4-d]pyrimidin-7-yl)piperazin-1-yl)-2-(4-methoxyphenoxy)ethanone
1-(4-(2-(4-fluorophenyl)thiazolo[5,4-d]pyrimidin-7-yl)piperazin-1-yl)-2-(4-chlorophenoxy)ethanone
1-(4-(2-(4-fluorophenethyl)thiazolo[5,4-d]pyrimidin-7-yl)piperazin-1-yl)-2-(4-methoxyphenoxy)ethanone
1-(4-(2-(4-fluorophenethyl)thiazolo[5,4-d]pyrimidin-7-yl)piperazin-1-yl)-2-(4-chlorophenoxy)ethanone
2-(4-chlorophenoxy)-1-(4-(6-(4-fluorophenyl)thieno[2,3-d]pyrimidin-4-yl)piperazin-1-yl)ethanone
1-(4-(2-butyl-6-(4-fluorophenyl)thieno[2,3-d]pyrimidin-4-yl)piperazin-1-yl)-2-(4-chlorophenoxy)ethanone
N-(3-chloro-4-fluorophenyl)-6-(4-fluorophenyl)thieno[2,3-d]pyrimidin-4-amine
2-butyl-N-(3-chloro-4-fluorophenyl)-6-(4-fluorophenyl)thieno[2,3-d]pyrimidin-4-amine
2-(4-chlorophenoxy)-1-(4-(6-(4-fluorophenyl)-2-methylthieno[2,3-d]pyrimidin-4-yl)piperazin-1-yl)ethanone
1-(4-(2-amino-6-(4-fluorophenyl)thieno[2,3-d]pyrimidin-4-yl)piperazin-1-yl)-2-(4-chlorophenoxy)ethanone
2-amino-4-N-benzylamino-6-(4-fluorophenyl)-thieno[2,3-d]pyrimidine
2-amino-4-N-piperazinyl-6-phenyl-thieno[2,3-d]pyrimidine
1-(4-(2-amino-6-phenylthieno[2,3-d]pyrimidin-4-yl)piperazin-1-yl)-2-(4-chlorophenoxy)ethanone
4-(2-amino-6-phenylthieno[2,3-d]pyrimidin-4-yl)-N-m-tolylpiperazine-1-carboxamide
4-(2-amino-6-phenylthieno[2,3-d]pyrimidin-4-yl)-N-(4-chlorophenyl)piperazine-1-carboxamide
1-(4-(2-amino-6-phenylthieno[2,3-d]pyrimidin-4-yl)piperazin-1-yl)-2-phenoxyethanone
2-amino-4-N-homopiperazinyl-6-phenyl-thieno[2,3-d]pyrimidine
1-(4-(2-amino-6-phenylthieno[2,3-d]pyrimidin-4-yl)-1,4-diazepan-1-yl)-2-(4-chlorophenoxy)ethanone
1-(4-(2-amino-6-phenylthieno[2,3-d]pyrimidin-4-yl)-1,4-diazepan-1-yl)(4-chlorophenyl)methanone
2-(4-(2-amino-6-phenylthieno[2,3-d]pyrimidin-4-yl)piperazin-1-yl)-N-methyl-N-phenylacetamide
4-(4-(2-phenoxyethyl)piperazin-1-yl)-6-phenylthieno[2,3-d]pyrimidin-2-amine
(R)-tert-butyl 1-(2-amino-6-(4-fluorophenyl)thieno[2,3-d]pyrimidin-4-yl)pyrrolidin-3-ylcarbamate
(R)-4-(3-aminopyrrolidin-1-yl)-6-(4-fluorophenyl)thieno[2,3-d]pyrimidin-2-amine
(R)-N-(1-(2-amino-6-(4-fluorophenyl)thieno[2,3-d]pyrimidin-4-yl)pyrrolidin-3-yl)-2-(4-chlorophenoxy)acetamide
(R)-N-(1-(2-amino-6-(4-fluorophenyl)thieno[2,3-d]pyrimidin-4-yl)pyrrolidin-3-yl)-4-chlorobenzamide
2-amino-4-N-piperazinyl-6-(4-fluorophenyl)-thieno[2,3-d]pyrimidine 1-(4-(2-amino-6-(4-fluorophenyl)thieno[2,3-d]pyrimidin-4-yl)piperazin-1-yl)-3-phenylpropan-1-one
4-(4-(benzylsulfonyl)piperazin-1-yl)-6-(4-fluorophenyl)thieno[2,3-d]pyrimidin-2-amine
(4-(2-amino-6-(4-fluorophenyl)thieno[2,3-d]pyrimidin-4-yl)piperazin-1-yl)(cyclohexyl)methanone
4-(2-amino-6-(4-fluorophenyl)thieno[2,3-d]pyrimidin-4-yl)piperazin-1-yl)(pyridin-3-yl)methanone
4-(2-amino-6-(4-fluorophenyl)thieno[2,3-d]pyrimidin-4-yl)-N,N-diisopropylpiperazine-1-carboxamide
(1-(2-amino-6-(4-fluorophenyl)thieno[2,3-d]pyrimidin-4-yl)piperidin-4-yl)(phenyl)methanone
2-amino-4-N-piperazino-thieno[2,3-d]pyrimidine
1-(4-(2-aminothieno[2,3-d]pyrimidin-4-yl)piperazin-1-yl)-2-(4-chlorophenoxy)ethanone
2-(4-chlorophenoxy)-1-(4-(6-(4-fluorophenyl)-2-phenylthieno[2,3-d]pyrimidin-4-yl)piperazin-1-yl)ethanone
ethyl 4-(4-(2-(4-chlorophenoxy)acetyl)piperazin-1-yl)-6-(4-fluorophenyl)thieno[2,3-d]pyrimidine-2-carboxylate
ethyl 2-(4-(2-(4-chlorophenoxy)acetyl)piperazin-1-yl)-6-(4-fluorophenyl)thieno[2,3-d]pyrimidin-2-yl)acetate
4-(4-(2-(4-chlorophenoxy)acetyl)piperazin-1-yl)-6-(4-fluorophenyl)thieno[2,3-d]pyrimidine-2-carboxamide
4-(4-(2-(4-chlorophenoxy)acetyl)piperazin-1-yl)-6-(4-fluorophenyl)-N-(2-methoxyethyl)thieno[2,3-d]pyrimidine-2-carboxamide
4-(4-(2-(4-chlorophenoxy)acetyl)piperazin-1-yl)-6-(4-fluorophenyl)thieno[2,3-d]pyrimidine-2-carboxylic acid
2-(4-(4-(2-(4-chlorophenoxy)acetyl)piperazin-1-yl)-6-(4-fluorophenyl)thieno[2,3-d]pyrimidin-2-yl)acetamide
4-(2-amino-6-(4-fluorophenyl)thieno[2,3-d]pyrimidin-4-yl)-N-m-tolylpiperazine-1-carboxamide
4-(6-(4-fluorophenyl)-2-phenylthieno[2,3-d]pyrimidin-4-yl)-N-m-tolylpiperazine-1-carboxamide
ethyl 6-(4-fluorophenyl)-4-(4-(m-tolylcarbamoyl)piperazin-1-yl)thieno[2,3-d]pyrimidine-2-carboxylate
6-(4-fluorophenyl)-4-(4-(m-tolylcarbamoyl)piperazin-1-yl)thieno[2,3-d]pyrimidine-2-carboxamide
4-ethoxy-6-(4-fluorophenyl)thieno[2,3-d]pyrimidin-2-amine
6-(4-fluorophenyl)-4-morpholinothieno[2,3-d]pyrimidin-2-amine
N-(3-chloro-4-fluorophenyl)-6-(4-fluorophenyl)-2-methylthieno[2,3-d]pyrimidin-4-amine
ethyl 4-(3-chloro-4-fluorophenylamino)-6-(4-fluorophenyl)thieno[2,3-d]pyrimidine-2-carboxylate
1-(4-(2-amino-6-phenylthieno[2,3-d]pyrimidin-4-yl)piperazin-1-yl)-2-(4-methoxyphenoxy)ethanone
1-(4-(2-amino-6-phenylthieno[2,3-d]pyrimidin-4-yl)piperazin-1-yl)-2-(4-fluorophenoxy)ethanone
1-(4-(2-amino-6-phenylthieno[2,3-d]pyrimidin-4-yl)piperazin-1-yl)-2-(m-tolyloxy)ethanone
1-(4-(2-amino-6-phenylthieno[2,3-d]pyrimidin-4-yl)piperazin-1-yl)-2-(4-bromophenoxy)ethanone
1-(4-(2-amino-6-phenylthieno[2,3-d]pyrimidin-4-yl)piperazin-1-yl)-2-(4-chlorophenoxy)-2-methylpropan-1-one
1-(4-(2-amino-8-(4-fluorophenyl)-9H-purin-6-yl)piperazin-1-yl)-2-(4-chlorophenoxy)ethanone
1-(4-(2-amino-8-(3,4-dimethoxyphenyl)-9H-purin-6-yl)piperazin-1-yl)-2-(4-chlorophenoxy)ethanone
1-(4-(2-amino-8-(4-bromophenyl)-9H-purin-6-yl)piperazin-1-yl)-2-(4-chlorophenoxy)ethanone
1-(4-(2-amino-8-(4-chlorophenyl)-9H-purin-6-yl)piperazin-1-yl)-2-(4-chlorophenoxy)ethanone
1-(4-(2-amino-8-(3-chlorophenyl)-9H-purin-6-yl)piperazin-1-yl)-2-(4-chlorophenoxy)ethanone
1-(4-(2-amino-8-(4-(trifluoromethyl)phenyl)-9H-purin-6-yl)piperazin-1-yl)-2-(4-chlorophenoxy)ethanone
1-(4-(2-amino-8-(4-(trifluoromethoxy)phenyl)-9H-purin-6-yl)piperazin-1-yl)-2-(4-chlorophenoxy)ethanone
1-(4-(2-amino-8-p-tolyl-9H-purin-6-yl)piperazin-1-yl)-2-(4-chlorophenoxy)ethanone
1-(4-(2-amino-8-propyl-9H-purin-6-yl)piperazin-1-yl)-2-(4-chlorophenoxy)ethanone
1-(4-(2-amino-8-cyclopropyl-9H-purin-6-yl)piperazin-1-yl)-2-(4-chlorophenoxy)ethanone
1-(4-(2-amino-8-tert-butyl-9H-purin-6-yl)piperazin-1-yl)-2-(4-chlorophenoxy)ethanone
1-(4-(2-amino-8-methyl-9H-purin-6-yl)piperazin-1-yl)-2-(4-chlorophenoxy)ethanone
1-(4-(2-amino-8-(4-fluorophenyl)-9H-purin-6-yl)piperazin-1-yl)-2-phenoxyethanone
1-(4-(2-amino-8-(4-fluorophenyl)-9H-purin-6-yl)piperazin-1-yl)(3-methoxyphenyl)methanone
1-(4-(2-amino-8-(4-fluorophenyl)-9H-purin-6-yl)piperazin-1-yl)-2-(thiophen-2-yl)ethanone
(4-(2-amino-8-(4-fluorophenyl)-9H-purin-6-yl)piperazin-1-yl)(4-chlorophenyl)methanone
6-(4-(benzylsulfonyl)piperazin-1-yl)-8-(4-fluorophenyl)-9H-purin-2-amine
(4-(2-amino-8-(4-fluorophenyl)-9H-purin-6-yl)piperazin-1-yl)(naphthalen-1-yl)methanone
1-(4-(2-amino-8-(4-fluorophenyl)-9H-purin-6-yl)piperazin-1-yl)ethanone
8-(4-fluorophenyl)-6-(4-(thiazol-2-yl)piperazin-1-yl)-9H-purin-2-amine
2-(4-(2-amino-8-(4-fluorophenyl)-9H-purin-6-yl)piperazin-1-yl)-1-(pyrrolidin-1-yl)ethanone
2-(4-(2-amino-8-(4-fluorophenyl)-9H-purin-6-yl)piperazin-1-yl)-1-morpholinoethanone
2-(4-(2-amino-8-(4-fluorophenyl)-9H-purin-6-yl)piperazin-1-yl)-N-(pyridin-3-yl)acetamide
2-(4-(2-amino-8-(4-fluorophenyl)-9H-purin-6-yl)piperazin-1-yl)-N-methyl-N-phenylacetamide
6-(4-(4-chlorophenyl)piperazin-1-yl)-8-(4-fluorophenyl)-9H-purin-2-amine
8-(4-fluorophenyl)-6-(4-(4-fluorophenyl)piperazin-1-yl)-9H-purin-2-amine
2-(4-(2-amino-8-(4-fluorophenyl)-9H-purin-6-yl)piperazin-1-yl)-N-(pyridin-2-yl)acetamide
2-(4-(2-amino-8-(4-fluorophenyl)-9H-purin-6-yl)piperazin-1-yl)-N-(thiazol-2-yl)acetamide
6-(4-(4-fluorobenzyl)piperazin-1-yl)-8-(4-fluorophenyl)-9H-purin-2-amine
8-(4-fluorophenyl)-6-(4-(pyridin-4-yl)piperazin-1-yl)-9H-purin-2-amine
6-(1,4-diazepan-1-yl)-8-(4-fluorophenyl)-9H-purin-2-amine
1-(4-(2-amino-8-(4-fluorophenyl)-9H-purin-6-yl)-1,4-diazepan-1-yl)-2-(4-chlorophenoxy)ethanone
4-(2-amino-8-(4-fluorophenyl)-9H-purin-6-yl)-N-m-tolyl-1,4-diazepane-1-carboxamide
1-(4-(2-amino-8-thioxo-8,9-dihydro-7H-purin-6-yl)piperazin-1-yl)-2-(4-chlorophenoxy)ethanone
1-(4-(2-amino-8-(methylthio)-9H-purin-6-yl)piperazin-1-yl)-2-(4-chlorophenoxy)ethanone
1-(4-(2-amino-8-(propylthio)-9H-purin-6-yl)piperazin-1-yl)-2-(4-chlorophenoxy)ethanone 1-(4-(2-amino-8-(benzylthio)-9H-purin-6-yl)piperazin-1-yl)-2-(4-chlorophenoxy)ethanone
1-(4-(2-amino-8-(phenethylthio)-9H-purin-6-yl)piperazin-1-yl)-2-(4-chlorophenoxy)ethanone
1-(4-(2-amino-9-methyl-8-(methylthio)-9H-purin-6-yl)piperazin-1-yl)-2-(4-chlorophenoxy)ethanone
1-(4-(2-amino-8-(cyclopentylthio)-9H-purin-6-yl)piperazin-1-yl)-2-(4-chlorophenoxy)ethanone
1-(4-(2-amino-8-(4-fluorophenyl)-9-methyl-9H-purin-6-yl)piperazin-1-yl)-2-(4-chlorophenoxy)ethanone
1-(4-(2-amino-9-benzyl-8-(4-fluorophenyl)-9H-purin-6-yl)piperazin-1-yl)-2-(4-chlorophenoxy)ethanone
2-amino-6-(piperazin-1-yl)-8-(4-fluorophenyl)-9H-purine
1-(4-(2-amino-8-(4-fluorophenyl)-9H-purin-6-yl)piperazin-1-yl)-3-phenylpropan-1-one
4-(5-amino-2-(pyridin-3-yl)thiazolo[5,4-d]pyrimidin-7-yl)-N-(4-(trifluoromethyl)phenyl)piperazine-1-carboxamide
4-(5-amino-2-(pyridin-3-yl)thiazolo[5,4-d]pyrimidin-7-yl)-N-phenylpiperazine-1-carboxamide
4-(5-amino-2-(pyridin-3-yl)thiazolo[5,4-d]pyrimidin-7-yl)-N-cyclohexylpiperazine-1-carboxamide
5-amino-7-[4-(N-4-fluorophenylcarboxamide)piperazin-1-yl]-2-(pyridine-3-yl)thiazolo[5,4-d]pyrimidine
4-(5-amino-2-(pyridin-3-yl)thiazolo[5,4-d]pyrimidin-7-yl)-N-hexylpiperazine-1-carboxamide
4-(5-amino-2-(pyridin-3-yl)thiazolo[5,4-d]pyrimidin-7-yl)-N-p-tolylpiperazine-1-carbothioamide
4-(5-amino-2-(pyridin-3-yl)thiazolo[5,4-d]pyrimidin-7-yl)-N-methyl-N-p-tolylpiperazine-1-carboxamide
p-tolyl 4-(5-amino-2-(pyridin-3-yl)thiazolo[5,4-d]pyrimidin-7-yl)piperazine-1-carboxylate.

In another particular embodiment, the invention relates to thiazolo[5,4-d]pyrimidine, oxazolo[5,4-d]pyrimidine, thieno[2,3-d]pyrimidine and purine derivatives of formula I, II, III, or IV, as well as pharmaceutical compositions comprising such thiazolo[5,4-d]pyrimidine, oxazolo[5,4-d]pyrimidine, thieno[2,3-d]pyrimidine and purine derivatives as active principle, represented by the above mentioned structural formula I, II, III, or V and being in the form of a pharmaceutically acceptable salt. The latter include any therapeutically active nontoxic addition salt which compounds represented by structural formula I, II, III, or IV are able to form with a salt-forming agent. Such addition salts may conveniently be obtained by treating the thiazolo[5,4-d]pyrimidine, oxazolo[5,4-d]pyrimidine, thieno[2,3-d]pyrimidine and purine derivatives of the invention with an appropriate salt-forming acid or base. For instance, thiazolo[5,4-d]pyrimidine, oxazolo[5,4-d]pyrimidine, thieno[2,3-d]pyrimidine and purine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluenesulfonate, salicylate, p-aminosalicylate, palmoate, bitartrate, camphorsulfonate, edetate, 1,2-ethanedisulfonate, fumarate, glucoheptonate, gluconate, glutamate, hexylresorcinate, hydroxynaphthoate, hydroxyethanesulfonate, mandelate, methylsulfate, pantothenate, stearate, as well as salts derived from ethanedioic, propanediol, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like. Thiazolo[5,4-d]pyrimidine, oxazolo[5,4-d]pyrimidine, thieno[2,3-d]pyrimidine and purine derivatives of this invention, including the ones represented by the structural formula I, II, III, or IV, having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, $N_1N^1$-dibenzylethylenediamine, chloroprocaine, choline, diethanolamine, ethylene-diamine, N-methylglucamine, procaine and the like.

Reaction conditions for treating the thiazolo[5,4-d]pyrimidine, oxazolo[5,4-d]pyrimidine, thieno[2,3-d]pyrimidine or purine derivatives of this invention, including the ones represented by the structural formula I, II, III, or IV, with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the thiazolo(5,4-d)pyrimidine or oxazolo(5,4-d)pyrimidine derivative of this invention.

Another aspect of the present invention relates to the process for the preparation of the thiazolo(5,4-d)pyrimidine derivatives of this invention, and comprises the steps of: (a) acylation of 2,5-diamino-4,6-dihydroxypyrimidine; (b) treatment with a thionation reagent; (c) treatment with iodomethane; (d) oxidation reaction by adding an oxidating agent; and (e) a nucleophilic aromatic substitution reaction.

In a specific embodiment, in step (a) said acylation is performed with a carboxylic acid ($R^2COOH$) or an acid chloride ($R^2C(O)Cl$) and/or step (a) further comprises the addition of a coupling reagent such as N,N'-dicyclohexylcarbodiimide (DCC) or N,N'-diisopropylcarbodiimide (DIC) or 1-(3-dimethylaminopropyl)-3-ethylcarbodiimide hydrochloride (EDCl) and optionally step (a) further comprises the addition of additives such as 1-hydroxybenzotriazole (HOBt) and 1-hydroxy-7-azabenzotriazole (HOAt). In a specific embodiment, in step (b) said thionation reagent is phosphorus pentasulfide or a Lawesson's reagent and said treatment with a thionation reagent is performed in high-boiling solvents such as pyridine, toluene or xylene. In a specific embodiment, step (c) is performed in alkaline conditions. In a specific embodiment, in step (d) said oxidating agent is m-chloro-peroxybenzoic acid or hydrogen peroxide. In a specific embodiment, in step (e) a piperazine is introduced at position 7. In another specific embodiment, the present invention relates to the process for the preparation of the thiazolo(5,4-d)pyrimidine derivatives of this invention wherein said thiazolo(5,4-d)pyrimidine derivatives are $R^2$-substituted 5-amino-7-N-piperazino thiazolo(5,4-d)pyrimidine derivatives, and wherein $R^2$ has any of the values as described herein.

Another aspect of the present invention relates to the thiazolo[5,4-d]pyrimidine oxazolo[5,4-d]pyrimidine, thieno[2,3-d]pyrimidine and purine derivatives of the invention, including the thiazolo[5,4-d]pyrimidine, oxazolo(5,4-d)pyrimidine, thieno[2,3-d]pyrimidine and purine derivatives of formula I, for use as a medicine and to the use of said thiazolo [5,4-d]pyrimidine, oxazolo[5,4-d]pyrimidine, thieno[2,3-d]pyrimidine or purine derivatives as a medicine, more in particular to the use of said thiazolo[5,4-d]pyrimidine, oxazolo [5,4-d]pyrimidine, thieno[2,3-d]pyrimidine or purine derivatives to treat or prevent an immune disorder in an animal, even more in particularly to treat or prevent autoimmune disorders and particular organ and cells transplant rejections in an animal, more specifically a mammal such as a human being.

Another aspect of the present invention relates to the pharmaceutical composition of the invention for use as a medicine and to the use of said pharmaceutical composition as a medicine, more in particular to the use of said pharmaceutical composition to treat or prevent an immune disorder in an animal, even more in particularly to treat or prevent autoimmune disorders and particular organ and cells transplant rejections in an animal, more specifically a mammal such as a human being.

The present invention further provides the use of thiazolo [5,4-d]pyrimidine, oxazolo[5,4-d]pyrimidine, thieno[2,3-d] pyrimidine and purine derivatives of this invention, including the ones represented by the structural formula I, II, III, or IV, or a pharmaceutically acceptable salt or a solvate thereof, as a biologically active ingredient, i.e. active principle, especially as a medicine or a diagnostic agent or for the manufacture of a medicament or a diagnostic kit. In a particular embodiment, said medicament may be for the prevention or treatment of a immune disorders, in particular organ and cells transplant rejections, and autoimmune disorders.

The present invention further provides the use of the thiazolo[5,4-d]pyrimidine, oxazolo[5,4-d]pyrimidine, thieno[2,3-d]pyrimidine and purine derivatives of this invention, including the ones represented by the structural formula I, II, III, or IV, or a pharmaceutically acceptable salt or a solvate thereof, as a biologically active ingredient, i.e. active principle, especially as a medicine or for the manufacture of a medicament for treating an immune disorder or for preventing a transplant rejection.

The pathologic conditions and disorders concerned by the said use, and the corresponding methods of prevention or treatment, are detailed herein below. Any of the uses mentioned with respect to the present invention may be restricted to a nonmedical use (e.g. in a cosmetic composition), a non-therapeutic use, a non-diagnostic use, a non-human use (e.g. in a veterinary composition), or exclusively an in-vitro use, or a use with cells remote from an animal. The invention further relates to a pharmaceutical composition comprising: (a) one or more thiazolo[5,4-d]pyrimidine, oxazolo[5,4-d]pyrimidine, thieno[2,3-d]pyrimidine and/or purine derivatives of this invention, including the ones represented by the structural formula I, II, III, or IV, and (b) one or more pharmaceutically acceptable carriers.

In another embodiment, this invention provides combinations, preferably synergistic combinations, of one or more thiazolo[5,4-d]pyrimidine, oxazolo[5,4-d]pyrimidine, thieno [2,3-d]pyrimidine and/or purine derivatives of this invention with one or more biologically active drugs being preferably selected from the group consisting of immunosuppressant and/or immunomodulator drugs. As is conventional in the art, the evaluation of a synergistic effect in a drug combination may be made by analyzing the quantification of the interactions between individual drugs, using the median effect principle described by Chou et al. in Adv. Enzyme Reg. (1984) 22:27. Briefly, this principle states that interactions (synergism, additivity, antagonism) between two drugs can be quantified using the combination index (hereinafter referred as CI) defined by the following equation: wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein below, this principle may be applied to a number of desirable effects such as, but not limited to, an activity against transplant rejection, an activity against immunosuppression or immunomodulation. For instance the present invention relates to a pharmaceutical composition or combined preparation having synergistic effects against immuno-suppression or immunomodulation and containing: (a) one or more immunosuppressant and/or immunomodulator drugs, and (b) at least one thiazolo[5,4-d] pyrimidine, oxazolo[5,4-d]pyrimidine, thieno[2,3-d]pyrimidine and/or purine derivative of the invention, including the ones represented by the structural formula I, II, III, or IV and (c) optionally one or more pharmaceutical excipients or pharmaceutically acceptable carriers, for simultaneous, separate or sequential use in the treatment or prevention of autoimmune disorders and/or in transplant-rejections.

Suitable immunosuppressant drugs for inclusion in the synergistic compositions or combined preparations of this invention belong to a well known therapeutic class. They are preferably selected from the group consisting of cyclosporine A, substituted xanthines (e.g. methylxanthines such as pentoxyfylline), daltroban, sirolimus, tacrolimus, rapamycin (and derivatives thereof such as defined below), leflunomide (or its main active metabolite A771726, or analogs thereof called malononitrilamides), mycophenolic acid and salts thereof (including the sodium salt marketed under the trade name Mofetil®), adrenocortical steroids, azathioprine, brequinar, gusperimus, 6-mercaptopurine, mizoribine, chloroquine, hydroxy-chloroquine and monoclonal antibodies with immunosuppressive properties (e.g. etanercept, infliximab or kineret). Adrenocortical steroids within the meaning of this invention mainly include glucocorticoids such as but not limited to ciprocinonide, desoxycorticosterone, fludrocortisone, flumoxonide, hydrocortisone, naflocort, procinonide, timobesone, tipredane, dexamethasone, methylprednisolone, methotrexate, prednisone, prednisolone, triamcinolone and pharmaceutically acceptable salts thereof. Rapamycin derivatives as referred herein include O-alkylated derivatives, particularly 9-deoxorapamycins, 26-dihydrorapamycins, 40-O-substituted rapamycins and 28,40-0,0-disubstituted rapamycins (as disclosed in U.S. Pat. No. 5,665,772) such as 40-O-(2-hydroxy)ethyl rapamycin—also known as SDZ-RAD-, pegylated rapamycin (as disclosed in U.S. Pat. No. 5,780,462), ethers of 7-desmethylrapamycin (as disclosed in U.S. Pat. No. 6,440,991) and polyethylene glycol esters of SDZ-RAD (as disclosed in U.S. Pat. No. 6,331,547).

Suitable immunomodulator drugs for inclusion into the synergistic immunomodulating pharmaceutical compositions or combined preparations of this invention are preferably selected from the group consisting of acemannan, amiprilose, bucillamine, dimepranol, ditiocarb sodium, imiquimod, Inosine Pranobex, interferon-β, interferon-γ, lentinan, levamisole, lisophylline, pidotimod, romurtide, platonin, procodazole, propagermanium, thymomodulin, thymopentin and ubenimex.

Synergistic activity of the pharmaceutical compositions or combined preparations of this invention against immunosuppression or immuno-modulation may be readily determined by means of one or more lymphocyte activation tests. Usually activation is measured via lymphocyte proliferation. Inhibition of proliferation thus always means immunosuppression under the experimental conditions applied. There exist different stimuli for lymphocyte activation, in particular: a) co-culture of lymphocytes of different species (mixed lymphocyte reaction, hereinafter referred as MLR) in a so-called mixed lymphocyte culture test: lymphocytes expressing different minor and major antigens of the HLA-DR type (=alloantigens) activate each other non-specifically; b) a CD3 assay wherein there is an activation of the T-lymphocytes via an exogenously added antibody (OKT3). This antibody reacts against a CD3 molecule located on the lymphocyte membrane which has a co-stimulatory function. Interaction between OKT3 and CD3 results in T-cell activation which proceeds via the $Ca^{2+}$/calmodulin/calcineurin system and can be inhibited e.g. by cyclosporine A (hereinafter referred as CyA); and c) a CD28 assay wherein specific activation of the T-lymphocyte proceeds via an exogenously added antibody against a CD28 molecule which is also located on the lymphocyte membrane and delivers strong co-stimulatory signals. This activation is $Ca^{2+}$-independent and thus cannot be inhibited by CyA. Determination of the immunosuppressing or immunomodulating activity of the thiazolo[5,4-d]pyrimidine, oxazolo[5,4-d]pyrimidine, thieno[2,3-d]pyrimidine or purine derivatives of this invention, as well as synergistic combinations comprising them, is preferably based on the determination of one or more, preferably at least three lymphocyte activation in vitro tests, more preferably including at least one of the MLR test, CD3 assay and CD28 assay referred above. Preferably the lymphocyte activation in vitro tests used include at least two assays for two different clusters of differentiation preferably belonging to the same general type of such clusters and more preferably belonging to type I transmembrane proteins. Optionally the determination of the immuno-suppressing or immunomodulating activity may be performed on the basis of other lymphocyte activation in vitro tests, for instance by performing a TNF-α assay or an IL-1 assay or an IL-6 assay or an IL-10 assay or an IL-12 assay or an assay for a cluster of differentiation belonging to a further general type of such clusters and more preferably belonging to type II transmembrane proteins such as, but not limited to, CD69, CD71 or CD134.

The synergistic effect may be evaluated by the median effect analysis method described herein before. Such tests may for instance, according to standard practice in the art, involve the use of equipment, such as flow cytometer, being able to separate and sort a number of cell subcategories at the end of the analysis, before these purified batches can be analyzed further.

Synergistic activity of the pharmaceutical compositions of this invention in the prevention or treatment of transplant rejection may be readily determined by means of one or more leukocyte activation tests performed in a Whole Blood Assay (hereinafter referred as WBA) described for instance by Lin et al. in Transplantation (1997) 63:1734-1738. WBA used herein is a lymphoproliferation assay performed in vitro using lymphocytes present in the whole blood, taken from animals that were previously given the thiazolo[5,4-d]pyrimidine, oxazolo[5,4-d]pyrimidine, thieno[2,3-d]pyrimidine or purine derivative of this invention, and optionally the other immunosuppressant drug, in vivo. Hence this assay reflects the in vivo effect of substances as assessed by an in vitro read-out assay. The synergistic effect may be evaluated by the median effect analysis method described herein before. Various organ transplantation models in animals are also available in vivo, which are strongly influenced by different immunogenicities, depending on the donor and recipient species used and depending on the nature of the transplanted organ. The survival time of transplanted organs can thus be used to measure the suppression of the immune response.

The pharmaceutical composition or combined preparation with synergistic activity against immunosuppression or immunomodulation according to this invention may contain the thiazolo[5,4-d]pyrimidine, oxazolo[5,4-d]pyrimidine, thieno[2,3-d]pyrimidine and/or purine derivative of this invention, including the ones represented by the structural formulae I, II, III, or IV over a broad content range depending on the contemplated use and the expected effect of the preparation. Typically, the thiazolo[5,4-d]pyrimidine, oxazolo[5,4-d]pyrimidine, thieno[2,3-d]pyrimidine and/or purine derivative content in the combined preparation is within the range of 0.1 to 99.9% by weight, preferably from 1 to 99% by weight, more preferably from about 5 to 95% by weight.

Auto-immune disorders to be prevented or treated by the pharmaceutical compositions or combined preparations of this invention include both:
- systemic auto-immune diseases such as, but not limited to, lupus erythematosus, psoriasis, vasculitis, polymyositis, scleroderma, multiple sclerosis, ankylosing spondilytis, rheumatoid arthritis and Sjogren syndrome; auto-immune endocrine disorders such as thyroiditis; and
- organ-specific auto-immune diseases such as, but not limited to, Addison disease, hemolytic or pernicious anemia, Goodpasture syndrome, Graves disease, idiopathic thrombocytopenic purpura, insulin-dependent diabetes mellitus, juvenile diabetes, uveitis, Crohn's disease, ulcerative colitis, pemphigus, atopic dermatitis, autoimmune hepatitis, primary biliary cirrhosis, autoimmune pneumonitis, autoimmune carditis, myasthenia gravis, glomerulonephritis and spontaneous infertility.

Transplant rejections to be prevented or treated by the pharmaceutical compositions or combined preparations of this invention include the rejection of transplanted or grafted organs or cells (both allografts and xenografts), such as but not limited to host versus graft reaction disease. The term "organ" as used herein means all organs or parts of organs in mammals, in particular humans, such as but not limited to kidney, lung, bone marrow, hair, cornea, eye (vitreous), heart, heart valve, liver, pancreas, blood vessel, skin, muscle, bone, intestine or stomach. The term "rejection" as used herein means all reactions of the recipient body or the transplanted organ which in the end lead to cell or tissue death in the transplanted organ or adversely affect the functional ability and viability of the transplanted organ or the recipient. In particular, this means acute and chronic rejection reactions. Also included in this invention is preventing or treating the rejection of cell transplants and xenotransplantation. The major hurdle for xenotransplantation is that even before the T lymphocytes, responsible for the rejection of allografts, are activated, the innate immune system, especially T-independent B lymphocytes and macrophages are activated. This provokes two types of severe and early acute rejection called hyperacute rejection and vascular rejection, respectively. The present invention addresses the problem that conventional immunosuppressant drugs like cyclosporine A are ineffective in xeno-transplantation. The ability of the compounds of this invention to suppress T-independent xeno-antibody production as well as macrophage activation may be evaluated in the ability to prevent xenograft rejection in athymic, T-deficient mice receiving xenogenic hamster-heart grafts.

The term "pharmaceutically acceptable carrier or excipient" as used herein in relation to pharmaceutical compositions and combined preparations means any material or substance with which the active principle, i.e. the thiazolo[5,4-d]pyrimidine, oxazolo[5,4-d]pyrimidine, thieno[2,3-d]pyrimidine and purine derivative of this invention, including the ones represented by the structural formula I, II, III, or IV, and optionally the immunosuppressant or immunomodulator may be formulated in order to facilitate its application or dissemination to the locus to be treated, for instance by dissolving, dispersing or diffusing said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders. Suitable pharmaceutical carriers for use in said pharmaceutical compositions and their formulation are well known to those skilled in the art. There is no particular restriction to their selection within the present invention although, due to the usually low or very low water-solubility of the thiazolo[5,4-d]pyrimidine, oxazolo[5,4-d]pyrimidine, thieno[2,3-d]pyrimidine and purine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents, may also be prepared by micronisation, for instance in view to obtain them in the form of microspheres usually having a diameter of about 1 to 10 μm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylene-diamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals. A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants" (Chemical Publishing Co., New York, 1981). Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof. Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxy-methylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems including, but not limited to liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof.

Other modes of local drug administration can also be used. For example, the selected active agent may be administered by way of intracavernosal injection, or may be administered topically, in an ointment, gel or the like, or transdermal, including transscrotally, using a conventional transdermal drug delivery system. Intracavernosal injection can be carried out by use of a syringe or any other suitable device. An example of a hypodermic syringe useful herein is described in U.S. Pat. No. 4,127,118, injection being made on the dorsum of the penis by placement of the needle to the side of each dorsal vein and inserting it deep into the corpora.

Since, in the case of combined preparations including the thiazolo[5,4-d]pyrimidine, oxazolo[5,4-d]pyrimidine, thieno[2,3-d]pyrimidine and purine derivative of this invention and an immunosuppressant or immunomodulator both ingredients do not necessarily bring out their synergistic therapeutic effect directly at the same time in the patient to be treated, the said combined preparation may be in the form of a medical kit or package containing the two ingredients in separate but adjacent form. In the latter context, each ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention further relates to a method for preventing or treating a disease selected from the group consisting of immune and auto-immune disorders, transplant rejections, in a patient, preferably a mammal, more preferably a human being. The method of this invention consists of administering to the patient in need thereof an effective amount of a thiazolo[5,4-d]pyrimidine, oxazolo[5,4-d]pyrimidine, thieno[2,3-d]pyrimidine and/or purine derivative of this invention, including the ones represented by the structural formula I, II, III, or IV, optionally together with an effective amount of another immunosuppressant or immunomodulator or antineoplastic drug or antiviral agent or phosphodiesterase-4 inhibitor, or a pharmaceutical composition comprising the same, such as disclosed above in extensive details. The effective amount is usually in the range of about 0.01 mg to 20 mg, preferably about 0.1 mg to 5 mg, per day per kg bodyweight for humans. Depending upon the pathologic condition to be treated and the patient's condition, the said effective amount may be divided into several sub-units per day or may be administered at more than one day intervals. The patient to be treated may be any warm-blooded animal, preferably a mammal, more preferably a human being, suffering from said pathologic condition.

The preferred compounds of the present invention are non-sedating. In other words, a dose of such compounds that is twice the minimum dose sufficient to provide analgesia in an animal model for determining pain relief causes only transient (i.e. lasting for no more than half the time that pain relief lasts) or preferably no statistically significant sedation in an animal model assay of sedation (using the method described by Fitzgerald et al. in Toxicology (1988) 49:433-9). Preferably, a dose that is five times the minimum dose sufficient to provide analgesia does not produce statistically significant sedation. More preferably, a compound provided herein does not produce sedation at intravenous doses of less than 10 mg/kg per day or at oral doses of less than 30 mg/kg per day. If desired, compounds provided herein may be evaluated for toxicity (a preferred compound is non-toxic when an immunomodulating amount or a cell anti-proliferative amount is administered to a subject) and/or side effects (a preferred compound produces side effects comparable to placebo when a therapeutically effective amount of the compound is administered to a subject). Toxicity and side effects may be assessed using any standard method. In general, the term "non-toxic" as used herein shall be understood as referring to any substance that, in keeping with established criteria, is susceptible to approval by the United States Federal Drug Administration for administration to mammals, preferably humans. Toxicity may be also evaluated using assays including bacterial reverse mutation assays, such as an Ames test, as well as standard teratogenicity and tumorogenicity assays. Preferably, administration of compounds provided herein within the therapeutic dose ranges disclosed hereinabove does not result in prolongation of heart QT intervals (e.g. as determined by electrocardiography in guinea pigs, minipigs or dogs). When administered daily, such doses also do not cause liver enlargement resulting in an increase of liver to body weight ratio of more than 50% over matched controls in laboratory rodents (e.g. mice or rats). Such doses also preferably do not cause liver enlargement resulting in an increase of liver to body weight ratio of more than 10% over matched untreated controls in dogs or other non-rodent mammals. The preferred compounds of the present invention also do not promote substantial release of liver enzymes from hepatocytes in vivo, i.e. the therapeutic doses do not elevate serum levels of such enzymes by more than 50% over matched untreated controls in vivo in laboratory rodents.

Another embodiment of this invention includes the various precursor or "prodrug" forms of the compounds of the present invention. It may be desirable to formulate the compounds of the present invention in the form of a chemical species which itself is not significantly biologically active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "prodrug" or "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome. The present invention will be further described with reference to certain more specific embodiments and examples, but the present invention is not limited thereto. The following examples are given by way of illustration only.

DEFINITIONS

When describing the compounds of the invention, the terms used are to be construed in accordance with the following definitions, unless a context dictates otherwise.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl (terbutyl), 2-methylbutyl, n-pentyl, dimethylpropyl, n-hexyl, 2-methylpentyl, 3-methylpentyl, n-heptyl and the like. By analogy, the term "$C_{1-12}$ alkyl" refers to such radicals having from 1 to 12 carbon atoms, i.e. up to and including dodecyl.

As used herein with respect to a substituting radical, and unless otherwise stated, the term "acyl" broadly refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a substituent derived from an organic sulfonic acid, wherein said acids comprise an aliphatic, aromatic or heterocyclic group in the molecule. In a more specific embodiment of the invention said acyl group, within the scope of the above definition, refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below. In a more specific embodiment of the invention said "sulfonyl" group, within the scope of the above definition, refers to a sulfonyl group adjacent to a $C_{1-7}$ alkyl, a $C_{3-10}$ cycloalkyl, an aryl, an arylalkyl or a heterocyclic group, all of them being such as herein defined.

Acyl and sulfonyl groups originating from aliphatic or cycloaliphatic monocarboxylic acids or sulfonic acids are designated herein as aliphatic or cycloaliphatic acyl and sulfonyl groups and include, but are not limited to, the following:

alkanoyl (for example formyl, acetyl, propionyl, butyryl, isobutyryl, valeryl, isovaleryl, pivaloyl and the like);

cycloalkanoyl (for example cyclobutanecarbonyl, cyclopentanecarbonyl, cyclohexanecarbonyl, 1-adamantanecarbonyl and the like);

cycloalkyl-alkanoyl (for example cyclohexylacetyl, cyclopentylacetyl and the like);

alkenoyl (for example acryloyl, methacryloyl, crotonoyl and the like);

alkylthioalkanoyl (for example methylthioacetyl, ethylthioacetyl and the like);

alkanesulfonyl (for example mesyl, ethanesulfonyl, propanesulfonyl and the like);

alkoxycarbonyl (for example methoxycarbonyl, ethoxycarbonyl, propoxycarbonyl, isopropoxycarbonyl, butoxycarbonyl, isobutoxycarbonyl and the like);

alkylcarbamoyl (for example methylcarbamoyl and the like);

(N-alkyl)-thiocarbamoyl (for example (N-methyl)-thiocarbamoyl and the like);

alkylcarbamidoyl (for example methylcarbamidoyl and the like); and alkoxalyl (for example methoxalyl, ethoxalyl, propoxalyl and the like);

Acyl and sulfonyl groups may also originate from aromatic monocarboxylic acids and include, but are not limited to, the following:

aroyl (for example benzoyl, toluoyl, xyloyl, 1-naphthoyl, 2-naphthoyl and the like);

aralkanoyl (for example phenylacetyl and the like);

aralkenoyl (for example cinnamoyl and the like);

aryloxyalkanoyl (for example phenoxyacetyl and the like);

arylthioalkanoyl (for example phenylthioacetyl and the like);

arylaminoalkanoyl (for example N-phenylglycyl, and the like);

arylsulfonyl (for example benzenesulfonyl, toluenesulfonyl, naphthalene sulfonyl and the like);

aryloxycarbonyl (for example phenoxycarbonyl, naphthyloxycarbonyl and the like);

aralkoxycarbonyl (for example benzyloxycarbonyl and the like);

arylcarbamoyl (for example phenylcarbamoyl, naphthylcarbamoyl and the like);

arylglyoxyloyl (for example phenylglyoxyloyl and the like).

arylthiocarbamoyl (for example phenylthiocarbamoyl and the like); and arylcarbamidoyl (for example phenylcarbamidoyl and the like).

Acyl groups may also originate from an heterocyclic monocarboxylic acids and include, but are not limited to, the following:

heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like); and heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imidazolyl propionyl, tetrazolylacetyl, 2-(2-amino-4-thiazolyl)-2-methoxyiminoacetyl and the like).

As used herein with respect to a substituting radical, and unless otherwise stated, the term "thioacyl" refers to an acyl group as defined herein-above but wherein a sulfur atom replaces the oxygen atom of the carbonyl (oxo) moiety.

As used herein with respect to a substituting radical, and unless otherwise stated, the term "$C_{1-7}$ alkylene" means the divalent hydrocarbon radical corresponding to the above defined $C_{1-7}$ alkyl, such as methylene, bis(methylene), tris(methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkyl-alkyl" refers to an aliphatic saturated hydrocarbon monovalent radical (preferably a $C_{1-7}$ alkyl such as defined above) to which a $C_{3-10}$ cycloalkyl (such as defined above) is already linked such as, but not limited to, cyclohexylmethyl, cyclopentylmethyl and the like.

As used herein with respect to a substituting radical, and unless otherwise stated, the term "$C_{3-10}$ cycloalkylene" means the divalent hydrocarbon radical corresponding to the above defined $C_{3-10}$ cycloalkyl.

As used herein with respect to a substituting radical, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_4\beta$ cycloalkyl radicals (the latter being as defined above) such as, for instance, indanyl, tetrahydronaphthyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, e.g. with respect to a substituting radical such as the combination of substituents in certain positions of the thiazolo[5,4-d]pyrimidine, oxazolo[5,4-d]pyrimidine, thieno[2,3-d]pyrimidine or purine ring together with the carbon atoms in the same positions of said ring, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance said combination of substituents may form a $C_{2-6}$ alkylene radical, such as tetramethylene, which cyclizes with the carbon atoms in certain positions of the thiazolo[5,4-d]pyrimidine, oxazolo[5,4-d]pyrimidine, thieno[2,3-d]pyrimidine or purine ring.

As used herein with respect to a substituting radical (including the combination of substituents in certain positions of the thiazolo[5,4-d]pyrimidine, oxazolo[5,4-d]pyrimidine, thieno[2,3-d]pyrimidine or purine ring together with the carbon atoms in the same positions of said ring), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphtho-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepine, benzodioxepinyl, benzodithiepinyl, benzoxazocinyl, benzo-thiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphto-triazolyl, naphtopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofutyl, furoyl, hydantoinyl, dioxolanyl, dioxolyl, dithianyl, dithienyl, dithiinyl, thienyl, indolyl, indazolyl, benzofutyl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkyl-amino, hydroxylalkylamino, mercaptoalkylamino, heterocyclic-substituted alkylamino, heterocyclic amino, heterocyclic-substituted arylamino, hydrazino, alkylhydrazino, phenylhydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkylhydrazino, phenylhydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, tricarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl and alkylaryl.

As used herein with respect to a substituting radical, and unless otherwise stated, the terms "$C_{1-7}$ alkoxy", "$C_{3-10}$ cycloalkoxy", "aryloxy", "arylalkyloxy", "oxyheterocyclic", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl or heterocyclic radical (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl, cresoxy, and the like.

As used herein with respect to a substituting atom, and unless otherwise stated, the term "halogen" or "halo" means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cycloheptadienyl, cycloheptatrienyl, cyclooctenyl, cyclooctadienyl and the like, or a $C_{7-10}$ polycyclic mono- or polyunsaturated hydrocarbon monovalent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the terms "arylalkyl", "arylalkenyl" and "heterocyclic-substituted alkyl" refer to an aliphatic saturated or ethylenically unsaturated hydrocarbon monovalent radical (preferably a $C_{1-7}$ alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-ylethyl, benzodioxolylmethyl and 2-furylmethyl.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above such as, but not limited to, o-toluyl, m-toluyl, p-toluyl, 2,3-xylyl, 2,4-xylyl, 3,4-xylyl, o-cumenyl, m-cumenyl, p-cumenyl, o-cymenyl, m-cymenyl, p-cymenyl, mesityl, ter-butylphenyl, lutidinyl (i.e. dimethylpyridyl), 2-methylaziridinyl, methyl-benzimidazolyl, methylbenzofuranyl, methylbenzothiazolyl, methylbenzotriazolyl, methylbenzoxazolyl and methylbenzselenazolyl.

As used herein with respect to a substituting radical, and unless otherwise stated, the term "alkoxyaryl" refers to an aryl radical (such as defined above) onto which is (are) bonded one or more $C_{1-7}$ alkoxy radicals as defined above, preferably one or more methoxy radicals, such as, but not limited to, 2-methoxyphenyl, 3-methoxyphenyl, 4-methoxyphenyl, 3,4-dimethoxyphenyl, 2,4,6-trimethoxyphenyl, methoxynaphtyl and the like.

As used herein with respect to a substituting radical, and unless otherwise stated, the terms "alkylamino", "cycloalkylamino", "alkenylamino", "cyclo-alkenylamino", "arylamino", "arylalkylamino", "heterocyclic-substituted alkylamino", "heterocyclic-substituted arylamino", "heterocyclic amino", "hydroxy-alkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic-substituted alkyl, heterocyclic-substituted aryl, heterocyclic (provided in this case the nitrogen atom is attached to a carbon atom of the heterocyclic ring), mono- or polyhydroxy $C_{1-7}$ alkyl, mono- or polymercapto $C_{1-7}$ alkyl, or $C_{2-7}$ alkynyl radical(s) (each of them as defined herein, respectively, and including the presence of optional substituents independently selected from the group consisting of halogen, amino, hydroxyl, sulfhydryl, $C_{1-7}$ alkyl, $C_{1-7}$ alkoxy, trifluoromethyl and nitro) is/are attached to a nitrogen atom through a single bond such as, but not limited to, anilino, 2-bromoanilino, 4-bromoanilino, 2-chloroanilino, 3-chloroanilino, 4-chloroanilino, 3-chloro-4-methoxyanilino, 5-chloro-2-methoxyanilino, 2,3-dimethylanilino, 2,4-dimethylanilino, 2,5-dimethylanilino, 2,6-dimethylanilino, 3,4-dimethylanilino, 2-fluoroanilino, 3-fluoroanilino, 4-fluoroanilino, 3-fluoro-2-methoxyanilino, 3-fluoro-4-methoxyanilino, 2-fluoro-4-methylanilino, 2-fluoro-5-methylanilino, 3-fluoro-2-methylanilino, 3-fluoro-4-methylanilino, 4-fluoro-2-methylanilino, 5-fluoro-2-methylanilino, 2-iodoanilino, 3-iodoanilino, 4-iodoanilino, 2-methoxy-5-methylanilino, 4-methoxy-2-methylanilino, 5-methoxy-2-methylanilino, 2-ethoxyanilino, 3-ethoxyanilino, 4-ethoxyanilino, benzylamino, 2-methoxybenzylamino, 3-methoxybenzylamino, 4-methoxybenzylamino, 2-fluorobenzylamino, 3-fluorobenzylamino, 4-fluoro-benzylamino, 2-chlorobenzylamino, 3-chlorobenzylamino, 4-chlorobenzylamino, 2-aminobenzylamino, diphenylmethylamino, α-naphthylamino, methylamino, dimethylamino, ethylamino, diethylamino, isopropylamino, propenylamino, n-butylamino, ter-butylamino, dibutylamino, 1,2-diaminopropyl, 1,3-diaminopropyl, 1,4-diaminobutyl, 1,5-diaminopentyl, 1,6-diaminohexyl, morpholinomethylamino, 4-morpholinoanilino, hydroxymethylamino, β-hydroxyethylamino and ethynylamino; this definition also includes mixed disubstituted amino radicals wherein the nitrogen atom is attached to two such radicals belonging to two different sub-sets of radicals, e.g. an alkyl radical and an alkenyl radical, or to two different radicals within the same subset of radicals, e.g. methylethylamino; among di-substituted amino radicals, symmetrically-substituted amino radicals are more easily accessible and thus usually preferred from a standpoint of ease of preparation.

As used herein with respect to a substituting radical, and unless otherwise stated, the terms "(thio)carboxylic acid-ester", "(thio)carboxylic acid thioester" and "(thio)carboxylic acid amide" refer to radicals wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic-substituted alkylamino, heterocyclic amino, heterocyclic-substituted arylamino, hydroxyalkylamino, mercapto-alkylamino or alkynylamino (such as above defined, respectively). As used herein with respect to a substituting radical, and unless otherwise stated, the term "amino-acid" refers to a radical derived from a molecule having the chemical formula $H_2N$—$CHR$—$COOH_1$ wherein R is the side group of atoms characterizing the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of formula I, II, III, or IV may possess, in particular all possible stereochemicalˆ and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a thiazolo[5,4-d]pyrimidine, oxazolo[5,4-d]pyrimidine, thieno[2,3-d]pyrimidine or purine derivative of this invention with a suitable inorganic solvent (e.g. hydrates) or organic solvent, such as but not limited to alcohols, ketones, esters, ethers, nitriles and the like.

The following examples illustrate the present invention.

EXAMPLES

General

For all reactions, analytical grade solvents were used. All moisture-sensitive reactions were carried out in oven-dried glass-ware (135° C.). $^1$H and $^{13}$C NMR spectra were recorded with a Bruker Advance 300 ($^1$H NMR: 300 MHz, $^{13}$C NMR: 75 MHz), using tetramethylsilane as internal standard for $^1$H NMR spectra and DMSO-$d_6$ (39.5 ppm) or CDCl$_3$ (77.2 ppm) for $^{13}$C NMR spectra. Abbreviations used are: s=singlet, d=doublet, t=triplet, q=quartet, m=multiplet, br s=broad signal. Coupling constants are expressed in Hertz. Mass spectra are obtained with a Finnigan LCQ advantage Max (ion trap) mass spectrophotometer from Thermo Finnigan, San Jose, Calif., USA. Exact mass measurements are performed on a quadrupole time-of-flight mass spectrometer (Q-tof-2, Micromass, Manchester, UK) equipped with a standard electrospray-ionization (ESI) interface. Samples were infused in i-PrOH/H$_2$O (1:1) at 3 µl/min. Melting points are determined on a Barnstead IA 9200 apparatus and are uncorrected. Precoated aluminum sheets (Fluka Silica gel/TLC-cards, 254 nm) were used for TLC. Column chromatography was performed on ICN silica gel 63-200, 60 Å.

Example 1

Synthesis of diethyl 2-(4-fluorobenzamido)malonate

To a solution of diethyl aminomalonate hydrochloride (5.0 g, 23.6 mmol) in pyridine (7.64 ml, 94.5 mmol) and dimethylformamide (60 ml) was added p-fluorobenzoyl chloride (4.19 ml, 35.4 mmol). The reaction mixture was stirred at room temperature for 15 hours. After removing the solvents, the residue was redissolved in dichloromethane, washed with water, brine and dried over Na$_2$SO$_4$. After removing the solvents, the crude residue was purified by flash chromatography on silica (CH$_2$Cl$_2$/MeOH 30:1) to yield the title compound as a white solid (4.9 g, 70%).

$^1$H NMR (300 MHz, DMSO, 25° C.): δ=9.37 (d, J=7.5 Hz, 1H, NH), 7.96-8.01 (m, 2H, PhH), 7.33 (t, J=8.8 Hz, 2H, PhH), 5.30 (d, J=7.5 Hz, 1H, CH), 4.12-4.28 (m, 4H, CH$_2$), 1.22 (t, J=7.1 Hz, 6H, CH$_3$) ppm.

HRMS: calcd for C$_{14}$H$_{17}$FNO$_5$ 298.1091, found 298.1092.

Example 2

Synthesis of diethyl 2-(2-(4-fluorophenyl)acetamido)malonate

To a solution of 4-fluorophenylacetic acid (4.5 g, 29.3 mmol) and 1-hydroxybenzotriazole (4.35 g, 32.2 mmol) in dichloromethane (140 ml) was added dicyclohexylcarbodiimide (6.65 g, 32.2 mmol). The reaction mixture was stirred at room temperature for 2 hours. The resulting solution was cooled to 0° C., and then a solution of diethyl aminomalonate hydrochloride (6.2 g, 29.3 mmol) in pyridine (4.5 ml, 29.3 mmol) and DMF (10 ml) was added. The temperature was allowed to rise to ambient temperature. After 1 hour, the reaction mixture was concentrated under reduced pressure, and the residue was partitioned between ethyl acetate and a 5% NaHCO$_3$ solution. The organic layer was washed with water, brine and dried over Na$_2$SO$_4$. After removing the solvents, the crude residue was purified by flash chromatography on silica (CH$_2$Cl$_2$/MeOH 50:1) to yield the title compound as a white solid (8.5 g, 93%).

$^1$H NMR (300 MHz, CDCl$_3$, 25° C.): δ=7.26-7.29 (m, 2H, PhH), 7.05 (t, J=8.7 Hz, 2H, PhH), 6.44 (d, J=6.9 Hz, 1H, NH), 5.12 (d, J=6.9 Hz, 1H, CH), 4.16-4.32 (m, 4H, CH$_2$), 3.61 (s, 2H, CH$_2$Ph), 1.27 (t, J=7.1 Hz, 6H, CH$_3$) ppm.

HRMS: calcd for C$_{15}$H$_{19}$FNO$_5$ 312.1247, found 312.1247.

Example 3

Synthesis of dimethyl 2-(3-(4-fluorophenyl)propanamido)malonate

This compound was synthesized from dimethyl aminomalonate according to the procedure for the preparation of example 2 using 4-fluorophenylpropionic acid. The crude residue was purified by flash chromatography on silica (CH$_2$Cl$_2$/MeOH 50:1) to yield the title compound as a white solid (53%).

$^1$H NMR (300 MHz, CDCl$_3$, 25° C.): δ=7.13-7.18 (m, 2H, PhH), 6.96 (t, J=8.7 Hz, 2H, PhH), 6.50 (d, J=6.7 Hz, 1H, NH), 5.19 (d, J=6.7 Hz, 1H, CH), 3.80 (s, 6H, CH$_3$), 2.95 (t, J=7.4 Hz, 2H, CH$_2$), 2.58 (t, J=7.4 Hz, 2H, CH$_2$) ppm.

HRMS: calcd for C$_{14}$H$_{17}$FNO$_5$ 298.10908, found 298.10827.

Example 4

Synthesis of dimethyl 2-(3-(4-fluorophenoxy)propanamido)malonate

This compound was synthesized from dimethyl aminomalonate according to the procedure for the preparation of example 2 using 3-(4-fluorophenoxy)propionic acid. The crude residue was purified by flash chromatography on silica (CH$_2$Cl$_2$/MeOH 50:1) to yield the title compound as a white solid (80%).

$^1$H NMR (300 MHz, CDCl$_3$, 25° C.): δ=7.01 (br s, 1H, NH), 6.96 (t, J=9.1 Hz, 2H, PhH), 6.86-6.91 (m, 2H, PhH), 5.22 (d, J=6.8 Hz, 1H, CH), 4.23 (t, J=5.9 Hz, 2H, OCH$_2$), 3.82 (s, 6H, CH$_3$), 2.76 (t, J=5.9 Hz, 2H, CH$_2$) ppm.

HRMS: calcd for C$_{14}$H$_{17}$FNO$_6$ 314.10399, found 314.10315.

Example 5

Synthesis of N-(2-amino-4,6-dihydroxypyrimidin-5-yl)-4-fluorobenzamide

Guanidine hydrochloride (1.35 g, 14.1 mmol) and diethyl 2-(4-fluorobenzamido)malonate (example 1, 3.0 g, 10.1 mmol) were added to a solution of sodium (0.46 g, 20.2 mmol) in ethanol (50 ml). The reaction mixture was refluxed for 3 hours. The reaction was cooled down to room temperature. The solid product was filtered off and washed with ethanol. The product was dissolved in a minimal volume of water and acidified to pH 4-5 with 5M HCl. The precipitate was collected, washed with water and dried to give the title compound as a white solid (1.41 g, 53%).

$^1$H NMR (300 MHz, DMSO, 25° C.): δ=10.62 (s, 2H, OH), 8.81 (s, 1H, NH), 7.96-8.01 (m, 2H, PhH), 7.28 (t, J=8.8 Hz, 2H, PhH), 6.63 (s, 2H, NH$_2$) ppm.

HRMS: calcd for C$_{11}$H$_{10}$FN$_4$O$_3$ 265.07369, found 265.07148.

Example 6

Synthesis of N-(2-amino-4,6-dihydroxypyrimidin-5-yl)-2-(4-fluorophenyl)acetamide This compound was synthesized from example 2 (yield of 77%) using a similar procedure as for the preparation of example 5.

$^1$H NMR (300 MHz, DMSO, 25° C.): δ=10.61 (s, 2H, OH), 8.57 (s, 1H, NH), 7.32-7.36 (m, 2H, PhH), 7.10 (t, J=8.8 Hz, 2H, PhH), 6.57 (s, 2H, NH$_2$), 3.50 (s, 2H, CH$_2$) ppm.

HRMS: calcd for C$_{12}$H$_{12}$FN$_4$O$_3$ 279.08934, found 279.08846.

Example 7

Synthesis of N-(2-amino-4,6-dihydroxypyrimidin-5-yl)-3-(4-fluorophenyl)propanamide This compound was prepared from example 3 in a yield of 76%, according to the procedure for the synthesis of example 5.

$^1$H NMR (300 MHz, DMSO, 25° C.): δ=10.67 (s, 2H, OH), 8.41 (s, 1H, NH), 7.26-7.31 (m, 2H, PhH), 7.07 (t, J=8.8 Hz, 2H, PhH), 6.61 (s, 2H, NH$_2$), 2.82 (t, J=7.2 Hz, 2H, CH$_2$), 2.50 (t, J=7.2 Hz, 2H, CH$_2$) ppm.

HRMS: calcd for C$_{13}$H$_{14}$FN$_4$O$_3$ 293.10499, found 293.10424

Example 8

Synthesis of N-(2-amino-4,6-dihydroxypyrimidin-5-yl)-3-(4-fluorophenoxy)propanamide This compound was prepared from example 4 in a yield of 34%, according to the procedure for the synthesis of example 5.

$^1$H NMR (300 MHz, DMSO, 25° C.): δ=10.65 (s, 2H, OH), 8.51 (s, 1H, NH), 7.10 (t, J=8.7 Hz, 2H, PhH), 6.90-6.97 (m, 2H, PhH), 6.55 (s, 2H, NH$_2$), 4.15 (t, J=6.2 Hz, 2H, OCH$_2$), 2.66 (t, J=6.2 Hz, 2H, CH$_2$) ppm.

MS 307 [M−H]

Example 9

Synthesis of N-(4,6-dihydroxy-2-methylpyrimidin-5-yl)-4-fluorobenzamide

Acetamidine hydrochloride (1.05 g, 11.1 mmol) and dimethyl 2-(4-fluorobenzamido)malonate (1.0 g, 3.71 mmol) were added to a solution of sodium (0.26 g, 11.1 mmol) in ethanol (37 ml). The reaction mixture was refluxed for 3 hours. Then, after cooling, the solid product was collected and washed with ethanol. The product was dissolved in a minimal volume of water and acidified to pH 4-5 with 5M HCl. The precipitate was collected, washed with water and dried to give the title compound as a white solid (0.77 g, 79%).

$^1$H NMR (300 MHz, DMSO, 25° C.): δ=12.0 (s, 2H, OH), 9.09 (s, 1H, NH), 8.00 (br s, 2H, PhH), 7.30 (t, J=8.0 Hz, 2H, PhH), 2.28 (s, 3H, CH$_3$) ppm.

MS: 261.8 [M−H]

Example 10

Synthesis of N-(4,6-dihydroxy-2-mercaptopyrimidin-5-yl)-4-fluorobenzamide

Thiourea (0.72 g, 9.4 mmol) and diethyl 2-(4-fluorobenzamido)malonate (example 1, 2.0 g, 6.7 mmol) were added to a solution of sodium (0.16 g, 6.7 mmol) in ethanol (50 ml). The reaction mixture was refluxed for 3 hours and then cooled down to room temperature. The precipitate was filtered off and washed with ethanol. The product was dissolved in a minimal volume of water and acidified to pH 4-5 with 5M HCl. The precipitate was collected, washed with water and dried, furnishing the title compound as a white solid (0.78 g, 41%).

$^1$H NMR (300 MHz, DMSO, 25° C.): δ=12.47 (s, 1H, SH), 12.32 (s, 2H, OH), 9.15 (s, 1H, NH), 8.00 (br s, 2H, PhH), 7.31 (t, J=6.8 Hz, 2H, PhH) ppm.

HRMS: calcd for C$_{11}$H$_9$FN$_3$O$_3$S 282.03487, found 282.03402.

Example 11

Synthesis of 5-amino-2-(4-fluorophenyl)thiazolo[5,4-d]pyrimidine-7-thiol

A solution of N-(2-amino-4,6-dihydroxypyrimidin-5-yl)-4-fluorobenzamide (example 5, 1.3 g, 4.92 mmol) and phosphorus pentasulfide (2.19 g, 9.84 mmol) in dry pyridine (25 ml) was refluxed for 6 hours. The solvents were evaporated in vacuo. The crude residue was purified by flash chromatography on silica (CH$_2$Cl$_2$/MeOH 30:1), yielding the title compound as a yellow solid (1.28 g, 93%).

$^1$H NMR (300 MHz, DMSO, 25° C.): δ=12.51 (s, 1H, SH), 7.96-8.01 (m, 2H, PhH), 7.38 (t, J=8.8 Hz, 2H, PhH), 7.10 (s, 2H, NH$_2$) ppm.

HRMS: calcd for C$_{11}$H$_8$FN$_4$S$_2$ 279.0174, found 279.0165.

Example 12

Synthesis of 5-amino-2-(4-fluorobenzyl)thiazolo[5,4-d]pyrimidine-7-thiol

This compound was prepared from example 6 in a yield of 76%, according to the procedure for the synthesis of example 11.

$^1$H NMR (300 MHz, DMSO, 25° C.): δ=12.40 (s, 1H, SH), 7.37-7.42 (m, 2H, PhH), 7.19 (t, J=8.9 Hz, 2H, PhH), 6.98 (s, 2H, NH$_2$), 4.29 (s, 2H, CH$_2$) ppm.

HRMS: calcd for C$_{12}$H$_{10}$FN$_4$S$_2$ 293.03309, found 293.03260.

Example 13

Synthesis of 5-amino-2-(4-fluorophenethyl)-thiazolo[5,4-d]pyrimidine-7-thiol This compound was prepared from example 7 in a yield of 76%, according to the procedure for the synthesis of example 11.

$^1$H NMR (300 MHz, DMSO, 25° C.): δ=12.39 (s, 1H, SH), 7.31-7.36 (m, 2H, PhH), 7.11 (t, J=8.8 Hz, 2H, PhH), 6.96 (s, 2H, NH$_2$), 3.23 (t, J=7.4, 2H, CH$_2$), 3.03 (t, J=7.4, 2H, CH$_2$) ppm.

HRMS: calcd for C$_{13}$H$_{12}$FN$_4$S$_2$ 307.04874, found 307.04792.

Example 14

Synthesis of 2-(4-fluorophenyl)-5-methyl-thiazolo[5,4-d]pyrimidine-7-thiol

This compound was prepared from example 9 in a yield of 73%, according to the procedure for the synthesis of example 11.

¹H NMR (300 MHz, DMSO, 25° C.): δ=14.09 (s, 1H, SH), 8.07-8.15 (m, 2H, PhH), 7.42 (t, J=8.8 Hz, 2H, PhH), 2.50 (s, 3H, CH$_3$) ppm.
MS 278.1 [M+H]$^+$

Example 15

Synthesis of 2-(4-fluorophenyl)-thiazolo[5,4-d]pyrimidine-5,7-dithiol

This compound was prepared from example 10 in a yield of 57%, according to the procedure for the synthesis of example 11.

¹H NMR (300 MHz, DMSO, 25° C.): δ=13.62 (s, 1H, SH), 8.00-8.05 (m, 2H, PhH), 7.39 (t, J=8.7 Hz, 2H, PhH) ppm.
HRMS: calcd for C$_{11}$H$_7$FN$_3$S$_3$ 295.97861, found 295.97777.

Example 16

Synthesis of 2-(4-fluorophenyl)-7-(methylthio)thiazolo[5,4-d]pyrimidin-5-amine

To a solution of 5-amino-2-(4-fluorophenyl)thiazolo[5,4-d]pyrimidine-7-thiol (1.2 g, 4.31 mmol) and triethylamine (1.50 ml, 10.8 mmol) in DMSO (25 ml) was added iodomethane (0.54 ml, 8.62 mmol). The reaction mixture was stirred for 12 h under N$_2$ at 25° C. The mixture was poured into water and extracted with EtOAc. The organic extracts were dried over Na$_2$SO$_4$ and the solvents were removed under reduced pressure. The crude residue was purified by flash chromatography on silica (CH$_2$Cl$_2$/MeOH 80:1), yielding the title compound as a light yellow solid (0.76 g, 60%).

¹H NMR (300 MHz, DMSO, 25° C.): δ=7.98-8.03 (m, 2H, PhH), 7.39 (t, J=8.8 Hz, 2H, PhH), 7.09 (s, 2H, NH$_2$), 2.59 (s, 3H, CH$_3$) ppm.
HRMS: calcd for C$_{12}$H$_{10}$FN$_4$S$_2$ 293.0331, found 293.0328.

Example 17

Synthesis of 2-(4-fluorobenzyl)-7-(methylthio)thiazolo[5,4-d]pyrimidin-5-amine

This compound was prepared from example 12 in a yield of 87%, according to the procedure for the synthesis of example 16.

¹H NMR (300 MHz, CDCl$_3$, 25° C.): δ=7.27-7.32 (m, 2H, PhH), 7.03 (t, J=8.6 Hz, 2H, PhH), 5.02 (s, 2H, NH$_2$), 4.31 (s, 2H, CH$_2$), 2.61 (s, 3H, CH$_3$) ppm.
HRMS: calcd for C$_{13}$H$_{12}$FN$_4$S$_2$ 307.0487, found 307.0482.

Example 18

Synthesis of 2-(4-fluorophenethyl)-7-methylthio-thiazolo[5,4-d]pyrimidin-5-amine This compound was prepared from example 13 in a yield of 61%, according to the procedure for the synthesis of example 16.

¹H NMR (300 MHz, CDCl$_3$, 25° C.): δ=7.16-7.21 (m, 2H, PhH), 6.97 (t, J=8.7 Hz, 2H, PhH), 5.30 (s, 2H, NH$_2$), 3.30 (t, J=8.3, 2H, CH$_2$), 3.11 (t, J=8.3, 2H, CH$_2$) ppm.
HRMS: calcd for C$_{14}$H$_{14}$FN$_4$S$_2$ 321.06439, found 321.06362.

Example 19

Synthesis of 2-(2-(4-fluorophenoxy)ethyl)-7-(methylthio)thiazolo[5,4-d]pyrimidin-5-amine A solution of N-(2-amino-4,6-dihydroxypyrimidin-5-yl)-3-(4-fluorophenoxy)propanamide (2.5 g, 8.11 mmol) and phosphorus pentasulfide (3.60 g, 16.2 mmol) in dry pyridine (40 ml) was refluxed for 6 hours. After cooling down to room temperature, the precipitate was filtered off, washed with ethylacetate and dried. The crude 5-amino-2-(2-(4-fluorophenoxy)ethyl)-thiazolo[5,4-d]pyrimidine-7-thiol (2.0 g, 6.20 mmol) was redissolved in DMSO (30 ml). Triethylamine (0.85 ml, 6.12 mmol) and iodomethane (0.31 ml, 4.90 mmol) were added. The reaction mixture was stirred for 12 hours at room temperature under a nitrogen atmosphere. The mixture was poured into water and extracted with EtOAc. The combined organic layers were dried over Na$_2$SO$_4$ and the solvents were removed under reduced pressure. The crude residue was purified by chromatography on silica gel (CH$_2$Cl$_2$/MeOH 100:1), yielding the title compound as a light yellow solid (0.45 g, 15% over 2 steps).

¹H NMR (300 MHz, CDCl$_3$, 25° C.): δ=6.96 (t, J=9.1 Hz, 2H, PhH), 6.34-6.88 (m, 2H, PhH), 5.19 (s, 2H, NH$_2$), 4.31 (t, J=6.2, 2H, CH$_2$), 3.48 (t, J=6.2, 2H, CH$_2$) ppm.
HRMS: calcd for C$_{14}$H$_{14}$FN$_4$OS$_2$ 337.0593, found 337.05827.

Example 20

Synthesis of 2-(4-fluorophenyl)-5-methyl-7-methylthio-thiazolo[5,4-d]pyrimidine

This compound was prepared from example 14 in a yield of 95%, according to the procedure for the synthesis of example 16.

¹H NMR (300 MHz, CDCl$_3$, 25° C.): δ=8.07-8.11 (m, 2H, PhH), 7.19 (t, J=8.7 Hz, 2H, PhH), 2.78 (s, 3H, CH$_3$), 2.71 (s, 3H, CH$_3$) ppm.

Example 21

Synthesis of 2-(4-fluorophenyl)-7-methylsulfonyl-thiazolo[5,4-d]pyrimidin-5-amine To a solution of 2-(4-fluorophenyl)-7-methylthio)-thiazolo[5,4-d]pyrimidin-5-amine (0.30 g, 1.03 mmol) in dichloromethane (5 ml) was added mCPBA (70%, 0.44 g, 2.57 mmol) at 0° C. The reaction mixture was stirred for 3 hours, whereby the reaction temperature was gradually increased from 0° C. to room temperature. The reaction mixture was diluted with CHCl$_3$ and was washed with a saturated NaHCO$_3$ solution, brine and dried over Na$_2$SO$_4$. After removing the solvents under reduced pressure, the residue was purified by flash chromatography on silica (CH$_2$Cl$_2$/MeOH 50:1), affording the title compound as a white solid (0.31 g, 93%).

¹H NMR (300 MHz, DMSO, 25° C.): δ=8.11-8.16 (m, 2H, PhH), 7.12 (s, 2H, NH$_2$), 7.44 (t, J=8.8 Hz, 2H, PhH), 3.58 (s, 3H, CH$_3$) ppm.
HRMS: calcd for C$_{12}$H$_{10}$FN$_4$O$_2$S$_2$ 325.02292, found 325.02221.

Example 22

Synthesis of 2-(4-fluorobenzyl)-7-methylsulfonyl-thiazolo[5,4-d]pyrimidin-5-amine This compound was prepared from example 17 in a yield of 71%, according to the procedure for the synthesis of example 21.

$^1$H NMR (300 MHz, DMSO, 25° C.): δ=7.58 (s, 2H, NH$_2$), 7.43-7.48 (m, 2H, PhH), 7.22 (t, J=6.8 Hz, 2H, PhH), 4.47 (s, 2H, CH$_2$), 3.51 (s, 3H, CH$_3$) ppm.

HRMS: calcd for C$_{13}$H$_{12}$FN$_4$O$_2$S$_2$ 339.03857, found 339.03804.

Example 23

Synthesis of 2-(4-fluorophenethyl)-7-methylsulfonyl-thiazolo[5,4-d]pyrimidin-5-amine This compound was prepared from example 18 in a yield of 35%, according to the procedure for the synthesis of example 21.

$^1$H NMR (300 MHz, CDCl$_3$, 25° C.): δ=7.17-7.22 (m, 2H, PhH), 6.98 (t, J=8.6 Hz, 2H, PhH), 5.43 (s, 2H, NH$_2$), 3.43 (s, 3H, CH$_3$), 3.41 (t, J=7.9, 2H, CH$_2$), 3.17 (t, J=7.9, 2H, CH$_2$) ppm.

HRMS: calcd for C$_{14}$H$_{14}$FN$_4$O$_2$S$_2$ 353.05422, found 353.05363.

Example 24

Synthesis of 2-(2-(4-fluorophenoxy)ethyl)-7-methylsulfonyl-thiazolo[5,4-d]pyrimidin-5-amine This compound was prepared from example 19 in a yield of 28%, according to the procedure for the synthesis of example 21.

$^1$H NMR (300 MHz, DMSO, 25° C.): δ=7.57 (s, 2H, NH$_2$), 7.13 (t, J=8.9 Hz, 2H, PhH), 6.98-7.03 (m, 2H, PhH), 4.39 (t, J=5.9, 2H, CH$_2$), 3.55 (t, J=5.9, 2H, CH$_2$) 3.49 (s, 3H, CH$_3$) ppm.

HRMS: calcd for C$_{14}$H$_{14}$FN$_4$O$_3$S$_2$ 369.04913, found 369.04842.

Example 25

Synthesis of 2-(4-fluorophenyl)-7-(piperazin-1-yl)-thiazolo[5,4-d]pyrimidin-5-amine To a solution of 2-(4-fluorophenyl)-7-methylsulfonyl-thiazolo[5,4-d]pyrimidin-5-amine (0.40 g, 1.23 mmol) and triethylamine (0.26 ml, 1.85 mmol) in dioxane (6 ml) was added piperazine (0.16 g, 1.85 mmol). The reaction mixture was heated at 60° C. for 5 hours. After cooling, the volatiles were removed under reduced pressure. The crude residue was purified by flash chromatography on silica (CH$_2$Cl$_2$/MeOH 15:1), furnishing the title compound as a light yellow solid (0.27 g, 67%).

$^1$H NMR (300 MHz, DMSO, 25° C.): δ=9.09 (t, J=9.2 Hz, 1H, NH), 7.98-8.03 (m, 2H, PhH), 7.37 (t, J=8.8 Hz, 2H, PhH), 6.58 (s, 2H, NH$_2$), 4.45 (br s, 4H, N(CH$_2$)$_2$), 3.26 (br s, 4H, NH(C<u>H</u>$_2$)$_2$) ppm.

HRMS: calcd for C$_{15}$H$_{16}$FN$_6$S 331.11412, found 331.11290.

Example 26

Synthesis of 2-(4-fluorobenzyl)-7-(piperazin-1-yl)-thiazolo[5,4-d]pyrimidin-5-amine This compound was prepared from example 22 in a yield of 50%, according to the procedure for the synthesis of example 25.

$^1$H NMR (300 MHz, DMSO, 25° C.): δ=7.36-7.41 (m, 2H, PhH), 7.17 (t, J=8.9 Hz, 2H, PhH), 6.26 (s, 2H, NH$_2$), 4.27 (s, 2H, CH$_2$), 4.14 (br s, 4H, N(CH$_2$)$_2$), 2.85 (t, J=4.7 Hz, 4H, NH(C<u>H</u>$_2$)$_2$) ppm.

HRMS: calcd for C$_{16}$H$_{18}$FN$_6$S 345.12977, found 345.12883.

Example 27

Synthesis of 2-(4-fluorophenethyl)-7-(piperazin-1-yl)thiazolo[5,4-d]pyrimidin-5-amine This compound was prepared from example 23 in a yield of 76%, according to the procedure for the synthesis of example 25.

$^1$H NMR (300 MHz, DMSO, 25° C.): δ=7.26-7.31 (m, 2H, PhH), 7.08 (t, J=8.9 Hz, 2H, PhH), 6.19 (s, 2H, NH$_2$) 3.95 (br s, 4H, N(CH$_2$)$_2$), 3.23 (t, J=7.4, 2H, CH$_2$), 3.02 (t, J=7.4, 2H, CH$_2$), 2.74 (br s, 4H, HN(C<u>H</u>$_2$)$_2$) ppm.

HRMS: calcd for C$_{17}$H$_{20}$FN$_6$S 359.14542, found 359.14456.

Example 28

Synthesis of 7-(benzylthio)-2-(4-fluorophenyl)thiazolo[5,4-d]pyrimidin-5-amine

To a solution of 5-amino-2-(4-fluorophenyl)thiazolo[5,4-d]pyrimidine-7-thiol (50 mg, 0.18 mmol) and triethylamine (63 μl, 0.45 mmol) in DMSO (1 ml) was added benzyl bromide (43 μl, 0.36 mmol). The reaction mixture was stirred under N$_2$ at 25° C. for 3 hours. The mixture was poured onto water and extracted with EtOAc. The organic extracts were dried over Na$_2$SO$_4$ and the solvents were removed under reduced pressure. The residue was purified by flash chromatography on silica (CH$_2$Cl$_2$/MeOH 100:1) to yield the title compound as a light yellow solid (40 mg, 60%).

$^1$H NMR (300 MHz, CDCl$_3$, 25° C.): δ=7.95-7.98 (m, 2H, PhH), 7.44 (d, J=6.6 Hz, 2H, PhH), 7.28-7.35 (m, 3H, PhH), 7.15 (t, J=8.6 Hz, 2H, PhH), 5.09 (s, 2H, NH$_2$), 4.53 (s, 2H, CH$_2$) ppm.

HRMS: calcd for C$_{18}$H$_{14}$FN$_4$S$_2$ 369.06439, found 369.06332.

Example 29

Synthesis of 2-(4-fluorophenyl)-7-(2-methoxyethoxy)-thiazolo[5,4-d]pyrimidin-5-amine To a solution of Na (2.0 mg, 0.07 mmol) in 2-methoxyethanol (1 ml) was added 2-(4-fluorophenyl)-7-methylthio-thiazolo[5,4-d]pyrimidin-5-amine (40 mg, 0.14 mmol). The reaction mixture was heated at 80° C. for 20 hours. After cooling, the mixture was neutralized with 1N HCl and the solvent was removed under reduced pressure. The crude residue was extracted by ethyl acetate, brine and dried over Na$_2$SO$_4$. After removing the solvents under reduced pressure, the residue was purified by flash chromatography on silica (CH$_2$Cl$_2$/MeOH 100:1) to yield the title compound as a white solid (35 mg, 80%).

$^1$H NMR (300 MHz, CDCl$_3$, 25° C.): δ=7.98-8.02 (m, 2H, PhH), 7.14 (t, J=8.5 Hz, 2H, PhH), 5.02 (s, 2H, NH$_2$), 4.70 (t, J=5.0 Hz, 2H, OCH$_2$), 3.85 (t, J=5.0 Hz, 2H, CH$_2$OCH$_3$), 3.46 (s, 3H, CH$_3$) ppm.

HRMS: calcd for C$_{14}$H$_{14}$FN$_4$O$_2$S 321.0821, found 321.0812.

Example 30

Synthesis of 7-ethoxy-2-(4-fluorophenyl)thiazolo[5,4-d]pyrimidin-5-amine

This compound was synthesized according to the procedure for the synthesis of example 29 using ethanol. The crude residue was purified by chromatography on silica gel (ethyl acetate/heptane 1:10) to yield the title compound as a white solid (67%).

$^1$H NMR (300 MHz, CDCl$_3$, 25° C.): δ=7.97-8.02 (m, 2H, PhH), 7.14 (t, J=8.6 Hz, 2H, PhH), 5.04 (s, 2H, NH$_2$), 4.61 (q, J=7.1 Hz, 2H, CH$_2$), 1.51 (t, J=7.1 Hz, 3H, CH$_3$) ppm.

HRMS: calcd for C$_{13}$H$_{12}$FN$_4$OS 291.0716, found 291.0717.

Example 31

Synthesis of 7-ethoxy-2-(4-fluorobenzyl)thiazolo[5,4-d]pyrimidin-5-amine

This compound was synthesized from example 17 in a yield of 36%, according to the procedure for the synthesis of example 29.

$^1$H NMR (300 MHz, CDCl$_3$, 25° C.): δ=7.26-7.31 (m, 2H, PhH), 7.02 (t, J=9.0 Hz, 2H, PhH), 4.95 (s, 2H, NH$_2$), 4.58 (q, J=7.1 Hz, 2H, CH$_2$), 4.32 (s, 2H, CH$_2$), 1.50 (t, J=7.1 Hz, 3H, CH$_3$) ppm.

HRMS: calcd for C$_{14}$H$_{14}$FN$_4$OS 305.08723, found 305.08635.

Example 32

Synthesis of 2-(4-fluorophenyl)-N-7-(3-methoxypropyl)thiazolo[5,4-d]pyrimidine-5,7-diamine To a solution of 2-(4-fluorophenyl)-7-methylsulfonyl-thiazolo[5,4-d]pyrimidin-5-amine (50 mg, 0.15 mmol) and triethylamine (32 μl, 0.23 mmol) in dioxane (1 ml) was added 3-methoxypropylamine (21 μl, 0.20 mmol). The reaction mixture was heated at 60° C. for 5 hours. After cooling, the volatiles were removed under reduced pressure. The crude residue was purified by flash chromatography on silica (CH$_2$Cl$_2$/MeOH 70:1), yielding the title compound as a white solid (32 mg, 62%).

$^1$H NMR (300 MHz, CDCl$_3$, 25° C.): δ=7.89-7.94 (m, 2H, PhH), 7.13 (t, J=8.7 Hz, 2H, PhH), 6.37 (br s, 1H, NH), 4.84 (s, 2H, NH$_2$), 3.68 (q, J=6.3, 2H, NHCH$_2$), 3.56 (t, J=5.9 Hz, 2H, OCH$_2$), 3.41 (s, 3H, OCH$_3$), 1.97 (quint, J=6.3, 2H, CH$_2$) ppm.

HRMS: calcd for C$_{15}$H$_{17}$FN$_5$OS 334.1138, found 334.1121.

Example 33

Synthesis of 2-(4-fluorophenyl)-7-morpholino-thiazolo[5,4-d]pyrimidin-5-amine

This compound was synthesized from example 21 using morpholine, according to the procedure for the synthesis of example 32. The crude residue was purified by flash chromatography on silica (CH$_2$Cl$_2$/MeOH 50:1) to yield the title compound as a light yellow solid (77%).

$^1$H NMR (300 MHz, CDCl$_3$, 25° C.): δ=7.86-7.90 (m, 2H, PhH), 7.14 (t, J=8.6 Hz, 2H, PhH), 4.77 (s, 2H, NH$_2$), 4.35 (br s, 4H, O(CH$_2$)$_2$), 3.85 (t, J=3.9 Hz, 4H, N(CH$_2$)$_2$) ppm.

HRMS: calcd for C$_{15}$H$_{15}$FN$_5$OS 332.0981, found 332.0975.

Example 34

Synthesis of 2-(4-fluorobenzyl)-7-morpholino-thiazolo[5,4-d]pyrimidin-5-amine

This compound was synthesized from example 22 in a yield of 67%, according to the procedure for the synthesis of example 32.

$^1$H NMR (300 MHz, CDCl$_3$, 25° C.): δ=7.24-7.28 (m, 2H, PhH), 7.02 (t, J=8.7 Hz, 2H, PhH), 4.69 (s, 2H, NH$_2$), 4.27 (br s, 4H, O(CH$_2$)$_2$), 4.21 (s, 2H, CH$_2$), 3.80 (t, J=5.0 Hz, 4H, N(CH$_2$)$_2$) ppm.

HRMS: calcd for C$_{16}$H$_{17}$FN$_5$OS 346.1138, found 346.1125.

Example 35

Synthesis of 2-(4-fluorophenyl)-7-(4-m-tolylpiperazin-1-yl)-thiazolo[5,4-d]pyrimidin-5-amine This compound was synthesized according to the procedure for the preparation of example 32, using 1-m-tolylpiperazine. The crude residue was purified by flash chromatography on silica (CH$_2$Cl$_2$/MeOH 40:1) to yield the title compound as a white solid (60%).

$^1$H NMR (300 MHz, CDCl$_3$, 25° C.): δ=7.89-7.93 (m, 2H, PhH), 7.12-7.22 (m, 4H, PhH, tolyl H), 6.72-6.82 (m, 3H, tolyl H), 4.77 (s, 2H, NH$_2$), 4.51 (br s, 4H, N(CH$_2$)$_2$), 3.33 (t, J=5.0 Hz, 4H, N(CH$_2$)$_2$), 2.34 (s, 3H, CH$_3$) ppm.

HRMS: calcd for C$_{22}$H$_{22}$FN$_6$S 421.16107, found 421.15992.

Example 36

Synthesis of 2-(4-fluorophenyl)-7-(4-(thiazol-2-yl)piperazin-1-yl)thiazolo[5,4-d]pyrimidin-5-amine This compound was synthesized according to the procedure for example 32, using 1-(thiazol-2-yl)piperazine. The crude residue was purified by flash chromatography on silica (CH$_2$Cl$_2$/MeOH 50:1), yielding the pure title compound as a white solid (43%).

$^1$H NMR (300 MHz, CDCl$_3$, 25° C.): δ=7.87-7.92 (m, 2H, PhH), 7.24 (d, J=3.6 Hz, 1H, thiazolyl H), 7.15 (t, J=8.6 Hz, 2H, PhH), 6.63 (d, J=3.6 Hz, 1H, thiazolyl H), 4.81 (s, 2H, NH$_2$), 4.50 (br s, 4H, N(CH$_2$)$_2$), 3.66 (t, J=5.3 Hz, 4H, N(CH$_2$)$_2$) ppm.

HRMS: calcd for $C_{18}H_{17}FN_7S_2$ 414.09709, found 414.09592.

Example 37

Synthesis of 2-(4-fluorophenyl)-7-(4-pentylpiperazin-1-yl)thiazolo[5,4-d]pyrimidin-5-amine This compound was synthesized using a similar procedure as for the preparation of example 32, using 1-pentylpiperazine. The crude residue was purified by flash chromatography on silica ($CH_2Cl_2$/MeOH 50:1) to yield the title compound as a white solid (40%).

$^1$H NMR (300 MHz, $CDCl_3$, 25° C.): δ=7.86-7.91 (m, 2H, PhH), 7.14 (t, J=8.6 Hz, 2H, PhH), 4.77 (s, 2H, $NH_2$), 4.38 (br s, 4H, $N(CH_2)_2$), 2.61 (br s, 4H, pentylN(C$\underline{H}_2$)$_2$), 2.41 (t, J=7.8 Hz, 2H, NC$\underline{H}_2$CH$_2$CH$_2$CH$_2$CH$_3$), 2.00 (br s, 2H, NCH$_2$C$\underline{H}_2$CH$_2$CH$_2$CH$_3$), 1.56 (quint, J=6.7 Hz, 2H, NCH$_2$CH$_2$C$\underline{H}_2$CH$_2$CH$_3$), 1.28-1.34 (m, 2H, NCH$_2$CH$_2$CH$_2$C$\underline{H}_2$CH$_3$), 0.91 (t, J=6.5 Hz, 3H, NCH$_2$CH$_2$CH$_2$CH$_2$C$\underline{H}_3$) ppm.

HRMS: calcd for $C_{20}H_{26}FN_6S$ 401.19237, found 401.19102.

Example 38

Synthesis of 2-(4-(5-amino-2-(4-fluorophenyl)thiazolo[5,4-d]pyrimidin-7-yl)piperazin-1-yl)-1-morpholinoethanone This compound was synthesized according to the procedure for the synthesis of example 32, using 1-morpholino-2-(piperazin-1-yl)ethanone. The crude residue was purified by flash chromatography on silica ($CH_2Cl_2$/MeOH 60:1), affording the title compound as a light yellow solid (48%).

$^1$H NMR (300 MHz, $CDCl_3$, 25° C.): δ=7.85-7.89 (m, 2H, PhH), 7.13 (t, J=8.4 Hz, 2H, PhH), 4.75 (s, 2H, $NH_2$), 4.37 (br s, 4H, $N(CH_2)_2$), 3.71 (br s, 4H, morpholinyl H), 3.66 (br s, 4H, morpholinyl H), 3.25 (S, 2H, $CH_2$), 2.67 (t, J=4.9 Hz, 4H, $CH_2N(C\underline{H}_2)_2$) ppm.

HRMS: calcd for $C_{21}H_{25}FN_7O_2S$ 458.17745, found 458.17603.

Example 39

Synthesis of 7-(4-benzylpiperazin-1-yl)-2-(4-fluorophenyl)thiazolo[5,4-d]pyrimidin-5-amine This compound was synthesized according to the procedure for the preparation of example 32, using 1-benzylpiperazine. The crude residue was purified by flash chromatography on silica ($CH_2Cl_2$/MeOH 60:1) to yield the title compound as a white solid (81%).

$^1$H NMR (300 MHz, $CDCl_3$, 25° C.): δ=7.84-7.88 (m, 2H, PhH), 7.26-7.37 (m, 5H, PhH), 7.12 (t, J=8.4 Hz, 2H, PhH), 4.73 (s, 2H, $NH_2$), 4.36 (br s, 4H, $N(CH_2)_2$), 3.57 (s, 2H, $CH_2$), 2.59 (t, J=4.7 Hz, 4H, $CH_2N(C\underline{H}_2)_2$) ppm.

HRMS: calcd for $C_{22}H_{22}FN_6S$ 421.16107, found 421.15986.

Example 40

Synthesis of benzyl-4-(5-amino-2-(4-fluorophenyl)thiazolo[5,4-d]pyrimidin-7-yl)piperazine-1-carboxylate To a solution of 2-(4-fluorophenyl)-7-(piperazin-1-yl)thiazolo[5,4-d]pyrimidin-5-amine (50 mg, 0.15 mmol) and pyridine (18 μl, 0.23 mmol) in DMF (1 ml) was added benzyl chloroformate (24 μl, 0.17 mmol). The reaction mixture was stirred for 3 hours at room temperature. The reaction mixture was quenched with water, extracted with EtOAc, brine and dried over $Na_2SO_4$. After removing the solvents, the crude residue was purified by flash chromatography on silica ($CH_2Cl_2$/MeOH 100:1) to yield the title compound as a white solid (54 mg, 77%).

$^1$H NMR (300 MHz, $CDCl_3$, 25° C.): δ=7.85-7.89 (m, 2H, PhH), 7.40-7.35 (m, 5H, PhH), 7.13 (t, J=8.6 Hz, 2H, PhH), 5.19 (s, 2H, $CH_2$), 4.82 (s, 2H, $NH_2$), 4.34 (br s, 4H, $N(CH_2)_2$), 3.66 (br s, 4H, $CON(CH_2)_2$) ppm.

HRMS: calcd for $C_{23}H_{22}FN_6O_2S$ 465.15090, found 465.15005.

Example 41

Synthesis of 2-(4-fluorophenyl)-7-(4-(phenylsulfonyl)piperazin-1-yl)thiazolo[5,4-d]pyrimidin-5-amine To a solution of 2-(4-fluorophenyl)-7-(piperazin-1-yl)thiazolo[5,4-d]pyrimidin-5-amine (50 mg, 0.15 mmol) and pyridine (18 μl, 0.23 mmol) in DMF (1 ml) was added benzenesulfonyl chloride (21 μl, 0.17 mmol). The reaction mixture was stirred for 3 hours at room temperature. The reaction was quenched with water and extracted with EtOAc. The combined organic layers were dried over $Na_2SO_4$. After removing the solvents, the crude residue was purified by flash chromatography on silica ($CH_2Cl_2$/MeOH 80:1) to yield the title compound as a white solid (32 mg, 45%).

$^1$H NMR (300 MHz, DMSO, 25° C.): δ=7.94-7.98 (m, 2H, PhH), 7.64-7.79 (m, 5H, PhH), 7.35 (t, J=8.6 Hz, 2H, PhH), 6.48 (s, 2H, $NH_2$), 4.35 (br s, 4H, $N(CH_2)_2$), 3.06 (br s, 4H, S—$N(CH_2)_2$) ppm.

HRMS: calcd for $C_{21}H_{20}FN_6O_2S_2$ 471.10732, found 471.10694.

Example 42

Synthesis of 4-(5-amino-2-(4-fluorophenyl)-thiazolo[5,4-d]pyrimidin-7-yl)-N-p-tolylpiperazine-1-carboxamide To a solution of 2-(4-fluorophenyl)-7-(piperazin-1-yl)thiazolo[5,4-d]pyrimidin-5-amine (50 mg, 0.15 mmol) in DMF (1 ml) was added p-tolyl isocyanate (21 μl, 0.17 mmol) in DMF (0.3 ml). The reaction mixture was stirred for 2 hours at room temperature. The reaction was quenched with water and extracted with EtOAc. The combined organic layers were dried over $Na_2SO_4$. After removing the solvents in vacuo, the crude residue was purified by flash chromatography on silica ($CH_2Cl_2$/MeOH 100:1) to yield the title compound as a white solid (31 mg, 44%).

$^1$H NMR (300 MHz, $CDCl_3$, 25° C.): δ=7.86-7.91 (m, 2H, PhH), 7.26 (d, J=1.6 Hz, 2H, tolyl H), 7.10-7.23 (m, 4H, PhH, tolyl H), 6.34 (s, 1H, NH), 4.81 (s, 2H, $NH_2$), 4.42 (br s, 4H, $N(CH_2)_2$), 3.28 (t, J=5.3 Hz, 4H, $CON(C\underline{H}_2)_2$), 2.31 (s, 3H, $CH_3$) ppm.

HRMS: calcd for $C_{23}H_{23}FN_7OS$ 464.1669, found 464.1671.

Example 43

Synthesis of 4-(5-amino-2-(4-fluorophenyl)thiazolo[5,4-d]pyrimidin-7-yl)-N-m-tolylpiperazine-1-carboxamide This compound was prepared according to the procedure for the synthesis of example 42, using m-tolylisocyanate in a yield of 57%.

¹H NMR (300 MHz, CDCl₃, 25° C.): δ=7.86-7.91 (m, 2H, PhH), 7.25 (s, 1H, tolyl H), 7.12-7.22 (m, 4H, PhH, tolyl H), 6.88 (d, J=7.2 Hz, 1H, tolyl H), 6.41 (s, 1H, NH), 4.84 (s, 2H, NH₂), 4.42 (br s, 4H, N(CH₂)₂), 3.68 (t, J=5.3 Hz, 4H, CON(C$\underline{H}_2$)₂), 2.33 (s, 3H, CH₃) ppm.

HRMS: calcd for C₂₃H₂₃FN₇OS 464.1669, found 464.1673.

Example 44

Synthesis of 4-(5-amino-2-(4-fluorobenzyl)thiazolo[5,4-d]pyrimidin-7-yl)-N-m-tolylpiperazine-1-carboxamide This compound was prepared from example 26 in a yield of 72%, according to the procedure for the synthesis of example 42.

¹H NMR (300 MHz, CDCl₃, 25° C.): δ=7.06-7.29 (m, 5H, PhH, tolyl H), 7.04 (d, J=4.7 Hz, 2H, PhH), 6.89 (d, J=6.2 Hz, 1H, tolyl H), 6.30 (s, 1H, NH), 4.71 (s, 2H, NH₂), 4.34 (br s, 4H, N(CH₂)₂), 4.23 (s, 2H, CH₂), 3.61-3.65 (m, 4H, CON(C$\underline{H}_2$)₂), 2.34 (s, 3H, CH₃) ppm.

HRMS: calcd for C₂₄H₂₅FN₇OS 478.1825, found 478.1823.

Example 45

Synthesis of 1-(4-(5-amino-2-(4-fluorophenyl)thiazolo[5,4-d]pyrimidin-7-yl)piperazin-1-yl)-2-(4-chlorophenoxy)ethanone To a solution of 2-(4-fluorophenyl)-7-(piperazin-1-yl)thiazolo[5,4-d]pyrimidin-5-amine (40 mg, 0.12 mmol) and pyridine (15 μl, 0.18 mmol) in DMF (1 ml) was added 4-chlorophenoxyacetyl chloride (27 mg, 0.13 mmol). The reaction mixture was stirred for 2 hours at room temperature. The reaction mixture was quenched with water, extracted with EtOAc, brine and was dried over Na₂SO₄. After removing the solvents, the crude residue was purified by flash chromatography on silica (CH₂Cl₂/MeOH 100:1) to yield the title compound as a white solid (32 mg, 53%).

¹H NMR (300 MHz, CDCl₃, 25° C.): δ=7.86-7.91 (m, 2H, PhH), 7.26 (d, J=9.0 Hz, 2H, tolyl H), 7.15 (t, J=8.4 Hz, 2H, PhH), 6.93 (d, J=9.0 Hz, 2H, tolyl H), 4.81 (s, 2H, NH₂), 4.75 (s, 2H, CH₂), 4.32 (br s, 4H, N(CH₂)₂), 3.75 (quint, J=5.0 Hz, 4H, CON(C$\underline{H}_2$)₂) ppm.

HRMS: calcd for C₂₃H₂₁ClFN₆O₂S 499.1119, found 499.1130.

Example 46

Synthesis of 1-(4-(5-amino-2-(4-fluorobenzyl)thiazolo[5,4-d]pyrimidin-7-yl)piperazin-1-yl)-2-(4-chlorophenoxy)ethanone This compound was prepared from example 26 in a yield of 31%, according to the procedure for the synthesis of example 45.

¹H NMR (300 MHz, CDCl₃, 25° C.): δ=7.23-7.28 (m, 4H, PhH), 7.02 (t, J=8.7 Hz, 2H, PhH), 6.92 (d, J=9.1 Hz, 2H, PhH), 4.74 (s, 2H, OCH₂), 4.71 (s, 2H, NH₂), 4.23-4.28 (br s, 4H, N(CH₂)₂), 4.22 (s, 2H, CH₂), 3.67-3.75 (m, 4H, CON(C$\underline{H}_2$)₂) ppm.

HRMS: calcd for C₂₄H₂₃ClFN₆O₂S 513.12758, found 513.12732.

Example 47

Synthesis of 2-(4-chlorophenoxy)-1-(4-(2-(4-fluorophenyl)-5-methylthiazolo[5,4-d]pyrimidin-7-yl)piperazin-1-yl)ethanone To a solution of 7-chloro-2-(4-fluorophenyl)-5-methylthiazolo[5,4-d]pyrimidine (30 mg, 0.11 mmol) and triethylamine (22 μl, 0.16 mmol) in dioxane (1 ml) was added 2-(4-chlorophenoxy)-1-(piperazin-1-yl)ethanone (38 mg, 0.16 mmol). The reaction mixture was heated at 70° C. for 3 hours. After cooling, the volatiles were removed under reduced pressure. The crude residue was purified by chromatography on silica gel (CH₂Cl₂/MeOH 70:1) to yield the title compound as a white solid (40 mg, 75%).

¹H NMR (300 MHz, CDCl₃, 25° C.): δ=7.93-7.97 (m, 2H, PhH), 7.26 (d, J=9.1 Hz, 2H, tolyl H), 7.17 (t, J=8.7 Hz, 2H, PhH), 6.93 (d, J=9.1 Hz, 2H, tolyl H), 4.76 (s, 2H, CH₂), 4.42 (br s, 4H, N(CH₂)₂), 3.79 (br s, 4H, CON(C$\underline{H}_2$)₂) ppm.

HRMS: calcd for C₂₄H₂₂ClFN₅O₂S 498.11668, found 498.11541.

Example 48

Synthesis of 1-(4-(5-amino-2-(2-(4-fluorophenoxy)ethyl)thiazolo[5,4-d]pyrimidin-7-yl)piperazin-1-yl)-2-(4-chlorophenoxy)ethanone This compound was prepared from example 24 in a yield of 72%, according to the procedure for the synthesis of example 47.

¹H NMR (300 MHz, CDCl₃, 25° C.): δ=7.25 (d, J=5.3 Hz, 2H, PhH), 6.83-7.00 (m, 6H, PhH), 4.72 (s, 2H, CH₂), 4.31 (t, J=6.2 Hz, 2H, CH₂), 4.23 (br s, 4H, NCH₂), 3.71 (br s, 2H, CONC$\underline{H}_2$), 3.65 (br s, 2H, CONC$\underline{H}_2$), 3.40 (t, J=6.2 Hz, 2H, CH₂) ppm.

HRMS: calcd for C₂₅H₂₅ClFN₆O₃S 543.13814, found 543.13690.

Example 49

Synthesis of 1-(4-(5-amino-2-(4-fluorophenethyl)-thiazolo[5,4-d]pyrimidin-7-yl)piperazin-1-yl)-2-(4-chlorophenoxy)ethanone To a solution of 2-(4-fluorophenethyl)-7-(methylsulfonyl)thiazolo[5,4-d]pyrimidin-5-amine (50 mg, 0.14 mmol) and triethylamine (30 μl, 0.21 mmol) in dioxane (1 ml) was added 2-(4-chlorophenoxy)-1-(piperazin-1-yl)ethanone (51 mg, 0.21 mmol). The reaction mixture was heated at 70° C. for 3 hours. After cooling, the volatiles were removed under reduced pressure. The crude residue was purified by chromatography on silica gel (CH₂Cl₂/MeOH 70:1) to yield the title compound as a light yellow solid (64 mg, 85%).

¹H NMR (300 MHz, CDCl₃, 25° C.): δ=7.26 (d, J=8.9 Hz, 2H, PhH), 7.13-7.18 (m, 2H, PhH), 6.68 (d, J=8.9, 2H, PhH), 6.93 (t, J=9.1 Hz, 2H, PhH), 4.73 (br s, 4H, NH₂, OCH₂), 4.23 (br s, 4H, N(CH₂)₂), 3.71 (br s, 2H, CONC$\underline{H}_2$), 3.70 (br s, 2H, CONC$\underline{H}_2$), 3.23 (t, J=7.0, 2H, CH₂), 3.07 (t, J=7.0, 2H, CH₂) ppm.

HRMS: calcd for C₂₅H₂₅ClFN₆O₂S 527.14323, found 527.14215.

Example 50

Synthesis of 1-(4-(5-amino-2-(4-fluorophenethyl)thiazolo[5,4-d]pyrimidin-7-yl)piperazin-1-yl)-2-(4-methoxyphenoxy)ethanone To a solution of 2-(4-fluorophenethyl)-7-(methylsulfonyl)thiazolo[5,4-d]pyrimidin-5-amine (40 mg, 0.11 mmol) and 4-methoxyphenoxyacetic acid (30 mg, 0.17 mmol) in DMF (2 ml) was added TBTU (N,N,N',N'-tetramethyl-O-(benzotriazol-1-yl)uronium tetrafluoroborate, 54 mg, 0.17 mmol), followed by DIPEA (29 µl, 0.17 mmol. The reaction mixture was stirred at room temperature for 3 hours. The mixture was diluted with water and extracted with dichloromethane. The combined organic layers were washed with brine and dried over $Na_2SO_4$. After removing the solvents under reduced pressure, the crude residue was purified by flash chromatography on silica ($CH_2Cl_2$/MeOH 40:1), yielding the title compound as a white solid (40 mg, 69%).

$^1$H NMR (300 MHz, DMSO, 25° C.): δ=7.27-7.32 (m, 2H, PhH), 7.09 (t, J=8.9 Hz, 2H, PhH), 6.84-6.91 (m, 4H, PhH), 6.31 (br s, 2H, $NH_2$), 4.79 (s, 2H, $CH_2$), 4.22 (br s, 2H, $NCH_2$), 4.10 (br s, 2H, $NCH_2$), 3.69 (s, 3H, $CH_3$), 3.56 (br s, 4H, $CON(C\underline{H}_2)_2$), 3.25 (t, J=7.4, 2H, $CH_2$), 3.04 (t, J=7.4, 2H, $CH_2$) ppm.

HRMS: calcd for $C_{26}H_{28}FN_6O_3S$ 523.19276, found 523.19218.

Example 51

Synthesis of 1-(4-(5-amino-2-(4-fluorophenethyl)thiazolo[5,4-d]pyrimidin-7-yl)piperazin-1-yl)-2-(4-fluorophenoxy)ethanone This compound was prepared from example 27 using 4-fluorophenoxyacetic acid in a yield of 56%, according to the procedure for the synthesis of example 50.

$^1$H NMR (300 MHz, DMSO, 25° C.): δ=7.27-7.32 (m, 2H, PhH), 7.12 (t, J=8.9 Hz, 2H, PhH), 7.09 (t, J=8.6 Hz, 2H, PhH), 6.94-6.98 (m, 2H, PhH), 6.31 (br s, 2H, $NH_2$), 4.87 (s, 2H, $CH_2$), 4.23 (br s, 2H, $NCH_2$), 4.10 (br s, 2H, $NCH_2$), 3.56 (br s, 4H, $CON(C\underline{H}_2)_2$), 3.25 (t, J=7.3, 2H, $CH_2$), 3.05 (t, J=7.3, 2H, $CH_2$) ppm.

HRMS: calcd for $C_{25}H_{25}F_2N_6O_2S$ 511.17278, found 511.17170.

Example 52

Synthesis of 1-(4-(5-amino-2-(4-fluorophenethyl)thiazolo[5,4-d]pyrimidin-7-yl)piperazin-1-yl)-2-(4-bromophenoxy)ethanone This compound was prepared from example 27 using 4-bromophenoxyacetic acid in a yield of 47%, according to the procedure for the synthesis of example 50.

$^1$H NMR (300 MHz, DMSO, 25° C.): δ=7.44 (d, J=8.9 Hz, 2H, PhH), 7.27-7.32 (m, 2H, PhH), 7.09 (t, J=8.9 Hz, 2H, PhH), 6.92 (d, J=8.9 Hz, 2H, PhH), 6.31 (br s, 2H, $NH_2$), 4.91 (s, 2H, $CH_2$), 4.24 (br s, 2H, $NCH_2$), 4.10 (br s, 2H, $NCH_2$), 3.55 (br s, 4H, $CON(C\underline{H}_2)_2$), 3.25 (t, J=7.4, 2H, $CH_2$), 3.04 (t, J=7.4, 2H, $CH_2$) ppm.

Example 53

Synthesis of 1-(4-(5-amino-2-(4-fluorophenethyl)thiazolo[5,4-d]pyrimidin-7-yl)piperazin-1-yl)-2-(m-tolyloxy)ethanone This compound was prepared from example 27 using 3-methylphenoxyacetic acid in a yield of 44%, according to the procedure for the synthesis of example 50.

$^1$H NMR (300 MHz, DMSO, 25° C.): δ 7.28-7.32 (m, 2H, PhH), 7.16 (t, J=7.7 Hz, 1H, PhH), 7.09 (t, J=8.9 Hz, 2H, PhH), 6.73-6.78 (m, 3H, PhH), 6.31 (br s, 2H, $NH_2$), 4.84 (s, 2H, $CH_2$), 4.24 (br s, 2H, $NCH_2$), 4.10 (br s, 2H, $NCH_2$), 3.57 (br s, 4H, $CON(C\underline{H}_2)_2$), 3.25 (t, J=7.4, 2H, $CH_2$), 3.05 (t, J=7.4, 2H, $CH_2$), 2.27 (s, 3H, $CH_3$) ppm.

HRMS: calcd for $C_{26}H_{28}FN_6O_2S$ 507.19785, found 507.19725.

Example 54

Synthesis of 1-(4-(5-amino-2-(4-fluorophenethyl)thiazolo[5,4-d]pyrimidin-7-yl)piperazin-1-yl)-2-(2,4-dichlorophenoxy)ethanone This compound was prepared from example 27 using 2,4-dichlorophenoxyacetic acid in a yield of 43%, according to the procedure for the synthesis of example 50.

$^1$H NMR (300 MHz, DMSO, 25° C.): δ=7.58 (d, J2.6 Hz, 1H, PhH), 7.28-7.37 (m, 3H, PhH), 7.07-7.12 (m, 3H, PhH), 6.32 (br s, 2H, $NH_2$), 5.07 (s, 2H, $CH_2$), 4.25 (br s, 2H, $NCH_2$), 4.11 (br s, 2H, $NCH_2$), 3.56 (br s, 4H, $CON(C\underline{H}_2)_2$), 3.25 (t, J=7.5, 2H, $CH_2$), 3.04 (t, J=7.5, 2H, $CH_2$) ppm.

HRMS: calcd for $C_{26}H_{24}Cl_2FN_6O_2S$ 561.10425, found 561.10335.

Example 55

Synthesis of 1-(4-(5-amino-2-(4-fluorophenethyl)thiazolo[5,4-d]pyrimidin-7-yl)piperazin-1-yl)-3-(4-fluorophenoxy)propan-1-one This compound was prepared from example 27 using 3-(4-fluorophenoxy)propionic acid in a yield of 43%, according to the procedure for the synthesis of example 50.

$^1$H NMR (300 MHz, DMSO, 25° C.): δ=7.27-7.33 (m, 2H, PhH), 7.06-7.14 (m, 4H, PhH), 6.92-6.97 (m, 2H, PhH), 6.30 (br s, 2H, $NH_2$), 4.19 (t, J=5.8 Hz, 2H, $OCH_2$), 4.17 (br s, 2H, $NCH_2$), 4.09 (br s, 2H, $NCH_2$), 3.59 (br s, 4H, $CON(C\underline{H}_2)_2$), 3.25 (t, J=7.4, 2H, $CH_2$), 3.05 (t, J=7.4, 2H, $CH_2$), 2.86 (t, J=5.8, 2H, $CH_2$) ppm.

Example 56

Synthesis of 2-(4-fluorophenyl)-5-methyl-thiazolo[5,4-d]pyrimidin-7(6H)-one

To a solution of 2-(4-fluorophenyl)-7-(methylthio)thiazolo[5,4-d]pyrimidin-5-amine (0.15 g, 0.51 mmol) in dichloromethane (3 ml) was added mCPBA (70%, 0.32 g, 1.29 mmol) at 0° C. The temperature was gradually raised from 0° C. to room temperature and the reaction was stirred for another 3 hours. The reaction mixture was diluted with $CHCl_3$ and washed with a saturated $NaHCO_3$ solution, brine and dried over $Na_2SO_4$. After removing the solvents under reduced pressure, the residue was purified by chromatography on silica gel ($CH_2Cl_2$/MeOH 50:1) to yield the title compound as a white solid (0.10 g, 75%).

$^1$H NMR (300 MHz, DMSO, 25° C.): δ=12.80 (s, 1H, NH), 8.03-8.08 (m, 2H, PhH), 7.40 (t, J=8.8 Hz, 2H, PhH), 2.41 (s, 3H, $CH_3$) ppm.

HRMS: calcd for $C_{12}H_9FN_3OS$ 262.04504, found 262.04433.

Example 57

Synthesis of 7-chloro-2-(4-fluorophenyl)-5-methyl-thiazolo[5,4-d]pyrimidine

To a solution of 2-(4-fluorophenyl)-5-methyl-thiazolo[5,4-d]pyrimidin-7(6H)-one (0.40 g, 1.23 mmol) in $POCl_3$ was added diisopropylethylamine (0.13 ml, 0.77 mmol). The reaction mixture was stirred under $N_2$ at 90° C. for 3.5 hours. After cooling down to room temperature, the reaction mixture was poured into ice-water and the aqueous phase was extracted with diethyl ether. The combined organic layers were washed with a saturated $NaHCO_3$ solution and brine, dried over $Na_2SO_4$ and concentrated under reduced pressure. The crude residue was purified by chromatography on silica gel (hexane/EtOAc 10:1) to yield the title compound as a white solid (42.8 mg, 40%).

$^1$H NMR (300 MHz, $CDCl_3$, 25° C.): δ=8.09-8.14 (m, 2H, PhH), 7.22 (t, J=8.5 Hz, 2H, PhH), 2.83 (s, 3H, $CH_3$) ppm.

HRMS: calcd for $C_{12}H_8ClFN_3S$ 280.01115, found 280.01063.

Example 58

Synthesis of tert-butyl 4-(2-(4-chlorophenoxy)acetyl)piperazine-1-carboxylate To a solution of tert-butyl piperazine-1-carboxylate (0.30 g, 0.16 mmol) and triethylamine (0.34 ml, 2.42 mmol) in dichloromethane (8 ml) was added p-chlorophenoxyacetyl chloride (0.36 mg, 1.77 mmol). The reaction mixture was stirred at room temperature overnight. The mixture was diluted with dichloromethane and washed with water, brine and dried over $Na_2SO_4$. After removing the solvents, the crude residue was purified by chromatography on silica gel ($CH_2Cl_2$/MeOH 80:1) to yield the title compound as a white solid (0.57 g, 100%).

$^1$H NMR (300 MHz, $CDCl_3$, 25° C.): δ=7.25 (d, J=8.9 Hz, 2H, PhH), 6.88 (d, J=8.9 Hz, 2H, PhH), 4.68 (s, 2H, $CH_2$), 3.57 (br s, 4H, CON($CH_2$)$_2$), 3.41 (br s, 4H, CON($CH_2$)$_2$), 1.46 (s, 3H, $CH_3$) ppm.

HRMS: calcd for $C_{17}H_{24}ClN_2O_4$ 355.14246, found 355.14167.

Example 59

Synthesis of ethyl 4-(m-tolylcarbamoyl)piperazine-1-carboxylate

To a solution of ethyl piperazine-1-carboxylate (1.0 g, 6.32 mmol) in dichloromethane (30 ml) was added m-tolylisocyanate (0.90 mg, 6.95 mmol). The reaction mixture was stirred at room temperature for 2 hours. The mixture was diluted with dichloromethane and washed with water, brine and dried over $Na_2SO_4$. After removing the solvents, the residue was purified by chromatography on silica gel ($CH_2Cl_2$/MeOH 50:1) to yield the title compound as a white solid (1.6 g, 87%).

$^1$H NMR (300 MHz, $CDCl_3$, 25° C.): δ=7.18 (s, 1H, PhH), 7.10-7.15 (m, 2H, PhH), 6.83 (d, J=6.4 Hz, 1H, PhH), 4.14 (q, J=7.1 Hz, 2H, O$CH_2$$CH_3$), 3.42 (br s, 8H, N($CH_2$)$_2$), 2.27 (s, 3H, $CH_3$), 1.26 (t, J=7.1 Hz, 3H, O$CH_2$$CH_3$) ppm.

MS 289.7 [M−H]

Example 60

Synthesis of 2-(4-chlorophenoxy)-1-(piperazin-1-yl)ethanone

A suspension of tert-butyl 4-(2-(4-chlorophenoxy)acetyl)piperazine-1-carboxylate (example 58, 0.58 g, 0.16 mmol) in dichloromethane (8 ml) was treated dropwise at room temperature with TFA until the solid completely dissolved. The reaction mixture was stirred under nitrogen at room temperature overnight. The volatiles were evaporated to dryness, diluted with water and the solid was collected by filtration. The solid was washed with water and dried to yield the title compound as a white solid (0.30 g, 72%).

$^1$H NMR (300 MHz, DMSO, 25° C.): δ=9.02 (s, 1H, NH), 7.32 (d, J=8.8 Hz, 2H, PhH), 6.96 (d, J=8.8 Hz, 2H, PhH), 4.90 (s, 2H, $CH_2$), 3.65 (br s, 4H, CON($CH_2$)), 3.18 (br s, 2H, N$CH_2$), 3.10 (br s, 2H, N$CH_2$) ppm.

HRMS: calcd for $C_{12}H_{16}ClN_2O_2$ 255.09003, found 255.08913.

Example 61

Synthesis of N-m-tolylpiperazine-1-carboxamide

A suspension of ethyl 4-(m-tolylcarbamoyl)piperazine-1-carboxylate (example 59, 1.5 g, 5.15 mmol) in dichloromethane (25 ml) was treated dropwise at room temperature with iodotrimethylsilane (1.6 ml, 11.3 mmol). The reaction mixture was stirred under nitrogen at room temperature overnight. The volatiles were evaporated to dryness, diluted with methanol and the solid was filtered off. The solid was washed with methanol and dichloromethane and dried under vacuum to yield the title compound as a yellow solid (1.1 g, 100%).

$^1$H NMR (300 MHz, DMSO, 25° C.): δ=8.62 (s, 1H, NH), 7.29 (s, 1H, PhH), 7.27 (d, J=7.3 Hz, 1H, PhH), 7.13 (t, J=7.3 Hz, 1H, PhH), 6.79 (d, J=7.3 Hz, 1H PhH), 3.65 (br s, 4H, CON($CH_2$)), 3.17 (br s, 4H, N($CH_2$)$_2$), 2.26 (s, 3H, $CH_3$) ppm.

MS 227.8 [M−H]

Example 62

Synthesis of 2-(1-(4-fluorophenyl)ethyl)-7-methylthio-thiazolo[5,4-d]pyrimidin-5-amine To a solution of 2-(4-fluorobenzyl)-7-(methylthio)thiazolo[5,4-d]pyrimidin-5-amine (0.4 g, 1.31 mmol) and 2N NaOH (0.65 ml, 1.31 mmol) in DMSO (7 ml) was added iodomethane (81 μl, 1.31 mmol). The reaction mixture was stirred at room temperature for 2 hours. The mixture was poured into water and extracted with ethyl acetate, brine and dried over $Na_2SO_4$. After removing the solvents under reduced pressure, the residue was purified by chromatography on silica gel (hexane/EtOAc 5:1) yielding the title compound as a white solid (0.29 g, 69%).

$^1$H NMR (300 MHz, $CDCl_3$, 25° C.): δ=7.31 (br s, 2H, PhH), 7.02 (br s, 2H, PhH), 5.16 (s, 2H, $NH_2$), 4.47 (br s, 1H, CH), 2.58 (s, 3H, $CH_3$), 1.76 (d, J=6.6 Hz, 3H, CH$CH_3$) ppm.

HRMS: calcd for $C_{14}H_{14}FN_4S_2$ 321.06439, found 321.06377.

Example 63

Synthesis of 2-(1-(4-fluorophenyl)-2-phenylethyl)-7-(methylthio)thiazolo[5,4-d]pyrimidin-5-amine This compound was synthesized according to the procedure for the preparation of example 62, using benzyl bromide. The crude residue was purified by flash chromatography on silica gel (hexane/EtOAc 5:1) to yield the title compound as a white solid (67%).

$^1$H NMR (300 MHz, $CDCl_3$, 25° C.): δ=7.13-7.25(m, 5H, PhH), 7.07 (d, J=6.8 Hz, 2H, PhH), 6.96 (t, J=8.5 Hz, 2H,

PhH), 5.05 (s, 2H, NH$_2$), 4.52 (t, J=7.8 Hz, 1H, CH), 3.74 (dd, J=13.8, 7.8 Hz, 1H, benzylH), 3.30 (dd, J=13.8, 7.8 Hz, 1H, benzylH), 2.59 (s, 3H, CH$_3$) ppm.

HRMS: calcd for C$_{20}$H$_{18}$FN$_4$S$_2$ 397.09569, found 397.09495.

Example 64

Synthesis of 2-(1-(4-fluorophenyl)ethyl)-7-(methylsulfonyl)thiazolo[5,4-d]pyrimidin-5-amine This compound was synthesized from example 62 according to the procedure for the preparation of example 21. The crude residue was purified by flash chromatography on silica (CH$_2$Cl$_2$/MeOH 100:1) to yield the title compound as a white solid (77%).

$^1$H NMR (300 MHz, CDCl$_3$, 25° C.): δ=7.35-7.30 (m, 2H, PhH), 7.05 (t, J=8.6 Hz, 2H, PhH), 5.49 (s, 2H, NH$_2$), 4.54 (q, J=7.1, 1H, CH), 3.49 (s, 3H, CH$_3$), 1.83 (d, J=7.1 Hz, 3H, CHCH$_3$) ppm.

HRMS: calcd for C$_{14}$H$_{14}$FN$_4$O$_2$S$_2$ 353.05422, found 353.05356.

Example 65

Synthesis of 2-(1-(4-fluorophenyl)-2-phenylethyl)-7-(methylsulfonyl)thiazolo[5,4-d]pyrimidin-5-amine This compound was synthesized from example 63 according to the procedure for the preparation of example 21. The crude residue was purified by flash chromatography on silica (CH$_2$Cl$_2$/MeOH 100:1) to yield the title compound as a white solid (85%).

$^1$H NMR (300 MHz, DMSO, 25° C.): δ=7.59 (s, 2H, NH$_2$), 7.44-7.49 (m, 2H, PhH), 7.11-7.24 (m, 7H, PhH), 4.96 (t, J=7.8 Hz, 1H, CH), 3.67 (dd, J=13.8, 7.8 Hz, 1H, benzylH), 3.53 (s, 3H, CH$_3$), 3.35 (dd, J=13.8, 7.8 Hz, 1H, benzylH) ppm.

HRMS: calcd for C$_{20}$H$_{18}$FN$_4$O$_2$S$_2$ 429.08552, found 429.08481.

Example 66

Synthesis of 1-(4-(5-amino-2-(1-(4-fluorophenyl) ethyl)thiazolo[5,4-d]pyrimidin-7-yl)piperazin-1-yl)-2-(4-chlorophenoxy)ethanone To a solution of 2-(1-(4-fluorophenyl)ethyl)-7-(methylsulfonyl)thiazolo[5,4-d]pyrimidin-5-amine (50 mg, 0.14 mmol) and triethylamine (30 μl, 0.21 mmol) in dioxane (1 ml) was added 2-(4-chlorophenoxy)-1-(piperazin-1-yl)ethanone (51 mg, 0.21 mmol). The reaction mixture was heated at 70° C. for 3 hours. After cooling down to room temperature, the volatiles were removed under reduced pressure. The crude residue was purified by chromatography on silica gel (CH$_2$Cl$_2$/MeOH 70:1) furnishing the title compound as a white solid (50 mg, 67%).

$^1$H NMR (300 MHz, CDCl$_3$, 25° C.): δ=7.29-7.25 (m, 4H, PhH), 7.02 (t, J=8.1 Hz, 2H, PhH), 6.92 (d, J=8.9 Hz, 2H, PhH), 4.74 (s, 4H, OCH$_2$, NH$_2$), 4.33 (q, J=7.3 Hz, 1H, CH), 4.27 (br s, 4H, N(CH$_2$)$_2$), 3.71 (br s, 4H, CON(CH$_2$)$_2$), 1.73 (d, J=7.3 Hz, 3H, CHCH$_3$) ppm.

HRMS: calcd for C$_{25}$H$_{25}$ClFN$_6$O$_2$S 527.14323, found 527.14230.

Example 67

Synthesis of 1-(4-(5-amino-2-(1-(4-fluorophenyl)-2-phenylethyl)thiazolo[5,4-d]pyrimidin-7-yl)piperazin-1-yl)-2-(4-chlorophenoxy)ethanone This compound was synthesized from example 65 according to the procedure for the preparation of example 66. The crude residue was purified by flash chromatography on silica (CH$_2$Cl$_2$/MeOH 70:1) to yield the title compound as a white solid (60 mg, 83%).

$^1$H NMR (300 MHz, CDCl$_3$, 25° C.): δ=7.17-7.28 (m, 7H, PhH), 6.91-7.05 (m, 6H, PhH), 4.74 (s, 2H, OCH$_2$), 4.70 (s, 2H, NH$_2$), 4.48 (t, J=7.7 Hz, 1H, CH), 4.24 (br s, 4H, N(CH$_2$)$_2$), 3.72 (br s, 2H, CONCH$_2$), 3.66 (br s, 2H, CONCH$_2$), 3.62 (dd, J=13.8, 7.7 Hz, 1H, benzylH), 3.26 (dd, J=13.8, 7.8 Hz, 1H, benzylH) ppm.

HRMS: calcd for C$_{31}$H$_{29}$ClFN$_6$O$_2$S 603.17453, found 603.17371.

Example 68

Synthesis of 4-(5-amino-2-(1-(4-fluorophenyl)ethyl) thiazolo[5,4-d]pyrimidin-7-yl)-N-m-tolylpiperazine-1-carboxamide This compound was synthesized according to the procedure for the preparation of example 66, using N-m-tolylpiperazine-1-carboxamide. The crude residue was purified by flash chromatography on silica gel (CH$_2$Cl$_2$/MeOH 50:1) furnishing the title compound as a white solid (76%).

$^1$H NMR (300 MHz, DMSO, 25° C.): δ=8.50 (s, 1H, NH), 7.38-7.43 (m, 2H, PhH), 7.32 (s, 1H, PhH), 7.28 (d, J=8.5 Hz, 1H, PhH), 7.18 (t, J=8.9 Hz, 2H, PhH), 7.12 (t, J=7.8 Hz, 1H, PhH), 6.76 (d, J=7.4 Hz, 1H, PhH), 6.33 (s, 2H, NH$_2$), 4.51 (q, J=7.1 Hz, 1H, CH), 4.22 (br s, 4H, N(CH$_2$)$_2$), 3.57 (br s, 4H, CON(CH$_2$)$_2$), 2.25 (s, 3H, CH$_3$), 1.67 (d, J=7.1 Hz, 3H, CHCH$_3$) ppm.

Example 69

Synthesis of 2-(4-fluorophenyl)-5,7-bis(methylthio) thiazolo[5,4-d]pyrimidine

To a solution of 2-(4-fluorophenyl)thiazolo[5,4-d]pyrimidine-5,7-dithiol (0.20 g, 0.68 mmol) and triethylamine (0.33 ml, 2.37 mmol) in DMSO (3 ml) was added iodomethane (0.13 ml, 2.03 mmol). The reaction mixture was stirred for 12 hours under N$_2$ at 25° C. The mixture was poured into water and extracted with EtOAc. The organic extracts were dried over Na$_2$SO$_4$ and the solvent was removed under reduced pressure. The crude residue was purified by flash chromatography on silica (EtOAc/Hex 1:40), yielding the title compound as a light yellow solid (0.19 g, 87%).

$^1$H NMR (300 MHz, CDCl$_3$, 25° C.): δ=8.04-8.09 (m, 2H, PhH), 7.18 (t, J=8.6 Hz, 2H, PhH), 2.70 (s, 3H, CH$_3$), 2.66 (s, 3H, CH$_3$) ppm.

HRMS: calcd for C$_{13}$H$_{11}$FN$_3$S$_3$ 324.00991, found 324.00908.

Example 70

Synthesis of 5,7-bis(butylthio)-2-(4-fluorophenyl) thiazolo[5,4-d]pyrimidine

This compound was synthesized according to a procedure for the preparation of example 69, using n-butyl bromide. The crude residue was purified by flash chromatography on silica (EtOAc/Hex 1:100) to yield the title compound as a white solid (53%).

$^1$H NMR (300 MHz, CDCl$_3$, 25° C.): δ=8.03-8.08 (m, 2H, PhH), 7.18 (t, J=8.6 Hz, 2H, PhH), 3.34 (t, J=7.3 Hz, 2H, SCH$_2$), 3.24 (t, J=7.3 Hz, 2H, SCH$_2$), 1.73-1.82 (m, 4H, SCH$_2$CH$_2$CH$_2$CH$_3$), 1.48-1.55 (m, 4H, SCH$_2$CH$_2$CH$_2$CH$_3$), 0.98 (t, J=7.4 Hz, 3H, CH$_3$), 0.97 (t, J=7.4 Hz, 3H, CH$_3$) ppm.

HRMS: calcd for C$_{19}$H$_{23}$FN$_3$S$_3$ 408.10381, found 408.10259.

Example 71

Synthesis of 5,7-bis(benzylthio)-2-(4-fluorophenyl)thiazolo[5,4-d]pyrimidine This compound was synthesized according to a procedure for the preparation of example 69, using benzyl bromide. The crude residue was purified by flash chromatography on silica (EtOAc/Hex 1:100) to yield the title compound as a white solid (97%).

$^1$H NMR (300 MHz, CDCl$_3$, 25° C.): δ=8.01-8.04 (m, 2H, PhH), 7.41-7.45 (m, 4H, PhH), 7.28-7.32 (m, 6H, PhH), 7.17 (t, J=8.5 Hz, 2H, PhH), 4.54 (s, 2H, CH$_2$), 4.49 (s, 2H, CH$_2$) ppm.

HRMS: calcd for C$_{25}$H$_{19}$FN$_3$S$_3$ 476.0725, found 476.3023.

Example 72

Synthesis of 7-ethoxy-2-(4-fluorophenyl)-5-(methylthio)thiazolo[5,4-d]pyrimidine To a solution of Na (2.0 mg, 0.08 mmol) in ethanol (1 ml) was added 2-(4-fluorophenyl)-5,7-bis(methylthio)thiazolo[5,4-d]pyrimidine (50 mg, 0.15 mmol). The reaction mixture was heated at 80° C. for 3 hours. After cooling, the mixture was neutralized with 1N HCl and the solvent was removed under reduced pressure. The crude residue was redissolved in ethyl acetate, extracted with brine and dried over Na$_2$SO$_4$. After removing the solvents in vacuo, the residue was purified by flash chromatography on silica (EtOAc/Hex 1:50), yielding the title compound as a white solid (30 mg, 60%).

$^1$H NMR (300 MHz, CDCl$_3$, 25° C.): δ=8.02-8.07 (m, 2H, PhH), 7.17 (t, J=8.6 Hz, 2H, PhH), 4.71 (q, J=7.1 Hz, 2H, OCH$_2$), 2.63 (s, 3H, SCH$_3$) 1.54 (t, J=7.1 Hz, 3H, CH$_3$) ppm.

HRMS: calcd for C$_{14}$H$_{13}$FN$_3$OS$_2$ 322.04841, found 322.04753.

Example 73

Synthesis of 7-ethoxy-2-(4-fluorophenyl)-5-methylsulfonyl-thiazolo[5,4-d]pyrimidine This compound was synthesized according to a procedure for the preparation of example 21. The crude residue was purified by flash chromatography on silica (EtOAc/Hex 1:30) to yield the title compound as a white solid (61%).

$^1$H NMR (300 MHz, CDCl$_3$, 25° C.): δ=8.11-8.16 (m, 2H, PhH), 7.23 (t, J=8.6 Hz, 2H, PhH), 4.84 (q, J=7.1 Hz, 2H, CH$_2$), 1.61 (t, J=7.1 Hz, 3H, CH$_3$) ppm.

HRMS: calcd for C$_{14}$H$_{13}$FN$_3$O$_3$S$_2$ 354.03824, found 354.03748.

Examples 74-76

Synthesis of diethyl 2-(acylamino)malonate analogues

General Procedure

To a solution of diethyl 2-aminomalonate hydrochloride (4.23 g, 20 mmol) in pyridine (50 ml) was added an acid chloride (20 mmol). The resulting mixture was stirred at room temperature for 1 hour. The solvents were evaporated in vacuo. The residue was collected, washed with water and dried over P$_2$O$_5$, yielding the title compound.

The following compounds were synthesized according to this procedure:

Example 74

Synthesis of diethyl 2-(cyclopropanecarboxamido)malonate

This compound was synthesized in 91% yield, using cyclopropanecarbonyl chloride.

MS m/z (%): 244 ([M+H]$^+$, 100)

Example 75

Synthesis of diethyl 2-(2-methoxyacetamido)malonate

This compound was synthesized from 2-methoxyacetyl chloride in 97% yield.

MS m/z (%): 248 ([M+H]$^+$, 100)

Example 76

Synthesis of diethyl 2-hexanamidomalonate

This compound was synthesized from hexanoyl chloride in 95% yield.

MS m/z (%): 274 ([M+H]$^+$, 100)

Examples 77-79

Synthesis of 2-amino-4,6-dihydroxy-5-(acylamino)pyrimidine analogues

General Procedure

Sodium (0.58 g, 25 mmol) was added to absolute ethanol (50 ml). After sodium was completely dissolved, diethyl 2-(acylamino)malonate (2.43 g, 10 mmol) and guanidine hydrochloride (1.20 g, 12.5 mmol) were added. The resulting mixture was heated under reflux for 1.5 h. The reaction mixture was cooled down to room temperature. The precipitate was collected by filtration, and washed with ethanol. The precipitate was then dissolved in a small amount of water and neutralized to pH=3-4 with acetic acid. The precipitate was collected, washed with water and dried over P$_2$O$_5$, yielding the title compounds The following compounds were synthesized according to this procedure:

Example 77

Synthesis of 2-amino-4,6-dihydroxy-5-(cyclopropanamido)pyrimidine

This compound was synthesized from diethyl 2-(cyclopropanecarboxamido)malonate in 91% yield.

MS m/z (%): 209 ([M−H]$^−$, 100).

Example 78

Synthesis of 2-amino-4,6-dihydroxy-5-(2-methoxy-acetamido)pyrimidine

This compound was synthesized from diethyl 2-(2-methoxyacetamido)malonate in 65% yield.
MS m/z (%): 213 ([M−H]$^-$, 100)

Example 79

Synthesis of 2-amino-4,6-dihydroxy-5-hexanamidopyrimidine

This compound was synthesized from diethyl 2-hexanamidomalonate (2.73 g, 10 mmol) in 83% yield.
MS m/z (%): 239 ([M−H]$^-$, 100)

Examples 80-86

Synthesis of 2-amino-5-acylamino-4,6-dihydroxypyrimidine analogues

General Procedure
To an ice-cooled solution of 2,5-diaminopyrimidine-4,6-diol (1.78 g, 10 mmol) in 1 N NaOH (25 ml), was added slowly an appropriate acid chloride (10 mmol). The resulting mixture was stirred and warmed to room temperature over 1 hour. The reaction mixture was neutralized with HCl to pH 5. The precipitate was filtered off, washed with water and dried over P$_2$O$_5$, yielding the title compound.
The following compounds were synthesized according to this general procedure:

Example 80

Synthesis of 2-amino-5-cyclohexanecarboxamido-4,6-dihydroxypyrimidine

This compound was synthesized from cyclohexane carbonyl chloride in 87% yield.
MS m/z (%): 253 ([M+H]$^+$, 100)

Example 81

Synthesis of 2-amino-4,6-dihydroxy-5-nicotinamidopyrimidine

This compound was synthesized from nicotinoyl chloride hydrochloride in 81% yield.
MS m/z (%): 248 ([M+H]$^+$, 100)

Example 82

Synthesis of 2-amino-4,6-dihydroxy-5-(3-phenylpropanamido)pyrimidine

This compound was synthesized from 3-phenylpropanoyl chloride in 96% yield.
MS m/z (%): 275 ([M+H]$^+$, 100)

Example 83

Synthesis of 2-amino-4,6-dihydroxy-5-(4-chlorophenylacetamido)pyrimidine

This compound was synthesized from 4-chlorophenylacetyl chloride yielding the title compound in 95% yield.
MS m/z (%): 295 ([M+H]$^+$, 100)

Example 84

Synthesis of 2-amino-4,6-dihydroxy-5-(3,4-dichlorobenzamido)pyrimidine

This compound was synthesized from 3,4-dichlorobenzoyl chloride yielding the title compound in 89% yield.
MS m/z (%): 315 ([M+H]$^+$, 100)

Example 85

Synthesis of 2-amino-4,6-dihydroxy-5-(3-methoxybenzamido)pyrimidine

This compound was synthesized from 3-methoxybenzoyl chloride, yielding the title compound in 94% yield.
MS m/z (%): 277 ([M+H]$^+$, 100)

Example 86

Synthesis of ethyl 2-amino-4,6-dihydroxypyrimidin-5-ylcarbamate

This compound was synthesized from ethyl chloroformate yielding the title compound in 89% yield.

Examples 87-88

Synthesis of 2-amino-4,6-dihydroxy-5-(acylamino)pyrimidine analogues

General Procedure
A suspension of 1-phenylcyclopropanecarboxylic acid (973 mg, 6.0 mmol) in SOCl$_2$ (5 ml) was heated under reflux for 1 h. After concentration under reduced pressure, the residue was redissolved in dioxane (5 ml) and added to a stirring solution of 2,5-diamino-4,6-dihydroxypyrimidine (893 mg, 5.0 mmol) in 1 N NaOH (20 ml) at 0° C. The mixture was stirred and warmed to room temperature in 1 h. After neutralization with 1 N hydrochloride to pH=5, the precipitate was filtered off, washed with water and dried over P$_2$O$_5$, yielding the title compound.
The following compounds were synthesized according to this procedure:

Example 87

Synthesis of 2-amino-4,6-dihydroxy-5-(1-phenylcyclopropanecarboxamido)pyrimidine This compound was synthesized using 1-phenylcyclopropanecarboxylic acid, yielding the title compound in 87% yield.
MS m/z (%): 285 ([M−H]$^-$, 100)

Example 88

Synthesis of 2-amino-4,6-dihydroxy-5-(1-(4-chlorophenyl)cyclopropanecarboxamido)pyrimidine This compound was synthesized from 1-(4-chlorophenyl)cyclopropanecarboxylic acid yielding the title compound in 84% yield.
MS m/z (%): 321 ([M+H]$^+$, 100)

Examples 89-98

Synthesis of 5-amino-2-substituted-thiazolo[5,4-d]pyrimidine-7-thiol analogues General Procedure A suspension of the appropriate 2-amino-4,6-dihydroxy-5-(acylamino)pyrimidine analogue (630 mg, 3 mmol) and $P_2S_5$ (1.33 g, 6 mmol) in pyridine (15 ml) was heated under reflux for 6 hours. After concentration under reduced pressure, the residue was resuspended in 20 ml water. Sodium carbonate (1.27 g, 9 mmol) was added and the mixture was stirred at room temperature for 1 h. The precipitate was collected by filtration and washed with water, yielding the crude title compound which was used without further purification (450 mg, 67%).

The following compounds were synthesized according to this procedure:

Example 89

Synthesis of 5-amino-2-cyclopropylthiazolo[5,4-d]pyrimidine-7-thiol

This compound was synthesized from 2-amino-4,6-dihydroxy-5-(acylamino)pyrimidine in 67 yield.
MS m/z (%): 223 ([M–H]$^-$, 100)

Example 90

Synthesis of 5-amino-2-(2-phenylethyl)thiazolo[5,4-d]pyrimidine-7-thiol

This compound was synthesized from 2-amino-4,6-dihydroxy-5-(3-phenylpropanamido)pyrimidine (550 mg, 2.0 mmol), yielding the title compound (530 mg, 92%).
MS m/z (%): 289 ([M+H]$^+$, 100)

Example 91

Synthesis of 5-amino-2-(3-pyridinyl)thiazolo[5,4-d]pyrimidine-7-thiol

This compound was synthesized from 2-amino-4,6-dihydroxy-5-(3-nicotinamido)pyrimidine (494 mg, 2.0 mmol), yielding the title compound (260 mg, 50%).
MS m/z (%): 262 ([M+H]$^+$, 100)

Example 92

Synthesis of 5-amino-2-(cyclohexyl)thiazolo[5,4-d]pyrimidine-7-thiol

This compound was synthesized from 2-amino-4,6-dihydroxy-5-cyclohexanecarboxamidopyrimidine (504 mg, 2.0 mmol), yielding the title compound (400 mg, 75%).
MS m/z (%): 267 ([M+H]$^+$, 100)

Example 93

Synthesis of 5-amino-2-(4-chlorobenzyl)thiazolo[5,4-d]pyrimidine-7-thiol

This compound was synthesized from 2-amino-4,6-dihydroxy-5-(4-chlorophenylacetamido)pyrimidine (589 mg, 2.0 mmol), yielding the title compound (500 mg, 81%).
MS m/z (%): 309 ([M+H]$^+$, 100)

Example 94

Synthesis of 5-amino-2-(4-chlorophenyl)thiazolo[5,4-d]pyrimidine-7-thiol

This compound was synthesized from 2-amino-4,6-dihydroxy-5(4-chlorobenzamido)pyrimidine (560 mg, 2.0 mmol), yielding the title compound (450 mg, 76%).
MS m/z (%): 295 ([M+H]$^+$, 100)

Example 95

Synthesis of 5-amino-2-(3-methoxyphenyl)thiazolo[5,4-d]pyrimidine-7-thiol

This compound was synthesized from 2-amino-4,6-dihydroxy-5(4-methoxybenzamido)pyrimidine (1.10 g, 4.0 mmol), yielding the title compound (1.0 g, 86%).
MS m/z (%): 291 ([M+H]$^+$, 100)

Example 96

Synthesis of 5-amino-2-(3,4-dichlorophenyl)thiazolo[5,4-d]pyrimidine-7-thiol

This compound was synthesized from 2-amino-4,6-dihydroxy-5-(3,4-dichlorobenzamido)pyrimidine (1.26 g, 4.0 mmol), yielding the title compound (1.1 g, 83%).
MS m/z (%): 329 ([M+H]$^+$, 100)

Example 97

Synthesis of 5-amino-2-(1-phenylcyclopropyl)thiazolo[5,4-d]pyrimidine-7-thiol

This compound was synthesized from 2-amino-4,6-dihydroxy-5-(1-phenylcyclopropanecarboxamido)pyrimidine (1.15 g, 4.0 mmol), yielding the title compound (1.1 g, 92%).
MS m/z (%): 301 ([M+H]$^+$, 100)

Example 98

Synthesis of 5-amino-2-(1-(4-chlorophenyl)cyclopropyl)thiazolo[5,4-d]pyrimidine-7-thiol This compound was synthesized from 2-amino-4,6-dihydroxy-5-(1-phenylcyclopropanecarboxamido)pyrimidine (1.28 g, 4.0 mmol), yielding the title compound (1.1 g, 82%).
MS m/z (%): 335 ([M+H]$^+$, 100)

Examples 99-105

Synthesis of 5-amino-2-substituted-7-methylthio-thiazolo[5,4-d]pyrimidine analogues General Procedure To a suspension of an appropriate 5-amino-2-substituted-thiazolo[5,4-d]pyrimidine-7-thiol (340 mg, 1.5 mmol) in 1N NaOH (10 ml), was added MeI (112 µl, 1.8 mmol). The resulting mixture was stirred at room temperature for 30 minutes. The reaction mixture was extracted with dichloromethane and washed with water and brine. The organic layer was evaporated in vacuo and purified by flash chromatography on silica, the mobile phase being a mixture of methanol and dichloromethane (in a ratio of 1/50), yielding the pure title compounds.

The following compounds were synthesized according to this procedure:

Example 99

Synthesis of 5-amino-2-cyclopropyl-7-methylthio-thiazolo[5,4-d]pyrimidine

This compound was synthesized from 5-amino-2-cyclopropyl-thiazolo[5,4-d]pyrimidine-7-thiol in 92% yield.
MS m/z (%): 239 ([M+H]$^+$, 100)

Example 100

Synthesis of 5-amino-2-(2-phenylethyl)-7-methylthiothiazolo[5,4-d]pyrimidine

This compound was synthesized from 5-amino-2-(2-phenylethyl)thiazolo[5,4-d]pyrimidine-7-thiol (288 mg, 1.0 mmol), yielding the pure title compound (190 mg, 63%).
MS m/z (%): 303 ([M+H]$^+$, 100)

Example 101

Synthesis of 5-amino-2-cyclohexyl-7-methylthio-thiazolo[5,4-d]pyrimidine

This compound was synthesized from 5-amino-2-cyclohexylthiazolo[5,4-d]pyrimidine-7-thiol (133 mg, 0.5 mmol), yielding the pure title compound (80 mg, 57%).
MS m/z (%): 281 ([M+H]$^+$, 100)

Example 102

Synthesis of 5-amino-2-(3-pyridinyl)-7-methylthio-thiazolo[5,4-d]pyrimidine

This compound was synthesized from 5-amino-2-(3-pyridinyl)thiazolo[5,4-d]pyrimidine-7-thiol (261 mg, 1.0 mmol), yielding the pure title compound (150 mg, 54%).
MS m/z (%): 276 ([M+H]$^+$, 100)

Example 103

Synthesis of 5-amino-2-(4-chlorobenzyl)-7-methylthiothiazolo[5,4-d]pyrimidine

This compound was synthesized from 5-amino-2-(4-chlorobenzyl)thiazolo[5,4-d]pyrimidine-7-thiol (308 mg, 1.0 mmol), yielding the pure title compound (100 mg, 31%).
MS m/z (%): 323 ([M+H]$^+$, 100)

Example 104

Synthesis of 5-amino-2-(3-methoxyphenyl)-7-methylthiothiazolo[5,4-d]pyrimidine

This compound was synthesized from 5-amino-2-(3-methoxyphenyl)thiazolo[5,4-d]pyrimidine-7-thiol (290 mg, 1.0 mmol), yielding the pure title compound (250 mg, 82%).
MS m/z (%): 305 ([M+H]$^+$, 100)

Example 105

Synthesis of 5-amino-2-(4-chlorophenyl)-7-(methylthio)thiazolo[5,4-d]pyrimidine

This compound was synthesized from 5-amino-2-(4-chlorophenyl)thiazolo[5,4-d]pyrimidine-7-thiol (443 mg, 1.5 mmol), yielding the pure title compound (380 mg, 82%).
MS m/z (%): 309 ([M+H]$^+$, 100)

Example 106

Synthesis of 5-amino-2-cyclopropyl-7-methylsulfonylthio-thiazolo[5,4-d]pyrimidine To an ice-cooled suspension of 5-amino-2-cyclopropyl-7-methylthiothiazolo[5,4-d]pyrimidine (120 mg, 0.5 mmol) in dichloromethane (5 ml), was added mCPBA (1250 mg, 1.0 mmol). The resulting mixture was stirred at 0° C. for 1 hour and then warmed to room temperature. The reaction mixture was evaporated in vacuo and purified by flash chromatography on silica, the mobile phase being a mixture of acetone and dichloromethane (in a ratio of 1/30), yielding the pure title compound (81 mg, 60%).
MS m/z (%): 271 ([M+H]$^+$, 100)

Example 107

Synthesis of 5-amino-2-cyclopropyl-7-methoxythiazolo[5,4-d]pyrimidine

A mixture of 5-amino-2-cyclopropyl-7-(methylsulfonyl)thiazolo[5,4-d]pyrimidine (54 mg, 0.2 mmol) and K$_2$CO$_3$ (69 mg, 0.5 mmol) in dioxane (10 ml) and methanol (5 ml) was stirred at room temperature overnight. The reaction mixture was evaporated in vacuo and purified by flash chromatography on silica, the mobile phase being a mixture of methanol and dichloromethane (in a ratio of 1/60), yielding the pure title compound (40 mg, 90%).
MS m/z (%): 223 ([M+H]$^+$, 100)

Example 108

Synthesis of 5-amino-2-cyclopropyl-7-N-piperazinothiazolo[5,4-d]pyrimidine

To a solution of 5-amino-2-cyclopropyl-7-(methylsulfonyl)thiazolo[5,4-d]pyrimidine (54 mg, 0.2 mmol) in dioxane (5 ml) was added piperazine (86 mg, 1.0 mmol). The resulting mixture was stirred at room temperature for 12 h. The solvents were evaporated in vacuo and purified by flash chromatography on silica, the mobile phase being a mixture of methanol and dichloromethane (in a ratio of 1/5), yielding the pure title compound (50 mg, 91%).
MS m/z (%): 277 ([M+H]$^+$, 100)

Examples 109-111

Synthesis of 5-amino-2-substituted-7-(N-piperazino)thiazolo[5,4-d]pyrimidine analogues General Procedure
A mixture of a 5-amino-2-substituted thiazolo[5,4-d]pyrimidine-7-thiol analogue (4.0 mmol) and piperazine (1.72 g, 20 mmol) in 1,1,1,3,3,3-hexamethyldisilazane (HMDS, 5 ml)

and pyridine (20 ml) was heated under reflux for 12 hours. The reaction mixture was evaporated in vacuo and purified by flash chromatography on silica, the mobile phase being a mixture of methanol and dichloromethane (in a ratio of 1/5), yielding the pure title compounds.

The following compounds were made according to this procedure:

Example 109

Synthesis of 5-amino-2-(3,4-dichlorophenyl)-7-(N-piperazino)thiazolo[5,4-d]pyrimidine This compound was synthesized from 5-amino-2-(3,4-chlorophenyl)thiazolo[5,4-d]pyrimidine-7-thiol in 51% yield.

MS m/z (%): 381 ([M+H]$^+$, 100)

Example 110

Synthesis of 5-amino-2-(1-phenylcyclopropyl)-7-(N-piperazino)thiazolo[5,4-d]pyrimidine This compound was synthesized from 5-amino-2-(1-phenylcyclopropyl)thiazolo[5,4-d]pyrimidine-7-thiol (600 mg, 2.0 mmol), yielding the pure title compound (450 mg, 64%).

MS m/z (%): 353 ([M+H]$^+$, 100)

Example 111

Synthesis of 5-amino-2-(1-(4-chlorophenyl)cyclopropyl)-7-(N-piperazino)thiazolo[5,4-d]pyrimidine This compound was synthesized from 5-amino-2-(1-phenylcyclopropyl)thiazolo[5,4-d]pyrimidine-7-thiol (1.34 g, 4.0 mmol), yielding the pure title compound (1.1 g, 71%).

MS m/z (%): 387 ([M+H]$^+$, 100)

Example 112

Synthesis of 5-amino-2-methylthio-7-oxo-thiazolo[5,4-d]pyrimidine

A suspension of ethyl 2-amino-4,6-dihydroxypyrimidin-5-ylcarbamate (0.43 g, 2.0 mmol) and $P_2S_5$ (1.33 g, 6 mmol) in pyridine (20 ml) was heated under reflux for 6 hours. After concentration under reduced pressure, the residue was suspended in water (20 ml). Sodium carbonate (1.27 g, 9 mmol) was added and the mixture was stirred at room temperature for 1 h. The reaction mixture was neutralized to pH=5-6, the precipitate was filtered off and washed with water. The crude product was dissolved in 1N NaOH (20 ml) and MeI (120 µl, 2.0 mmol) was added. The resulting mixture was stirred at room temperature for 30 minutes. The reaction mixture was extracted with dichloromethane and washed with water and brine. The organic layer was evaporated in vacuo and purified by flash chromatography on silica, the mobile phase being a mixture of methanol and dichloromethane (in a ratio of 1/50), yielding the pure title compound (210 mg, 49%).

MS m/z (%): 215 ([M+H]$^+$, 100)

Example 113

Synthesis of 5-amino-7-N-piperazino-2-methylthio-thiazolo[5,4-d]pyrimidine

To a suspension of 5-amino-7-oxo-2-thiomethyl-thiazolo[5,4-d]pyrimidine (107 mg, 0.5 mmol) in DMF (5 ml) were added piperazine (215 mg, 2.5 mmol), benzotriazol-1-yloxy-tris(dimethylamino)-phosphonium hexafluorophosphate (BOP, 290 mg, 0.66 mmol) and 1,8-diazabicyclo[5.4.0]undec-7-ene (DBU, 120 µl, 0.79 mmol), respectively. The resulting reaction mixture was stirred at room temperature for 6 h. The reaction mixture was diluted with dichloromethane and washed with water and brine. The organic phase was evaporated in vacuo and purified by flash chromatography on silica, the mobile phase being a mixture of methanol and dichloromethane (in a ratio of 1/8), yielding the pure title compound (130 mg, 82%).

MS m/z (%): 283([M+H]$^+$, 100)

Examples 114-117

Synthesis of 5-amino-7-[4-(4-chlorophenoxyacetyl)piperazin-1-yl]-2-substituted thiazolo[5,4-d]pyrimidine analogues General Procedure To a solution of a 5-amino-2-substituted-7-N-piperazino-thiazolo[5,4-d]pyrimidine analogue (260 mg, 1.0 mmol) in dioxane (10 ml), was added DIPEA (330 µl, 2.0 mmol) and 4-chlorophenoxyacetyl chloride (246 mg, 1.2 mmol) respectively. The resulting reaction mixture was stirred at room temperature for 30 minutes. The mixture was evaporated in vacuo and purified by flash chromatography on silica, the mobile phase being a mixture of methanol and dichloromethane (in a ratio of 1/40), yielding the pure title compounds.

The following compounds were synthesized according to this procedure:

Example 114

Synthesis of 5-amino-7-[4-(4-chlorophenoxyacetyl)piperazin-1-yl]-2-(1-phenylcyclopropyl)thiazolo[5,4-d]pyrimidine This compound was synthesized from 5-amino-2-(1-phenylcyclopropyl)-7-(N-piperazino)thiazolo[5,4-d]pyrimidine (35 mg, 0.1 mmol), yielding the pure title compound (49 mg, 92%).

MS m/z (%): 521 ([M+H]$^+$, 100)

Example 115

Synthesis of 5-amino-7-[4-(4-chlorophenoxyacetyl)piperazin-1-yl]-2-methylthio-thiazolo[5,4-d]pyrimidine This compound was synthesized from 5-amino-7-(N-piperazino)-2-methylthio-thiazolo[5,4-d]pyrimidine (113 mg, 0.36 mmol), yielding the pure title compound (120 mg, 75%).

MS m/z (%): 451 ([M+H]$^+$, 100)

Example 116

Synthesis of 5-amino-7-[4-(4-chlorophenoxyacetyl)piperazin-1-yl]-2-(3,4-dichlorophenyl)thiazolo[5,4-d]pyrimidine This compound was synthesized from 5-amino-2-(3,4-dichlorophenyl)-7-(N-piperazino)thiazolo[5,4-d]pyrimidine (190 mg, 0.5 mmol), yielding the pure title compound (150 mg, 55%).

$^1$H NMR (300 MHz, DMSO-d6, 25° C.): δ=8.13 (s, 1H, ArH), 7.91 (d, J=8.6 Hz, 1H, ArH), 7.74 (d, J=8.6 Hz, 1H, ArH), 7.32 (d, J=9.0 Hz, 2H, ArH), 6.97 (d, J=9.0 Hz, 2H, ArH), 4.93 (s, 2H, NH$_2$), 4.90 (s, 2H, CH$_2$), 4.42 (br s, 2H, NCH$_2$), 4.22 (br s, 2H, NCH$_2$), 3.64 (br s, 4H, NCH$_2$) ppm.
MS m/z (%): 549 ([M+H]$^+$, 98)

Example 117

Synthesis of 5-amino-7-[4-(4-chlorophenoxyacetyl) piperazin-1-yl]-2-(1-(4-chlorophenyl)cyclopropyl) thiazolo[5,4-d]pyrimidine This compound was synthesized from 5-amino-2-(1-(4-chlorophenyl)cyclopropyl)-7-(N-piperazino)thiazolo[5,4-d]pyrimidine (39 mg, 0.1 mmol), yielding the pure title compound (50 mg, 89%).
MS m/z (%): 555 ([M+H]$^+$, 100)

Examples 118-124

Synthesis of 5-amino-7-[4-(4-chlorophenoxyacetyl) piperazin-1-yl]-2-substituted-thiazolo[5,4-d]pyrimidine analogues General Procedure To a solution of a 5-amino-7-methylthio-2-substituted-thiazolo[5,4-d]pyrimidine analogue (76 mg, 0.25 mmol) in dichloromethane (10 ml) was added mCPBA (250 mg, 1.0 mmol). The solution was stirred at room temperature for 2 h. Then, a solution of piperazine (215 mg, 2.5 mmol) in dioxane (10 ml) was added. The resulting mixture was stirred at room temperature for another 2 h. The reaction mixture was diluted with dichloromethane and washed with water and brine. The organic phase was evaporated in vacuo and the residue was dissolved in dioxane (5 ml). Then, a solution of 4-chlorophenoxyacetyl chloride in dioxane (2 ml) was added. The mixture was stirred at room temperature for 1 h. The solvents were evaporated in vacuo and purified by flash chromatography on silica, the mobile phase being a mixture of methanol and dichloromethane (in a ratio of 1/50), yielding the pure title compound.
The following compounds were made according to this procedure:

Example 118

Synthesis of 5-amino-7-[4-(4-chlorophenoxyacetyl) piperazin-1-yl]-2-(2-phenylethyl)thiazolo[5,4-d]pyrimidine This compound was made from 5-amino-7-methylthio-2-(2-phenylethyl)thiazolo[5,4-d]pyrimidine in 71% yield.
MS m/z (%): 509 ([M+H]$^+$, 100)

Example 119

Synthesis of 5-amino-2-cyclopropyl-7-[4-(4-chlorophenoxyacetyl)piperazin-1-yl]-thiazolo[5,4-d]pyrimidine This compound was made from 5-amino-2-cyclopropyl-7-N-piperazino-thiazolo[5,4-d]pyrimidine (15 mg, 0.05 mmol), yielding the pure title compound (20 mg, 83%).
MS m/z (%): 445 ([M+H]$^+$, 100)

Example 120

Synthesis of 5-amino-7-[4-(4-chlorophenoxyacetyl) piperazin-1-yl]-2-cyclohexylthiazolo[5,4-d]pyrimidine This compound was made from 5-amino-2-cyclohexyl-7-methylthiothiazolo[5,4-d]pyrimidine (56 mg, 0.2 mmol), yielding the pure title compound (60 mg, 62%).
MS m/z (%): 487 ([M+H]$^+$, 100)

Example 121

Synthesis of 5-amino-7-[4-(4-chlorophenoxyacetyl) piperazin-1-yl]-2-(pyridine-3-yl)thiazolo[5,4-d]pyrimidine and 5-amino-7-[4-(4-chlorophenoxyacetyl) piperazin-1-yl]-2-(N-oxopyridine-3-yl)thiazolo[5,4-d]pyrimidine These compounds were prepared from 5-amino-7-(methylthio)-2-(pyridine-3-yl)thiazolo[5,4-d]pyrimidine (69 mg, 0.25 mmol), yielding examples 121a and 121b.

Example 121a 5-amino-7-[4-(4-chlorophenoxyacetyl)piperazin-1-yl]-2-(pyridine-3-yl)thiazolo[5,4-d]pyrimidine (50 mg, 41%)

MS m/z (%): 482 ([M+H]$^+$, 100) and

Example 121b 5-amino-7-[4-(4-chlorophenoxyacetyl)piperazin-1-yl]-2-(N-oxopyridine-3-yl)thiazolo[5,4-d]pyrimidine (20 mg, 17%).

MS m/z (%): 498 ([M+H]$^+$, 100)

Example 122

Synthesis of 5-amino-7-[4-(4-chlorophenoxyacetyl) piperazin-1-yl]-2-(4-chlorophenylmethyl)thiazolo[5,4-d]pyrimidine This compound was made from 5-amino-2-(4-chlorophenylmethyl)-7-methylthiothiazolo[5,4-d]pyrimidine (100 mg, 0.31 mmol), yielding the pure title compound (140 mg, 85%).
MS m/z (%): 529 ([M+H]$^+$, 100)

Example 123

Synthesis of 5-amino-7-[4-(4-chlorophenoxyacetyl) piperazin-1-yl]-2-(4-chlorophenyl)thiazolo[5,4-d] pyrimidine This compound was made from 5-amino-2-(4-chlorophenyl)-7-methylthiothiazolo[5,4-d]pyrimidine (154 mg, 0.5 mmol), yielding the pure title compound (190 mg, 74%).
$^1$H NMR (300 MHz, DMSO-d6, 25° C.): δ=7.94 (d, J=9.0 Hz, 2H, ArH), 7.58 (d, J=9.0 Hz, 2H, ArH), 7.34 (d, J=9.0 Hz, 2H, ArH), 6.99 (d, J=9.0 Hz, 2H, ArH), 6.55 (s, 2H, NH$_2$), 4.93 (s, 2H, CH$_2$), 4.35 (br s, 2H, NCH$_2$), 4.22 (br s, 2H, NCH$_2$), 3.64 (br s, 4H, NCH$_2$) ppm.
MS m/z (%): 515 ([M+H]$^+$, 100)

Example 124

Synthesis of 5-amino-7-[4-(4-chlorophenoxyacetyl)piperazin-1-yl]-2-(3-methoxyphenyl)thiazolo[5,4-d]pyrimidine This compound was made from 5-amino-2-(3-methoxyphenyl)-7-methylthiothiazolo[5,4-d]pyrimidine (152 mg, 0.5 mmol), yielding the pure title compound (120 mg, 47%).

$^1$H NMR (300 MHz, DMSO-d6, 25° C.): δ=7.51-7.41 (m, 3H, ArH), 7.32 (d, J=9.0 Hz, 2H, ArH), 7.09 (m, 1H, ArH), 6.97 (d, J=9.0 Hz, 2H, ArH), 6.52 (s, 2H, NH$_2$), 4.93 (s, 2H, CH$_2$), 4.36 (br s, 2H, NCH$_2$), 4.22 (br s, 2H, NCH$_2$), 3.84 (s, 3H, OCH$_3$), 3.64 (br s, 4H, NCH$_2$) ppm.

MS m/z (%): 511 ([M+H]$^+$, 100)

Example 125

Synthesis of 5-amino-7-[4-(4-chlorophenoxyacetyl)piperazin-1-yl]-2-(1-(4-chlorophenyl)ethyl)thiazolo[5,4-d]pyrimidine To a suspension of 5-amino-7-[4-(4-chlorophenoxyacetyl)piperazin-1-yl]-2-(4-chlorophenylmethyl)thiazolo[5,4-d]pyrimidine (53 mg, 0.1 mmol) in DMF (2 ml) was added 1N NaOH (150 μl, 0.15 mmol) and MeI (7 μl, 0.11 mmol). The resulting mixture was stirred at room temperature for 1 hour. The reaction mixture was diluted with dichloromethane and washed with water and brine. The organic layer was evaporated in vacuo and purified by flash chromatography on silica, the mobile phase being a mixture of methanol and dichloromethane (in a ratio of 1/80), yielding the pure title compound (40 mg, 74%).

MS m/z (%): 543 ([M+H]$^+$, 100)

Example 126

Synthesis of 5-amino-7-[4-(4-chlorophenoxyacetyl)piperazin-1-yl]-2-methylsulfinyl-thiazolo[5,4-d]pyrimidine To an ice cooled suspension of 5-amino-7-[4-(4-chlorophenoxyacetyl)piperazin-1-yl]-2-methylthio-thiazolo[5,4-d]pyrimidine (90 mg, 0.2 mmol) in dichloromethane (5 ml) was added mCPBA (125 mg, 0.5 mmol). The resulting mixture was stirred at 0° C. for 2 h. The solvents were evaporated in vacuo and the crude residue was purified by flash chromatography on silica, the mobile phase being a mixture of methanol and dichloromethane (in a ratio of 1/80), yielding the pure title compound (65 mg, 70%).

MS m/z (%): 467 ([M+H]$^+$, 100)

Example 127

Synthesis of 5-amino-7-[4-(4-chlorophenoxyacetyl)piperazin-1-yl]-2-(4-fluorophenylamino)-thiazolo[5,4-d]pyrimidine A mixture of 5-amino-7-[4-(4-chlorophenoxyacetyl)piperazin-1-yl]-2-methylsulfinyl-thiazolo[5,4-d]pyrimidine (47 mg, 0.1 mmol) and 4-fluoroaniline (95 μl, 1 mmol) in dioxane (5 ml) was heated under reflux for 12 hours. The reaction mixture was evaporated in vacuo and purified by flash chromatography on silica, the mobile phase being a mixture of methanol and dichloromethane (in a ratio of 1/80), yielding the pure title compound (45 mg, 88%).

MS m/z (%): 514 ([M+H]$^+$, 100)

Examples 128-129

Synthesis of 5-amino-2-(4-fluorophenyl)-7-(4-(2-aryloxyacetyl)-piperazin-1-yl)-thiazolo[5,4-d]pyrimidine analogues General Procedure To a solution of 5-amino-2-(4-fluorophenyl)-7-piperazin-1-yl-thiazolo[5,4-d]pyrimidine (50 mg, 0.15 mmol) and a 2-aryloxyacetic acid derivative (0.23 mmol) in DMF (2 ml) was added TBTU (0.23 mmol) followed by diisopropylethylamine (0.23 mmol, 37 μL). The reaction was stirred at room temperature for 24 hours after which the solvent was removed in vacuo. The resulting residue was purified by flash chromatography on silica, the mobile phase being a mixture of methanol and dichloromethane (in a ratio gradually ranging from 100% CH$_2$Cl$_2$ to 1% CH$_3$OH in CH$_2$Cl$_2$), yielding the pure title compounds which were characterized by their mass spectra as indicated below.

The following compounds were synthesized according to this procedure:

Example 128

Synthesis of 5-amino-2-(4-fluorophenyl)-7-(4-[2-(4-bromophenoxy)acetyl]-piperazin-1-yl)-thiazolo[5,4-d]pyrimidine This compound was obtained from 2-(4-bromophenoxy)acetic acid (43 mg);

MS m/z (%): 543 ([M+H]$^+$, 100).

Example 129

Synthesis of 5-amino-2-(4-fluorophenyl)-7-(4-[2-(3-nitrophenoxy)acetyl]-piperazin-1-yl)-thiazolo[5,4-d]pyrimidine This compound was obtained from 2-(3-nitrophenoxy)acetic acid (49 mg).

MS m/z (%): 510 ([M+H]$^+$, 100).

Example 130

Synthesis of 5-amino-2-(4-fluorophenyl)-7-(4-(2-phenoxyacetyl)-piperazin-1-yl)-thiazolo[5,4-d]pyrimidine To a solution of 5-amino-2-(4-fluorophenyl)-7-piperazin-1-yl-thiazolo[5,4-d]pyrimidine (50 mg, 0.15 mmol) in DMF (2 ml) was added diisopropylethylamine (0.33 mmol, 55 μL) followed by phenoxyacetyl chloride (0.17 mmol). The reaction was stirred at room temperature for 4 hours after which the solvent was removed in vacuo. The resulting residue was purified by flash chromatography on silica, the mobile phase being a mixture of methanol and dichloromethane (in a ratio gradually ranging from 100% CH$_2$Cl$_2$ to 0.5% CH$_3$OH in CH$_2$Cl$_2$), yielding the pure title compound (30 mg) which was characterized by its mass spectrum: MS m/z (%): 465 ([M+H]$^+$, 100).

Example 131

Synthesis of 5-amino-2-[2-(4-fluorophenyl)ethyl]-7-(4-[2-(3-nitrophenoxy)acetyl]piperazin-1-yl)-thiazolo[5,4-d]pyrimidine To a solution of 5-amino-2-[2-(4-fluorophenyl)ethyl]-7-piperazin-1-yl-thiazolo[5,4-d]pyrimidine (50 mg, 0.14 mmol) and 3-nitrophenoxyacetic acid (0.23 mmol) in DMF (2 ml) was added TBTU (0.21 mmol) followed by diisopropylethylamine (0.21 mmol, 35 μL). The reaction was stirred at room temperature for 24 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 0.5% $CH_3OH$ in $CH_2Cl_2$), yielding the pure title compound (41 mg) which was characterized by its mass spectrum: MS m/z (%): 538 ([M+H]$^+$, 100).

Example 132

Synthesis of 5-amino-2-[2-(4-fluorophenyl)ethyl]-7-(4-[2-(4-chlorophenyl)acetyl]piperazin-1-yl)-thiazolo[5,4-d]pyrimidine To a solution of 5-amino-2-[2-(4-fluorophenyl)ethyl]-7-piperazin-1-yl-thiazolo[5,4-d]pyrimidine (50 mg, 0.14 mmol) and 4-chlorophenylacetic acid (0.21 mmol) in DMF (2 ml) was added TBTU (0.21 mmol) followed by diisopropylethylamine (0.21 mmol, 35 μL). The reaction was stirred at room temperature for 24 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 1% $CH_3OH$ in $CH_2Cl_2$), yielding the pure title compound (44 mg) which was characterized by its mass spectrum: MS m/z (%): 511 ([M+H]$^+$, 100).

Example 133

Synthesis of 5-amino-2-[2-(4-fluorophenyl)ethyl]-7-(4-m-tolylcarbamoylpiperazin-1-yl)-thiazolo[5,4-d]pyrimidine To a solution of 5-amino-2-[2-(4-fluorophenyl)ethyl]-7-piperazin-1-yl-thiazolo[5,4-d]pyrimidine (50 mg, 0.14 mmol) in dichloromethane (4 ml) was added 3-methylphenylisocyanate (0.15 mmol). The reaction was stirred at room temperature for 2 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 2% $CH_3OH$ in $CH_2Cl_2$), yielding the pure title compound (28 mg) which was characterized by its mass spectrum: MS m/z (%): 492 ([M+H]$^+$, 100).

Example 134

Synthesis of 5-amino-2-[2-(4-fluorophenyl)ethyl]-7-(4-[2-phenoxyacetyl]piperazin-1-yl)-thiazolo[5,4-d]pyrimidine To a solution of 5-amino-2-[2-(4-fluorophenyl)ethyl]-7-piperazin-1-yl-thiazolo[5,4-d]pyrimidine (50 mg, 0.14 mmol) in dichloromethane (4 ml) was added diisopropylethylamine (0.33 mmol, 55 μL) followed by phenoxyacetyl chloride (0.17 mmol). The reaction was stirred at room temperature for 4 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 2% $CH_3OH$ in $CH_2Cl_2$), yielding the pure title compound (34 mg) which was characterized by its mass spectrum: MS m/z (%): 493 ([M+H]$^+$, 100).

Example 135

Synthesis of 5-amino-2-[2-(4-fluorophenyl)ethyl]-7-[4-(4-chlorobenzoyl)piperazin-1-yl]-thiazolo[5,4-d]pyrimidine To a solution of 5-amino-2-[2-(4-fluorophenyl)ethyl]-7-piperazin-1-yl-thiazolo[5,4-d]pyrimidine (50 mg, 0.14 mmol) in dichloromethane (4 ml) was added diisopropylethylamine (0.33 mmol, 55 μL) and 4-chlorobenzoyl chloride (0.15 mmol). The reaction was stirred at room temperature for 16 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 1% $CH_3OH$ in $CH_2Cl_2$), yielding the pure title compound (31 mg) which was characterized by its mass spectrum: MS m/z (%): 497 ([M+H]$^+$, 100).

Example 136

Synthesis of 5-amino-2-[2-(4-fluorophenyl)ethyl]-7-[4-(3-phenylpropionyl)piperazin-1-yl]-thiazolo[5,4-d]pyrimidine To a solution of 5-amino-2-[2-(4-fluorophenyl)ethyl]-7-piperazin-1-yl-thiazolo[5,4-d]pyrimidine (80 mg, 0.22 mmol) in dichloromethane (4 ml) was added diisopropylethylamine (0.49 mmol, 81 μL) and 3-phenylpropionyl chloride (0.25 mmol). The reaction was stirred at room temperature for 16 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 1% $CH_3OH$ in $CH_2Cl_2$), yielding the pure title compound (43 mg) which was characterized by its mass spectrum: MS m/z (%): 491 ([M+H]$^+$, 100).

Example 137

Synthesis of 5-amino-2-[2-(4-fluorophenyl)ethyl]-7-[4-phenylmethanesulfonylpiperazin-1-yl]-thiazolo[5,4-d]pyrimidine To a solution of 5-amino-2-[2-(4-fluorophenyl)ethyl]-7-piperazin-1-yl-thiazolo[5,4-d]pyrimidine (80 mg, 0.22 mmol) in 1,4-dioxane (4 ml) was added diisopropylethylamine (0.49 mmol, 81 μL) and phenylmethanesulfonyl chloride (0.25 mmol). The reaction was stirred at 90° C. for 16 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 1% $CH_3OH$ in $CH_2Cl_2$), yielding the pure title compound (13 mg) which was characterized by its mass spectrum: MS m/z (%): 513 ([M+H]$^+$, 100).

Example 138

Synthesis of 5-amino-2-[2-(4-fluorophenyl)ethyl]-7-(4-[2-(4-chlorophenoxy)acetyl]homopiperazin-1-yl)-thiazolo[5,4-d]pyrimidine To a solution of 5-amino-2-[2-(4-fluorophenyl)ethyl]-7-methanesulfonyl-thiazolo[5,4-d]pyrimidine (50 mg, 0.14 mmol) in dichloromethane (4 ml) was added homopiperazine (1.4 mmol). The reaction mixture was stirred at room temperature for 2 hours. The mixture was extracted, the organic phase was dried over MgSO$_4$ after which the solvent was removed in vacuo. The residue was dissolved in dichloromethane whereupon diisopropylethylamine (0.28 mmol, 47 μL) followed by 4-chlorophenoxyacetyl chloride (0.14 mmol) were added. The reaction was stirred at room temperature for 24 hours after which the solvent was removed in vacuo. The resulting residue was purified by flash chromatography on silica, the mobile phase being a mixture of methanol and dichloromethane (in a ratio gradually ranging from 100% CH$_2$Cl$_2$ to 1% CH$_3$OH in CH$_2$Cl$_2$), yielding the pure title compound (38 mg) which was characterized by its mass spectrum: MS m/z (%): 541 ([M+H]$^+$, 100).

Examples 139-141

Synthesis of 5-amino-2-[2-(4-fluorophenyl)ethyl]-7-(4-[alkyl(aryl)methylphenylcarbamoyl)methyl]piperazin-1-yl)-thiazolo[5,4-d]pyrimidine analogues General Procedure To a solution of 5-amino-2-[2-(4-fluorophenyl)ethyl]-7-methanesulfonyl-thiazolo[5,4-d]pyrimidine (100 mg, 0.28 mmol) in dichloromethane (5 ml) was added diisopropylethylamine (0.59 mmol, 98 μL) and a piperazine derivative (0.31 mmol). The reaction mixture was stirred at room temperature for 18 hours whereupon the solvent was removed in vacuo. The resulting residue was purified by flash chromatography on silica, the mobile phase being a mixture of methanol and dichloromethane (in a ratio gradually ranging from 100% CH$_2$Cl$_2$ to 1% CH$_3$OH in CH$_2$Cl$_2$), yielding the pure title compounds which were characterized by their mass spectra as indicated below.

The following compounds were made according to this procedure:

Example 139

Synthesis of 5-amino-2-[2-(4-fluorophenyl)ethyl]-7-(4-[(methylphenylcarbamoyl)-methyl]piperazin-1-yl)-thiazolo[5,4-d]pyrimidine This compound was obtained from N-methyl-N-phenyl-2-piperazin-1-yl-acetamide (62 mg).
MS m/z (%): 506 ([M+H]$^+$, 100).

Example 140

Synthesis of 5-amino-2-[2-(4-fluorophenyl)ethyl]-7-(4-thiazol-2-yl-piperazine-1-yl)-thiazolo[5,4-d]pyrimidine This compound was obtained from 4-thiazol-2-yl-piperazine (65 mg).
MS m/z (%): 442 ([M+H]$^+$, 100).

Example 141

Synthesis of 5-amino-2-[2-(4-fluorophenyl)ethyl]-7-(4-(phenethylcarbamoyl-methyl)piperazin-1-yl)-thiazolo[5,4-d]pyrimidine This compound was obtained from 4-(phenethylcarbamoyl-methyl)piperazine (84 mg).
MS m/z (%): 520 ([M+H]$^+$, 100).

Example 142

Synthesis of 5-amino-2-[2-(4-fluorophenyl)ethyl]-7-((3-(R)-tert-butoxycarbonylamino)pyrrolidin-1-yl)-thiazolo[5,4-d]pyrimidine To a solution of 5-amino-2-[2-(4-fluorophenyl)ethyl]-7-methanesulfonyl-thiazolo[5,4-d]pyrimidine (150 mg, 0.42 mmol) in dichloromethane (10 ml) was added diisopropylethylamine (0.94 mmol, 155 μL) and 3-(R)-tert-(butoxycarbonylamino)pyrrolidine (0.47 mmol). The reaction mixture was stirred at room temperature for 24 hours. The reaction mixture was extracted with a saturated sodium bicarbonate solution and the organic phase was collected and dried over magnesium sulfate. The solvent was removed in vacuo and the resulting residue was purified by flash chromatography on silica, the mobile phase being a mixture of methanol and dichloromethane (in a ratio gradually ranging from 100% CH$_2$Cl$_2$ to 1% CH$_3$OH in CH$_2$Cl$_2$), yielding the pure title compound (168 mg) which was characterized by its mass spectrum: MS m/z (%): 459 ([M+H]$^+$, 100).

Examples 143-144

Synthesis of 5-amino-2-[2-(4-fluorophenyl)ethyl]-7-(3-(R)-acylaminopyrrolidin-1-yl)-thiazolo[5,4-d]pyrimidine analogues General Procedure To a solution of 5-amino-2-[2-(4-fluorophenyl)ethyl]-7-((3-(R)-tert-butoxycarbonylamino)pyrrolidin-1-yl)-thiazolo[5,4-d]pyrimidine (70 mg, 0.15 mmol) in dichloromethane (3 ml) was added trifluoroacetic acid (3 ml). The reaction mixture was stirred at room temperature for 2 hours after which the solvents were removed in vacuo. The residue was dissolved in dichloromethane (3 ml) and diisopropylethylamine (1.5 mmol, 252 μL) and an acyl chloride (0.17 mmol) were added. The reaction mixture was stirred at room temperature for 16 hours whereupon the solvent was removed in vacuo. The resulting residue was purified by flash chromatography on silica, the mobile phase being a mixture of methanol and dichloromethane (in a ratio gradually ranging from 100% CH$_2$Cl$_2$ to 1.5% CH$_3$OH in CH$_2$Cl$_2$), yielding the pure title compounds which were characterized by their mass spectra as indicated below.

The following compounds were made according to this procedure:

Example 143

Synthesis of 5-amino-2-[2-(4-fluorophenyl)ethyl]-7-(3-(R)-[2-(4-chlorophenoxy)-acetylamino]pyrrolidin-1-yl)-thiazolo[5,4-d]pyrimidine This compound was obtained from 4-chlorophenoxyacetyl chloride (43 mg);
MS m/z (%): 527 ([M+H]$^+$, 100).

Example 144

Synthesis of 5-amino-2-[2-(4-fluorophenyl)ethyl]-7-(3-(R)-(4-chlorobenzoylamino)-pyrrolidin-1-yl)-thiazolo[5,4-d]pyrimidine This compound was obtained from 4-chlorobenzoyl chloride (44 mg).
MS m/z (%): 497 ([M+H]$^+$, 100).

Example 145

Synthesis of 5-amino-2-[2-(4-fluorophenyl)ethyl]-7-(1-benzyloxycarbonylpiperidin-3-ylamino)-thiazolo[5,4-d]pyrimidine To a solution of 5-amino-2-[2-(4-fluorophenyl)ethyl]-7-methanesulfonyl-thiazolo[5,4-d]pyrimidine (50 mg, 0.14 mmol) in 1,4-dioxane (5 ml) was added potassium carbonate (0.42 mmol) and benzyl 3-aminopiperidine-1-carboxylate hydrogen chloride (0.15 mmol). The reaction mixture was stirred at room temperature for 24 hours whereupon the solvent was removed in vacuo. The resulting residue was purified by flash chromatography on silica, the mobile phase being a mixture of methanol and dichloromethane (in a ratio gradually ranging from 100% CH$_2$Cl$_2$ to 1% CH$_3$OH in CH$_2$Cl$_2$), yielding the pure title compound (59 mg) which was characterized by its mass spectrum: MS m/z (%): 507 ([M+H]$^+$, 100).

Example 146

Synthesis of 5-amino-2-[2-(4-fluorophenyl)ethyl]-7-(1-tert-butoxycarbonylpyrrolidin-3-(S)-ylamino)-thiazolo[5,4-d]pyrimidine To a solution of 5-amino-2-[2-(4-fluorophenyl)ethyl]-7-methanesulfonyl-thiazolo[5,4-d]pyrimidine (150 mg, 0.42 mmol) in dichloromethane (10 ml) was added diisopropylethylamine (3.0 mmol, 492 µL) and tert-butyl 3-(S)-aminopyrrolidine-1-carboxylate (2.1 mmol). The reaction mixture was refluxed for 40 hours whereupon the mixture was extracted with a saturated sodium bicarbonate solution. The organic phase was dried over magnesium sulfate and the solvent was removed in vacuo. The resulting residue was purified by flash chromatography on silica, the mobile phase being a mixture of methanol and dichloromethane (in a ratio gradually ranging from 100% CH$_2$Cl$_2$ to 1% CH$_3$OH in CH$_2$Cl$_2$), yielding the pure title compound (81 mg) which was characterized by its mass spectrum: MS m/z (%): 459 ([M+H]$^+$, 100).

Example 147

Synthesis of 5-amino-2-[2-(4-fluorophenyl)ethyl]-7-(1-(4-chlorophenoxyacetyl)pyrrolidin-3-(S)-ylamino)-thiazolo[5,4-d]pyrimidine To a solution of 5-amino-2-[2-(4-fluorophenyl)ethyl]-7-(1-tert-butoxycarbonyl-pyrrolidin-3-(S)-ylamino)-thiazolo[5,4-d]pyrimidine (70 mg, 0.15 mmol) in dichloromethane (1 ml) was added trifluoroacetic acid (1 ml). The reaction mixture was stirred at room temperature for 2 hours after which the solvents were removed in vacuo. The residue was dissolved in dichloromethane (3 ml) and diisopropylethylamine (1.5 mmol, 252 µL) and 4-chlorophenoxyacetyl chloride (0.17 mmol) were added. The reaction mixture was stirred at room temperature for 16 hours whereupon the solvent was removed in vacuo. The resulting residue was purified by flash chromatography on silica, the mobile phase being a mixture of methanol and dichloromethane (in a ratio gradually ranging from 100% CH$_2$Cl$_2$ to 1.5% CH$_3$OH in CH$_2$Cl$_2$), yielding the pure title compound (37 mg) which was characterized by its mass spectrum: MS m/z (%): 527 ([M+H]$^+$, 100).

Example 148

Synthesis of 5-amino-2-[2-(4-fluorophenyl)ethyl]-7-(4-benzoylpiperidine-1-yl)-thiazolo[5,4-d]pyrimidine To a solution of 5-amino-2-[2-(4-fluorophenyl)ethyl]-7-methanesulfonyl-thiazolo[5,4-d]pyrimidine (50 mg, 0.14 mmol) in acetonitrile (5 ml) was added diisopropylethylamine (0.45 mmol, 74 µL) and 4-benzoylpiperidine hydrogen chloride (0.15 mmol). The reaction mixture was stirred at room temperature for 16 hours whereupon the solvent was removed in vacuo. The resulting residue was purified by flash chromatography on silica, the mobile phase being a mixture of methanol and dichloromethane (in a ratio gradually ranging from 100% CH$_2$Cl$_2$ to 1% CH$_3$OH in CH$_2$Cl$_2$), yielding the pure title compound (59 mg) which was characterized by its mass spectrum: MS m/z (%): 462 ([M+H]$^+$, 100).

Example 149

Synthesis of 5-amino-2-[2-(4-fluorophenyl)ethyl]-7-(4-(2-phenoxyethyl)piperazin-1-yl)-thiazolo[5,4-d]pyrimidine To a solution of 5-amino-2-[2-(4-fluorophenyl)ethyl]-6H-thiazolo[5,4-d]pyrimidin-7-one (133 mg, 0.46 mmol) in DMF (5 ml) was added DBU (0.69 mmol), BOP (0.59 mmol) and 1-(2-phenoxyethyl)piperazine (1.37 mmol). The reaction mixture was stirred at room temperature for 3 hours whereupon the solvent was removed in vacuo. The resulting residue was purified by flash chromatography on silica, the mobile phase being a mixture of methanol and dichloromethane (in a ratio gradually ranging from 100% CH$_2$Cl$_2$ to 2% CH$_3$OH in CH$_2$Cl$_2$), yielding the pure title compound (56 mg) which was characterized by its mass spectrum: MS m/z (%): 479 ([M+H]$^+$, 100).

Example 150

Synthesis of 5-amino-2-[1-(4-fluorophenyl)propyl]-7-(4-[2-(4-chlorophenoxy)acetyl]piperazin-1-yl)thiazolo[5,4-d]pyrimidine To a solution of 5-amino-2-(4-fluorobenzyl)-7-methylsulfanylthiazolo[5,4-d]pyrimidine (100 mg, 0.33 mmol) in DMSO (1.5 ml) was added sodium hydroxide (2N, 171 µL) and ethyl iodide (0.34 mmol). The reaction mixture was stirred at room temperature for 16 hours whereupon the mixture was extracted with ethyl acetate and brine. The organic phase was dried over magnesium sulfate and concentrated by evaporation in vacuo. The resulting residue was dissolved in dichloromethane (3 ml), cooled to 0° C. and m-chloroperoxybenzoic acid (0.81 mmol) was added. The reaction mixture was stirred at room temperature for 7 hours. The mixture was first extracted with a saturated sodium bicarbonate solution, then with brine. The combined organic phases were dried over magnesium sulfate. After evaporating the solvents in vacuo, the residue was dissolved again in dichloromethane (3 ml) and piperazine (3.3 mmol) was added. The reaction mixture was stirred at room temperature for 16 hours whereupon the mixture was extracted with brine. The organic phase was dried over magnesium sulfate and evaporated in vacuo. The crude residue was reacted at room temperature for 16 hours with 4-chlorophenoxyacetyl chloride (0.35 mmol) in the presence of diisopropylethylamine (0.72 mmol, 119 μL). After removing the solvent in vacuo, the crude mixture was purified by flash chromatography on silica, the mobile phase being a mixture of methanol and dichloromethane (in a ratio gradually ranging from 100% $CH_2Cl_2$ to 1.5% $CH_3OH$ in $CH_2Cl_2$), yielding the pure title compound (30 mg) which was characterized by its mass spectrum: MS m/z (%): 541 ($[M+H]^+$, 100).

Example 151

Synthesis of 5-amino-2-[cyclopentyl-(4-fluorophenyl)methyl]-7-(4-[2-(4-chlorophenoxy)acetyl]piperazin-1-yl)thiazolo[5,4-d]pyrimidine To a solution of 5-amino-2-(4-fluorobenzyl)-7-methylsulfanylthiazolo[5,4-d]pyrimidine (100 mg, 0.33 mmol) in DMSO (1.5 ml) was added sodium hydroxide (2N, 171 μL) and cyclopentyl iodide (0.34 mmol). The reaction mixture was stirred at room temperature for 16 hours whereupon the mixture was extracted with ethyl acetate and brine. The organic phase was dried over magnesium sulfate and concentrated by evaporation in vacuo. The resulting residue was dissolved in dichloromethane (3 ml), cooled to 0° C. and m-chloroperoxybenzoic acid (0.81 mmol) was added. The reaction mixture was stirred at room temperature for 7 hours. The mixture was first extracted with a saturated sodium bicarbonate solution, then with brine. The combined organic phases were dried over magnesium sulfate. After evaporating the solvents in vacuo, the residue was redissolved in dichloromethane (3 ml) and piperazine (3.3 mmol) was added. The reaction mixture was stirred at room temperature for 16 hours whereupon the mixture was extracted with brine. The organic phase was dried over magnesium sulfate and evaporated in vacuo. The crude residue was reacted at room temperature for 16 hours with 4-chlorophenoxyacetyl chloride (0.35 mmol) in the presence of diisopropylethylamine (0.72 mmol, 119 μL). After removing the solvent in vacuo, the crude mixture was purified by flash chromatography on silica, the mobile phase being a mixture of methanol and dichloromethane (in a ratio gradually ranging from 100% $CH_2Cl_2$ to 1.5% $CH_3OH$ in $CH_2Cl_2$), yielding the pure title compound (47 mg) which was characterized by its mass spectrum: MS m/z (%): 581 ($[M+H]^+$, 100).

Example 152

Synthesis of N-(2-amino-4,6-dihydroxypyrimidin-5-yl)-3-thiophen-2-yl-propionamide To a solution of 2,5-diaminopyrimidine-4,6-diol hydrogen chloride (1.04 g, 5.8 mmol) in sodium hydroxide (17.8 mmol) solution (25 ml of $H_2O$) was added 3-thiophen-2-ylpropionyl chloride (6.4 mmol). The latter was prepared by refluxing 3-thiophen-2-ylpropionic acid (6.4 mmol) in thionyl chloride (500 μL) for 1 hour whereupon the excess of thionyl chloride was removed by evaporation in vacuo. The reaction mixture was stirred at room temperature for 18 hours. The pH of the suspension was adjusted to approximately 6 and the solids were filtered off. The title compound (1.25 g) was characterized by its mass spectrum: MS m/z (%): 515 ($[M+H]^+$, 100).

Example 153

Synthesis of 5-amine-7-piperazin-1-yl-2-(2-thiophen-2-yl-ethyl)-thiazolo[5,4-d]pyrimidine To a suspension of N-(2-amino-4,6-dihydroxypyrimidin-5-yl)-3-thiophen-2-yl-propionamide (example 153, 1 g, 3.6 mmol) in o-xylene (25 ml) was added phosphorus pentasulfide (5.3 mmol, $P_4S_{10}$). The reaction mixture was refluxed until all starting material was consumed (TLC monitoring) whereupon the mixture was cooled down to room temperature. The reaction was quenched by adding potassium carbonate (32 mmol) and the mixture was stirred at room temperature for one additional hour. The precipitate was filtered off and the solids were extensively washed with water and subsequently dried. Next, the solids were dissolved in pyridine (20 ml) and piperazine (17.8 mmol), ammonium sulfate (36 mg), p-toluenesulfonic acid (36 mg) and 1,1,1,3,3,3-hexamethyldisilazane (3.6 ml) were added. The reaction mixture was refluxed for 24 hours after which the solvent was evaporated in vacuo. The resulting residue was purified by flash chromatography on silica, the mobile phase being a mixture of methanol and dichloromethane (in a ratio gradually ranging from 100% $CH_2Cl_2$ to 5% $CH_3OH$ in $CH_2Cl_2$), yielding the pure title compound (656 mg) which was characterized by its mass spectrum: MS m/z (%): 347 ($[M+H]^+$, 100).

Examples 154-156

Synthesis of 5-amino-2-(2-thiophen-2-ylethyl)-7-(4-acylpiperazin-1-yl)thiazolo[5,4-d]pyrimidine General Procedure To a solution of 5-amine-7-piperazin-1-yl-2-(2-thiophen-2-yl-ethyl)-thiazolo[5,4-d]pyrimidine (example 154, 50 mg, 0.14 mmol) in dichloromethane (3 ml) was added diisopropylethylamine (35 mmol) and an acyl chloride (0.17 mmol). The reaction mixture was stirred at room temperature for 16 hours whereupon the solvent was removed in vacuo. The resulting residue was purified by flash chromatography on silica, the mobile phase being a mixture of methanol and dichloromethane (in a ratio gradually ranging from 100% $CH_2Cl_2$ to 1% $CH_3OH$ in $CH_2Cl_2$), yielding the pure title compounds which were characterized by their mass spectra as indicated below.

The following compounds were synthesized according to this procedure:

Example 154

Synthesis of 5-amino-2-(2-thiophen-2-ylethyl)-7-(4-[2-(4-chloro-phenoxy)acetyl]piperazin-1-yl)thiazolo[5,4-d]pyrimidine This compound was obtained from 4-chlorophenoxyacetyl chloride (31 mg). MS m/z (%): 515 ($[M+H]^+$, 100).

Example 155

Synthesis of 5-amino-2-(2-thiophen-2-ylethyl)-7-(4-[2-(4-chloro-phenyl)acetyl]piperazin-1-yl)thiazolo[5,4-d]pyrimidine This compound was obtained from 4-chlorophenylacetic chloride (23 mg).
MS m/z (%): 499 ($[M+H]^+$, 100).

Example 156

Synthesis of 5-amino-2-(2-thiophen-2-ylethyl)-7-(4-(4-chloro-benzoyl)piperazin-1-yl)thiazolo[5,4-d]pyrimidine This compound was obtained from 4-chlorobenzoyl chloride (29 mg).

MS m/z (%): 485 ([M+H]$^+$, 100).

Example 157

Synthesis of 5-amino-2-(2-thiophen-2-ylethyl)-7-(4-m-tolylcarbamoylpiperazin-1-yl)thiazolo[5,4-d]pyrimidine To a solution of 5-amine-7-piperazin-1-yl-2-(2-thiophen-2-yl-ethyl)-thiazolo[5,4-d]pyrimidine (50 mg, 0.14 mmol) in dichloromethane (3 ml) was added 3-methylphenylisocyanate (0.17 mmol). The reaction mixture was stirred at room temperature for 16 hours whereupon the solvent was removed in vacuo. The resulting residue was purified by flash chromatography on silica, the mobile phase being a mixture of methanol and dichloromethane (in a ratio gradually ranging from 100% CH$_2$Cl$_2$ to 0.5% CH$_3$OH in CH$_2$Cl$_2$), yielding the pure title compound (33 mg) which was characterized by its mass spectrum: MS m/z (%): 480 ([M+H]$^+$, 100).

Example 158

Synthesis of N-(4,6-dihydroxypyrimidin-5-yl)-4-fluorobenzamide

Formamidine acetate (0.46 g, 4.46 mmol) and dimethyl 2-(4-fluorobenzamido)malonate (1.0 g, 3.71 mmol) were added to a solution of sodium (0.17 g, 7.43 mmol) in ethanol (37 ml). The reaction mixture was refluxed for 3 hours. After cooling down, the precipitate was filtered off and washed with ethanol. The product was dissolved in a minimal volume of water and acidified to pH 4-5 with 5M HCl. The precipitate was collected, washed with water and dried to yield the title compound as a white solid (0.60 g, 64%).

$^1$H NMR (300 MHz, DMSO, 25° C.): δ=12.03 (s, 2H, OH), 9.25 (s, 1H, CH), 8.01-8.05 (m, 3H, PhH, NH), 7.32 (t, J=8.3 Hz, 2H, PhH) ppm.

MS: 247.8 [M–H]

Example 159

Synthesis of N-(4,6-dihydroxypyrimidin-5-yl)-2-(4-fluorophenyl)acetamide

This compound was prepared from example 2 in a yield of 24%, according to the procedure for the synthesis of example 158.

$^1$H NMR (300 MHz, DMSO, 25° C.): δ=12.00 (s, 2H, OH), 9.09 (s, 1H, NH), 7.97 (s, 1H, CH), 7.33-7.37 (m, 2H, PhH), 7.12 (t, J=8.6 Hz, 2H, PhH), 3.59 (s, 2H, CH$_2$) ppm.

HRMS: calcd for C$_{12}$H$_{11}$FN$_3$O$_3$ 264.07844, found 264.07769.

Example 160

Synthesis of N-(4,6-dihydroxy-2-methyl-pyrimidin-5-yl)-2-(4-fluorophenyl)acetamide This compound was prepared from example 2 in a yield of 29%, according to the procedure for the synthesis of example 9.

$^1$H NMR (300 MHz, DMSO, 25° C.): δ=11.97 (s, 2H, OH), 8.89 (s, 1H, NH), 7.32-7.37 (m, 2H, PhH), 7.12 (t, J=8.6 Hz, 2H, PhH), 3.56 (s, 2H, CH$_2$), 2.24 (s, 3H, CH$_3$) ppm.

HRMS: calcd for C$_{13}$H$_{13}$FN$_3$O$_3$ 278.09409, found 278.09331.

Example 161

Synthesis of 7-chloro-2-(4-fluorophenyl)-oxazolo[5,4-d]pyrimidine

To a solution of N-(4,6-dihydroxypyrimidin-5-yl)-4-fluorobenzamide (0.30 g, 1.20 mmol) in POCl$_3$ (6 ml) was added diisopropylethylamine (0.42 ml, 2.41 mmol). The reaction mixture was stirred under N$_2$ at 90° C. for 3.5 hours. The reaction mixture was allowed to cool down to room temperature and the volatiles were evaporated to dryness. The residue was diluted with water and the aqueous phase was extracted with diethyl ether. The combined organic layers were washed with a saturated NaHCO$_3$ solution and brine, dried over Na$_2$SO$_4$, and concentrated under reduced pressure. The residue was purified by chromatography on silica gel (CH$_2$Cl$_2$/MeOH 100:1) to yield the title compound as a white solid (0.13 g, 30%).

$^1$H NMR (300 MHz, CDCl$_3$, 25° C.): δ=8.64 (s, 1H, CH), 8.23-8.27 (m, 2H, PhH), 7.25 (t, J=8.2 Hz, 2H, PhH) ppm.

Example 162

Synthesis of 7-chloro-2-(4-fluorophenyl)-5-methyloxazolo[5,4-d]pyrimidine

This compound was prepared from example 9 in a yield of 40%, according to the procedure for the synthesis of example 161.

$^1$H NMR (300 MHz, CDCl$_3$, 25° C.): δ=8.28-8.33 (m, 2H, PhH), 7.26 (t, J=8.6 Hz, 2H, PhH), 2.84 (s, 3H, CH$_3$) ppm.

HRMS: calcd for C$_{12}$H$_8$ClFN$_3$O 264.03399, found 264.03318.

Example 163

Synthesis of 7-chloro-2-(4-fluorophenyl)-oxazolo[5,4-d]pyrimidin-5-amine

This compound was prepared from example 5 in a yield of 28%, according to the procedure for the synthesis of example 161.

$^1$H NMR (300 MHz, DMSO, 25° C.): δ=8.13-8.18 (m, 2H, PhH), 7.48 (s, 2H, NH$_2$), 7.45 (t, J=8.9 Hz, 2H, PhH) ppm.

HRMS: calcd for C$_{11}$H$_7$ClFN$_4$O 265.02924, found 265.02851.

Example 164

Synthesis of 7-chloro-2-(4-fluorobenzyl)-oxazolo[5,4-d]pyrimidine

This compound was prepared from example 159 in a yield of 73%, according to the procedure for the synthesis of example 160.

¹H NMR (300 MHz, CDCl₃, 25° C.): δ=8.77 (s, 1H, CH), 7.36-7.41 (m, 2H, PhH), 7.06 (t, J=8.6 Hz, 2H, PhH), 4.32 (s, 2H, CH₂) ppm.

HRMS: calcd for $C_{12}H_8ClFN_3O$ 264.03399, found 264.03349.

Example 165

Synthesis of 7-chloro-2-(4-fluorobenzyl)-5-methyl-oxazolo[5,4-d]pyrimidine

This compound was prepared from example 159 in a yield of 40%, according to the procedure for the synthesis of example 161.

¹H NMR (300 MHz, CDCl₃, 25° C.): δ=7.35-7.40 (m, 2H, PhH), 7.08 (t, J=8.6 Hz, 2H, PhH), 4.14 (s, 2H, CH₂), 2.68 (s, 3H, CH₃) ppm.

Example 166

Synthesis of 7-chloro-2-(4-fluorophenethyl)-oxazolo[5,4-d]pyrimidin-5-amine

This compound was prepared from example 7 in a yield of 34%, according to the procedure for the synthesis of example 161.

¹H NMR (300 MHz, DMSO, 25° C.): δ=7.28-7.33 (m, 2H, PhH), 7.10 (t, J=8.8 Hz, 2H, PhH), 6.43 (s, 2H, NH₂), 3.16 (br s, 4H, CH₂CH₂) ppm.

Example 167

Synthesis of 2-(4-chlorophenoxy)-1-(4-(2-(4-fluorophenyl)oxazolo[5,4-d]pyrimidin-7-yl)piperazin-1-yl)ethanone This compound was prepared from example 161 in a yield of 60%, according to the procedure for the synthesis of example 47.

¹H NMR (300 MHz, CDCl₃, 25° C.): δ=8.34 (s, 1H, CH), 7.90-7.94 (m, 2H, PhH), 7.18-7.24 (m, 4H, PhH), 6.83 (d, J=6.8 Hz, 2H, PhH), 4.66 (s, 2H, CH₂), 3.77 (br s, 2H, NCH₂), 3.68 (br s, 2H, NCH₂), 3.65 (s, 4H, CON(CH2) ppm.

HRMS: calcd for $C_{23}H_{21}ClFN_6O_3$ 483.13477, found 483.13334.

Example 168

Synthesis of 2-(4-chlorophenoxy)-1-(4-(2-(4-fluorophenyl)-5-methyl-oxazolo[5,4-d]pyrimidin-7-yl)piperazin-1-yl)ethanone This compound was prepared from example 162 in a yield of 93%, according to the procedure for the synthesis of example 47.

¹H NMR (300 MHz, CDCl₃, 25° C.): δ=8.13-8.18 (m, 2H, PhH), 7.27 (d, J=8.9 Hz, 2H, PhH), 7.20 (t, J=8.5 Hz, 2H, PhH), 6.93 (d, J=8.9 Hz, 2H, PhH), 4.76 (s, 2H, CH₂), 4.27 (br s, 4H, N(CH₂)₂), 3.78 (br s, 4H, CON(CH₂), 2.59 (s, 3H, CH₃) ppm.

HRMS: calcd for $C_{24}H_{22}ClFN_5O_3$ 482.13952, found 482.13800.

Example 169

Synthesis of 1-(4-(5-amino-2-(4-fluorophenyl)oxazolo[5,4-d]pyrimidin-7-yl)piperazin-1-yl)-2-(4-chlorophenoxy)ethanone This compound was prepared from example 163 in a yield of 55%, according to the procedure for the synthesis of example 47.

¹H NMR (300 MHz, CDCl₃, 25° C.): δ=8.03-8.08 (m, 2H, PhH), 7.40 (t, J=8.8 Hz, 2H, PhH), 7.33 (d, J=8.8 Hz, 2H, PhH), 6.98 (d, J=8.8 Hz, 2H, PhH), 6.54 (s, 2H, NH₂), 4.93 (s, 2H, CH₂), 4.19 (br s, 2H, NCH₂), 4.09 (br s, 2H, N(CH₂)₂), 3.62 (br s, 4H, CON(CH₂)₂) ppm.

HRMS: calcd for $C_{23}H_{21}ClFN_6O_3$ 483.13477, found 483.13367.

Example 170

Synthesis of 2-(4-chlorophenoxy)-1-(4-(2-(4-fluorobenzyl)oxazolo[5,4-d]pyrimidin-7-yl)piperazin-1-yl)ethanone This compound was prepared from example 164 in a yield of 58%, according to the procedure for the synthesis of example 47.

¹H NMR (300 MHz, CDCl₃, 25° C.): δ=8.33 (s, 1H, CH), 7.30-7.35 (m, 2H, PhH), 7.28 (d, J=6.8 Hz, 2H, PhH), 7.03 (t, J=8.7 Hz, 2H, PhH), 6.91 (d, J=6.8 Hz, 2H, PhH), 4.74 (s, 2H, OCH₂), 4.17 (s, 2H, CH₂), 4.17 (br s, 4H, N(CH₂)₂), 3.75 (br s, 4H, CON(CH₂)₂) ppm.

HRMS: calcd for $C_{24}H_{22}ClFN_5O_3$ 482.13952, found 482.13796.

Example 171

Synthesis of 2-(4-chlorophenoxy)-1-(4-(2-(4-fluorobenzyl)-5-methyloxazolo[5,4-d]pyrimidin-7-yl)piperazin-1-yl)ethanone This compound was prepared from example 165 in a yield of 68%, according to the procedure for the synthesis of example 47.

¹H NMR (300 MHz, CDCl₃, 25° C.): δ=7.25 (d, J=8.9 Hz, 2H, PhH), 7.10-7.15 (m, 2H, PhH), 6.99 (t, J=8.5 Hz, 2H, PhH), 6.86 (d, J=8.9 Hz, 2H, PhH), 4.67 (s, 2H, OCH₂), 3.66 (br s, 4H, N(CH₂)₂), 3.55 (s, 2H, CH₂), 3.53 (br s, 4H, CON(CH₂)₂), 2.61 (s, 3H, CH₃) ppm.

Example 172

Synthesis of 1-(4-(5-amino-2-(4-fluorophenethyl)oxazolo[5,4-d]pyrimidin-7-yl)piperazin-1-yl)-2-(4-chlorophenoxy)ethanone This compound was prepared from example 166 in a yield of 34%, according to the procedure for the synthesis of example 47.

¹H NMR (300 MHz, CDCl₃, 25° C.): δ=7.26 (d, J=8.9 Hz, 2H, PhH), 7.14-7.19 (m, 2H, PhH), 6.96 (t, J=8.7 Hz, 2H, PhH), 6.91 (d, J=8.9 Hz, 2H, PhH), 4.78 (s, 2H, NH₂), 4.73 (s, 2H, CH₂), 4.11 (br s, 4H, N(CH₂)₂), 3.68 (br s, 4H, CON(CH₂)₂), 3.07 (br s, 4H, CH₂CH₂) ppm.

Example 173

Synthesis of N-(3-chloro-4-fluorophenyl)-2-(4-fluorophenyl)-oxazolo[5,4-d]pyrimidin-7-amine To a solution of 7-chloro-2-(4-fluorophenyl)-oxazolo[5,4-d]pyrimidine (85 mg, 0.34 mmol) in 1,2-dichloroethane/t-BuOH (1:1, 2 ml) was added 3-chloro-4-fluoroaniline (50 mg, 0.34 mmol). The mixture was heated at 90° C. for 1 day. After cooling down to room temperature, the solvent was removed under reduced pressure. The crude residue was purified by silica gel chromatography ($CH_2Cl_2$/MeOH 50:1) to yield the title compound as a white solid (0.1 g, 82%).

$^1$H NMR (300 MHz, DMSO, 25° C.): δ=10.52 (s, 1H, NH), 8.55 (s, 1H, CH), 8.23-8.27 (m, 2H, PhH), 7.84-7.87 (m, 1H, PhH), 7.50 (t, J=8.8 Hz, 2H, PhH), 7.43 (t, J=9.1 Hz, 1H, PhH) ppm.

HRMS: calcd for $C_{17}H_{10}ClF_2N_4O$ 359.05112, found 359.05016.

Example 174

Synthesis of N-7-(3-chloro-4-fluorophenyl)-2-(4-fluorophenyl)-oxazolo[5,4-d]pyrimidine-5,7-diamine This compound was prepared from example 163 in a yield of 32%, according to the procedure for the synthesis of example 173.

$^1$H NMR (300 MHz, DMSO, 25° C.): δ=10.00 (s, 1H, NH), 8.22-8.26 (m, 1H, PhH), 8.08-8.12 (m, 2H, PhH), 7.95-7.99 (m, 1H, PhH), 7.44 (t, J=8.8 Hz, 2H, PhH), 7.35 (t, J=9.1 Hz, 1H, PhH), 6.81 (s, 2H, $NH_2$) ppm.

HRMS: calcd for $C_{17}H_{11}ClF_2N_5O$ 374.06202, found 374.06101.

Examples 175-179

Synthesis of 5-amino-7-chloro-2-substituted-oxazolo[5,4-d]pyrimidine analogues

General Procedure

To a suspension of a 2-amino-4,6-dihydroxy-5-substituted pyrimidine analogue (3.0 mmol) in toluene (20 ml) were added DIPEA (1.19 ml, 9 mmol) and $POCl_3$ (830 µl, 9 mmol) respectively. The resulting mixture was heated at 95° C. for 2 h. The solvents were evaporated in vacuo and purified by flash chromatography on silica, the mobile phase being a mixture of acetone and dichloromethane (in a ratio of 1/50), yielding the pure title compounds.

The following compounds were synthesized according to this procedure:

Example 175

Synthesis of 5-amino-7-chloro-2-cyclopropyloxazolo[5,4-d]pyrimidine

This compound was obtained from 2-amino-4,6-dihydroxy-5-(cyclopropanamido)pyrimidine (630 mg, 3.0 mmol) yielding the pure title compound (550 mg, 87%).

MS m/z (%): 211 ([M+H]$^+$, 100)

Example 176

Synthesis of 5-amino-7-chloro-2-methoxymethyloxazolo[5,4-d]pyrimidine

From 2-amino-4,6-dihydroxy-5-methoxyacetamidopyrimidine (642 mg, 3.0 mmol), yielding the pure title compound (430 mg, 67%).

MS m/z (%): 215 ([M+H]$^+$, 100)

Example 177

Synthesis of 5-amino-7-chloro-2-cyclohexyloxazolo[5,4-d]pyrimidine

From 2-amino-4,6-dihydroxy-5-cyclohexanecarboxamidopyrimidine (760 mg, 3.0 mmol), yielding the pure title compound (390 mg, 51%).

MS m/z (%): 253 ([M+H]$^+$, 100)

Example 178

Synthesis of 5-amino-7-chloro-2-pentyloxazolo[5,4-d]pyrimidine

From 2-amino-4,6-dihydroxy-5-hexanamidopyrimidine (720 mg, 3.0 mmol), yielding the pure title compound (480 mg, 67%).

MS m/z (%): 241 ([M+H]$^+$, 100)

Example 179

Synthesis of 5-amino-7-chloro-2-(2-phenylethyl)oxazolo[5,4-d]pyrimidine

From 2-amino-4,6-dihydroxy-5-phenylpropanamidopyrimidine (686 mg, 2.5 mmol), yielding the pure title compound (320 mg, 46%).

MS m/z (%): 276 ([M+H]$^+$, 100)

Examples 180-184

Synthesis of 5-amino-7-N-piperazino-2-substituted oxazolo[5,4-d]pyrimidine analogues General Procedure To a solution of the 5-amino-7-chloro-2-substituted oxazolo[5,4-d]pyrimidine (420 mg, 2.0 mmol) in dioxane (10 ml), was added piperazine (860 mg, 10 mmol). The resulting mixture was stirred at room temperature for 12 h. The mixture was evaporated in vacuo and purified by flash chromatography on silica, the mobile phase being a mixture of methanol and dichloromethane (in a ratio of 1/6), yielding the pure title compounds.

The following compounds were synthesized according to this general procedure:

Example 180

Synthesis of 5-amino-2-cyclopropyl-7-N-piperazino-oxazolo[5,4-d]pyrimidine

This compound was obtained in 92% yield from 5-amino-7-chloro-2-cyclopropyl-oxazolo[5,4-d]pyrimidine.

MS m/z (%): 261 ([M+H]$^+$, 100)

Example 181

Synthesis of 5-amino-2-methoxymethyl-7-N-piperazino-oxazolo[5,4-d]pyrimidine

This compound was obtained in 57% yield from 5-amino-7-chloro-2-methoxymethyl-oxazolo[5,4-d]pyrimidine.

MS m/z (%): 265 ([M+H]$^+$, 100)

Example 182

Synthesis of 5-amino-2-cyclohexyl-7-N-piperazino-oxazolo[5,4-d]pyrimidine

This compound was obtained in 97% yield from 5-amino-7-chloro-2-cyclohexyloxazolo[5,4-d]pyrimidine.
MS m/z (%): 303 ([M+H]$^+$, 100)

Example 183

Synthesis of 5-amino-2-pentyl-7-N-piperazino-oxazolo[5,4-d]pyrimidine

This compound was obtained in 86% yield from 5-amino-7-chloro-2-pentyloxazolo[5,4-d]pyrimidine.
MS m/z (%): 291 ([M+H]$^+$, 100)

Example 184

Synthesis of 5-amino-2-(2-phenylethyl)-7-N-piperazino-oxazolo[5,4-d]pyrimidine

This compound was obtained in 99% yield from 5-amino-7-chloro-2-(2-phenylethyl)oxazolo[5,4-d]pyrimidine.
MS m/z (%): 325 ([M+H]$^+$, 100)

Examples 185-189

Synthesis of 5-amino-2-substituted-7-[4-(4-chlorophenoxyacetyl)piperazin-1-yl]-oxazolo[5,4-d]pyrimidine analogues General Procedure To a solution of a 5-amino-2-substituted-7-N-piperazino-oxazolo[5,4-d]pyrimidine analogue (1.0 mmol) in dioxane (10 ml), was added DIPEA (330 µl, 2.0 mmol) and 4-chlorophenoxyacetyl chloride (246 mg, 1.2 mmol), respectively. The resulting mixture was stirred at room temperature for 30 minutes. The solvents were evaporated in vacuo and purified by flash chromatography on silica, the mobile phase being a mixture of methanol and dichloromethane (in a ratio of 1/40), yielding the pure title compounds.

The following compounds were synthesized according to this procedure:

Example 185

Synthesis of 5-amino-2-cyclopropyl-7-[4-(4-chlorophenoxyacetyl)piperazin-1-yl]-oxazolo[5,4-d]pyrimidine This compound was synthesized from 5-amino-2-cyclopropyl-7-N-piperazino-oxazolo[5,4-d]pyrimidine in 93% yield.
MS m/z (%): 429 ([M+H]$^+$, 100)

Example 186

Synthesis of 5-amino-7-[4-(4-chlorophenoxyacetyl) piperazin-1-yl]-2-methoxylmethyloxazolo[5,4-d] pyrimidine This compound was synthesized from 5-amino-2-methoxymethyl-7-N-piperazino-oxazolo[5,4-d]pyrimidine in 60% yield.
MS m/z (%): 433 ([M+H]$^+$, 100)

Example 187

Synthesis of 5-amino-2-cyclohexyl-7-[4-(4-chlorophenoxyacetyl)piperazin-1-yl]oxazolo[5,4-d]pyrimidine This compound was synthesized from 5-amino-2-cyclohexyl-7-N-piperazino-oxazolo[5,4-d]pyrimidine in 73% yield.
MS m/z (%): 471 ([M+H]$^+$, 100)

Example 188

Synthesis of 5-amino-7-[4-(4-chlorophenoxyacetyl) piperazin-1-yl]-2-pentyloxazolo[5,4-d]pyrimidine This compound was synthesized from 5-amino-2-pentyl-7-N-piperazino-oxazolo[5,4-d]pyrimidine in 71% yield.
MS m/z (%): 459 ([M+H]$^+$, 100)

Example 189

Synthesis of 5-amino-2-(2-phenylethyl)-7-[4-(4-chlorophenoxyacetyl)piperazin-1-yl]oxazolo[5,4-d] pyrimidine This compound was synthesized from 5-amino-2-pentyl-7-N-piperazino-oxazolo[5,4-d]pyrimidine in 85% yield.
MS m/z (%): 493 ([M+H]$^+$, 100)

Examples 190-192

Synthesis of 5-amino-2-(4-fluorophenyl)-7-piperazin-1-yl-oxazolo[5,4-d]pyrimidine analogues General Procedure To a solution of 5-amino-7-chloro-2-(4-fluorophenyl)-oxazolo[5,4-d]pyrimidine X (50 mg, 0.19 mmol) in dioxane (5 ml) was added diisopropylethylamine (0.28 mmol, 47 µL) and a piperazine derivative (0.28 mmol). The reaction was stirred at 70° C. for 6 hours after which the solvent was removed in vacuo. The resulting residue was purified by flash chromatography on silica, the mobile phase being a mixture of methanol and dichloromethane (in a ratio gradually ranging from 100% CH$_2$Cl$_2$ to 2% CH$_3$OH in CH$_2$Cl$_2$), yielding the pure title compounds which were characterized by their mass spectra as indicated below:

The following compounds were synthesized according to this procedure:

Example 190

Synthesis of 5-amino-2-(4-fluorophenyl)-7-(4-isobutylpiperazin-1-yl)-oxazolo[5,4-d]pyrimidine This compound was obtained from 1-isobutyl-piperazine (32 mg);
MS m/z (%): 371 ([M+H]$^+$, 100).

Example 191

Synthesis of 5-amino-2-(4-fluorophenyl)-7-(4-acetyl piperazin-1-yl)-oxazolo[5,4-d]pyrimidine This compound was obtained from 1-acetyl piperazine (27 mg).
MS m/z (%): 357 ([M+H]$^+$, 100).

Example 192

Synthesis of 5-amino-2-(4-fluorophenyl)-7-[4-(2-methoxyethyl)-piperazin-1-yl]-oxazolo[5,4-d]pyrimidine This compound was obtained from 1-(2-methoxyethyl)piperazine (30 mg).
MS m/z (%): 373 ([M+H]$^+$, 100).

Example 193

Synthesis of 5-amino-2-(4-fluorophenyl)-7-(4-[2-(3-nitrophenoxy)acetyl]-piperazin-1-yl)-oxazolo[5,4-d]pyrimidine To a solution of 5-amino-2-(4-fluorophenyl)-7-piperazin-1-yl-oxazolo[5,4-d]pyrimidine (50 mg, 0.15 mmol) and 2-(3-nitrophenoxy)acetic acid (0.22 mmol) in DMF (2 ml) was added TBTU (0.22 mmol) followed by diisopropylethylamine (0.22 mmol, 36 µL). The reaction was stirred at room temperature for 24 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 1% $CH_3OH$ in $CH_2Cl_2$), yielding the pure title compound which was characterized by its mass spectrum: MS m/z (%): 522 ([M+H]$^+$, 100).

Examples 194-195

Synthesis of 5-amino-2-[2-(4-fluorophenyl)ethyl]-7-(4-[2-alkylacetyl]piperazin-1-yl)-oxazolo[5,4-d]pyrimidine General Procedure To a solution of 5-amino-2-(4-fluorophenyl)-7-piperazin-1-yl-oxazolo[5,4-d]pyrimidine (50 mg, 0.15 mmol) in dichloromethane (4 ml) was added diisopropylethylamine (0.32 mmol, 53 µL) followed by an acyl chloride (0.16 mmol). The reaction was stirred at room temperature for 16 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 1% $CH_3OH$ in $CH_2Cl_2$), yielding the pure title compounds which were characterized by their mass spectra as indicated below.

The following compounds were synthesized according to this procedure:

Example 194

Synthesis of 5-amino-2-[2-(4-fluorophenyl)ethyl]-7-(4-[2-(4-chlorophenyl)acetyl]-piperazin-1-yl)-oxazolo[5,4-d]pyrimidine This compound was obtained from 4-chlorophenylacetyl chloride (57 mg);
MS m/z (%): 495 ([M+H]$^+$, 100).

Example 195

Synthesis of 5-amino-2-[2-(4-fluorophenyl)ethyl]-7-(4-[4-chlorobenzoyl]piperazin-1-yl)-oxazolo[5,4-d]pyrimidine This compound was obtained from 4-chlorobenzoyl chloride (62 mg).
MS m/z (%): 481 ([M+H]$^+$, 100).

Example 196

Synthesis of 5-amino-2-[2-(4-fluorophenyl)ethyl]-7-(4-m-tolylcarbamoylpiperazin-1-yl)-oxazolo[5,4-d]pyrimidine To a solution of 5-amino-2-[2-(4-fluorophenyl)ethyl]-7-piperazin-1-yl-oxazolo[5,4-d]pyrimidine (50 mg, 0.15 mmol) in dichloromethane (4 ml) was added 3-methylphenylisocyanate (0.16 mmol). The reaction was stirred at room temperature for 2 hours after which the solvent was removed in vacuo. The resulting residue was purified by flash chromatography on silica, the mobile phase being a mixture of methanol and dichloromethane (in a ratio gradually ranging from 100% $CH_2Cl_2$ to 2% $CH_3OH$ in $CH_2Cl_2$), yielding the pure title compound (30 mg) which was characterized by its mass spectrum: MS m/z (%): 476 ([M+H]$^+$, 100).

Examples 197-198

Synthesis of 5-amino-2-[2-(4-fluorophenyl)ethyl]-7-(4-alkylpiperazin-1-yl)-oxazolo[5,4-d]pyrimidine analogues General Procedure To a solution of 5-amino-2-[2-(4-fluorophenyl)ethyl]-6H-oxazolo[5,4-d]pyrimidin-7-one (50 mg, 0.18 mmol) in DMF (2 ml) was added DBU (0.27 mmol), BOP (0.23 mmol) and a piperazine derivative (0.23 mmol). The reaction mixture was stirred at room temperature for 16 hours whereupon the solvent was removed in vacuo. The resulting residue was purified by flash chromatography on silica, the mobile phase being a mixture of methanol and dichloromethane (in a ratio gradually ranging from 100% $CH_2Cl_2$ to 2% $CH_3OH$ in $CH_2Cl_2$), yielding the pure title compounds which were characterized by their mass spectra as indicated below.

The following compounds were made according to this general procedure:

Example 197

Synthesis of 5-amino-2-[2-(4-fluorophenyl)ethyl]-7-(4-(2-phenoxyethyl)piperazin-1-yl)-oxazolo[5,4-d]pyrimidine This compound was obtained from 1-(2-phenoxyethyl)-piperazine (57 mg).
MS m/z (%): 463 ([M+H]$^+$, 100).

Example 198

Synthesis of 5-amino-2-[2-(4-fluorophenyl)ethyl]-7-(4-[(methylphenyl-carbamoyl)methyl]piperazin-1-yl)-oxazolo[5,4-d]pyrimidine This compound was obtained from N-methyl-N-phenyl-2-piperazin-1-yl-acetamide (27 mg).
MS m/z (%): 371 ([M+H]$^+$, 100).

Examples 199-201

Synthesis of 2-amino-5-acylamino-4,6-dihydroxypyrimidine analogues

General Procedure

To a solution of 2,5-diamino-4,6-dihydroxypyrimidine (1 g, 5.6 mmol) in water (15 ml) was added sodium hydroxide (17 mmol, 672 mg) and an appropriate acid chloride (6.72 mmol) at 0° C. The reaction was then stirred at room temperature for 3 hours. The reaction mixture was acidified till pH=5. A light pink precipitate was formed, which was filtered off yielding the pure title compounds, in yields varying from 85-95%.

The following compounds were made according to this procedure:

Example 199

Synthesis of 2-amino-5-benzamido-4,6-dihydroxypyrimidine

This compound was synthesized according to the general procedure using benzoyl chloride.

$^1$H NMR (300 MHz, DMSO): δ=10.82 (br s, 2H, 2×OH), 8.73 (s, 1H, arom H), 7.9 (m, 2H, arom H), 7.45 (m, 3H, arom H), 6.97 (br s, 2H, NH$_2$) ppm.

Example 200

Synthesis of 2-amino-5-(2-furancarboxamido)-4,6-dihydroxypyrimidine

This compound was synthesized according to the general procedure using 2-furoyl chloride $^1$H NMR (300 MHz, DMSO): δ=10.67 (br s, 2H, 2×OH), 8.56 (s, 1H, arom H), 7.81 (s, 1H, arom H), 7.16 (s, 1H, arom H), 6.65 (br s, 2H, NH$_2$) ppm.

Example 201

Synthesis of 2-amino-5-(4-fluorobenzamido)-4,6-dihydroxypyrimidine

This compound was synthesized according to the general procedure using 4-fluorobenzoyl chloride

Examples 202-204

Synthesis of 5-amino-2-substituted-thiazolo[5,4-d]pyrimidine-7-thiol analogues General Procedure A suspension of the appropriate 2-amino-4,6-dihydroxy-5-(acylamino)pyrimidine analogue (4.24 mmol) and P$_2$S$_5$ (8.47 mmol, 3.77 g) in pyridine (20 ml) was heated under reflux for 12 hours. After concentration under reduced pressure, the residue was resuspended in water (15 ml). Potassium carbonate (1.76 g, 13 mmol) was added and the mixture was stirred at room temperature for 1 h. The precipitate was collected by filtration and washed with water, yielding the crude title compound which was used without further purification.

The following compounds were synthesized according to this procedure:

Example 202

Synthesis of 5-amino-2-phenyl-thiazolo[5,4-d]pyrimidine-7-thiol

This compound was synthesized from 2-amino-5-benzamido-4,6-dihydroxypyrimidine

Example 203

Synthesis of 5-amino-2-(2-fury))-thiazolo[5,4-d]pyrimidine-7-thiol

This compound was synthesized from 2-amino-5-(2-furancarboxamido)-4,6-dihydroxypyrimidine

Example 204

Synthesis of 5-amino-2-(4-fluoro-phenyl)-thiazolo[5,4-d]pyrimidine-7-thiol

This compound was synthesized from 2-amino-5-(4-fluorobenzamido)-4,6-dihydroxypyrimidine

Examples 205-207

Synthesis of 5-amino-7-N-piperazinyl-2-substituted-thiazolo[5,4-d]pyrimidine analogues General Procedure To a solution of a 5-amino-2-substituted-thiazolo[5,4-d]pyrimidine-7-thiol analogue (3.37 mmol) in pyridine (20 ml) was added 1,1,1,3,3,3-hexamethyldisilazane (HMDS, 6.1 ml) and piperazine (33.7 mmol, 2.9 g). The reaction mixture was refluxed overnight. After cooling down to room temperature, the solvents were evaporated in vacuo. The residue was adsorbed on silica and purified by silica gel flash chromatography, the mobile phase being a mixture of methanol and dichloromethane (in a gradient gradually raising from 8% to 9% methanol in dichloromethane), yielding the title compounds as yellow powders, in yields ranging from 40-50%.

The following compounds were made according to this procedure:

Example 205

Synthesis of 5-amino-2-phenyl-7-N-piperazinyl-thiazolo[5,4-d]pyrimidine

This compound was synthesized from 5-amino-2-phenyl-thiazolo[5,4-d]pyrimidine-7-thiol.

Example 206

Synthesis of 5-amino-2-(2-furyl)-7-N-piperazinyl-thiazolo[5,4-d]pyrimidine

This compound was synthesized from 5-amino-2-(2-fury))-thiazolo[5,4-d]pyrimidine-7-thiol.

Example 207

Synthesis of 5-amino-2-(4-fluoro-phenyl)-7-N-piperazinyl-thiazolo[5,4-d]pyrimidine This compound was synthesized from 5-amino-2-(4-fluoro-phenyl)-thiazolo[5,4-d]pyrimidine-7-thiol.

Examples 208-214

Synthesis of 5-amino-7-N-(acylpiperazinyl)-2-substituted-thiazolo[5,4-d]pyrimidine analogues General Procedure To a solution of a 5-amino-7-N-piperazinyl-2-substituted-thiazolo[5,4-d]pyrimidine analogue (0.65 mmol) in DMF (10 ml) was added diisopropylamine (1.3 mmol, 215 µl), O-(benzotriazol-1-yl)-N,N,N',N'-tetramethyluronium tetrafluoroborate (TBTU, 0.78 mmol, 251 mg) and an appropriate carboxylic acid (0.78 mmol). The reaction was stirred at room temperature for 2 hours. An extraction was carried out (water/dichloromethane) and the solvents were evaporated in vacuo. The residue was purified by silica gel flash chromatography, the mobile phase being a mixture of methanol and dichloromethane (in a ratio gradually raising from 1% to 1.5% methanol in dichloromethane), yielding pure final compounds in yields varying from 70 to 80%.

The following compounds were made according to this procedure:

Example 208

Synthesis of 1-(4-(5-amino-2-phenylthiazolo[5,4-d]pyrimidin-7-yl)piperazin-1-yl)-2-(4-methoxyphenoxy)ethanone This compound was obtained from 5-amino-2-phenyl-7-N-piperazinyl-thiazolo[5,4-d]pyrimidine and 4-methoxy-phenoxyacetic acid.

$^1$H NMR (300 MHz, DMSO): δ=7.91 (m, 2H, arom H), 7.49 (m, 3H, arom H), 6.87 (q, 4H, arom H), 6.51 (br s, 2H, NH$_2$), 4.81 (s, 2H, CH$_2$), 4.36 (br s, 2H, piperazine H), 4.21 (br s, 2H, piperazine H), 3.68 (s, 3H, OCH$_3$), 3.62 (br s, 4H, piperazine H) ppm.

Example 209

Synthesis of 1-(4-(5-amino-2-(furan-2-yl)thiazolo[5,4-d]pyrimidin-7-yl)piperazin-1-yl)-2-(4-fluorophenoxy)ethanone This compound was obtained from 5-amino-2-(2-furyl)-7-N-piperazinyl-thiazolo[5,4-d]pyrimidine and 4-fluoro-phenoxyacetic acid.

$^1$H NMR (300 MHz, DMSO): δ=7.91 (s, 1H, arom H), 7.10-7.14 (m, 3H, arom H), 6.96-6.98 (m, 2H, arom H), 6.72 (q, 1H, arom H), 6.52 (br s, 2H, NH$_2$), 4.89 (s, 2H, CH$_2$), 4.33*br s, 2H, piperazine H), 4.19 (br s, 2H, piperazine H), 3.62 (br s, 4H, piperazine H) ppm.

Example 210

Synthesis of 1-(4-(5-amino-2-(furan-2-yl)thiazolo[5,4-d]pyrimidin-7-yl)piperazin-1-yl)-2-(m-tolyloxy)ethanone This compound was obtained from 5-amino-2-(2-furyl)-7-N-piperazinyl-thiazolo[5,4-d]pyrimidine and 3-methyl-phenoxyacetic acid.

$^1$H NMR (300 MHz, DMSO): δ=7.89 (s, 1H, arom H), 7.13-7.16 (m, 2H, arom H), 6.72-6.78 (m, 4H, arom H), 6.49 (br s, 2H, NH$_2$), 4.85 (s, 2H, CH$_2$), 4.32 (br s, 2H, piperazine H), 4.18 (br s, 2H, piperazine H), 3.63 (br s, 4H, piperazine H), 2.27 (s, 3H, CH$_3$) ppm.

Example 211

Synthesis of 1-(4-(5-amino-2-(4-fluorophenyl)thiazolo[5,4-d]pyrimidin-7-yl)piperazin-1-yl)-2-(m-tolyloxy)ethanone This compound was obtained from 5-amino-2-(4-fluoro-phenyl)-7-N-piperazinyl-thiazolo[5,4-d]pyrimidine and 3-methyl-phenoxyacetic acid.

$^1$H NMR (300 MHz, DMSO): δ=7.96-8.00 (m, 2H, arom H), 7.36 (t, 2H, arom H), 7.16 (t, 1H, arom H), 6.76-6.79 (m, 3H, arom H), 6.51 (br s, 2H, NH$_2$), 4.86 (s, 2H, CH$_2$), 4.35 (br s, 2H, piperazine H), 4.22 (br s, 2H, piperazine H), 3.65 (br s, 4H, piperazine H), 2.28 (s, 3H, CH$_3$) ppm.

Example 212

Synthesis of 1-(4-(5-amino-2-(4-fluorophenyl)thiazolo[5,4-d]pyrimidin-7-yl)piperazin-1-yl)-2-(2,4-dichlorophenoxy)ethanone This compound was obtained from 5-amino-2-(4-fluoro-phenyl)-7-N-piperazinyl-thiazolo[5,4-d]pyrimidine and 2,4-dichloro-phenoxyacetic acid.

$^1$H NMR (300 MHz, DMSO): δ=7.95-8.00 (m, 2H, arom H), 7.58 (d, 2H, arom H), 7.36 (m, 3H, arom H), 7.01 (d, 1H, arom H), 6.52 (br s, 2H, NH$_2$), 5.09 (s, 2H, CH$_2$), 4.36 (br s, 2H, piperazine H), 4.22 (br s, 2H, piperazine H), 3.64 (br s, 4H, piperazine H) ppm.

Example 213

Synthesis of 1-(4-(5-amino-2-(4-fluorophenyl)thiazolo[5,4-d]pyrimidin-7-yl)piperazin-1-yl)-2-(4-chloro-2-methylphenoxy)ethanone This compound was obtained from 5-amino-2-(4-fluoro-phenyl)-7-N-piperazinyl-thiazolo[5,4-d]pyrimidine and 4-chloro-o-tolyl-oxyacetic acid.

$^1$H NMR (300 MHz, DMSO): δ=7.95-8.00 (m, 2H, arom H), 7.33-7.39 (t, 2H, arom H), 7.16-7.23 (m, 2H, arom H), 6.90 (d, 1H, arom H), 6.51 (br s, 2H, NH$_2$), 4.94 (s, 2H, CH$_2$), 4.35 (br s, 2H, piperazine H), 4.22 (br s, 2H, piperazine H), 3.64 (br s, 4H, piperazine H), 2.20 (s, 3H, CH$_3$) ppm.

Example 214

Synthesis of 1-(4-(5-amino-2-(4-fluorophenyl)thiazolo[5,4-d]pyrimidin-7-yl)piperazin-1-yl)-2-(3-chlorophenoxy)ethanone This compound was obtained from 5-amino-2-(4-fluoro-phenyl)-7-N-piperazinyl-thiazolo[5,4-d]pyrimidine and 3-chloro-phenoxyacetic acid.

$^1$H NMR (300 MHz, DMSO): δ=7.97 (m, 2H, arom H), 7.36 (m, 3H, arom H), 6.93-6.99 (m, 3H, arom H), 6.51 (br s, 2H, arom H), 4.96 (s, 2H, CH$_2$), 4.36 (br s, 2H, piperazine H), 4.23 (br s, 2H, piperazine H), 3.64 (br s, 4H, piperazine H) ppm.

Example 215

Synthesis of 1-(4-(5-amino-2-phenylthiazolo[5,4-d]pyrimidin-7-yl)piperazin-1-yl)-2-(4-chlorophenoxy)ethanone To a solution of 5-amino-2-phenyl-7-N-piperazinyl-thiazolo[5,4-d]pyrimidine (90 mg, 0.28 mmol) in dioxane (5 ml) was added triethylamine (0.86 mmol, 120 µl) and 4-chlorophenoxyacetyl chloride (0.35 mmol, 71 mg). The reaction was stirred at room temperature for 2 hours. The solvents were evaporated and the residue was purified by silica gel flash chromatography, the mobile phase being a mixture of methanol and dichloromethane (in a ratio gradually raising from 1% to 2% methanol in dichloromethane), yielding the pure title compound.

$^1$H NMR (300 MHz, DMSO): δ=7.92 (m, 2H, arom H), 7.51 (m, 3H, arom H), 7.32-7.35 (m, 2H, arom H), 6.97-7.00 (m, 2H, arom H), 6.51 (br s, 2H, arom H), 4.93 (s, 2H, $CH_2$), 4.38 (br s, 2H, piperazine H), 4.22 (br s, 2H, piperazine H), 3.64 (br s, 4H, piperazine H) ppm.

Examples 216-220

Synthesis of 5-amino-7-N-(carbamoylpiperazinyl)-2-substituted-thiazolo[5,4-d]pyrimidine analogues General Procedure To a solution of a 5-amino-7-N-piperazinyl-2-substituted-thiazolo[5,4-d]pyrimidine analogue (0.61 mmol) in DMF (10 ml) was added diisopropylamine (1.2 mmol, 200 µl) and an appropriate isocyanate (0.91 mmol). The reaction was stirred at room temperature for 2 hours. The solvents were evaporated in vacuo. The residue was purified by silica gel flash chromatography, the mobile phase being a mixture of methanol and dichloromethane (in a ratio gradually raising from 1% to 1.5% methanol in dichloromethane), yielding pure final compounds in yields varying from 70 to 80%.

The following compounds were made according to this procedure:

Example 216

Synthesis of 4-(5-amino-2-(4-fluorophenyl)thiazolo[5,4-d]pyrimidin-7-yl)-N-(4-cyanophenyl)piperazine-1-carboxamide This compound was obtained from 5-amino-2-(4-fluorophenyl)-7-N-piperazinyl-thiazolo[5,4-d]pyrimidine and 4-cyanophenylisocyanate.

$^1$H NMR (300 MHz, DMSO): δ=9.08 (s, 1H, NH), 7.95-7.99 (m, 2H, arom H), 7.70 (s, 4H, arom H), 7.37 (t, 2H, arom H), 6.51 (br s, 2H, $NH_2$), 4.31 (br s, 4H, piperazine H), 3.66 (br s, 4H, piperazine H) ppm.

Example 217

Synthesis of 4-(5-amino-2-(4-fluorophenyl)thiazolo[5,4-d]pyrimidin-7-yl)-N-(2,4-difluorophenyl)piperazine-1-carboxamide This compound was obtained from 5-amino-2-(4-fluorophenyl)-7-N-piperazinyl-thiazolo[5,4-d]pyrimidine and 2,4-difluoro-phenylisocyanate.

$^1$H NMR (300 MHz, DMSO): δ=8.40 (s, 1H, NH), 7.97 (m, 2H, arom H), 7.36 (m, 5H, arom H), 7.04 (m, 1H, arom H), 6.50 (br s, 2H, $NH_2$), 4.30 (br s, 4H, piperazine H), 3.62 (br s, 4H, piperazine H) ppm.

Example 218

Synthesis of 4-(5-amino-2-(4-fluorophenyl)thiazolo[5,4-d]pyrimidin-7-yl)-N-(4-bromophenyl)piperazine-1-carboxamide This compound was obtained from 5-amino-2-(4-fluorophenyl)-7-N-piperazinyl-thiazolo[5,4-d]pyrimidine and 4-bromo-phenylisocyanate.

$^1$H NMR (300 MHz, DMSO): δ=8.72 (s, 1H, NH), 7.95-7.98 (m, 2H, arom H), 7.43-7.48 (m, 6H, arom H), 6.49 (br s, 2H, $NH_2$), 4.30 (br s, 4H, piperazine H), 3.63 (br s, 4H, piperazine H) ppm.

Example 219

Synthesis of 4-(5-amino-2-(4-fluorophenyl)thiazolo[5,4-d]pyrimidin-7-yl)-N-(2-methoxyphenyl)piperazine-1-carboxamide This compound was obtained from 5-amino-2-(4-fluorophenyl)-7-N-piperazinyl-thiazolo[5,4-d]pyrimidine and 2-methoxy-phenylisocyanate.

Example 220

Synthesis of 4-(5-amino-2-phenylthiazolo[5,4-d]pyrimidin-7-yl)-N-m-tolylpiperazine-1-carboxamide This compound was obtained from 5-amino-2-phenyl-7-N-piperazinyl-thiazolo[5,4-d]pyrimidine and 3-methyl-phenylisocyanate.

$^1$H NMR (300 MHz, DMSO): δ=8.52 (s, 1H, NH), 7.91 (dd, 2H, arom H), 7.50 (m, 3H, arom H), 7.32 (m, 2H, arom H), 7.12 (t, 1H, arom H), 6.76 (d, 1H, arom H), 6.52 (br s, 2H, $NH_2$), 4.30 (br s, 4H, piperazine H), 3.62 (br s, 4H, piperazine H), 2.26 (s, 3H, $CH_3$) ppm.

Example 221

Synthesis of 5-amino-7-(N-piperazin-1-yl)-2-(pyridine-3-yl)thiazolo[5,4-d]pyrimidine A mixture of 5-amino-7-thiol-2-(pyridine-3-yl)thiazolo[5,4-d]pyrimidine (1.31 g, 5 mmol), piperazine (2.15 g, 25 mmol) and 1,1,1,3,3,3-hexamethyldisilazane (HMDS, 5 ml) in pyridine (40 ml) was heated in a microwave oven (CEM discover, 150° C., 150 W) for 30 minutes. The reaction mixture was evaporated in vacuo and purified by flash chromatography on silica, the mobile phase being a mixture of methanol and dichloromethane (in a ratio of 1/3), yielding the pure title compound as a yellowish solid (0.95 g, 60%).

MS m/z (%): 314 ([M+H]$^+$, 100)

Example 222

Synthesis of 4-(5-amino-2-(pyridin-3-yl)thiazolo[5,4-d]pyrimidin-7-yl)-N-p-tolylpiperazine-1-carboxamide To a suspension of 5-amino-7-(piperazin-1-yl)-2-(pyridine-3-yl)thiazolo[5,4-d]pyrimidine (150 mg, 0.48 mmol) in dioxane (10 ml) was added 4-tolyl isocyanate (63 µl, 0.5 mmol). The resulting reaction mixture was stirred at room temperature for 30 minutes. The solvents were evaporated in vacuo and the residue was purified by flash chromatography on silica, the mobile phase being a mixture of methanol and dichloromethane (in a ratio of 1/25), yielding the pure title compound as a yellowish solid (170 mg, 79%).

MS m/z (%): 447 ([M+H]$^+$, 100)

Example 223

Synthesis of 1-(4-(5-amino-2-(4-fluorophenethyl)thiazolo[5,4-d]pyrimidin-7-yl)piperazin-1-yl)-3-(4-bromophenyl)propan-1-one This compound was prepared from example 27 using 3-(4-bromophenyl)propionic acid in a yield of 71%, according to the procedure for the synthesis of example 50.

$^1$H NMR (300 MHz, CDCl$_3$, 25° C.): δ=7.42 (d, 2H, PhH), 7.10-7.24 (m, 4H, PhH), 6.6 (t, 2H, PhH), 4.69 (s, 2H, NH$_2$), 4.17 (br s, 4H, N(CH$_2$)$_2$), 3.71 (br s, 2H, NCH$_2$), 3.47 (br s, 2H, NCH$_2$), 3.23 (t, 2H, CH$_2$), 3.07 (t, 2H, CH$_2$), 2.97 (t, 2H, CH$_2$), 2.65 (t, 2H, CH$_2$) ppm.

Example 224

Synthesis of 1-(4-(5-amino-2-(4-fluorophenethyl)thiazolo[5,4-d]pyrimidin-7-yl)piperazin-1-yl)-2-(4-hydroxyphenoxy)ethanone This compound was prepared from example 27 using 4-hydroxyphenoxyacetic acid in a yield of 12%, according to the procedure for the synthesis of example 50.

$^1$H NMR (300 MHz, CDCl$_3$, 25° C.): δ=7.13-7.18 (m, 2H, PhH), 6.96 (t, 2H, PhH), 6.76-6.87 (m, 4H, PhH), 4.71 (s, 2H, NH$_2$), 4.69 (s, 2H, OCH$_2$), 4.25 (br s, 2H, NCH$_2$), 4.21 (br s, 2H, NCH$_2$), 3.70 (br s, 4H, N(CH$_2$)$_2$), 3.23 (t, 2H, CH$_2$), 3.07 (t, 2H, CH$_2$) ppm.

Example 225

Synthesis of methyl 4-(2-(4-(5-amino-2-(4-fluorophenethyl)thiazolo[5,4-d]pyrimidin-7-yl)piperazin-1-yl)-2-oxoethoxy)benzoate This compound was prepared from example 27 using 4-methoxycarbonylphenoxyacetic acid in a yield of 41%, according to the procedure for the synthesis of example 50.

$^1$H NMR (300 MHz, CDCl$_3$, 25° C.): δ=8.01 (d, 2H, PhH), 7.13-7.18 (m, 2H, PhH), 7.01 (d, 2H, PhH), 6.96 (t, 2H, PhH), 4.81 (s, 2H, OCH$_2$), 4.71 (s, 2H, NH$_2$), 4.25 (br s, 2H, NCH$_2$), 4.20 (br s, 2H, NCH$_2$), 3.88 (s, 3H, CH$_3$), 3.73 (br s, 2H, NCH$_2$), 3.65 (br s, 2H, NCH$_2$), 3.23 (t, 2H, CH$_2$), 3.07 (t, 2H, CH$_2$) ppm

Example 226

Synthesis of 1-(4-(5-amino-2-(4-fluorophenethyl)thiazolo[5,4-d]pyrimidin-7-yl)piperazin-1-yl)-2-(4-(trifluoromethoxy)phenoxy)ethanone This compound was prepared from example 27 using 4-trifluoromethoxyphenoxyacetic acid in a yield of 54%, according to the procedure for the synthesis of example 50.

$^1$H NMR (300 MHz, CDCl$_3$, 25° C.): δ=7.13-7.18 (m, 4H, PhH), 6.93-6.99 (m, 4H, PhH), 4.75 (s, 2H, OCH$_2$), 4.71 (s, 2H, NH$_2$), 4.26 (br s, 2H, NCH$_2$), 4.21 (br s, 2H, NCH$_2$), 3.72 (br s, 2H, NCH$_2$), 3.65 (br s, 2H, NCH$_2$), 3.23 (t, 2H, CH$_2$), 3.07 (t, 2H, CH$_2$) ppm

Example 227

Synthesis of 2-(4-acetylphenoxy)-1-(4-(5-amino-2-(4-fluorophenethyl)thiazolo[5,4-d]pyrimidin-7-yl)piperazin-1-yl)ethanone This compound was prepared from example 27 using 4-acetylphenoxyacetic acid in a yield of 67%, according to the procedure for the synthesis of example 50.

$^1$H NMR (300 MHz, CDCl$_3$, 25° C.): δ=7.97 (d, 2H PhH), 7.13-7.18 (m, 4H, PhH), 693-7.04 (m, 4H, PhH), 4.82 (s, 2H, OCH2), 4.71 (s, 2H, NH2), 4.25 (br s, 2H, NCH2), 4.20 (br s, 2H, NCH2), 3.72 (br s, 2H, NCH2), 3.65 (br s, 2H, NCH2), 3.23 (t, 2H, CH2), 3.07 (t, 2H, CH2), 2.56 (s, 3H, CH3) ppm

Example 228

Synthesis of 1-(4-(5-amino-2-(4-fluorophenethyl)thiazolo[5,4-d]pyrimidin-7-yl)piperazin-1-yl)-2-(3-chlorophenoxy)ethanone This compound was prepared from example 27 using 3-chlorophenoxyacetic acid in a yield of 51%, according to the procedure for the synthesis of example 50.

$^1$H NMR (300 MHz, CDCl$_3$, 25° C.): δ=7.00-7.23 (m, 3H, PhH), 6.93-6.99 (m, 4H, PhH), 6.87 (d, 1H, PhH), 4.73 (s, 2H, OCH$_2$), 4.72 (s, 2H, NH$_2$), 4.26 (br s, 2H, NCH$_2$), 4.22 (br s, 2H, NCH$_2$), 3.71 (t, 2H, NCH$_2$), 3.64 (t, 2H, NCH$_2$), 3.23 (t, 2H, CH$_2$), 3.07 (t, 2H, CH$_2$) ppm

Example 229

Synthesis of 4-(5-amino-2-(4-fluorophenethyl)thiazolo[5,4-d]pyrimidin-7-yl)-N-(4-cyanophenyl)piperazine-1-carboxamide This compound was prepared from example 27 using 4-cyanophenyl isocyanate in a yield of 64%, according to the procedure for the synthesis of example 42.

$^1$H NMR (300 MHz, DMSO, 25° C.): δ=9.06 (s, 1H, NH), 7.69 (s, 4H, PhH), 7.28-7.33 (m, 2H, PhH), 7.10 (t, 2H, PhH), 6.30 (s, 2H, NH$_2$), 4.20 (br s, 4H, N(CH$_2$)$_2$), 3.59 (br s, 4H, N(CH$_2$)$_2$) 3.26 (t, 2H, CH$_2$), 3.05 (t, 2H, CH$_2$) ppm.

Example 230

Synthesis of 1-(4-(5-amino-2-(4-fluorobenzyl)thiazolo[5,4-d]pyrimidin-7-yl)piperazin-1-yl)-2-(4-methoxyphenoxy)ethanone This compound was prepared from example 26 using 4-methoxyphenoxyacetic acid in a yield of 59%, according to the procedure for the synthesis of example 50.

$^1$H NMR (300 MHz, CDCl$_3$, 25° C.): δ=7.23-7.28 (m, 2H, PhH), 7.02 (t, 2H, PhH), 8.82-6.93 (m, 4H, PhH), 4.78 (s, 2H, NH$_2$), 4.70 (s, 2H, OCH$_2$), 4.28 (br s, 4H, N(CH$_2$)$_2$), 4.21 (s, 2H), CH$_2$), 3.77 (s, 3H, CH$_3$), 3.73 (br s, 4H, N(CH$_2$)$_2$) ppm

Example 231

Synthesis of 1-(4-(5-amino-2-(4-fluorobenzyl)thiazolo[5,4-d]pyrimidin-7-yl)piperazin-1-yl)-2-(4-bromophenoxy)ethanone This compound was prepared from example 26 using 4-bromophenoxyacetic acid in a yield of 80%, according to the procedure for the synthesis of example 50.

$^1$H NMR (300 MHz, CDCl$_3$, 25° C.): δ=7.40 (d, 2H, PhH), 7.23-7.27 (m, 2H, PhH), 7.02 (t, 2H, PhH), 6.87 (d, 2H, PhH), 4.78 (s, 2H, NH$_2$), 4.73 (s, 2H, OCH$_2$), 4.28 (br s, 4H, N(CH$_2$)$_2$), 4.21 (s, 2H, CH$_2$), 3.67-3.72 (m, 4H, N(CH$_2$)$_2$) ppm

Example 232

Synthesis of 4-(5-amino-2-(4-fluorobenzyl)thiazolo[5,4-d]pyrimidin-7-yl)-N-(4-cyanophenyl)piperazine-1-carboxamide This compound was prepared from example 26 using 4-cyanophenyl isocyanate in a yield of 58%, according to the procedure for the synthesis of example 42.

$^1$H NMR (300 MHz, DMSO, 25° C.): δ=9.06 (s, 1H, NH), 7.69 (s, 4H, PhH), 7.37-7.42 (m, 2H, PhH), 7.18 (t, 2H, PhH), 6.33 (s, 2H, NH$_2$), 4.29 (s, 2H, CH2), 4.22 (br s, 4H, N(CH$_2$)$_2$), 3.60 (br s, 4H, N(CH$_2$)$_2$) ppm.

Example 233

Synthesis of 1-(4-(5-amino-2-(4-fluorophenyl)thiazolo[5,4-d]pyrimidin-7-yl)piperazin-1-yl)-2-(4-fluorophenoxy)ethanone This compound was prepared from example 25 using 4-fluorophenoxyacetic acid in a yield of 58%, according to the procedure for the synthesis of example 50.

$^1$H NMR (500 MHz, DMSO, 25° C.): δ=7.95-7.98 (m, 2H PhH), 7.35 (t, 2H, PhH), 7.11 (t, 2H, PhH), 6.95-6.98 (m, 2H PhH), 6.51 (s, 2H, NH$_2$), 4.88 (s, 2H, CH$_2$), 4.35 (br s, 2H NCH$_2$), 4.21 (br s, 2H, NCH$_2$), 3.63 (br s, 4H N(CH$_2$)$_2$) ppm

Example 234

Synthesis of 1-(4-(5-amino-2-(4-fluorophenyl)thiazolo[5,4-d]pyrimidin-7-yl)piperazin-1-yl)-2-(4-methoxyphenoxy)ethanone This compound was prepared from example 25 using 4-methoxyphenoxyacetic acid in a yield of 95%, according to the procedure for the synthesis of example 50.

$^1$H NMR (300 MHz, DMSO, 25° C.): δ=7.95-8.00 (m, 2H, PhH), 7.35 (t, 2H, PhH), 6.84-6.92 (m, 4H, PhH), 6.51 (s, 2H, NH$_2$), 4.81 (s, 2H, OCH$_2$), 4.33 (br s, 2H, NCH$_2$), 4.21 (br s, 2H, NCH$_2$), 3.69 (s, 3H, CH$_3$), 3.64 (br s, 4H, N(CH$_2$)$_2$) ppm.

Example 235

Synthesis of 1-(4-(5-amino-2-(4-fluorophenyl)thiazolo[5,4-d]pyrimidin-7-yl)piperazin-1-yl)-2-(4-bromophenoxy)ethanone This compound was prepared from example 25 using 4-bromophenoxyacetic acid in a yield of 47%, according to the procedure for the synthesis of example 50.

$^1$H NMR (500 MHz, DMSO, 25° C.): δ=7.95-7.98 (m, 2H PhH), 7.47 (d, 2H, PhH), 7.35 (t, 2H, PhH), 6.92 (d, 2H, PhH), 6.50 (s, 2H, NH$_2$), 4.91 (s, 2H, CH$_2$), 4.37 (br s, 2H NCH$_2$), 4.21 (br s, 2H, NCH$_2$), 3.63 (br s, 4H N(CH$_2$)$_2$) ppm.

Example 236

Synthesis of 1-(4-(5-amino-2-(4-fluorophenyl)thiazolo[5,4-d]pyrimidin-7-yl)piperazin-1-yl)-3-(4-fluorophenyl)propan-1-one This compound was prepared from example 25 using 3-(4-fluoropheny)propionic acid in a yield of 62%, according to the procedure for the synthesis of example 50.

$^1$H NMR (300 MHz, CDCl$_3$, 25° C.): δ=7.85-7.89 (m, 2H, PhH), 7.11-7.22 (m, 4H, PhH), 6.98 (t, 2H, PhH), 4.84 (s, 2H, NH$_2$), 4.29 (br s, 4H, N(CH$_2$)$_2$), 3.78 (t, 2H, NCH$_2$), 3.55 (t, 2H, NCH$_2$), 3.00 (t, 2H, CH$_2$), 2.67 (t, 2H, CH$_2$) ppm.

Example 237

Synthesis of 1-(4-(5-amino-2-(4-fluorophenyl)thiazolo[5,4-d]pyrimidin-7-yl)piperazin-1-yl)-2-(4-chlorophenoxy)-2-methylpropan-1-one This compound was prepared from example 25 using 2-(4-chlorophenoxy)-2-methylpropanoic acid in a yield of 58%, according to the procedure for the synthesis of example 50.

$^1$H NMR (300 MHz, DMSO, 25° C.): δ=7.94-7.98 (m, 2H, PhH), 7.32-7.38 (m, 4H, PhH), 6.87 (d, 2H, PhH), 6.46 (s, 2H, NH$_2$), 4.14 (br s, 2H, NCH$_2$), 3.93 (br s, 4H, N(CH$_2$)$_2$), 3.68 (br s, 2H, NCH$_2$), 1.56 (s, 6H, CH$_3$, CH$_3$) ppm.

Examples 238-240

Synthesis of 2-amino-4,6-dihydroxy-5-(acylamino)pyrimidine analogues

General Procedure

A suspension of a carboxylic acid (6.7 mmol) in SOCl$_2$ (5 ml) was heated under reflux for 1 h. After concentration under reduced pressure, the residue was redissolved in dioxane (5 ml) and added to a stirring solution of 2,5-diamino-4,6-dihydroxypyrimidine hydrochloride (1.0 g, 5.6 mmol) in 1 N NaOH (20 ml) at 0° C. The mixture was stirred and warmed to room temperature over 1 hour. After neutralization with 1 N hydrochloric acid to pH=5, the precipitate was filtered off, washed with water and dried over P$_2$O$_5$, yielding the title compound.

The following compounds were synthesized according to this procedure:

Example 238

Synthesis of N-(2-amino-4,6-dihydroxypyrimidin-5-yl)-3-(3-methoxyphenyl)propanamide This compound was synthesized using 3-(3-methoxyphenyl)propionic acid, yielding the title compound in 87% yield.

Example 239

Synthesis of N-(2-amino-4,6-dihydroxypyrimidin-5-yl)-3-(3,4-dimethoxyphenyl)propanamide This compound was synthesized using 3-(3,4-dimethoxyphenyl)propionic acid, yielding the title compound in 46% yield.

Example 240

Synthesis of N-(2-amino-4,6-dihydroxypyrimidin-5-yl)-3-p-tolylpropanamide

This compound was synthesized using 3-(4-tolyl)propionic acid, yielding the title compound in 67% yield.

Examples 241-243

Synthesis of 5-amino-2-substituted-thiazolo[5,4-d]pyrimidine-7-thiol analogues

General Procedure

A suspension of a 2-amino-4,6-dihydroxy-5-N-acylamino-pyrimidine analogue (3.3 mmol) and $P_2S_5$ (1.68 g, 7.6 mmol) in pyridine (15 ml) was heated under reflux for 6 hours. After concentration under reduced pressure, the residue was purified by flash chromatography on silica ($CH_2Cl_2$/MeOH 30:1), yielding the title compounds as a yellow solid.

The following compounds were synthesized according to this procedure:

Example 241

Synthesis of 5-amino-2-(3-methoxyphenethyl)thiazolo[5,4-d]pyrimidine-7-thiol

This compound was synthesized from N-(2-amino-4,6-dihydroxypyrimidin-5-yl)-3-(3-methoxyphenyl)propanamide, yielding the title compound in 82% yield.

Example 242

Synthesis of 5-amino-2-(3,4-dimethoxyphenethyl)thiazolo[5,4-d]pyrimidine-7-thiol This compound was synthesized from N-(2-amino-4,6-dihydroxypyrimidin-5-yl)-3-(3,4-dimethoxyphenyl)propanamide, yielding the title compound in 48% yield.
MS m/z (%):349 ([M+H]$^+$, 100)

Example 243

Synthesis of 5-amino-2-(4-methylphenethyl)thiazolo[5,4-d]pyrimidine-7-thiol

This compound was synthesized from N-(2-amino-4,6-dihydroxypyrimidin-5-yl)-3-p-tolylpropanamide, yielding the title compound in 76% yield.

Examples 244-246

Synthesis of 5-amino-2-substituted-7-methylthio-thiazolo[5,4-d]pyrimidine analogues General Procedure To a solution of 5-amino-2-substituted-thiazolo[5,4-d]pyrimidine-7-thiol (2.4 mmol) and triethylamine (0.83 ml, 5.97 mmol) in DMSO (10 ml) was added iodomethane (0.29 ml, 4.77 mmol). The reaction mixture was stirred for 12 h under $N_2$ at 25° C. The mixture was poured into water and extracted with EtOAc. The organic extracts were dried over $Na_2SO_4$ and the solvents were removed under reduced pressure. The crude residue was purified by flash chromatography on silica ($CH_2Cl_2$/MeOH 80:1), yielding the title compound as a light yellow solid.

The following compounds were synthesized according to this procedure:

Example 244

Synthesis of 2-(3-methoxyphenethyl)-7-(methylthio)thiazolo[5,4-d]pyrimidin-5-amine This compound was synthesized from 5-amino-2-(3-methoxyphenethyl)thiazolo[5,4-d]pyrimidine-7-thiol, yielding the title compound in 73% yield.

Example 245

Synthesis of 2-(3,4-dimethoxyphenethyl)-7-(methylthio)thiazolo[5,4-d]pyrimidin-5-amine This compound was synthesized from 5-amino-2-(3,4-dimethoxyphenethyl)thiazolo[5,4-d]pyrimidine-7-thiol, yielding the title compound in 96% yield.

Example 246

Synthesis of 2-(4-methylphenethyl)-7-(methylthio)thiazolo[5,4-d]pyrimidin-5-amine This compound was synthesized from 5-amino-2-(4-methylphenethyl)thiazolo[5,4-d]pyrimidine-7-thiol, yielding the title compound in 55% yield.

Examples 247-249

Synthesis of 5-amino-2-substituted-7-methylsulfonyl-thiazolo[5,4-d]pyrimidine analogues General Procedure To a solution of a 2-substituted-7-(methylthio)thiazolo[5,4-d]pyrimidin-5-amine analogue (0.90 mmol) in dichloromethane (5 ml) was added mCPBA (70%, 0.39 g, 2.26 mmol) at 0° C. The reaction mixture was stirred for 3 hours, whereby the reaction temperature was gradually increased from 0° C. to room temperature. The reaction mixture was diluted with $CHCl_3$ and was washed with a saturated $NaHCO_3$ solution, brine and dried over $Na_2SO_4$. After removing the solvents under reduced pressure, the residue was purified by flash chromatography on silica ($CH_2Cl_2$/MeOH 50:1), affording the title compound.

The following compounds were synthesized according to this procedure:

Example 247

Synthesis of 2-(3-methoxyphenethyl)-7-(methylsulfonyl)thiazolo[5,4-d]pyrimidin-5-amine This compound was synthesized from 2-(3-methoxyphenethyl)-7-(methylthio)thiazolo[5,4-d]pyrimidin-5-amine, yielding the title compound in 85% yield.

Example 248

Synthesis of 2-(3,4-dimethoxyphenethyl)-7-(methylsulfonyl)thiazolo[5,4-d]pyrimidin-5-amine This compound was synthesized from 2-(3,4-dimethoxyphenethyl)-7-(methylthio)thiazolo[5,4-d]pyrimidin-5-amine, yielding the title compound in 69% yield.

Example 249

Synthesis of 2-(4-methylphenethyl)-7-(methylsulfonyl)thiazolo[5,4-d]pyrimidin-5-amine This compound was synthesized from 2-(4-methylphenethyl)-7-(methylthio)thiazolo[5,4-d]pyrimidin-5-amine, yielding the title compound in 51% yield.

Examples 250-252

Synthesis of 5-amino-2-substituted-7-piperazinyl-thiazolo[5,4-d]pyrimidine analogues General Procedure To a solution of a 2-substituted-7-(methylsulfonyl)thiazolo[5,4-d]pyrimidin-5-amine analogue (0.55 mmol) and triethylamine (0.12 ml, 0.82 mmol) in dioxane (4 ml) was added piperazine (71 mg, 0.82 mmol). The reaction mixture was heated at 60° C. for 5 hours. After cooling, the volatiles were removed under reduced pressure. The crude residue was purified by flash chromatography on silica ($CH_2Cl_2$/MeOH 15:1), furnishing the title compound.

The following compounds were synthesized according to this procedure:

Example 250

Synthesis of 2-(3-methoxyphenethyl)-7-(piperazin-1-yl)thiazolo[5,4-d]pyrimidin-5-amine This compound was synthesized from 2-(3-methoxyphenethyl)-7-(methylsulfonyl)thiazolo[5,4-d]pyrimidin-5-amine, yielding the title compound in 98% yield.

Example 251

Synthesis of 2-(3,4-dimethoxyphenethyl)-7-(piperazin-1-yl)thiazolo[5,4-d]pyrimidin-5-amine This compound was synthesized from 2-(3,4-dimethoxyphenethyl)-7-(methylsulfonyl)thiazolo[5,4-d]pyrimidin-5-amine, yielding the title compound in 89% yield.

Example 252

Synthesis of 2-(4-methylphenethyl)-7-(piperazin-1-yl)thiazolo[5,4-d]pyrimidin-5-amine This compound was synthesized from 2-(4-methylphenethyl)-7-(methylsulfonyl)thiazolo[5,4-d]pyrimidin-5-amine, yielding the title compound in 79% yield.

Example 253

Synthesis of 1-(4-(5-amino-2-(3-methoxyphenethyl)thiazolo[5,4-d]pyrimidin-7-yl)piperazin-1-yl)-2-(4-methoxyphenoxy)ethanone This compound was prepared from 2-(3-methoxyphenethyl)-7-(piperazin-1-yl)thiazolo[5,4-d]pyrimidin-5-amine using 4-methoxyphenoxyacetic acid in a yield of 66%, according to the procedure for the synthesis of example 50.

$^1$H NMR (300 MHz, $CDCl_3$, 25° C.): δ=7.22 (t, 1H, PhH), 6.81-6.93 (m, 4H, PhH), 6.73-6.81 (m, 3H, PhH), 4.76 (s, 2H, $NH_2$), 4.69 (s, 2H, $OCH_2$), 4.25 (br s, 2H, $NCH_2$), 4.19 (br s, 2H, $NCH_2$), 3.77 (s, 3H, $CH_3$), 3.76 (s, 3H, $CH_3$), 3.69 (br s, 4H, $N(CH_2)_2$), 3.25 (t, 2H, $CH_2$), 3.07 (t, 2H, $CH_2$) ppm.

Example 254

Synthesis of 1-(4-(5-amino-2-(3-methoxyphenethyl)thiazolo[5,4-d]pyrimidin-7-yl)piperazin-1-yl)-2-(4-bromophenoxy)ethanone This compound was prepared from 2-(3-methoxyphenethyl)-7-(piperazin-1-yl)thiazolo[5,4-d]pyrimidin-5-amine using 4-bromophenoxyacetic acid in a yield of 65%, according to the procedure for the synthesis of example 50.

$^1$H NMR (300 MHz, $CDCl_3$, 25° C.): δ=7.39 (d, 2H PhH), 7.20 (t, 1H, PhH), 6.86 (d, 2H, PhH), 6.73-6.81 (m, 3H, PhH), 4.77 (s, 2H, $NH_2$), 4.72 (s, 2H, $OCH_2$), 4.25 (br s, 2H, $NCH_2$), 4.19 (br s, 2H, $NCH_2$), 3.77 (s, 3H, $CH_3$), 3.70 (br s, 2H, $NCH_2$), 3.64 (br s, 2H, $NCH_2$), 3.25 (t, 2H, $CH_2$), 3.07 (t, 2H, $CH_2$) ppm.

Example 255

Synthesis of 1-(4-(5-amino-2-(3-methoxyphenethyl)thiazolo[5,4-d]pyrimidin-7-yl)piperazin-1-yl)-2-(4-chlorophenoxy)ethanone This compound was prepared from 2-(3-methoxyphenethyl)-7-(piperazin-1-yl)thiazolo[5,4-d]pyrimidin-5-amine using 4-chlorophenoxyacetic acid in a yield of 48%, according to the procedure for the synthesis of example 50.

$^1$H NMR (300 MHz, $CDCl_3$, 25° C.): δ=7.26 (d, 2H, PhH), 7.20 (t, 1H, PhH), 6.92 (d, 2H PhH), 6.73-6.82 (m, 3H, PhH), 4.73 (s, 2H, $OCH_2$), 4.71 (2, 2H, $NH_2$), 4.26 (br s, 2H, $NCH_2$), 4.20 (br s, 2H, $NCH_2$), 3.78 (s, 3H, $CH_3$), 3.70 (br s, 2H, $NCH_2$), 3.67 (br s, 2H, $NCH_2$), 3.26 (t, 2H, $CH_2$), 3.07 (t, 2H, $CH_2$) ppm.

Example 256

Synthesis of 1-(4-(5-amino-2-(3,4-dimethoxyphenethyl)thiazolo[5,4-d]pyrimidin-7-yl)piperazin-1-yl)-2-(4-bromophenoxy)ethanone This compound was prepared from 2-(3,4-dimethoxyphenethyl)-7-(piperazin-1-yl)thiazolo[5,4-d]pyrimidin-5-amine using 4-bromophenoxyacetic acid in a yield of 74%, according to the procedure for the synthesis of example 50.

$^1$H NMR (300 MHz, $CDCl_3$, 25° C.): δ=7.39 (d, 2H, PhH), 6.87 (d, 2H, PhH), 6.72-6.78 (m, 3H, PhH), 4.73 (s, 2H, $OCH_2$), 4.69 (s, 2H, $NH_2$), 4.24 (br s, 4H, $N(CH_2)_2$), 3.85 (s, 6H, $CH_3$, $CH_3$), 3.71 (br s, 2H, $NCH_2$), 3.65 (br s, 2H, $NCH_2$), 3.24 (t, 2H, $CH_2$), 3.04 (t, 2H, $CH_2$) ppm.

Example 257

Synthesis of 1-(4-(5-amino-2-(3,4-dimethoxyphenethyl)thiazolo[5,4-d]pyrimidin-7-yl)piperazin-1-yl)-2-(4-methoxyphenoxy)ethanone This compound was prepared from 2-(3,4-dimethoxyphenethyl)-7-(piperazin-1-yl)thiazolo[5,4-d]pyrimidin-5-amine using 4-methoxyphenoxyacetic acid in a yield of 71%, according to the procedure for the synthesis of example 50.

$^1$H NMR (300 MHz, $CDCl_3$, 25° C.): δ=6.73-6.93 (m, 7H, PhH), 4.76 (s, 2H, $NH_2$), 4.70 (s, 2H, $OCH_2$), 4.26 (br s, 2H,

NCH$_2$), 4.22 (br s, 2H, NCH$_2$), 3.85 (s, 3H, CH$_3$), 3.84 (s, 3H, CH$_3$), 3.76 (s, 3H, CH$_3$), 3.71 (br s, 4H, N(CH$_2$)$_2$), 3.23 (t, 2H, CH$_2$), 3.04 (t, 2H, CH$_2$) ppm.

Example 258

Synthesis of 1-(4-(5-amino-2-(4-methylphenethyl) thiazolo[5,4-d]pyrimidin-7-yl)piperazin-1-yl)-2-(4-bromophenoxy)ethanone This compound was prepared from 2-(4-methylphenethyl)-7-(piperazin-1-yl)thiazolo[5,4-d]pyrimidin-5-amine using 4-bromophenoxyacetic acid in a yield of 47%, according to the procedure for the synthesis of example 50.

$^1$H NMR (300 MHz, CDCl$_3$, 25° C.): δ=7.39 (d, 2H, PhH), 7.10 (s, 4H, PhH), 6.87 (d, 2H, PhH), 4.73 (s, 2H, OCH$_2$), 4.70 (s, 2H, NH$_2$), 4.27 (br s, 2H, NCH$_2$), 4.20 (br s, 2H, NCH$_2$), 3.64-3.72 (m, 4H, N(CH$_2$)$_2$), 3.24 (t, 2H, CH$_2$), 3.06 (t, 2H, CH$_2$), 2.32 (s, 3H, CH$_3$) ppm.

Example 259

Synthesis of 1-(4-(5-amino-2-(4-methylphenethyl) thiazolo[5,4-d]pyrimidin-7-yl)piperazin-1-yl)-2-(4-methoxyphenoxy)ethanone This compound was prepared from 2-(4-methylphenethyl)-7-(piperazin-1-yl)thiazolo[5,4-d]pyrimidin-5-amine using 4-methoxyphenoxyacetic acid in a yield of 68%, according to the procedure for the synthesis of example 50.

$^1$H NMR (300 MHz, CDCl$_3$, 25° C.): δ=7.10 (s, 4H, PhH), 6.82-6.93 (m, 4H, PhH), 4.70 (s, 4H, NH$_2$, OCH$_2$), 4.27 (br s, 2H, NCH$_2$), 4.21 (br s, 2H, NCH$_2$), 3.76 (s, 3H, OCH$_3$), 3.70 (br s, 4H, N(CH$_2$)$_2$), 3.23 (t, 2H, CH$_2$), 3.05 (t, 2H, CH$_2$), 2.31 (s, 3H, CH$_3$) ppm

Example 260

Synthesis of 1-(4-(5-amino-2-(4-methylphenethyl) thiazolo[5,4-d]pyrimidin-7-yl)piperazin-1-yl)-2-(4-chlorophenoxy)ethanone This compound was prepared from 2-(4-methylphenethyl)-7-(piperazin-1-yl)thiazolo[5,4-d]pyrimidin-5-amine using 4-chlorophenoxyacetic acid in a yield of 51%, according to the procedure for the synthesis of example 50.

$^1$H NMR (300 MHz, CDCl$_3$, 25° C.): δ=7.26 (d, 2H, PhH), 7.10 (s, 4H, PhH), 6.92 (d, 2H, PhH), 4.73 (s, 2H, OCH$_2$), 4.71 (s, 2H, NH$_2$), 4.27 (br s, 2H, NCH$_2$), 4.20 (br s, 2H, NCH$_2$), 3.66-3.72 (m, 4H, N(CH$_2$)$_2$), 3.23 (t, 2H, CH$_2$), 3.05 (t, 2H, CH$_2$), 2.31 (s, 3H, CH$_3$) ppm.

Example 261

Synthesis of 4,6-dichloropyrimidine-2,5-diamine

A suspension of 2,5-diamino-4,6-dihydroxypyrimidine hydrochloride (5.0 g, 28 mmol) and tetraethylammonium chloride (27.8 g, 0.167 mmol) in phosphorus oxychloride (80 ml) was heated at 105° C. for 20 hours. After cooling down to room temperature, the excess phosphorus oxychloride was distilled off under vacuum. The reaction mixture was poured into ice water and the pH was adjusted to 4, and the mixture was stirred for 1 hour at 50° C. The pH was adjusted to 7 and the product was extracted with ethyl acetate, washed with a saturated NaHCO$_3$ solution, brine and dried over Na$_2$SO$_4$. After removing the solvents under reduced pressure, the residue was purified by flash chromatography on silica (CH$_2$Cl$_2$/MeOH 50:1), affording the title compound (3.21 g, 64%).

Examples 262-263

Synthesis of tert-butyl 4-(5-amino-2-substituted-6-chloropyrimidin-4-yl)piperazine-1-carboxylate analogues General Procedure To a solution of a 4,6-dichloropyrimidine analogue (11.2 mmol) and DIPEA (2.9 ml, 16.8 mmol) in dioxane (40 ml) was added tert-butyl piperazine-1-carboxylate (3.12 g, 16.8 mmol). The reaction mixture was heated at 100° C. for overnight. After cooling, the volatile was removed under reduced pressure. The crude residue was diluted with CHCl$_3$ and was washed with a saturated NaHCO$_3$ solution, brine and dried over Na$_2$SO$_4$. After removing the solvents under reduced pressure, the residue was purified by flash chromatography on silica (CH$_2$Cl$_2$/MeOH 50:1), affording the title compound.

The following compounds were synthesized according to this procedure:

Example 262

Synthesis of tert-butyl 4-(2,5-diamino-6-chloropyrimidin-4-yl)piperazine-1-carboxylate This compound was synthesized from 2,5-diamino-4,6-dichloropyrimidine, yielding the title compound in 94% yield.

Example 263

Synthesis of tert-butyl 4-(5-amino-6-chloropyrimidin-4-yl)piperazine-1-carboxylate This compound was synthesized from 5-amino-4,6-dichloropyrimidine, yielding the title compound in 91% yield.

Examples 264-265

Synthesis of tert-butyl 4-(5-amino-2-substituted-6-mercaptopyrimidin-4-yl)piperazine-1-carboxylate analogues General Procedure To a solution of a tert-butyl 4-(2,5-diamino-6-chloropyrimidin-4-yl)piperazine-1-carboxylate analogue (6.1 mmol) in DMSO (15 ml) was added sodium sulfide nonahydrate (2.9 g, 12.1 mmol). The reaction mixture was heated at 50° C. overnight. After cooling down to room temperature, water (15 ml) was added and the solution was evaporated under reduced pressure. The crude residue was diluted with water (20 ml) and neutralized with HCl. The precipitate was collected by filtration, washed with water and dried over P$_2$O$_5$, yielding the title compound.

The following compounds were synthesized according to this procedure:

Example 264

Synthesis of tert-butyl 4-(2,5-diamino-6-mercaptopyrimidin-4-yl)piperazine-1-carboxylate

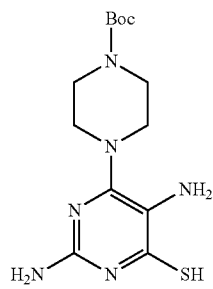 [SMILES: CC(C)(C)OC(=O)N1CCN(c2nc(N)nc(S)c2N)CC1]

This compound was synthesized from tert-butyl 4-(2,5-diamino-6-chloropyrimidin-4-yl)piperazine-1-carboxylate, yielding the title compound in 61% yield.

Example 265

Synthesis of tert-butyl 4-(5-amino-6-mercaptopyrimidin-4-yl)piperazine-1-carboxylate

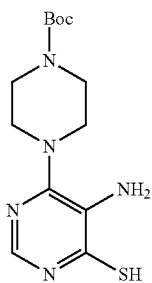

This compound was synthesized from tert-butyl 4-(5-amino-6-chloropyrimidin-4-yl)piperazine-1-carboxylate, yielding the title compound in 80% yield.

Examples 266-269

Synthesis of 7-(piperazin-1-yl)-2-substituted-thiazolo[5,4-d]pyrimidin-5-amine analogues General Procedure To a solution of a tert-butyl 4-(6-mercaptopyrimidin-4-yl)piperazine-1-carboxylate analogue (6.1 mmol) in DMSO (10 ml) was added an appropriate aldehyde (2.36 mmol). The reaction mixture was heated at 150° C. for 1 hour. After cooling down to room temperature, the mixture was diluted with ethyl acetate and washed with water, brine and dried over $Na_2SO_4$. After removing the solvents under reduced pressure, the residue was diluted with dichloromethane (5 ml) and treated with TFA (1.6 ml, 21.4 mmol). The reaction mixture was stirred at room temperature overnight. The volatiles were evaporated under reduced pressure and the residue was diluted with water and neutralized with 1N NaOH. The precipitate was collected by filtration, washed with water and dried over $P_2O_5$, yielding the title compound. The following compounds were synthesized according to this procedure:

Example 266

Synthesis of 7-(piperazin-1-yl)-2-(pyridin-3-yl)thiazolo[5,4-d]pyrimidin-5-amine This compound was synthesized using nicotinaldehyde, yielding the title compound in 56% yield.

Example 267

Synthesis of 7-(piperazin-1-yl)-2-(pyridin-2-yl)thiazolo[5,4-d]pyrimidin-5-amine This compound was synthesized using picolinaldehyde, yielding the title compound in 44% yield.

Example 268

Synthesis of 7-(piperazin-1-yl)-2-(pyridin-4-yl)thiazolo[5,4-d]pyrimidin-5-amine This compound was synthesized using isonicotinaldehyde, yielding the title compound in 46% yield.

Example 269

Synthesis of 2-(4-chlorophenyl)-7-(piperazin-1-yl)thiazolo[5,4-d]pyrimidin-5-amine This compound was synthesized using 4-chlorobenzaldehyde, yielding the title compound in 60% yield.

Example 270

Synthesis of 1-(4-(5-amino-2-(4-chlorophenyl)thiazolo[5,4-d]pyrimidin-7-yl)piperazin-1-yl)-2-(4-methoxyphenoxy)ethanone This compound was prepared from 2-(4-chlorophenyl)-7-(piperazin-1-yl)thiazolo[5,4-d]pyrimidin-5-amine using 4-methoxyphenoxyacetic acid in a yield of 63%, according to the procedure for the synthesis of example 50.

$^1$H NMR (300 MHz, $CDCl_3$, 25° C.): δ=7.82 (d, 2H, PhH), 7.43 (d, 2H, PhH), 6.83-6.94 (m, 4H, PhH), 4.80 (s, 2H, $NH_2$), 4.72 (s, 2H, $CH_2$), 4.37 (br s, 2H, $NCH_2$), 4.32 (br s, 2H, $NCH_2$), 3.77 (s, 7H, $CH_3$, $N(CH_2)_2$) ppm.

Example 271

Synthesis of 1-(4-(5-amino-2-(pyridin-3-yl)thiazolo[5,4-d]pyrimidin-7-yl)piperazin-1-yl)-2-(4-methoxyphenoxy)ethanone This compound was prepared from 7-(piperazin-1-yl)-2-(pyridin-3-yl)thiazolo[5,4-d]pyrimidin-5-amine using 4-methoxyphenoxyacetic acid in a yield of 52%, according to the procedure for the synthesis of example 50.

$^1$H NMR (300 MHz, DMSO, 25° C.): δ=9.14 (s, 1H, 2-pyridyl-H), 8.66 (d, J=4.7 Hz, 1H, 4-pyridyl-H), 8.30 (d, J=5.5 Hz, 1H, 6-pyridyl-H), 7.53-7.57 (m, 1H, 5-pyridyl-H), 6.84-6.93 (m, 4H, PhH), 6.58 (s, 2H, $NH_2$), 4.81 (s, 2H, $OCH_2$), 4.34 (br s, 2H, $CH_2$), 4.23 (br s, 2H, $CH_2$), 3.70 (s, 3H, $CH_3$), 3.66 (br s, 4H, $CH_2$) ppm.

Example 272

Synthesis of 1-(4-(5-amino-2-(pyridin-3-yl)thiazolo[5,4-d]pyrimidin-7-yl)piperazin-1-yl)-2-(4-fluorophenoxy)ethanone This compound was prepared from 7-(piperazin-1-yl)-2-(pyridin-3-yl)thiazolo[5,4-d]pyrimidin-5-amine using 4-fluorophenoxyacetic acid in a yield of 67%, according to the procedure for the synthesis of example 50

$^1$H NMR (300 MHz, DMSO, 25° C.): δ=9.14 (d, J=2.0 Hz, 1H, 2-pyridyl-H), 8.66 (d, J=3.6 Hz, 1H, 4-pyridyl-H), 8.29 (d, J=8.0 Hz, 1H, 6-pyridyl-H), 7.53-7.57 (m, 1H, 5-pyridyl-H), 7.12 (t, J=8.9 Hz, 2H, PhH), 6.95-6.99 (m, 2H, PhH), 6.58 (s, 2H, NH$_2$), 4.89 (s, 2H, OCH$_2$), 4.37 (br s, 2H, CH$_2$), 4.24 (br s, 2H, CH$_2$), 3.66 (br s, 4H, CH$_2$) ppm.

Example 273

Synthesis of 1-(4-(5-amino-2-(pyridin-3-yl)thiazolo[5,4-d]pyrimidin-7-yl)piperazin-1-yl)-2-(4-trifluoromethoxyphenoxy)ethanone This compound was prepared from 7-(piperazin-1-yl)-2-(pyridin-3-yl)thiazolo[5,4-d]pyrimidin-5-amine using 4-trifluoromethoxyphenoxyacetic acid in a yield of 45%, according to the procedure for the synthesis of example 50.

$^1$H NMR (300 MHz, DMSO, 25° C.): δ=9.14 (d, J=1.7 Hz, 1H, 2-pyridyl-H), 8.66 (dd, J=4.7 Hz, J=1.5 Hz, 1H, 4-pyridyl-H), 8.28 (dd, J=8.2 Hz, j=2.0 Hz, 1H, 6-pyridyl-H), 7.53-7.57 (m, 1H, 5-pyridyl-H), 7.30 (d, J=8.6 Hz, 2H, PhH), 7.05 (d, J=8.6 Hz, 2H, PhH), 6.58 (s, 2H, NH$_2$), 4.96 (s, 2H, OCH$_2$), 4.38 (br s, 2H, CH$_2$), 4.25 (br s, 2H, CH$_2$), 3.65 (br s, 4H, CH$_2$) ppm.

Example 274

Synthesis of 1-(4-(5-amino-2-(pyridin-3-yl)thiazolo[5,4-d]pyrimidin-7-yl)piperazin-1-yl)-2-(4-chlorophenoxy)-2-methylpropan-1-one This compound was prepared from 7-(piperazin-1-yl)-2-(pyridin-3-yl)thiazolo[5,4-d]pyrimidin-5-amine using 2-(4-chlorophenoxy)-2-methylpropanoic acid in a yield of 45%, according to the procedure for the synthesis of example 50.

$^1$H NMR (300 MHz, DMSO, 25° C.): δ=9.12 (d, J=2.3 Hz, 1H, 2-pyridyl-H), 8.66 (d, J=4.7 Hz, 1H, 4-pyridyl-H), 8.27 (d, J=8.0 Hz, 1H, 6-pyridyl-H), 7.52-7.56 (m, 1H, 5-pyridyl-H), 7.34 (d, J=8.8 Hz, 2H, PhH), 6.86 (d, J=8.8 Hz, 2H, PhH), 6.53 (s, 2H, NH$_2$), 3.94 (br s, 4H, CH$_2$), 3.69 (br s, 4H, CH$_2$), 1.59 (s, 6H, CH$_3$) ppm.

Example 275

Synthesis of 1-(4-(5-amino-2-(pyridin-3-yl)thiazolo[5,4-d]pyrimidin-7-yl)piperazin-1-yl)-2-(m-tolyloxy)ethanone This compound was prepared from 7-(piperazin-1-yl)-2-(pyridin-3-yl)thiazolo[5,4-d]pyrimidin-5-amine using 3-tolyloxyacetic acid in a yield of 45%, according to the procedure for the synthesis of example 50.

$^1$H NMR (300 MHz, DMSO, 25° C.): δ=9.13 (s, 1H, pyridyl-H), 8.66 (d, 1H, pyridyl-H), 8.28 (d, 1H, pyridyl-H), 7.52-7.56 (m, 1H, pyridyl-H), 7.16 (t, 1H, PhH), 6.73-6.78 (m, 3H, PhH), 6.56 (s, 2H, NH$_2$), 4.85 (s, 2H, CH$_2$), 4.36 (br s, 2H, NCH$_2$), 4.23 (br s, 2H, NCH$_2$), 3.65 (br s, 4H, N(CH$_2$)$_2$), 2.27 (s, 3H, CH$_3$) ppm.

Example 276

Synthesis of 4-(5-amino-2-(pyridin-3-yl)thiazolo[5,4-d]pyrimidin-7-yl)-N-m-tolylpiperazine-1-carboxamide This compound was prepared from 7-(piperazin-1-yl)-2-(pyridin-3-yl)thiazolo[5,4-d]pyrimidin-5-amine using 3-tolyl isocyanate in a yield of 42%, according to the procedure for the synthesis of example 42.

$^1$H NMR (300 MHz, DMSO, 25° C.): δ=9.13 (d, J=1.7 Hz, 1H, 2-pyridyl-H), 8.66-8.68 (m, 1H, 4-pyridyl-H), 8.52 (s, 1H, NH), 8.28 (d, J=5.9 Hz, 1H, 6-pyridyl-H), 7.53-7.57 (m, 1H, 5-pyridyl-H), 7.32 (s, 1H, 2-tolyl-H), 7.29 (d, J=8.5 Hz, 1H, 6-tolyl-H), 7.12 (t, J=7.6 Hz, 1H, 5-tolyl-H), 6.77 (d, J=7.0 Hz, 1H, 4-tolyl-H), 6.57 (s, 2H, NH$_2$), 4.30 (br s, 4H, CH$_2$), 3.62 (br s, 4H, CH$_2$), 2.26 (s, 3H, CH$_3$) ppm.

Example 277

Synthesis of 4-(5-amino-2-(pyridin-3-yl)thiazolo[5,4-d]pyrimidin-7-yl)-N-(4-chlorophenyl)piperazine-1-carboxamide This compound was prepared from 7-(piperazin-1-yl)-2-(pyridin-3-yl)thiazolo[5,4-d]pyrimidin-5-amine using 4-chlorophenyl isocyanate in a yield of 38%, according to the procedure for the synthesis of example 42.

$^1$H NMR (300 MHz, DMSO, 25° C.): δ==9.13 (d, J=2.3 Hz, 1H, 2-pyridyl-H), 8.73 (s, 1H, NH), 8.66 (d, J=4.7 Hz, 1H, 4-pyridyl-H), 8.28 (d, J=8.0 Hz, 1H, 6-pyridyl-H), 7.54-7.57 (m, 1H, 5-pyridyl-H), 7.53 (d, J=8.9 Hz, 2H, PhH), 7.30 (d, J=8.9 Hz, 2H, PhH), 6.60 (s, 2H, NH$_2$), 4.32 (br s, 4H, CH$_2$), 3.64 (br s, 4H, CH$_2$) ppm.

Example 278

Synthesis of 4-(5-amino-2-(pyridin-3-yl)thiazolo[5,4-d]pyrimidin-7-yl)-N-(4-methoxybenzyl)piperazine-1-carboxamide This compound was prepared from 7-(piperazin-1-yl)-2-(pyridin-3-yl)thiazolo[5,4-d]pyrimidin-5-amine using 4-methoxybenzyl isocyanate in a yield of 40%, according to the procedure for the synthesis of example 42.

$^1$H NMR (300 MHz, DMSO, 25° C.): δ=9.11 (s, 1H, 2-pyridyl-H), 8.66 (d, J=4.6 Hz, 1H, 4-pyridyl-H), 8.27 (d, J=8.1 Hz, 1H, 6-pyridyl-H), 7.53-7.57 (m, 1H, 5-pyridyl-H), 7.21 (d, J=8.8 Hz, 2H, PhH), 7.08 (s, 1H, NH), 6.87 (d, J=8.8 Hz, 2H, PhH), 6.54 (s, 2H, NH$_2$), 4.20 (br s, 6H, CH$_2$, NHC$\underline{H}_2$), 3.72 (s, 3H, CH$_3$), 3.50 (br s, 4H, CH$_2$) ppm

Example 279

Synthesis of 4-(5-amino-2-(pyridin-3-yl)thiazolo[5,4-d]pyrimidin-7-yl)-N-(4-cyanophenyl)piperazine-1-carboxamide This compound was prepared from 7-(piperazin-1-yl)-2-(pyridin-3-yl)thiazolo[5,4-d]pyrimidin-5-amine using 4-cyanophenyl isocyanate in a yield of 53%, according to the procedure for the synthesis of example 42.

¹H NMR (300 MHz, DMSO, 25° C.): δ=9.14 (s, 1H, NH), 9.09 (s, 1H, 2-pyridyl-H), 8.67 (d, J=4.9 Hz, 1H, 4-pyridyl-H), 8.29 (d, J=6.3 Hz, 1H, 6-pyridyl-H), 7.69 (s, 4H, PhH), 7.54-7.57 (m, 1H, 5-pyridyl-H), 6.57 (s, 2H, NH$_2$), 4.32 (br s, 4H, CH$_2$), 3.67 (br s, 4H, CH$_2$) ppm.

Example 280

Synthesis of 1-(4-(5-amino-2-(4-chlorophenyl)thiazolo[5,4-d]pyrimidin-7-yl)piperazin-1-yl)-2-(4-methoxyphenoxy)ethanone This compound was prepared from 7-(piperazin-1-yl)-2-(pyridin-3-yl)thiazolo[5,4-d]pyrimidin-5-amine using phenylmethanesulfonyl chloride in a yield of 40%, according to the procedure for the synthesis of example 41.

¹H NMR (300 MHz, DMSO, 25° C.): δ=9.14 (s, 1H, 2-pyridyl-H), 8.67 (d, J=4.4 Hz, 1H, 4-pyridyl-H), 8.29 (d, J=7.3 Hz, 1H, 6-pyridyl-H), 7.53-7.57 (m, 1H, 5-pyridyl-H), 7.36-7.41 (m, 5H, PhH), 6.59 (s, 2H, NH$_2$), 4.45 (s, 2H, SCH$_2$), 4.31 (br s, 4H, CH$_2$), 3.35 (br s, 4H, CH$_2$) ppm.

Example 281

Synthesis of 1-(4-(5-amino-2-(pyridin-4-yl)thiazolo [5,4-d]pyrimidin-7-yl)piperazin-1-yl)-2-(4-chlorophenoxy)ethanone This compound was prepared from 7-(piperazin-1-yl)-2-(pyridin-4-yl)thiazolo[5,4-d]pyrimidin-5-amine using 4-chlorophenoxyacetic acid in a yield of 43%, according to the procedure for the synthesis of example 50.

¹H NMR (300 MHz, DMSO, 25° C.): δ=8.71 (d, 2H, pyridyl-H), 7.87 (d, 2H, pyridyl-H), 7.34 (d, 2H, PhH), 6.99 (d, 2H, PhH), 6.66 (s, 2H, NH$_2$), 4.93 (s, 2H, CH$_2$), 4.37 (br s, 2H, NCH$_2$), 4.25 (br s, 2H, NCH$_2$), 3.65 (br s, 4H, N(CH$_2$)$_2$) ppm.

Example 282

Synthesis of 1-(4-(5-amino-2-(pyridin-2-yl)thiazolo [5,4-d]pyrimidin-7-yl)piperazin-1-yl)-2-(4-chlorophenoxy)ethanone This compound was prepared from 7-(piperazin-1-yl)-2-(pyridin-2-yl)thiazolo[5,4-d]pyrimidin-5-amine using 4-chlorophenoxyactic acid in a yield of 57%, according to the procedure for the synthesis of example 50.

¹H NMR (300 MHz, DMSO, 25° C.): δ=8.63 (d, 1H, pyridyl-H), 8.16 (d, 1H, pyridyl-H), 7.96 (t, 1H, pyridyl-H), 7.48 (t, 1H, pyridyl-H), 7.33 (d, 2H, PhH), 6.99 (d, 2H, PhH), 6.54 (s, 2H, NH$_2$), 4.93 (s, 2H, CH$_2$), 4.36 (br s, 2H, NCH$_2$), 4.25 (br s, 2H, NCH$_2$), 3.65 (br s, 4H, N(CH$_2$)$_2$) ppm.

Examples 283-287

Synthesis of 7-(piperazin-1-yl)-2-substituted-thiazolo[5,4-d]pyrimidin-5-amine analogues General Procedure A suspension of an appropriate carboxylic acid (0.42 mmol) in SOCl$_2$ (1 ml) was heated under reflux for 1 hour. After concentration under reduced pressure, the residue was redissolved in dioxane (1 ml) and added to a stirring solution of tert-butyl 4-(5-amino-6-mercaptopyrimidin-4-yl)piperazine-1-carboxylate (0.1 g, 0.32 mmol) and DIPEA (0.22 ml, 1.28 mmol) in DMF (3 ml). The reaction mixture was stirred for 2 hours. The mixture was extracted with ethyl acetate, washed with water, brine and dried over sodium sulfate. After removing solvent under reduced pressure, the crude mixture was diluted with dioxane (5 ml) and 3M HCl in dioxane (1 ml) was added and the mixture was heated at 60° C. for 5 hours. After cooling, the mixture was concentrated under reduced pressure and the residue was diluted with water and neutralized with 1N NaOH. The precipitate was collected by filtration, washed with water and dried over P$_2$O$_5$, yielding the title compound.

The following compounds were synthesized according to this procedure:

Example 283

Synthesis of 2-(4-fluorophenethyl)-7-(piperazin-1-yl)thiazolo[5,4-d]pyrimidine

This compound was synthesized from tert-butyl 4-(5-amino-6-mercaptopyrimidin-4-yl)piperazine-1-carboxylate using 3-(4-fluorophenyl)propionic acid, yielding the title compound in 80% yield.

Example 284

Synthesis of 2-(4-fluorophenyl)-7-(piperazin-1-yl)thiazolo[5,4-d]pyrimidine

This compound was synthesized from tert-butyl 4-(5-amino-6-mercaptopyrimidin-4-yl)piperazine-1-carboxylate using 4-fluorobenzoic acid, yielding the title compound in 74% yield.

Example 285

Synthesis of 2-(3-(4-fluorophenyl)propyl)-7-(piperazin-1-yl)thiazolo[5,4-d]pyrimidin-5-amine This compound was synthesized from tert-butyl 4-(2,5-diamino-6-mercaptopyrimidin-4-yl)piperazine-1-carboxylate using 4-(4-fluorophenyl)butanoic acid, yielding the title compound in 48% yield.

Example 286

Synthesis of 2-(4-(4-fluorophenyl)butyl)-7-(piperazin-1-yl)thiazolo[5,4-d]pyrimidin-5-amine This compound was synthesized from tert-butyl 4-(2,5-diamino-6-mercaptopyrimidin-4-yl)piperazine-1-carboxylate using 4-(4-fluorophenyl)butanoic acid, yielding the title compound in 58% yield.

Example 287

Synthesis of 2-(4-bromophenethyl)-7-(piperazin-1-yl)thiazolo[5,4-d]pyrimidin-5-amine This compound was synthesized from tert-butyl 4-(2,5-diamino-6-mercaptopyrimidin-4-yl)piperazine-1-carboxylate using 3-(4-bromophenyl)propionic acid, yielding the title compound in 70% yield.

Examples 288-289

Synthesis of 7-(N-piperazin-1-yl)-2-substituted-thiazolo[5,4-d]pyrimidin-5-amine analogues General Procedure To a solution of tert-butyl 4-(2,5-diamino-6-mercaptopyrimidin-4-yl)piperazine-1-carboxylate (0.1 g, 0.31 mmol) and pyridine (37 μl, 0.46 mmol) in DMF (3 ml) was added an appropriate acid chloride (0.34 mmol). The reaction mixture was stirred for 2 hours. The mixture was extracted with ethyl acetate, washed with water, brine and dried over sodium sulfate. After removing solvent under reduced pressure, the crude mixture was diluted with dioxane (5 ml) and 3M HCl in dioxane (1 ml) was added and the mixture was heated at 60° C. for 5 hours. After cooling, the mixture was concentrated under reduced pressure and the residue was diluted with water and neutralized with 1N NaOH. The precipitate was collected by filtration, washed with water and dried over $P_2O_5$, yielding the title compound.

The following compounds were synthesized according to this procedure:

Example 288

Synthesis of 2-pentyl-7-(piperazin-1-yl)thiazolo[5,4-d]pyrimidin-5-amine

This compound was synthesized from tert-butyl 4-(2,5-diamino-6-mercaptopyrimidin-4-yl)piperazine-1-carboxylate using hexanoyl chloride, yielding the title compound in 67% yield.

Example 289

Synthesis of 7-(piperazin-1-yl)-2-p-tolylthiazolo[5,4-d]pyrimidin-5-amine

This compound was synthesized from tert-butyl 4-(2,5-diamino-6-mercaptopyrimidin-4-yl)piperazine-1-carboxylate using p-toluoyl chloride, yielding the title compound in 80% yield.

Example 290

Synthesis of 1-(4-(5-amino-2-(3-(4-fluorophenyl)propyl)thiazolo[5,4-d]pyrimidin-7-yl)piperazin-1-yl)-2-(4-chlorophenoxy)ethanone This compound was prepared from 2-(3-(4-fluorophenyl)propyl)-7-(piperazin-1-yl)thiazolo[5,4-d]pyrimidin-5-amine using 4-chlorophenoxyacetic acid in a yield of 33%, according to the procedure for the synthesis of example 50.

$^1$H NMR (300 MHz, CDCl$_3$, 25° C.): δ=7.24 (d, 2H, PhH), 7.10-7.15 (m, 2H, PhH), 6.96 (t, 2H, PhH), 6.90 (d, 2H, PhH), 4.71 (s, 4H, NH$_2$, OCH$_2$), 4.27 (br s, 2H, NCH$_2$), 4.23 (br s, 2H, NCH$_2$), 3.65-3.73 (m, 4H, N(CH$_2$)$_2$), 2.92 (t, 2H, CH$_2$), 2.68 (t, 2H, CH$_2$), 2.07 (quint, 2H, CH$_2$) ppm.

Example 291

Synthesis of 1-(4-(5-amino-2-(3-(4-fluorophenyl)propyl)thiazolo[5,4-d]pyrimidin-7-yl)piperazin-1-yl)-2-(4-methoxyphenoxy)ethanone This compound was prepared from 2-(3-(4-fluorophenyl)propyl)-7-(piperazin-1-yl)thiazolo[5,4-d]pyrimidin-5-amine using 4-methoxyphenoxyacetic acid in a yield of 30%, according to the procedure for the synthesis of example 50.

$^1$H NMR (300 MHz, CDCl$_3$, 25° C.): δ=7.7.11-7.16 (m, 2H, PhH), 6.94 (t, 2H, PhH), 6.82-6.93 (m, 4H, PhH), 4.71 (s, 2H, NH$_2$), 4.70 (s, 2H, OCH$_2$), 4.29 (br s, 2H, NCH$_2$), 4.24 (br s, 2H, NCH$_2$), 3.76 (s, 3H, CH$_3$), 3.71 (br s, 4H, N(CH$_2$)$_2$), 2.94 (t, 2H, CH$_2$), 2.70 (t, 2H, CH$_2$), 2.08 (quint, 2H, CH$_2$) ppm

Example 292

Synthesis of 1-(4-(5-amino-2-(4-(4-fluorophenyl)butyl)thiazolo[5,4-d]pyrimidin-7-yl)piperazin-1-yl)-2-(4-chlorophenoxy)ethanone This compound was prepared from 2-(4-(4-fluorophenyl)butyl)-7-(piperazin-1-yl)thiazolo[5,4-d]pyrimidin-5-amine using 4-chlorophenoxyacetic acid in a yield of 23%, according to the procedure for the synthesis of example 50.

$^1$H NMR (300 MHz, CDCl$_3$, 25° C.): δ=7.28 (d, 2H, PhH), 7.12-7.16 (m, 2H PhH), 7.00 (t, 2H, PhH), 6.94 (d, 2H PhH), 4.75 (s, 4H, NH$_2$, OCH$_2$), 4.30 (br s, 2H, NCH$_2$), 4.26 (br s, 2H, NCH$_2$), 3.75 (t, 2H, NCH$_2$), 3.69 (t, 2H, NCH$_2$), 2.98 (t, 2H, CH$_2$), 2.66 (t, 2H, CH$_2$), 1.78-1.87 (m, 2H, CH$_2$), 1.70-1.74 (m, 2H CH$_2$) ppm

Example 293

Synthesis of 1-(4-(5-amino-2-(4-(4-fluorophenyl)butyl)thiazolo[5,4-d]pyrimidin-7-yl)piperazin-1-yl)-2-(4-methoxyphenoxy)ethanone This compound was prepared from 2-(4-(4-fluorophenyl)butyl)-7-(piperazin-1-yl)thiazolo[5,4-d]pyrimidin-5-amine using 4-methoxyphenoxyacetic acid in a yield of 35%, according to the procedure for the synthesis of example 50.

$^1$H NMR (300 MHz, CDCl$_3$, 25° C.): δ=7.08-7.13 (m, 2H, PhH), 6.95 (t, 2H, PhH), 6.82-6.93 (m, 4H, PhH), 4.69 (s, 4H, NH$_2$, OCH$_2$), 4.27 (br s, 2H, NCH$_2$), 4.23 (br s, 2H, NCH$_2$), 3.76 (s, 3H, CH$_3$), 3.71 (br s, 4H, N(CH$_2$)$_2$), 2.95 (t, 2H, CH$_2$), 2.63 (t, 2H, CH$_2$), 1.75-1.84 (m, 2H, CH$_2$), 1.60-1.72 (m, 2H CH$_2$) ppm

Example 294

Synthesis of 1-(4-(5-amino-2-p-tolylthiazolo[5,4-d]pyrimidin-7-yl)piperazin-1-yl)-2-(4-methoxyphenoxy)ethanone This compound was prepared from 7-(piperazin-1-yl)-2-p-tolylthiazolo[5,4-d]pyrimidin-5-amine using 4-methoxyphenoxyacetic acid in a yield of 41%, according to the procedure for the synthesis of example 50.

$^1$H NMR (300 MHz, CDCl$_3$, 25° C.): δ=7.78 (d, 2H, PhH), 7.25 (d, 2H, PhH), 6.83-6.94 (m, 4H, PhH), 4.76 (s, 2H, NH$_2$), 4.72 (s, 2H, CH$_2$), 3.77 (br s, 7H, OCH$_3$, N(CH$_2$)$_2$), 42.41 (s, 3H, CH$_3$) ppm

Example 295

Synthesis of 1-(4-(5-amino-2-p-tolylthiazolo[5,4-d]pyrimidin-7-yl)piperazin-1-yl)-2-(4-chlorophenoxy)ethanone This compound was prepared from 7-(piperazin-1-yl)-2-p-tolylthiazolo[5,4-d]pyrimidin-5-amine using 4-chlorophenoxyacetic acid in a yield of 32%, according to the procedure for the synthesis of example 50.

$^1$H NMR (300 MHz, CDCl$_3$, 25° C.): δ=7.78 (d, 2H, PhH), 7.24-7.27 (m, 4H, PhH), 6.93 (d, 2H, PhH), 4.77 (s, 2H, NH$_2$), 4.75 (s, 2H, CH$_2$), 4.38 (br s, 2H, NCH$_2$), 4.32 (br s, 2H, NCH$_2$), 3.71-3.79 (m, 4H, N(CH$_2$)$_2$), 2.41 (s, 3H, CH$_3$) ppm Example 296

Synthesis of 1-(4-(5-amino-2-pentylthiazolo[5,4-d]pyrimidin-7-yl)piperazin-1-yl)-2-(4-methoxyphenoxy)ethanone This compound was prepared from 2-pentyl-7-(piperazin-1-yl)thiazolo[5,4-d]pyrimidin-5-amine using 4-methoxyphenoxyacetic acid in a yield of 34%, according to the procedure for the synthesis of example 50.

$^1$H NMR (300 MHz, DMSO, 25° C.): δ=6.89-6.90 (m, 4H, PhH), 6.30 (s, 2H, NH$_2$), 4.79 (s, 2H, CH$_2$), 4.26 (br s, 2H, NCH$_2$), 4.13 (br s, 2H, NCH$_2$), 3.69 (s, 3H, OCH$_3$), 3.58 (br s, 4H, N(CH$_2$)$_2$), 2.91 (t, 2H, CH$_2$), 1.71 (qiuint, 2H, CH$_2$), 1.31-1.36 (m, 4H, CH$_2$, CH$_2$), 0.87 (t, 3H, CH$_3$) ppm.

Example 297

Synthesis of 1-(4-(5-amino-2-pentylthiazolo[5,4-d]pyrimidin-7-yl)piperazin-1-yl)-2-(4-chlorophenoxy)ethanone This compound was prepared from 2-pentyl-7-(piperazin-1-yl)thiazolo[5,4-d]pyrimidin-5-amine using 4-chlorophenoxyacetic acid in a yield of 30%, according to the procedure for the synthesis of example 50.

$^1$H NMR (500 MHz, CDCl$_3$, 25° C.): δ=7.25 (d, 2H, PhH), 6.91 (d, 2H, PhH), 4.73 (s, 2H, OCH2), 4.69 (s, 2H, NH$_2$), 4.29 (br s, 2H, NCH$_2$), 4.24 (br s, 2H, NCH$_2$), 3.73 (br s, 2H, NCH$_2$), 3.68 (br s, 2H, NCH$_2$), 2.92 (t, 2H, CH$_2$), 1.78 (quint, 2H, CH$_2$), 1.37 (m, 4H, CH$_2$, CH$_2$), 0.91 (t, 3H, CH$_3$) ppm Example 298

Synthesis of 1-(4-(5-amino-2-(4-bromophenethyl)thiazolo[5,4-d]pyrimidin-7-yl)piperazin-1-yl)-2-(4-methoxyphenoxy)ethanone This compound was prepared from 2-(4-bromophenethyl)-7-(piperazin-1-yl)thiazolo[5,4-d]pyrimidin-5-amine using 4-methoxyphenoxyacetic acid in a yield of 40%, according to the procedure for the synthesis of example 50.

$^1$H NMR (300 MHz, CDCl$_3$, 25° C.): δ=7.40 (d, 2H, PhH), 7.07 (d, 2H, PhH), 6.82-6.93 (m, 4H, PhH), 4.71 (s, 2H, NH$_2$), 4.70 (s, 2H, OCH$_2$), 4.23 (br s, 2H, NCH$_2$), 4.19 (br s, 2H, NCH$_2$), 3.77 (s, 3H, CH$_3$), 3.67-3.75 (m, 4H, N(CH$_2$)$_2$), 3.23 (t, 2H, CH$_2$), 3.05 (t, 2H, CH$_2$) ppm Example 299

Synthesis of 1-(4-(5-amino-2-(4-bromophenethyl)thiazolo[5,4-d]pyrimidin-7-yl)piperazin-1-yl)-2-(4-chlorophenoxy)ethanone This compound was prepared from 2-(4-bromophenethyl)-7-(piperazin-1-yl)thiazolo[5,4-d]pyrimidin-5-amine using 4-chlorophenoxyacetic acid in a yield of 29%, according to the procedure for the synthesis of example 50.

$^1$H NMR (300 MHz, CDCl$_3$, 25° C.): δ=7.40 (d, 2H, PhH), 7.26 (d, 2H, PhH), 7.07 (d, 2H, PhH), 6.92 (d, 2H, PhH), 4.73 (s, 2H, OCH$_2$), 4.71 (s, 2H, NH$_2$), 4.20 (br s, 4H, N(CH$_2$)$_2$), 3.71 (t, 2H, NCH$_2$), 3.65 (t, 2H, NCH$_2$), 3.23 (t, 2H, CH$_2$), 3.05 (t, 2H, CH$_2$) ppm Example 300

Synthesis of 1-(4-(2-(4-fluorophenyl)thiazolo[5,4-d]pyrimidin-7-yl)piperazin-1-yl)-2-(4-methoxyphenoxy)ethanone This compound was prepared from 2-(4-fluorophenyl)-7-(piperazin-1-yl)thiazolo[5,4-d]pyrimidine using 4-methoxyphenoxyacetic acid in a yield of 51%, according to the procedure for the synthesis of example 50.

$^1$H NMR (300 MHz, CDCl$_3$, 25° C.): δ=8.44 (s, 1H, CH), 7.95-8.00 (m, 2H, PhH), 7.19 (t, 2H, PhH), 6.83-6.95 (m, 4H, PhH), 4.73 (s, 2H, CH$_2$), 4.42 (br s, 4H, N(CH$_2$)$_2$), 3.81 (br s, 4H, N(CH$_2$)$_2$), 3.77 (s, 3H, CH$_3$) ppm.

Example 301

Synthesis of 1-(4-(2-(4-fluorophenyl)thiazolo[5,4-d]pyrimidin-7-yl)piperazin-1-yl)-2-(4-chlorophenoxy)ethanone This compound was prepared from 2-(4-fluorophenyl)-7-(piperazin-1-yl)thiazolo[5,4-d]pyrimidine using 4-chlorophenoxyacetic acid in a yield of 48%, according to the procedure for the synthesis of example 50.

$^1$H NMR (300 MHz, CDCl$_3$, 25° C.): δ=8.45 (s, 1H, CH), 7.95-8.00 (m, 2H, PhH), 7.27 (d, 2H, PhH), 7.19 (d, 2H, PhH), 6.93 (d, 2H, PhH), 4.76 (s, 2H, CH$_2$), 4.43 (br s, 4H, N(CH$_2$)$_2$), 3.81 (br s, 4H, N(CH$_2$)$_2$) ppm.

Example 302

Synthesis of 1-(4-(2-(4-fluorophenethyl)thiazolo[5,4-d]pyrimidin-7-yl)piperazin-1-yl)-2-(4-methoxyphenoxy)ethanone This compound was prepared from 2-(4-fluorophenethyl)-7-(piperazin-1-yl)thiazolo[5,4-d]pyrimidine using 4-methoxyphenoxyacetic acid in a yield of 39%, according to the procedure for the synthesis of example 50.

$^1$H NMR (300 MHz, CDCl$_3$, 25° C.): δ=8.40 (s, 1H, CH), 7.14-7.19 (m, 2H, PhH), 6.97 (t, 2H, PhH), 6.82-6.91 (m, 4H, PhH), 4.71 (s, 2H, NH$_2$), 4.31 (br s, 4H, N(CH$_2$)$_2$), 3.76 (s, 3H, CH$_3$), 3.74 (br s, 4H, N(CH$_2$)$_2$), 3.34 (t, 2H, CH$_2$), 3.12 (t, 2H, CH$_2$) ppm.

Example 303

Synthesis of 1-(4-(2-(4-fluorophenethyl)thiazolo[5,4-d]pyrimidin-7-yl)piperazin-1-yl)-2-(4-chlorophenoxy)ethanone This compound was prepared from 2-(4-fluorophenethyl)-7-(piperazin-1-yl)thiazolo[5,4-d]pyrimidine using 4-chlorophenoxyacetic acid in a yield of 48%, according to the procedure for the synthesis of example 50.

$^1$H NMR (300 MHz, CDCl$_3$, 25° C.): δ=8.41 (s, 1H, CH), 7.26 (d, 2H, PhH), 7.14-7.19 (m, 2H, PhH), 6.97 (t, 2H, PhH), 6.91 (d, 2H, PhH), 4.74 (s, 2H, NH$_2$), 4.31 (br s, 4H, N(CH$_2$)$_2$), 3.75 (br s, 2H, NCH$_2$), 3.69 (br s, 2H, NCH$_2$), 3.35 (t, 2H, CH$_2$), 3.12 (t, 2H, CH$_2$) ppm.

Example 304

Synthesis of thieno[2,3-d]pyrimidin-4(3H)-one

A solution of methyl 2-aminothiophene-3-carboxylate (3.0 g, 19.1 mmol) in formamide (95 ml) was heated at 190° C. for 4 hours. The cooled mixture was poured into water. The precipitate was filtered off, washed with water and dried. The crude product was purified by silica gel chromatography ($CH_2Cl_2$/MeOH 50:1) to yield the title compound as a white solid (1.93 g, 66%).

$^1$H NMR (300 MHz, DMSO, 25° C.): δ=12.49 (s, 1H, NH), 8.13 (s, 1H, CH), 7.58 (d, J=5.8 Hz, 1H, CH), 7.39 (d, J=5.8 Hz, 1H, CH) ppm.

HRMS: calcd for $C_6H_5N_2OS$ 153.01226, found 153.01155.

Example 305

Synthesis of 2-methylthieno[2,3-d]pyrimidin-4(3H)-one

To a solution of ethyl 2-aminothiophene-3-carboxylate (0.1 g, 0.64 mmol) and acetonitrile (50 µl, 0.95 mmol) in dioxane (3 ml) was added 4M HCl in dioxane (3 ml). The mixture was stirred at room temperature overnight. The solvents were removed under reduced pressure. The residue was diluted with water and made alcaline with a saturated aqueous sodium bicarbonate solution. The precipitate was filtered off, washed with water and dried. The crude residue was purified by flash chromatography on silica gel ($CH_2Cl_2$/MeOH 50:1) to yield the title compound as a white solid (42 mg, 40%).

$^1$H NMR (300 MHz, CDCl$_3$, 25° C.): δ=12.92 (s, 1H, NH), 7.46 (d, J=5.8 Hz, 1H, CH), 7.21 (d, J=5.8 Hz, 1H, CH), 2.61 (s, 3H, CH$_3$) ppm.

Example 306

Synthesis of 2-aminothieno[2,3-d]pyrimidin-4(3H)-one

A mixture of ethyl 2-aminothiophene-3-carboxylate (0.5 g, 3.18 mmol), chloroformamidine hydrochloride (0.91 g, 7.95 mmol) and dimethylsulfone (1.50 g, 15.9 mmol) was heated at 120-130° C. for 30 minutes. After cooling down to room temperature, water (10 ml) was added and ammonium hydroxide was used to neutralize the suspension. The solid was filtered off, washed with water and dried. The crude residue was purified by flash chromatography on silica gel ($CH_2Cl_2$/MeOH 10:1) to yield the title compound as a white solid (0.24 g, 45%).

$^1$H NMR (300 MHz, DMSO, 25° C.): δ=10.89 (s, 1H, NH), 7.09 (d, J=5.8 Hz, 1H, CH), 6.97 (d, J=5.8 Hz, 1H, CH), 6.52 (s, 2H, NH$_2$) ppm.

HRMS: calcd for $C_6H_6N_3OS$ 168.02316, found 168.02239.

Example 307

Synthesis of 4-chlorothieno[2,3-d]pyrimidine

DMF (1.53 ml, 19.7 mmol) in dichloromethane (50 ml) was cooled to 0° C. and oxalyl chloride (2.5 ml, 29.6 mmol) was added slowly forming a white gel. Thieno[2,3-d]pyrimidin-4(3H)-one (1.5 g, 9.86 mmol) was added and the reaction mixture was refluxed for 3 hours. The mixture was cooled down to room temperature and poured into water. The mixture was extracted with dichloromethane, dried over sodium sulfate and concentrated in vacuo. The crude residue was purified by silica gel chromatography (EtOAc/hexane 15:1) to yield the title compound as a white solid (1.61 g, 96%).

$^1$H NMR (300 MHz, CDCl$_3$, 25° C.): δ=8.88 (s, 1H, CH), 7.64 (d, J=6.0 Hz, 1H, CH), 7.47 (d, J=5.8 Hz, 1H, CH) ppm.

HRMS: calcd for $C_6H_4ClN_2S$ 170.97837, found 170.97804.

Examples 308 and 309

Synthesis of 6-bromo-4-chlorothieno[2,3-d]pyrimidine and 6-bromo-2-butyl-4-chlorothieno[2,3-d]pyrimidine n-BuLi (1.6 M in hexane, 1.9 ml, 2.5 mmol) in THF (8 ml) was cooled to −78° C. 4-Chlorothieno[2,3-d]pyrimidine (0.34 g, 2.0 mmol) was dissolved in THF (2 ml) and slowly added to the reaction mixture over 5 minutes. After 20 min, CBr$_4$ (0.73 g, 2.2 mmol) in THF (3 ml) was slowly added to the reaction mixture. The temperature was maintained at −78° C. for 20 minutes and then warmed to room temperature for 2 hours. The mixture was poured into water and extracted with chloroform, dried over sodium sulfate, and concentrated in vacuo. The crude residue was purified by silica gel chromatography (EtOAc/hexane 40:1) to yield two pure compounds a white solid (example 203: 0.13 g, 25% and example 204: 0.16 g, 26%).

Example 308

$^1$H NMR (300 MHz, CDCl$_3$, 25° C.): δ=8.82 (s, 1H, H-2), 7.49 (s, 1H, H-5) ppm.

Example 309

$^1$H NMR (300 MHz, CDCl$_3$, 25° C.): δ=7.4 (s, 1H, H-5), 2.99 (t, J=7.5 Hz, 2H, CH$_2$CH$_2$CH$_2$CH$_3$), 1.83 (quint, J=7.6 Hz, 2H, CH$_2$CH$_2$CH$_2$CH$_3$), 1.42 (sixtet, J=7.4 Hz, 2H, CH$_2$CH$_2$CH$_2$CH$_3$), 0.96 (t, J=7.4 Hz, 2H, CH$_2$CH$_2$CH$_2$CH$_3$) ppm.

Example 310

Synthesis of 4-Chloro-6-(4-fluorophenyl)thieno[2,3-d]pyrimidine

A solution of 6-bromo-4-chlorothieno[2,3-d]pyrimidine (0.12 g, 0.48 mmol), 4-fluorophenylboronic acid (67 mg, 0.48 mmol), K$_2$CO$_3$ (0.266 g, 1.92 mmol) and Pd(PPh$_3$)$_4$ in dioxane/H$_2$O (3:1, 3 ml) was refluxed under N$_2$ for 2 hours. After cooling to room temperature, 1N HCl was added slowly to neutralize the mixture to pH=7-8. The mixture was extracted with CH$_2$Cl$_2$, washed with water and brine and dried over Na$_2$SO$_4$. After removing the solvents under reduced pressure, the crude residue was purified by silica gel chromatography (hexane/EtOAc 30:1) to yield the title compound as a pale yellow solid (60 mg, 47%).

$^1$H NMR (300 MHz, CDCl$_3$, 25° C.): δ=8.82 (s, 1H, CH-2), 7.70-7.74 (m, 2H, PhH), 7.52 (s, 1H, CH-5), 7.19 (t, J=8.4 Hz, 2H, PhH) ppm.

HRMS: calcd for $C_{12}H_7ClFN_2S$ 265.00025, found 264.99949.

Example 311

Synthesis of 2-butyl-4-chloro-6-(4-fluorophenyl)thieno[2,3-d]pyrimidine

This compound was prepared from example 309 in a yield of 57%, according to the procedure for the synthesis of example 310.

$^1$H NMR (300 MHz, CDCl$_3$, 25° C.): δ=7.57-7.62 (m, 2H, PhH), 7.36 (s, 1H, H-5), 7.08 (t, J=8.4 Hz, 2H, PhH), 2.94 (t, J=7.6 Hz, 2H, CH$_2$CH$_2$CH$_2$CH$_3$), 1.78 (quint, J=7.6 Hz, 2H, CH$_2$CH$_2$CH$_2$CH$_3$), 1.36 (sixtet, J=7.5 Hz, 2H, CH$_2$CH$_2$CH$_2$CH$_3$), 0.89 (t, J=7.4 Hz, 2H, CH$_2$CH$_2$CH$_2$CH$_3$) ppm.

HRMS: calcd for C$_{16}$H$_{15}$ClFN$_2$S 321.06285, found 321.06206.

Example 312

Synthesis of 2-(4-chlorophenoxy)-1-(4-(6-(4-fluorophenyl)thieno[2,3-d]pyrimidin-4-yl)piperazin-1-yl)ethanone To a solution of 4-chloro-6-(4-fluorophenyl)thieno[2,3-d]pyrimidine (20 mg, 0.08 mmol) and triethylamine (42 μl, 0.3 mmol) in dioxane (1 ml) was added 2-(4-chlorophenoxy)-1-(piperazin-1-yl)ethanone (25 mg, 0.1 mmol). The mixture was heated at 60° C. for 2 hours.

After cooling down to room temperature, the solvents were removed under reduced pressure. The crude residue was purified by silica gel chromatography (CH$_2$Cl$_2$/MeOH 50:1) to yield the title compound as a white solid (27 mg, 75%).

$^1$H NMR (300 MHz, CDCl$_3$, 25° C.): δ=8.51 (s, 1H, CH-2), 7.60-7.65 (m, 2H, PhH), 7.36 (s, 1H, CH-5), 7.26 (d, J=8.8 Hz, PhH), 7.14 (t, J=8.5 Hz, 2H, PhH), 6.91 (d, J=8.8 Hz, 2H, PhH), 4.75 (s, 2H, CH$_2$), 3.95 (br s, 4H, NCH$_2$), 3.82 (br s, 4H, NCH$_2$) ppm.

HRMS: calcd for C$_{24}$H$_{21}$ClFN$_4$O$_2$S 483.10578, found 483.10438.

Example 313

Synthesis of 1-(4-(2-butyl-6-(4-fluorophenyl)thieno[2,3-d]pyrimidin-4-yl)piperazin-1-yl)-2-(4-chlorophenoxy)ethanone This compound was prepared from example 311 in a yield of 57%, according to the procedure for the synthesis of example 312.

$^1$H NMR (300 MHz, CDCl$_3$, 25° C.): δ=7.58-7.63 (m, 2H, PhH), 7.32 (s, 1H, CH-5), 7.26 (d, J=9.0 Hz, PhH), 7.13 (t, J=8.6 Hz, 2H, PhH), 6.91 (d, J=9.0 Hz, 2H, PhH), 4.74 (s, 2H, CH$_2$), 3.95 (br s, 4H, N(CH$_2$)$_2$), 3.81 (br s, 4H, CON(CH$_2$)$_2$), 2.84 (t, J=7.6 Hz, 2H, CH$_2$CH$_2$CH$_2$CH$_3$), 1.80 (quint, J=7.6 Hz, 2H, CH$_2$CH$_2$CH$_2$CH$_3$), 1.4 (sixtet, J=7.6 Hz, 2H, CH$_2$CH$_2$CH$_2$CH$_3$), 0.96 (t, J=7.6 Hz, 2H, CH$_2$CH$_2$CH$_2$CH$_3$) ppm.

HRMS: calcd for C$_{28}$H$_{29}$ClFN$_4$O$_2$S 539.16838, found 539.16680.

Example 314

Synthesis of N-(3-chloro-4-fluorophenyl)-6-(4-fluorophenyl)thieno[2,3-d]pyrimidin-4-amine To a solution of 4-chloro-6-(4-fluorophenyl)thieno[2,3-d]pyrimidine (40 mg, 0.15 mmol) in 1,2-dichloroethane/t-BuOH (1:1, 1 ml) was added 3-chloro-4-fluoroaniline (22 mg, 0.15 mmol). The mixture was heated at 90° C. for 2 days. After cooling down to room temperature, the solvents were removed under reduced pressure. The crude residue was purified by silica gel chromatography (CH$_2$Cl$_2$/MeOH 100:1) to yield the title compound as a white solid (28 mg, 50%).

$^1$H NMR (300 MHz, CDCl$_3$, 25° C.): δ=8.61 (s, 1H, H-2), 7.89 (dd, J=6.5 Hz, J=2.6 Hz, 1H, PhH), 7.62-7.67 (m, 2H, PhH), 7.48-7.53 (m, 1H, PhH), 7.28 (s, 1H, H-5), 7.13-7.26 (m, 3H, PhH), 6.87 (s, 1H, NH) ppm.

HRMS: calcd for C$_{18}$H$_{11}$ClF$_2$N$_3$S 374.03303, found 374.03216.

Example 315

Synthesis of 2-butyl-N-(3-chloro-4-fluorophenyl)-6-(4-fluorophenyl)thieno[2,3-d]pyrimidin-4-amine This compound was prepared from example 311 in a yield of 47%, according to the procedure for the synthesis of example 314.

$^1$H NMR (300 MHz, CDCl$_3$, 25° C.): δ=8.03 (dd, J=6.30 Hz, J=2.3 Hz, 1H, PhH), 7.59-7.64 (m, 2H, PhH), 7.48-7.53 (m, 1H, PhH), 7.23 (s, 1H, H-5), 7.10-7.19 (m, 3H, PhH, PhH), 6.89 (s, 1H, NH), 2.93 (t, J=7.5 Hz, 2H, CH$_2$CH$_2$CH$_2$CH$_3$), 1.87 (quint, J=7.6 Hz, 2H, CH$_2$CH$_2$CH$_2$CH$_3$), 1.45 (sixtet, J=7.5 Hz, 2H, CH$_2$CH$_2$CH$_2$CH$_3$), 0.98 (t, J=7.3 Hz, 2H, CH$_2$CH$_2$CH$_2$CH$_3$) ppm.

Example 316

Synthesis of 2-(4-fluorophenyl)acetaldehyde

To a stirred suspension of pyridinium chlorochromate (6.9 g, 21.4 mmol) in CH$_2$Cl$_2$ (100 ml) was added a solution of 2-(4-fluorophenyl)ethanol (3.0 g, 21.4 mmol) in CH$_2$Cl$_2$ (10 ml). The resulting suspension was stirred for 2 hours at room temperature and was then diluted with ether. The resulting suspension was filtered through a pad of Celite and washed with ether. The solvents were removed under reduced pressure to yield the crude title compound as a green oil (2.6 g, 86%), which was used as such for further reaction.

$^1$H NMR (300 MHz, CDCl$_3$, 25° C.): δ=9.75 (s, 1H, CH), 7.19-7.22 (m, 2H, PhH), 7.06 (t, J=8.5 Hz, PhH), 3.68 (s, 2H, CH$_2$) ppm.

Example 317

Synthesis of ethyl 2-amino-5-(4-fluorophenyl)thiophene-3-carboxylate

Triethylamine (0.98 ml, 7.01 mmol) was added to a stirred suspension of ethyl cyanoacetate (2.79 ml, 13.7 mmol) and sulfur (0.44 g, 13.7 mmol) in DMF (70 ml). A solution of 2-(4-fluorophenyl)acetaldehyde (example 316, 1.9 g, 13.7 mmol) in DMF (5 ml) was added dropwise over a period of 50 minutes, while the temperature was maintained at 50° C. The solution was cooled down to room temperature and stirred overnight. The reaction was poured into water and the aqueous phase was extracted with diethylether. The organic layer was separated and washed with water, brine and dried over Na$_2$SO$_4$. The solvents were evaporated and the crude residue was purified by flash chromatography on silica gel (EtOAc/Hexane 1:15) to yield the title compound as a white solid (1.3 g, 38%).

$^1$H NMR (300 MHz, CDCl$_3$, 25° C.): δ=7.33-7.39 (m, 2H, PhH), 7.14 (s, 1H, CH), 6.99 (t, J=8.6 Hz, PhH), 6.06 (s, 2H, NH$_2$), 4.29 (q, J=7.1, 2H, CH$_2$), 1.36 (t, J=7.1, 3H, CH$_3$) ppm.

Example 318

Synthesis of ethyl 2-amino-5-phenyl-thiophene-3-carboxylate

This compound was synthesized using the procedure as described for example 317, using phenylacetaldehyde.

Example 319

Synthesis of 6-(4-fluorophenyl)-2-methylthieno[2,3-d]pyrimidin-4(3H)-one

To a solution of ethyl 2-amino-5-(4-fluorophenyl) thiophene-3-carboxylate (0.3 g, 1.13 mmol) and acetonitrile (0.56 ml, 11.3 mmol) in dioxane (4 ml) was added 4M HCl in dioxane (4 ml). The mixture was stirred at room temperature overnight. The solvents were removed under reduced pressure. The residue was diluted with water and made alcaline with a saturated aqueous sodium bicarbonate solution. The precipitate was filtered off, washed with water and dried. The crude residue was purified by flash chromatography on silica gel ($CH_2Cl_2$/MeOH 60:1) to yield the title compound as a white solid (0.29 g, 81%).

$^1$H NMR (300 MHz, DMSO, 25° C.): δ=12.47 (s, 1H, NH), 7.76-7.81 (m, 2H, PhH), 7.71 (s, 1H, CH), 7.28 (t, J=8.7 Hz, PhH), 2.38 (s, 3H, $CH_3$) ppm.

HRMS: calcd for $C_{13}H_{10}FN_2OS$ 261.04979, found 261.04889.

Example 320

Synthesis of 2-amino-6-(4-fluorophenyl)thieno[2,3-d]pyrimidin-4(3H)-one

A mixture of ethyl 2-amino-5-(4-fluorophenyl)thiophene-3-carboxylate (0.3 g, 1.13 mmol), chloroformamidine hydrochloride (0.33 g, 2.83 mmol) and dimethylsulfone (0.53 g, 5.65 mmol) was heated at 120-130° C. for 30 minutes. After cooling down to room temperature, water (10 ml) was added and ammonium hydroxide was used to neutralize the suspension. The solid was filtered off, washed with water and dried. The crude residue was purified by flash chromatography on silica gel ($CH_2Cl_2$/MeOH 10:1) to yield the title compound as a white solid (0.28 g, 95%).

$^1$H NMR (300 MHz, DMSO, 25° C.): δ=11.05 (s, 1H, NH), 7.66-7.71 (m, 2H, PhH), 7.51 (s, 1H, CH), 7.23 (t, J=8.8 Hz, PhH), 6.73 (s, 2H, $NH_2$) ppm.

HRMS: calcd for $C_{12}H_9FN_3OS$ 262.04504, found 262.04413.

Example 321

Synthesis of 2-amino-6-phenyl-thieno[2,3-d]pyrimidin-4(3H)-one

This compound was synthesized from example 318 according to the procedure mentioned for the synthesis of example 320.

MS m/z (%): 244 ([M+H]$^+$, 100)

HRMS: calcd for $C_{13}H_{13}FNO_2S$ 266.06510, found 266.06425.

Example 322

Synthesis of 6-(4-fluorophenyl)-2-phenylthieno[2,3-d]pyrimidin-4(3H)-one

To a solution of ethyl 2-amino-5-(4-fluorophenyl) thiophene-3-carboxylate (0.2 g, 0.75 mmol) and benzonitrile (0.23 g, 2.26 mmol) in dioxane (4 ml) was added 4M HCl in dioxane (4 ml). The mixture was stirred at room temperature overnight. The precipitate was filtered off, washed with diethyl ether and dried. The solid was redissolved in DMF and the mixture was heated at 100° C. for 3 hours. The solvents were removed under reduced pressure. The residue was diluted with water and the solid was filtered off, washed with water and dried. The crude residue was purified by flash chromatography on silica gel ($CH_2Cl_2$/MeOH 60:1) to yield the title compound as a white solid (0.20 g, 82%).

$^1$H NMR (300 MHz, DMSO, 25° C.): δ=12.78 (s, 1H, NH), 8.16 (d, J=7.4 Hz, 2H, PhH), 7.81-7.85 (m, 3H, PhH), 7.57 (s, 1H, CH), 7.55 (t, J=7.4 Hz, 2H, PhH), 7.30 (t, J=8.5 Hz, PhH) ppm.

HRMS: calcd for $C_{18}H_{12}FN_2OS$ 323.06544, found 323.06461.

Example 323

Synthesis of ethyl 6-(4-fluorophenyl)-4-oxo-3,4-dihydrothieno[2,3-d]pyrimidine-2-carboxylate This compound was prepared from example 317 in a yield of 96%, according to the procedure for the synthesis of example 322, using ethyl cyanoformate.

$^1$H NMR (300 MHz, DMSO, 25° C.): δ=12.97 (s, 1H, NH), 7.91 (s, 1H, CH), 7.86-7.89 (m, 2H, PhH), 7.32 (t, J=8.8 Hz, PhH), 4.38 (q, J=7.1 Hz, 2H, $CH_2$), 1.36 (t, J=7.1 Hz, 3H, $CH_3$) ppm.

HRMS: calcd for $C_{15}H_{12}FN_2O_3S$ 319.05527, found 319.05433.

Example 324

Synthesis of ethyl 2-(6-(4-fluorophenyl)-4-oxo-3,4-dihydrothieno[2,3-d]pyrimidin-2-yl)acetate This compound was prepared from example 317 in a yield of 93%, according to the procedure for the synthesis of example 322, using ethyl cyanoacetate.

$^1$H NMR (300 MHz, DMSO, 25° C.): δ=12.63 (s, 1H, NH), 7.79-7.84 (m, 2H, PhH), 7.77 (s, 1H, H-5), 7.30 (t, J=8.7 Hz, PhH), 4.15 (q, J=7.1 Hz, 2H, $OCH_2$), 3.79 (s, 2H, $CH_2$), 1.21 (t, J=7.1 Hz, 3H, $CH_3$) ppm.

HRMS: calcd for $C_{16}H_{14}FN_2O_3S$ 333.07092, found 333.07010.

Example 325

Synthesis of 2-(4-chlorophenoxy)-1-(4-(6-(4-fluorophenyl)-2-methylthieno[2,3-d]pyrimidin-4-yl)piperazin-1-yl)ethanone To a solution of 6-(4-fluorophenyl)-2-methylthieno[2,3-d]pyrimidin-4(3H)-one (40 mg, 0.15 mmol) and BOP (88 mg, 0.20 mmol) in $CH_3ON$ (1 ml) was added DBU (34 μl, 0.23 mmol). After stirring for 10 minutes at room temperature, 2-(4-chlorophenoxy)-1-(piperazin-1-yl)ethanone (59 mg, 0.23 mmol) was added. The reaction was stirred at room temperature overnight and then heated at 60° C. for 4 hours. The solvents were removed under reduced pressure, and the crude residue was purified by flash chromatography on silica gel ($CH_2Cl_2$/MeOH 100:1) to yield the title compound as a white solid (66 mg, 86%).

$^1$H NMR (300 MHz, $CDCl_3$, 25° C.): δ=7.56-7.61 (m, 2H, PhH), 7.31 (s, 1H, CH), 7.25 (d, J=8.9 Hz, 2H, PhH), 7.11 (t, J=8.5 Hz, PhH), 6.90 (d, J=8.9 Hz, 2H, PhH), 4.74 (s, 2H, $CH_2$), 3.92 (br s, 4H, $NCH_2$), 3.80 (br s, 4H, $NCH_2$), 2.60 (s, 3H, $CH_3$) ppm.

HRMS: calcd for $C_{25}H_{23}ClFN_4O_2S$ 497.12143, found 497.11983.

Example 326

Synthesis of 1-(4-(2-amino-6-(4-fluorophenyl)thieno[2,3-d]pyrimidin-4-yl)piperazin-1-yl)-2-(4-chlorophenoxy)ethanone This compound was prepared from example 320 in a yield of 55%, according to the procedure for the synthesis of example 325.

$^1$H NMR (300 MHz, DMSO, 25° C.): δ=7.52-7.57 (m, 2H, PhH), 7.27 (s, 1H, CH), 7.22 (d, J=8.9 Hz, 2H, PhH) 7.10 (t, J=8.7 Hz, PhH), 6.91 (d, J=8.9 Hz, 2H, PhH), 4.78 (s, 2H, $NH_2$), 4.74 (s, 2H, $CH_2$), 3.86 (br s, 4H, $NCH_2$), 3.78 (br s, 4H, $NCH_2$) ppm.

HRMS: calcd for $C_{24}H_{22}ClFN_5O_2S$ 498.11668, found 498.11511.

Example 327

Synthesis of 2-amino-4-N-benzylamino-6-(4-fluorophenyl)-thieno[2,3-d]pyrimidine

To a solution of 2-amino-6-(4-fluorophenyl)thieno[2,3-d]pyrimidin-4-(3H)-one (100 mg, 0.39 mmol) in acetonitrile (20 ml) was added 1,8-diazabicyclo[5.4.0]undec-7-ene (DBU, 0.58 mmol, 86 µl), benzotriazol-1-yloxytris(dimethylamino)-phosphonium hexafluorophosphate (BOP, 0.77 mmol, 84 µl) and benzylamine (0.77 mmol, 84 µl). The reaction was stirred at room temperature overnight. The reaction mixture was diluted with water and dichloromethane. The organic layer was washed with water. The combined organic layers were evaporated in vacuo and the residue was redissolved in ethylacetate. This solution was extracted with brine (3×). The combined organic layers were again evaporated and the crude residue was purified by flash chromatography on silica using a mixture of methanol and dichloromethane (in a ratio gradually ranging from 1:99 to 3:97) as mobile phase, yielding the title compound (86 mg, 63%).

MS m/z (%): 351 ([M+H]$^+$, 100)

Example 328

Synthesis of 2-amino-4-N-piperazinyl-6-phenyl-thieno[2,3-d]pyrimidine

This compound was synthesized from example 321 according to the procedure of example 327 in 71% yield, using piperazine.

MS m/z (%): 312 ([M+H]$^+$, 100)

Example 329

Synthesis of 1-(4-(2-amino-6-phenylthieno[2,3-d]pyrimidin-4-yl)piperazin-1-yl)-2-(4-chlorophenoxy)ethanone To a solution of 2-amino-4-N-piperazino-6-phenyl-thieno[2,3-d]pyrimidine (90 mg, 0.29 mmol) in dioxane (10 ml) was added diisopropylethylamine (0.58 mmol, 96 µl) and 4-chlorophenoxyacetyl chloride (0.35 mmol, 71 mg). The reaction was stirred at room temperature for 2 hours. The reaction mixture was diluted with dichloromethane and extracted with water and brine. The organic phase was evaporated in vacuo and purified by flash chromatography on silica, the mobile phase being a mixture of methanol and dichloromethane (in a ratio gradually ranging from 100% $CH_2Cl_2$ to 2% $CH_3OH$ in $CH_2Cl_2$), yielding the pure title compound (115 mg, 83%).

MS m/z (%): 480 ([M+H]$^+$, 100)

Example 330

Synthesis of 4-(2-amino-6-phenylthieno[2,3-d]pyrimidin-4-yl)-N-m-tolylpiperazine-1-carboxamide To a solution of 2-amino-4-N-piperazino-6-phenyl-thieno[2,3-d]pyrimidine (70 mg, 0.23 mmol) in dioxane (10 ml) was added m-tolylisocyanate (0.27 mmol, 35 µl). The reaction was stirred at room temperature for 2 hours. The reaction mixture was diluted with dichloromethane and extracted with water and brine. The organic phase was evaporated in vacuo and purified by flash chromatography on silica, the mobile phase being a mixture of methanol and dichloromethane (in a ratio gradually ranging from 100% $CH_2Cl_2$ to 2% $CH_3OH$ in $CH_2Cl_2$), yielding the pure title compound (59 mg, 58%).

MS m/z (%): 445 ([M+H]$^+$, 100)

$^1$H NMR (300 MHz, $CDCl_3$, 25° C.): δ=7.56-7.61 (m, 2H, arom H), 7.15-7.45 (m, 6H, arom H), 6.88 (s, 1H, arom H), 6.33 (s, 1H, arom H), 4.79 (2H, br s, $NH_2$), 4.01 (t, 4H, piperazine $CH_2$), 3.74 (br s, 4H, piperazine $CH_2$), 2.34 (br s, 3H, $CH_3$) ppm.

Example 331

Synthesis of 4-(2-amino-6-phenylthieno[2,3-d]pyrimidin-4-yl)-N-(4-chlorophenyl)piperazine-1-carboxamide This compound was synthesized in 76% yield from example 328 according to the procedure for the synthesis of example 330, using 4-chloro-phenylisocyanate.

MS m/z (%): 465 ([M+H]$^+$, 100)

Example 332

Synthesis of 1-(4-(2-amino-6-phenylthieno[2,3-d]pyrimidin-4-yl)piperazin-1-yl)-2-phenoxyethanone To a solution of 2-amino-4-(N-piperazin-1-yl)-6-phenyl-thieno[2,3-d]pyrimidine (48 mg, 0.15 mmol) and pyridine (15 µl, 0.18 mmol) in DMF (1 ml) was added phenoxyacetyl chloride (0.17 mmol). The reaction mixture was stirred for 2 hours at room temperature. The reaction mixture was quenched with water, extracted with EtOAc, brine and was dried over $Na_2SO_4$. After removing the solvents, the crude residue was purified by flash chromatography on silica (CH$_2$Cl$_2$/MeOH 100:1) to yield the title compound as a white solid (39 mg, 58%).
MS m/z (%): 446 ([M+H]$^+$, 100)

Example 333

Synthesis of 2-amino-4-N-homopiperazinyl-6-phenyl-thieno[2,3-d]pyrimidine

This compound was synthesized from example 321 according to the procedure of example 328, using homopiperazine, in 53% yield.
MS m/z (%): 326 ([M+H]$^+$, 100)

Example 334

Synthesis of 1-(4-(2-amino-6-phenylthieno[2,3-d]pyrimidin-4-yl)-1,4-diazepan-1-yl)-2-(4-chlorophenoxy)ethanone This compound was synthesized in 69% yield from example 333, according to the procedure described for the synthesis of example 332, using 4-chloro-phenoxyacetyl chloride.
MS m/z (%): 495 ([M+H]$^+$, 100)

Example 335

Synthesis of (4-(2-amino-6-phenylthieno[2,3-d]pyrimidin-4-yl)-1,4-diazepan-1-yl)(4-chlorophenyl)methanone This compound was synthesized from example 333 according to the procedure for the synthesis of example 332, using 4-chlorobenzoylchloride.
MS m/z (%): 464 ([M+H]$^+$, 100)

Example 336

Synthesis of 2-(4-(2-amino-6-phenylthieno[2,3-d]pyrimidin-4-yl)piperazin-1-yl)-N-methyl-N-phenylacetamide This compound was synthesized according to the procedure of example 327, using 2-(piperazin-1-yl)-acetic acid N-methyl-N-phenyl-amide in 52% yield.
MS m/z (%): 459 ([M+H]$^+$, 100)
$^1$H NMR (300 MHz, CDCl$_3$, 25° C.): δ=7.56 (d, 2H, arom H), 7.20-7.50 (m, 9H, arom H), 4.75 (br s, 2H, NH$_2$), 6.33 (s, 1H, arom H), 4.79 (2H, br s, NH$_2$), 4.01 (t, 4H, piperazine CH$_2$), 3.74 (br s, 4H, piperazine CH$_2$), 2.99 (2H, s, CH2), 2.34 (br s, 3H, CH$_3$) ppm Example 337

Synthesis of 4-(4-(2-phenoxyethyl)piperazin-1-yl)-6-phenylthieno[2,3-d]pyrimidin-2-amine This compound was synthesized according to the procedure of example 327, using 1-(2-phenoxyethyl)-piperazine in 49% yield.
MS m/z (%): 432 ([M+H]$^+$, 100)
$^1$H NMR (300 MHz, CDCl$_3$, 25° C.): δ=7.57 (d, 2H, arom H), 7.25-7.35 (m, 5H, arom H), 6.94 (m, 4H, arom H), 4.79 (br s, 2H, NH$_2$), 4.17 (2H, t, CH$_2$), 3.90 (t, 4H, piperazine CH$_2$), 2.89 (t, 2H, CH$_2$), 2.74 (4H, t, piperazine CH$_2$) ppm.

Example 338

Synthesis of (R)-tert-butyl 1-(2-amino-6-(4-fluorophenyl)thieno[2,3-d]pyrimidin-4-yl)pyrrolidin-3-ylcarbamate This compound was synthesized according to the procedure of example 327, in 61% yield, using (R)-3-N-Boc-aminopyrrolidine.
MS m/z (%): 430 ([M+H]$^+$, 100)
$^1$H NMR (300 MHz, CDCl$_3$, 25° C.): δ=7.51 (m, 2H, arom H), 7.35 (s, 1H, arom H), 7.07 (t, 2H, arom H), 4.78 (br s, 2H, NH$_2$), 4.38 (br s, 1H, NH), 4.06-3.70 (m, 5H), 2.27 (m, 1H, CH$_2$), 2.04 (m, 1H, CH$_2$) ppm.

Example 339

Synthesis of (R)-4-(3-aminopyrrolidin-1-yl)-6-(4-fluorophenyl)thieno[2,3-d]pyrimidin-2-amine To a solution of the compound of example 338 (66 mg, 0.15 mmol) in dichloromethane (6 ml) was added trifluoroacetic acid (3 ml). The solution was stirred at room temperature for 30 minutes. The solvents were evaporated in vacuo and co-evaporated with toluene. The residue was directly used for further reaction without any purification.
MS m/z (%): 330 ([M+H]$^+$, 100)

Example 340

Synthesis of (R)-N-(1-(2-amino-6-(4-fluorophenyl)thieno[2,3-d]pyrimidin-4-yl)pyrrolidin-3-yl)-2-(4-chlorophenoxy)acetamide This compound was synthesized in 78% yield from example 339 according to the procedure of example 332, using 4-chlorophenoxyacetyl chloride.
MS m/z (%): 498 ([M+H]$^+$, 100)
$^1$H NMR (300 MHz, DMSO, 25° C.): δ=8.42 (d, 1H, NH), 7.67 (d, 2H, arom H), 7.31 (t, 2H, arom H), 6.98 (d, 2H, arom H), 6.21 (br s, 2H, NH$_2$), 4.51 (s, 1H, CH2), 3.87-3.67 (m, 5H), 2.17 (m, 1H, CH$_2$), 1.99 (m, 1H, CH$_2$) ppm.

Example 341

Synthesis of (R)-N-(1-(2-amino-6-(4-fluorophenyl)thieno[2,3-d]pyrimidin-4-yl)pyrrolidin-3-yl)-4-chlorobenzamide This compound was synthesized from example 339 according to the procedure of example 332, using 4-chlorobenzoylchloride in 65% yield.
MS m/z (%): 468 ([M+H]$^+$, 100)

Example 342

Synthesis of 2-amino-4-N-piperazinyl-6-(4-fluorophenyl)-thieno[2,3-d]pyrimidine

This compound was synthesized according to the procedure of example 327, using piperazine in 54% yield.
MS m/z (%): 330 ([M+H]$^+$, 100)

Example 343

Synthesis of 1-(4-(2-amino-6-(4-fluorophenyl)thieno[2,3-d]pyrimidin-4-yl)piperazin-1-yl)-3-phenylpropan-1-one This compound was synthesized in 55% yield from 2-amino-4-N-piperazino-6-(4-fluorophenyl)-thieno[2,3-d]pyrimidine according to the procedure for the synthesis of example 329, using hydrocinnamoylchloride.
MS m/z (%): 462 ([M+H]$^+$, 100)

Example 344

Synthesis of 4-(4-(benzylsulfonyl)piperazin-1-yl)-6-(4-fluorophenyl)thieno[2,3-d]pyrimidin-2-amine This compound was synthesized in 51% yield from 2-amino-4-N-piperazino-6-(4-fluorophenyl)-thieno[2,3-d]pyrimidine according to the procedure for the synthesis of example 329, using α-toluenesulfonyl chloride.
MS m/z (%): 484 ([M+H]$^+$, 100)

Example 345

Synthesis of (4-(2-amino-6-(4-fluorophenyl)thieno[2,3-d]pyrimidin-4-yl)piperazin-1-yl)(cyclohexyl)methanone This compound was synthesized in 66% yield from 2-amino-4-N-piperazino-6-(4-fluorophenyl)-thieno[2,3-d]pyrimidine according to the procedure for the synthesis of example 329, using cyclohexanecarboxylic acid chloride.
MS m/z (%): 440 ([M+H]$^+$, 100)

Example 346

Synthesis of (4-(2-amino-6-(4-fluorophenyl)thieno[2,3-d]pyrimidin-4-yl)piperazin-1-yl)(pyridin-3-yl)methanone This compound was synthesized in 49% yield from 2-amino-4-N-piperazino-6-(4-fluorophenyl)-thieno[2,3-d]pyrimidine using nicotinoyl chloride according to the procedure for the synthesis of example 329.
MS m/z (%): 435 ([M+H]$^+$, 100)

Example 347

Synthesis of 4-(2-amino-6-(4-fluorophenyl)thieno[2,3-d]pyrimidin-4-yl)-N,N-diisopropylpiperazine-1-carboxamide This compound was synthesized in 61% yield from 2-amino-4-N-piperazino-6-(4-fluorophenyl)-thieno[2,3-d]pyrimidine using diisopropylcarbamoyl chloride according to the procedure for the synthesis of example 329, using diisopropylcarbamoyl chloride.
MS m/z (%): 457 ([M+H]$^+$, 100)

Example 348

Synthesis of (1-(2-amino-6-(4-fluorophenyl)thieno[2,3-d]pyrimidin-4-yl)piperidin-4-yl)(phenyl)methanone This compound was synthesized in 44% yield from 2-amino-4-N-piperazino-6-(4-fluorophenyl)-thieno[2,3-d]pyrimidine using 4-benzoylpiperidine hydrochloride according to the procedure for the synthesis of example 327, using 4-benzoylpiperidine hydrochloride.
MS m/z (%): 433 ([M+H]$^+$, 100)
$^1$H NMR (300 MHz, CHCl$_3$, 25° C.): δ=7.98 (d, 2H, arom H), 7.53 (m, 5H, arom H), 7.08 (t, 2H, arom H), 4.79 (br s, 2H, NH$_2$), 4.55 (d, 2H, NCH2), 3.61 (m, 1H, CH), 3.37 (t, 2H, NCH$_2$), 2.01 (m, 4H, CH$_2$) ppm.

Example 349

Synthesis of 2-amino-thieno[2,3-d]pyrimidin-4-(3H)-one

A suspension of ethyl 2-amino-thiophene-3-carboxylate (0.4 g, 2.34 mmol), chloroformamidine hydrochloride (0.67 g, 5.84 mmol) and dimethylsulfone (0.53 g, 11.7 mmol) was heated at 130° C. for 30 minutes. After cooling down to room temperature, water (10 ml) was added and ammonium hydroxide was used to neutralize the suspension till pH=8. The solid was filtered off, washed with water and dried, yielding the crude title compound (71%, 277 mg). The crude residue was used as such for further reaction.
MS m/z (%): 168 ([M+H]$^+$, 100)

Example 350

Synthesis of 2-amino-4-N-piperazino-thieno[2,3-d]pyrimidine

To a solution of 2-amino-thieno[2,3-d]pyrimidin-4-(3H)-one (250 mg, 1.5 mmol) in acetonitrile (20 ml) was added 1,8-diazabicyclo[5.4.0]undec-7-ene (DBU, 2.24 mmol, 335 µl), benzotriazol-1-yloxytris(dimethylamino)-phosphonium hexafluorophosphate (BOP, 862 mg) and piperazine (3 mmol, 258 mg). The reaction was stirred at room temperature overnight and then for 4 hours at 70° C. The solvents were evaporated in vacuo and the crude residue was purified by flash chromatography on silica, the mobile phase being a mixture of methanol, dichloromethane and a 33% aq. NH$_3$ solution (in a ratio gradually ranging from 3:96.5:0.5 to 5:94.5:0.5) yielding the title compound (48%, 169 mg).
MS m/z (%): 236 ([M+H]$^+$, 100)

Example 351

Synthesis of 1-(4-(2-aminothieno[2,3-d]pyrimidin-4-yl)piperazin-1-yl)-2-(4-chlorophenoxy)ethanone To a solution of 2-amino-4-N-piperazino-thieno[2,3-d]pyrimidine (100 mg, 0.43 mmol) in dioxane (15 ml) was added diisopropylethylamine (DIPEA, 0.85 mmol, 141 µl) and 4-chlorophenoxyacetylchloride (0.43 mmol, 88 mg). The reaction was stirred overnight at room temperature. The solvents were evaporated in vacuo. The residue was redissolved in ethylacetate and extracted with brine (3×). The combined organic layers were evaporated in vacuo and the crude residue was purified by silica gel flash chromatography, the mobile phase consisting of a mixture of methanol and dichloromethane (in a ratio gradually ranging from 1:99 to 2:98), yielding the pure title compound (121 mg, 70%).
MS m/z (%): 404 ([M+H]$^+$, 100)
$^1$H NMR (300 MHz, CHCl$_3$, 25° C.): δ=7.25 (d, 2H, arom H), 7.13 (d, 1H, arom H), 6.91 (d, 1H, arom H), 6.89 (d, 1H, arom H), 4.74 (br s, 2H, NH$_2$), 4.73 (s, 2H, CH$_2$), 3.83 (br s, 4H, CH$_2$), 3.77 (br s, 1H, CH$_2$) ppm.

Example 352

Synthesis of 2-(4-chlorophenoxy)-1-(4-(6-(4-fluorophenyl)-2-phenylthieno[2,3-d]pyrimidin-4-yl)piperazin-1-yl)ethanone This compound was prepared from example 322 in a yield of 77%, according to the procedure for the synthesis of example 325.

$^1$H NMR (300 MHz, CDCl$_3$, 25° C.): δ=8.41-8.45 (m, 2H, PhH), 7.58-7.63 (m, 2H, PhH), 7.45-7.47 (m, 3H, PhH), 7.33 (s, 1H, CH), 7.26 (d, J=8.9 Hz, 2H, PhH), 7.13 (t, J=8.5 Hz, PhH), 6.92 (d, J=8.9 Hz, 2H, PhH), 4.74 (s, 2H, CH$_2$), 4.01 (br s, 4H, NCH$_2$), 3.85 (br s, 4H, NCGH$_2$) ppm.

HRMS: calcd for C$_{30}$H$_{25}$ClFN$_4$O$_2$S 559.13708, found 559.13554.

Example 353

Synthesis of ethyl 4-(4-(2-(4-chlorophenoxy)acetyl)piperazin-1-yl)-6-(4-fluorophenyl)thieno[2,3-d]pyrimidine-2-carboxylate This compound was prepared from example 323 in a yield of 89%, according to the procedure for the synthesis of example 325.

$^1$H NMR (300 MHz, CDCl$_3$, 25° C.): δ=7.62-7.67 (m, 2H, PhH), 7.42 (s, 1H, CH), 7.26 (d, J=8.9 Hz, 2H, PhH), 7.16 (t, J=8.5 Hz, PhH), 6.91 (d, J=8.9 Hz, 2H, PhH), 4.75 (s, 2H, CH$_2$), 4.51 (q, J=7.1 Hz, 2H, CH$_2$), 4.09 (br s, 2H, NCH$_2$), 4.03 (br s, 2H, NCH$_2$), 3.84 (br s, 4H, NCH$_2$), 1.47 (t, J=7.1 Hz, 3H, CH$_3$) ppm.

HRMS: calcd for C$_{27}$H$_{25}$ClFN$_4$O$_4$S 555.12691, found 555.12507.

Example 354

Synthesis of ethyl 2-(4-(4-(2-(4-chlorophenoxy)acetyl)piperazin-1-yl)-6-(4-fluorophenyl)thieno[2,3-d]pyrimidin-2-yl)acetate This compound was prepared from example 324 in a yield of 58%, according to the procedure for the synthesis of example 325.

$^1$H NMR (300 MHz, CDCl$_3$, 25° C.): δ=7.56-7.60 (m, 2H, PhH), 7.32 (s, 1H, CH), 7.24 (d, J=8.8 Hz, 2H, PhH), 7.10 (t, J=8.5 Hz, PhH), 6.89 (d, J=8.8 Hz, 2H, PhH), 4.72 (s, 2H, OCH$_2$), 4.21 (q, J=7.1 Hz, 2H, CH$_2$), 3.92 (br s, 4H, NCH$_2$), 3.88 (s, 2H, CH$_2$), 3.78 (br s, 4H, NCH$_2$), 1.28 (t, J=7.1 Hz, 3H, CH$_3$) ppm.

HRMS: calcd for C$_{28}$H$_{27}$ClFN$_4$O$_4$S 569.1426, found 569.1426.

Example 355

Synthesis of 4-(4-(2-(4-chlorophenoxy)acetyl)piperazin-1-yl)-6-(4-fluorophenyl)thieno[2,3-d]pyrimidine-2-carboxamide A suspension of ethyl 4-(4-(2-(4-chlorophenoxy)acetyl)piperazin-1-yl)-6-(4-fluorophenyl)thieno[2,3-d]pyrimidine-2-carboxylate (40 mg, 0.07 mmol) in 7N NH$_3$ in MeOH (1 ml) was stirred at room temperature for 3 hours. The solvents were removed under reduced pressure, and the crude residue was purified by flash chromatography on silica gel (CH$_2$Cl$_2$/MeOH 40:1) to yield the title compound as a white solid (25 mg, 66%).

$^1$H NMR (300 MHz, DMSO, 25° C.): δ=8.14 (s, 1H, NH), 8.00 (s, 1H, CH), 7.90-7.95 (m, 2H, PhH), 7.35 (t, J=8.8 Hz, 2H, PhH), 7.33 (d, J=9.0 Hz, 2H, PhH), 6.99 (d, J=9.0 Hz, 2H, PhH), 4.94 (s, 2H, CH$_2$), 4.15 (br s, 2H, NCH$_2$), 4.08 (br s, 2H, NCH$_2$), 3.73 (br s, 4H, NCH$_2$) ppm.

HRMS: calcd for C$_{25}$H$_{22}$ClFN$_5$O$_3$S 526.11159 found 526.11031.

Example 356

Synthesis of 4-(4-(2-(4-chlorophenoxy)acetyl)piperazin-1-yl)-6-(4-fluorophenyl)-N-(2-methoxyethyl)thieno[2,3-d]pyrimidine-2-carboxamide To a suspension of ethyl 4-(4-(2-(4-chlorophenoxy)acetyl)piperazin-1-yl)-6-(4-fluorophenyl)thieno[2,3-d]pyrimidine-2-carboxylate (30 mg, 0.05 mmol) in MeOH (7 ml) was added 2-methoxyethylamine (0.7 ml). The mixture was stirred at room temperature for 3 hours. The solvents were removed under reduced pressure and the crude residue was purified by flash chromatography on silica gel (CH$_2$Cl$_2$/MeOH 50:1) to yield the title compound as a white solid (29 mg, 92%).

$^1$H NMR (300 MHz, CDCl$_3$, 25° C.): δ=8.20 (s, 1H, NH), 7.59-7.64 (m, 2H, PhH), 7.40 (s, 1H, CH), 7.25 (d, J=8.8 Hz, 2H, PhH), 7.14 (t, J=7.15 Hz, 2H, PhH), 6.91 (d, J=8.8 Hz, 2H, PhH), 4.75 (s, 2H, CH$_2$), 4.05 (br s, 2H, NCH$_2$), 3.99 (br s, 2H, NCH$_2$), 3.69 (br s, 4H, NCH$_2$), 3.69 (t, J=5.1 Hz, 2H, CH$_2$), 3.60 (t, J=5.1 Hz, 2H, CH$_2$), 3.41 (s, 3H, CH$_3$) ppm.

HRMS: calcd for C$_{28}$H$_{28}$ClFN$_5$O$_4$S 584.15346, found 584.15178.

Example 357

Synthesis of 4-(4-(2-(4-chlorophenoxy)acetyl)piperazin-1-yl)-6-(4-fluorophenyl)thieno[2,3-d]pyrimidine-2-carboxylic acid A solution of ethyl 4-(4-(2-(4-chlorophenoxy)acetyl)piperazin-1-yl)-6-(4-fluorophenyl)thieno[2,3-d]pyrimidine-2-carboxylate (0.12 g, 0.22 mmol) in methanol/2M NaOH/CH$_2$Cl$_2$ (5:5:1, 5 ml) was stirred at room temperature for 3 hours after which it was neutralized with a 2N HCl solution in dioxane. The solvents were removed under reduced pressure, and the crude residue was purified by flash chromatography on silica gel (CH$_2$Cl$_2$/MeOH 8:1) to yield the title compound as a pale yellow solid (50 mg, 44%).

$^1$H NMR (300 MHz, DMSO, 25° C.): δ=8.02 (s, 1H, CH), 7.92-7.97 (m, 2H, PhH), 7.32-7.39 (m, 4H, PhH), 6.98 (d, J=8.7 Hz, 2H, PhH), 4.93 (s, 2H, CH$_2$), 4.11 (br s, 2H, NCH$_2$), 4.04 (br s, 2H, NCH$_2$), 3.68 (br s, 4H, NCH$_2$) ppm.

HRMS: calcd for C$_{25}$H$_{21}$ClFN$_4$O$_4$S 527.09561, found 527.09421.

Example 358

Synthesis of 2-(4-(4-(2-(4-chlorophenoxy)acetyl)piperazin-1-yl)-6-(4-fluorophenyl)thieno[2,3-d]pyrimidin-2-yl)acetamide This compound was prepared from example 354 in a yield of 34%, according to the procedure for the synthesis of example 355.

$^1$H NMR (300 MHz, DMSO, 25° C.): δ=7.92 (s, 1H, H-5), 7.86-7.91 (m, 2H, PhH), 7.44 (s, 1H, NH), 7.30-7.36 (m, 4H, PhH, PhH), 6.99 (s, 1H, NH), 6.98 (d, J=9.1 Hz, 2H, PhH), 4.92 (s, 2H, OCH$_2$), 4.03 (br s, 2H, NCH$_2$), 3.98 (br s, 2H, NCH$_2$), 3.70 (br s, 4H, CON(CH$_2$)$_2$), 3.57 (s, 2H, CH$_2$) ppm.

HRMS: calcd for $C_{26}H_{24}ClFN_5O_3S$ 540.12724 found 540.12544.

Example 359

Synthesis of 4-(2-amino-6-(4-fluorophenyl)thieno[2,3-d]pyrimidin-4-yl)-N-m-tolylpiperazine-1-carboxamide This compound was prepared from example 320 in a yield of 46%, according to the procedure for the synthesis of example 325, using N-m-tolylpiperazine-1-carboxamide.

$^1$H NMR (300 MHz, CDCl$_3$, 25° C.): δ=8.50 (s, 1H, NH), 7.73-7.78 (m, 2H, PhH), 7.71 (s, 1H, PhH), 7.23-7.32 (m, 4H, PhH), 7.12 (t, J=7.3 Hz, PhH), 6.77 (d, J=7.3 Hz, 1H, PhH), 6.36 (s, 2H, NH$_2$), 3.88 (br s, 4H, NCH$_2$), 3.64 (br s, 4H, NCH$_2$), 2.26 (s, 3H, CH$_3$) ppm.

HRMS: calcd for $C_{24}H_{24}FN_6OS$ 463.1716, found 463.1702.

Example 360

Synthesis of 4-(6-(4-fluorophenyl)-2-phenylthieno[2,3-d]pyrimidin-4-yl)-N-m-tolylpiperazine-1-carboxamide This compound was prepared from example 322 in a yield of 69%, according to the procedure for the synthesis of example 325, using N-m-tolylpiperazine-1-carboxamide.

$^1$H NMR (300 MHz, DMSO, 25° C.): δ=8.54 (s, 1H, NH), 8.41-8.44 (m, 2H, 5-PhH), 7.99 (s, 1H, CH), 7.89-7.94 (m, 2H, 2-PhH), 7.50-7.52 (m, 3H, PhH), 7.28-7.38 (m, 4H, PhH), 7.13 (t, J=7.7 Hz, 1H, tolyl-H), 6.78 (d, J=7.4 Hz, 1H, tolyl-H), 4.13 (br s, 4H, NCH$_2$), 3.75 (br s, 4H, NCH$_2$), 2.27 (s, 3H, CH$_3$) ppm.

HRMS: calcd for $C_{30}H_{27}FN_5OS$ 524.1920, found 524.1921.

Example 361

Synthesis of ethyl 6-(4-fluorophenyl)-4-(4-(m-tolylcarbamoyl)piperazin-1-yl)thieno[2,3-d]pyrimidine-2-carboxylate This compound was prepared from example 323 in a yield of 61%, according to the procedure for the synthesis of example 325, using N-m-tolylpiperazine-1-carboxamide.

$^1$H NMR (300 MHz, CDCl$_3$, 25° C.): δ=7.60-7.65 (m, 2H, PhH), 7.46 (s, 1H, CH), 7.11-7.17 (m, 4H, PhH), 6.87 (br s, 1H, PhH), 6.66 (s, 1H, PhH), 4.50 (q, J=7.1 Hz, 2H, CH$_2$), 4.15 (br s, 4H, NCH$_2$), 3.79 (br s, 4H, NCH$_2$), 1.46 (t, J=7.1 Hz, 3H, CH$_3$) ppm.

HRMS: calcd for $C_{27}H_{27}FN_5O_3S$ 520.18186, found 520.17993.

Example 362

Synthesis of 6-(4-fluorophenyl)-4-(4-(m-tolylcarbamoyl)piperazin-1-yl)thieno[2,3-d]pyrimidine-2-carboxamide This compound was prepared from example 361 in a yield of 66%, according to the procedure for the synthesis of example 355.

$^1$H NMR (300 MHz, DMSO, 25° C.): δ=8.55 (s, 1H, NH), 8.15 (s, 1H, CONH), 8.02 (s, 1H, CH), 7.91-7.95 (m, 2H, PhH), 7.68 (s, 1H, CONH), 7.27-7.38 (m, 4H, PhH), 7.13 (t, J=7.7 Hz, 1H, PhH), 6.77 (d, J=7.7 Hz, 1H, PhH), 4.11 (br s, 4H, NCH$_2$), 3.71 (br s, 4H, NCH$_2$), 2.26 (s, 3H, CH$_3$) ppm.

HRMS: calcd for $C_{25}H_{24}FN_6O_2S$ 491.16655, found 491.16526.

Example 363

Synthesis of 4-ethoxy-6-(4-fluorophenyl)thieno[2,3-d]pyrimidin-2-amine

To a solution of 2-amino-6-(4-fluorophenyl)thieno[2,3-d]pyrimidin-4(3H)-one (50 mg, 0.19 mmol) and BOP (110 mg, 0.25 mmol) in EtOH (1 ml) was added DBU (43 μl, 0.29 mmol). The resulting mixture was heated at 60° C. for 4 hours. After cooling down to room temperature, sodium ethoxide (26 mg, 0.38 mmol) was added. The mixture was again heated at 60° C. overnight. The solvents were removed under reduced pressure and the crude residue was purified by flash chromatography on silica gel (CH$_2$Cl$_2$/MeOH 60:1) yielding the title compound as a white solid (30 mg, 54%).

mp 142° C.

$^1$H NMR (300 MHz, CDCl$_3$, 25° C.): δ=7.54-7.59 (m, 2H, PhH), 7.29 (s, 1H, PhH), 7.07 (t, J=8.6 Hz, PhH), 5.03 (s, 2H, NH$_2$), 4.49 (q, J=7.1 Hz, 2H, CH$_2$), 1.44 (t, J=7.1 Hz, 3H, CH$_3$) ppm.

HRMS: calcd for $C_{14}H_{13}FN_3OS$ 290.0763, found 290.0740.

Example 364

Synthesis of 6-(4-fluorophenyl)-4-morpholinothieno[2,3-d]pyrimidin-2-amine

This compound was prepared from example 320 using morpholine in a yield of 58%, according to the procedure for the synthesis of example 327.

$^1$H NMR (300 MHz, CDCl$_3$, 25° C.): δ=7.52-7.75 (m, 2H, PhH), 7.24 (s, 1H, CH), 7.09 (t, J=8.6 Hz, PhH), 4.82 (s, 2H, NH$_2$), 3.84 (br s, 8H, NCH$_2$, OCH$_2$) ppm.

HRMS: calcd for $C_{16}H_{16}FN_4OS$ 331.1029, found 331.1003.

Example 365

Synthesis of 4-chloro-6-(4-fluorophenyl)-2-methylthieno[2,3-d]pyrimidine

A solution of 6-(4-fluorophenyl)-2-methylthieno[2,3-d]pyrimidin-4(3H)-one (0.2 g, 0.77 mmol) and diisopropylethylamine (0.26 ml, 1.54 mmol) in POCl$_3$ (4 ml) was stirred under N$_2$ at 90° C. for 3.5 hours. The reaction mixture was allowed to cool down to room temperature and poured into an ice-bath. The aqueous phase was extracted with diethyl ether. The combined organic layers were washed with a half-saturated NaHCO$_3$ solution and brine, dried over Na$_2$SO$_4$, and concentrated under reduced pressure. The crude residue was purified by silica gel chromatography (CH$_2$Cl$_2$/MeOH 50:1) to yield the title compound as a white solid (14 mg, 6%).

$^1$H NMR (300 MHz, CDCl$_3$, 25° C.): δ=7.66-7.71 (m, 2H, PhH), 7.45 (s, 1H, CH), 7.16 (t, J=8.5 Hz, PhH), 2.81 (s, 3H, CH$_3$) ppm.

HRMS: calcd for $C_{13}H_9ClFN_2S$ 279.01590, found 279.01510.

Example 366

Synthesis of ethyl 4-chloro-6-(4-fluorophenyl)thieno[2,3-d]pyrimidine-2-carboxylate This compound was prepared from example 323 in a yield of 99%, according to the procedure for the synthesis of example 365.

$^1$H NMR (300 MHz, CDCl$_3$, 25° C.): δ=7.71-7.76 (m, 2H, PhH), 7.57 (s, 1H, CH), 7.19 (t, J=8.5 Hz, 2H, PhH), 4.58 (q, J=7.1 Hz, 2H, CH$_2$), 1.49 (t, J=7.1 Hz, 3H, CH$_3$) ppm.

HRMS: calcd for $C_{15}H_{11}ClFN_2O_2S$ 337.02138, found 337.02038.

Example 367

Synthesis of N-(3-chloro-4-fluorophenyl)-6-(4-fluorophenyl)-2-methylthieno[2,3-d]pyrimidin-4-amine To a solution of 4-chloro-6-(4-fluorophenyl)-2-methylthieno[2,3-d]pyrimidine (15 mg, 0.05 mmol) in 1,2-dichloroethane/t-BuOH (1:1, 2 ml) was added 3-chloro-4-fluoroaniline (16 mg, 0.11 mmol). The mixture was heated at 90° C. for 2 days. After cooling down to room temperature, the solvents were removed under reduced pressure. The crude residue was purified by silica gel chromatography (CH$_2$Cl$_2$/MeOH 100:1) to yield the title compound as a white solid (11 mg, 53%).

HRMS: calcd for $C_{19}H_{13}ClF_2N_3S$ 388.0487, found 388.0471.

Example 368

Synthesis of ethyl 4-(3-chloro-4-fluorophenylamino)-6-(4-fluorophenyl)thieno[2,3-d]pyrimidine-2-carboxylate This compound was prepared from example 366 in a yield of 38%, according to the procedure for the synthesis of example 367.

$^1$H NMR (300 MHz, DMSO, 25° C.): δ=10.04 (s, 1H, NH), 8.65-8.67 (m, 1H, PhH), 8.27 (s, 1H, PhH), 7.79-7.84 (m, 3H, PhH), 7.39-7.51 (m, 3H, PhH), 4.37 (q, J=7.0 Hz, 2H, CH$_2$), 1.39 (t, J=7.0 Hz, 3H, CH$_3$) ppm.

HRMS: calcd for $C_{21}H_{15}ClF_2N_3O_2S$ 446.05416, found 446.05311.

Examples 369-373

Synthesis of 2-amino-4-(N-acylpiperazinyl)-6-phenyl-thieno[2,3-d]pyrimidine analogues General Procedure To a solution of 2-amino-4-(N-piperazinyl)-6-phenyl-thieno[2,3-d]pyrimidine (0.65 mmol) in DMF (10 ml) was added diisopropylethylamine (1.3 mmol, 215 µl), O-(benzotriazol-1-yl)-N,N,N',N'-tetramethyluronium tetrafluoroborate (TBTU, 0.78 mmol, 250 mg) and an appropriate carboxylic acid (0.78 mmol). The reaction was stirred at room temperature overnight. The reaction was diluted with dichloromethane and extracted with water. The combined organic layers were evaporated in vacuo and the resulting residue was purified by silica gel flash chromatography, the mobile phase being a mixture of methanol and dichloromethane (in a ratio gradually raising from 1% to 2% methanol), yielding the pure title compounds in yields varying from 62% to 75%. The following compounds were made according to this procedure

Example 369

Synthesis of 1-(4-(2-amino-6-phenylthieno[2,3-d]pyrimidin-4-yl)piperazin-1-yl)-2-(4-methoxyphenoxy)ethanone This compound was obtained from 2-amino-4-(N-piperazinyl)-6-phenyl-thieno[2,3-d]pyrimidine and 4-methoxyphenoxyacetic acid.

$^1$H NMR (300 MHz, CDCl$_3$): δ=7.59 (d, 2H, arom H), 7.26-7.40 (m, 4H, arom H), 6.86-6.90 (m, 4H, arom H), 4.81 (br s, 2H, NH$_2$), 4.71 (s, 2H, CH$_2$), 3.79 (br s, 4H, piperazine H), 3.77 (br s, 7H, piperazine H and OCH$_3$) ppm.

Example 370

Synthesis of 1-(4-(2-amino-6-phenylthieno[2,3-d]pyrimidin-4-yl)piperazin-1-yl)-2-(4-fluorophenoxy)ethanone This compound was obtained from 2-amino-4-(N-piperazinyl)-6-phenyl-thieno[2,3-d]pyrimidine and 4-fluoro-phenoxyacetic acid.

$^1$H NMR (300 MHz, DMSO): δ=7.57 (m, 2H, arom H), 7.26-7.43 (m, 4H, arom H), 6.93-6.99 (m, 4H, arom H), 5.13 (br s, 2H, NH$_2$), 4.72 (s, 2H, CH$_2$), 3.91 (br s, 4H, piperazine H), 3.81 (br s, 4H, piperazine H) ppm.

Example 371

Synthesis of 1-(4-(2-amino-6-phenylthieno[2,3-d]pyrimidin-4-yl)piperazin-1-yl)-2-(m-tolyloxy)ethanone This compound was obtained from 2-amino-4-(N-piperazinyl)-6-phenyl-thieno[2,3-d]pyrimidine and 3-methylphenoxyacetic acid.

Example 372

Synthesis of 1-(4-(2-amino-6-phenylthieno[2,3-d]pyrimidin-4-yl)piperazin-1-yl)-2-(4-bromophenoxy)ethanone This compound was obtained from 2-amino-4-(N-piperazinyl)-6-phenyl-thieno[2,3-d]pyrimidine and 4-bromo-phenoxyacetic acid.

$^1$H NMR (300 MHz, CDCl$_3$): δ=7.57 (m, 2H, arom H), 7.26-7.41 (m, 4H, arom H), 6.86 (m, 4H, arom H), 4.73 (br s, 2H, NH$_2$), 4.64 (s, 2H, CH$_2$), 3.92 (br s, 4H, piperazine H), 3.80 (br s, 4H, piperazine H) ppm.

Example 373

Synthesis of 1-(4-(2-amino-6-phenylthieno[2,3-d]pyrimidin-4-yl)piperazin-1-yl)-2-(4-chlorophenoxy)-2-methylpropan-1-one This compound was obtained from 2-amino-4-(N-piperazinyl)-6-phenyl-thieno[2,3-d]pyrimidine and 2-(4-chlorophenoxy)-2-methylpropionic acid.

$^1$H NMR (300 MHz, CDCl$_3$): δ=7.57 (d, 2H, arom H), 7.39 (t, 2H, arom H), 7.19-7.32 (m, 4H, arom H), 6.79 (d, 2H, arom H), 4.78 (br s, 2H, NH$_2$), 4.01 (br s, 2H, piperazine H), 3.80 (br s, 4H, piperazine H), 3.56 (br s, 2H, piperazine H), 1.67 (s, 6H, 2×CH$_3$) ppm.

Example 374

Synthesis of 2,6-diamino-4-(N-piperazin-1-yl)pyrimidine

A mixture of 4-chloro-2,6-diaminopyrimidine (4.34 g, 30 mmol), piperazine (2.58 g, 30 mmol) and NaOH (1.2 g, 30 mmol) in water (50 ml) was heated under reflux for 3 hours. After cooling to room temperature, the precipitate was filtered off. The filtrate was concentrated under reduced pressure to yield the crude title product which was used in the following step without further purification.

MS m/z (%): 195 ([M+H]$^+$, 100)

Examples 375-381

Synthesis of 2,6-diamino-4-(N-acyl-piperazin-1-yl)-pyrimidine analogues

General Procedure

To a solution of 2,6-diamino-4-(N-piperazin-1-yl)pyrimidine (crude residue, +/−30 mmol) and potassium carbonate (8.28 g, 60 mmol) in dioxane/methanol (1:1; 100 ml), was added a solution of the appropriate acid chloride (36 mmol) in dioxane (20 ml). The resulting reaction mixture was stirred at room temperature for 1 hour. After concentration under reduced pressure, the residue was resuspended in water (50 ml). The solid was filtered off and washed with water. The precipitate was dried over P$_2$O$_5$, yielding the title compound in yields between 70-90% over 2 steps.

The following compounds were synthesized according to this procedure:

Example 375

2,6-diamino-4-[4-(4-chlorophenoxyacetyl)piperazin-1-yl]pyrimidine

This compound was synthesized using 4-chlorophenoxyacetyl chloride.

MS m/z (%): 363 ([M+H]$^+$, 100)

Example 376

2,6-diamino-4-[(4-phenoxyacetyl)piperazin-1-yl]pyrimidine

This compound was synthesized using phenoxyacetyl chloride.

MS m/z (%): 329 ([M+H]$^+$, 100)

Example 377

2,6-diamino-4-([3-methoxy-benzoyl)piperazin-1-yl]pyrimidine

This compound was synthesized using 3-methoxybenzoyl chloride.

MS m/z (%): 329 ([M+H]$^+$, 100)

Example 378

2,6-diamino-4-[(2-thiophene-acetyl)piperazin-1-yl]pyrimidine

This compound was synthesized using 2-thiophene-acetyl chloride.

MS m/z (%): 319 ([M+H]$^+$, 100)

Example 379

2,6-diamino-4-[(4-chloro-benzoyl)piperazin-1-yl]pyrimidine

This compound was synthesized using 4-chloro-benzoyl chloride.

MS m/z (%):333 ([M+H]$^+$, 100)

Example 380

2,6-diamino-4-[(4-α-toluenesulfonyl)piperazin-1-yl]pyrimidine

This compound was synthesized using α-toluenesulfonyl-chloride.

MS m/z (%):349 ([M+H]$^+$, 100)

Example 381

2,6-diamino-4-[(1-naphthoyl)piperazin-1-yl]pyrimidine

This compound was synthesized using 1-naphthoylchloride.

MS m/z (%):349 ([M+H]$^+$, 100)

Examples 382-388

Synthesis of 2,5,6-triamino-4-[(4-N-acyl-)piperazin-1-yl]pyrimidine analogues

General Procedure

To a suspension of 2,6-diamino-4-[4-acyl-piperazin-1-yl]pyrimidine (10 mmol) and sodium nitrite (0.86 g, 12.5 mmol) in a mixture of water/dioxane/methanol (4/2/1; 70 ml), was added acetic acid (1.5 g, 25 mmol). The resulting reaction mixture was stirred at room temperature for 2 hours. A pink precipitate was formed indicating the formation of the nitroso intermediate. To this violet suspension was added a 30% ammonia solution in water (75 mmol) and sodium dithionite (25 mmol). The reaction mixture was stirred at 50° C. till the violet color completely disappeared (about 2 hours). After concentration under reduced pressure, the residue was suspended in water (50 ml). The solid was filtered off, washed with water and dried over P$_2$O$_5$, yielding the title compound as white solids in yields varying from 60 to 90%. The following compounds were made according to this procedure:

Example 382

2,5,6-triamino-4-[4-(4-chlorophenoxyacetyl)piperazin-1-yl]pyrimidine

MS m/z (%): 378 ([M+H]$^+$, 100)

Example 383

2,5,6-triamino-4-[(4-phenoxyacetyl)piperazin-1-yl]pyrimidine

MS m/z (%): 344 ([M+H]$^+$, 100)

Example 384

2,5,6-triamino-4-[(3-methoxy-benzoyl)piperazin-1-yl]pyrimidine

MS m/z (%): 344 ([M+H]$^+$, 100)

Example 385

2,5,6-triamino-4-[(2-thiophene-acetyl)piperazin-1-yl]pyrimidine

MS m/z (%): 334 ([M+H]$^+$, 100)

Example 386

2,5,6-triamino-4-[(4-chloro-benzoyl)piperazin-1-yl]pyrimidine

MS m/z (%): 348 ([M+H]$^+$, 100)

Example 387

2,5,6-triamino-4-[(4-α-toluenesulfonyl)piperazin-1-yl]pyrimidine

MS m/z (%): 364 ([M+H]$^+$, 100)

Example 388

2,5,6-triamino-4-[(1-naphthoyl)piperazin-1-yl]pyrimidine

MS m/z (%): 378 ([M+H]$^+$, 100)

Examples 389-407

Synthesis of 2-amino-6-[4-(4-chlorophenoxyacetyl)piperazin-1-yl]-8-substituted-9H-purine analogues General Procedure A suspension of a 2,5,6-triamino-4-[4-acyl-piperazin-1-yl]pyrimidine analogue (0.5 mmol), an appropriate aldehyde (0.5 mmol) and a drop of acetic acid in methanol (10 ml) was stirred at room temperature for 1 hour, after which the Schiff base intermediate was formed. Then, FeCl$_3$ (0.75 mmol) was added. The mixture was stirred at room temperature overnight. The reaction mixture was evaporated in vacuo and purified by flash chromatography on silica, the mobile phase being a mixture of methanol and dichloromethane (in a ratio of 1:25), yielding the pure title compound.

The following compounds were synthesized according to this procedure:

Example 389

1-(4-(2-amino-8-(4-fluorophenyl)-9H-purin-6-yl)piperazin-1-yl)-2-(4-chlorophenoxy)ethanone This compound was synthesized from 2,5,6-triamino-4-[4-(4-chlorophenoxyacetyl)piperazin-1-yl]pyrimidine and 4-fluorobenzaldehyde, yielding the pure title compound in 83% yield.

MS m/z (%): 482 ([M+H]$^+$, 100)

Example 390

Synthesis of 1-(4-(2-amino-8-(3,4-dimethoxyphenyl)-9H-purin-6-yl)piperazin-1-yl)-2-(4-chlorophenoxy)ethanone This compound was synthesized from 2,5,6-triamino-4-[4-(4-chlorophenoxyacetyl)piperazin-1-yl]pyrimidine and 3,4-dimethoxybenzaldehyde yielding the pure title compound in 57% yield.

MS m/z (%): 524 ([M+H]$^+$, 100)

Example 391

1-(4-(2-amino-8-(4-bromophenyl)-9H-purin-6-yl)piperazin-1-yl)-2-(4-chlorophenoxy)ethanone This compound was synthesized from 2,5,6-triamino-4-[4-(4-chlorophenoxyacetyl)piperazin-1-yl]pyrimidine and 4-bromobenzaldehyde in 74% yield.

MS m/z (%): 543 ([M+H]$^+$, 100)

Example 392

1-(4-(2-amino-8-(4-chlorophenyl)-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and 4-chlorobenzaldehyde in 60% yield.

MS m/z (%): 498 ([M+H]$^+$, 100)

Example 393

1-(4-(2-amino-8-(3-chlorophenyl)-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and 3-chlorobenzaldehyde in 67% yield.

MS m/z (%): 498 ([M+H]$^+$, 100)

Example 394

1-(4-(2-amino-8-(4-(trifluoromethyl)phenyl)-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and p-trifluoromethylbenzaldehyde in 63% yield.

MS m/z (%): 532 ([M+H]$^+$, 100)

Example 395

Synthesis of 1-(4-(2-amino-8-(4-(trifluoromethoxy)phenyl)-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and p-trifluoromethoxybenzaldehyde in 61% yield.

MS m/z (%): 548 ([M+H]$^+$, 100)

Example 396

Synthesis of 1-(4-(2-amino-8-p-tolyl-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and p-methylbenzaldehyde in 56% yield.
MS m/z (%): 478 ([M+H]$^+$, 100)

Example 397

Synthesis of 1-(4-(2-amino-8-propyl-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and butyraldehyde in 47% yield.
MS m/z (%): 430 ([M+H]$^+$, 100)

Example 398

Synthesis of 1-(4-(2-amino-8-cyclopropyl-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and cyclopropanecarboxaldehyde, in 78% yield.
MS m/z (%): 428 ([M+H]$^+$, 100)

Example 399

Synthesis of 1-(4-(2-amino-8-tert-butyl-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and trimethylacetaldehyde in 45% yield.
MS m/z (%): 444 ([M+H]$^+$, 100)

Example 400

Synthesis of 1-(4-(2-amino-8-methyl-9H-purin-6-yl)piperazin-1-yl)-2-(4-chlorophenoxy)ethanone This compound was obtained from 2,5,6-triamino-4-[4-(4-chlorophenoxyacetyl)piperazin-1-yl]pyrimidine and acetaldehyde in 30% yield.
MS m/z (%): 402 ([M+H]$^+$, 100)

Example 401

Synthesis of 1-(4-(2-amino-8-(4-fluorophenyl)-9H-purin-6-yl)piperazin-1-yl)-2-phenoxyethanone This compound was obtained from 2,5,6-triamino-4-[(4-phenoxyacetyl)piperazin-1-yl]pyrimidine and 4-fluorobenzaldehyde in 37% yield.
MS m/z (%): 448 ([M+H]$^+$, 100)

Example 402

Synthesis of (4-(2-amino-8-(4-fluorophenyl)-9H-purin-6-yl)piperazin-1-yl)(3-methoxyphenyl)methanone This compound was obtained from 2,5,6-triamino-4-[(3-methoxy-benzoyl)piperazin-1-yl]pyrimidine and 4-fluorobenzaldehyde in 41% yield.
MS m/z (%): 448 ([M+H]$^+$, 100)

Example 403

Synthesis of 1-(4-(2-amino-8-(4-fluorophenyl)-9H-purin-6-yl)piperazin-1-yl)-2-(thiophen-2-yl)ethanone This compound was obtained from 2,5,6-triamino-4-[(2-thiophene-acetyl)piperazin-1-yl]pyrimidine and 4-fluorobenzaldehyde in 28% yield.
MS m/z (%): 438 ([M+H]$^+$, 100)

Example 404

Synthesis of (4-(2-amino-8-(4-fluorophenyl)-9H-purin-6-yl)piperazin-1-yl)(4-chlorophenyl)methanone This compound was obtained from 2,5,6-triamino-4-[(4-chloro-benzoyl)piperazin-1-yl]pyrimidine and 4-fluorobenzaldehyde in 31% yield.
MS m/z (%): 452 ([M+H]$^+$, 100)

Example 405

Synthesis of 6-(4-(benzylsulfonyl)piperazin-1-yl)-8-(4-fluorophenyl)-9H-purin-2-amine This compound was obtained from 2,5,6-triamino-4-[4-α-toluenesulfonyl)piperazin-1-yl]pyrimidine and 4-fluorobenzaldehyde in 21% yield
MS m/z (%): 468 ([M+H]$^+$, 100)

Example 406

Synthesis of (4-(2-amino-8-(4-fluorophenyl)-9H-purin-6-yl)piperazin-1-yl)(naphthalen-1-yl)methanone This compound was obtained from 2,5,6-triamino-4-[(1-naphthoyl)piperazin-1-yl]pyrimidine and 4-fluorobenzaldehyde in 41% yield.
MS m/z (%): 468 ([M+H]$^+$, 100)

Example 407

2-amino-6-hydroxy-8-(4-fluorophenyl)-9H-purine

This compound was synthesized from commercially available 2,5,6-triamino-4-hydroxypyrimidine (40 mmol) and 4-fluorobenzaldehyde (40 mmol), yielding the title compound in 60% yield.
MS m/z (%): 246 ([M+H]$^+$, 100)

Examples 408-420

Synthesis of 2-amino-6-substituted-8-(4-fluorophenyl)-9H-purine analogues

General Procedure
To a solution of 2-amino-6-hydroxy-8-(4-fluorophenyl)-9H-purine (0.4 mmol), a nitrogen nucleophile (0.6 mmol) and benzotriazol-1-yloxytris(dimethylamino)-phosphonium hexafluorophosphate (BOP, 0.65 mmol) in DMF (5 ml), was added 1,8-diazabicyclo[5.4.0]undec-7-ene (DBU, 0.5 mmol). The resulting reaction mixture was stirred at room temperature until all starting material disappeared on TLC (4-8 hours). The solvents were evaporated in vacuo. The crude residue was purified by flash chromatography on silica, the mobile phase being a mixture of methanol and dichloromethane (in a ratio of 1:30), yielding the pure title compounds.

The following compounds were synthesized according to this procedure:

Example 408

1-(4-(2-amino-8-(4-fluorophenyl)-9H-purin-6-yl) piperazin-1-yl)ethanone

This compound was obtained from 1-acetylpiperazine in 63% yield.
MS m/z (%): 356 ([M+H]$^+$, 100)

Example 409

8-(4-fluorophenyl)-6-(4-(thiazol-2-yl)piperazin-1-yl)-9H-purin-2-amine

This compound was obtained from 1-(thiazol-2-yl)piperazine in 63% yield.
MS m/z (%): 396 ([M+H]$^+$, 100)

Example 410

2-(4-(2-amino-8-(4-fluorophenyl)-9H-purin-6-yl) piperazin-1-yl)-1-(pyrrolidin-1-yl)ethanone This compound was synthesized from 1-(piperazin-1-yl)-2-(pyrrolidin-1-yl)ethanone in 45% yield.
MS m/z (%): 425 ([M+H]$^+$, 100)

Example 411

2-(4-(2-amino-8-(4-fluorophenyl)-9H-purin-6-yl) piperazin-1-yl)-1-morpholinoethanone This compound was synthesized from 1-morpholino-2-(piperazin-1-yl)ethanone in 45% yield.
MS m/z (%): 441 ([M+H]$^+$, 100)

Example 412

2-(4-(2-amino-8-(4-fluorophenyl)-9H-purin-6-yl) piperazin-1-yl)-N-(pyridin-3-yl)acetamide This compound was obtained from 2-(piperazin-1-yl)-N-(pyridin-3-yl)acetamide in 16% yield.
MS m/z (%): 448 ([M+H]$^+$, 100)

Example 413

2-(4-(2-amino-8-(4-fluorophenyl)-9H-purin-6-yl) piperazin-1-yl)-N-methyl-N-phenylacetamide This compound was obtained from 2-(piperazin-1-yl)-N-methyl-N-phenylacetamide in 43% yield.
MS m/z (%): 461 ([M+H]$^+$, 100)

Example 414

6-(4-(4-chlorophenyl)piperazin-1-yl)-8-(4-fluorophenyl)-9H-purin-2-amine

This compound was obtained from 1-(4-chlorophenyl)piperazine in 58% yield.
MS m/z (%): 424 ([M+H]$^+$, 100)

Example 415

8-(4-fluorophenyl)-6-(4-(4-fluorophenyl)piperazin-1-yl)-9H-purin-2-amine

This compound was obtained from 4-fluorophenylpiperazine in 55% yield.
MS m/z (%): 408 ([M+H]$^+$, 100)

Example 416

2-(4-(2-amino-8-(4-fluorophenyl)-9H-purin-6-yl) piperazin-1-yl)-N-(pyridin-2-yl)acetamide This compound was obtained from 2-(piperazin-1-yl)-N-(pyridin-2-yl)acetamide in 37% yield.
MS m/z (%): 448 ([M+H]$^+$, 100)

Example 417

2-(4-(2-amino-8-(4-fluorophenyl)-9H-purin-6-yl) piperazin-1-yl)-N-(thiazol-2-yl)acetamide This compound was obtained from 2-(piperazin-1-yl)-N-(thiazol-2-yl)acetamide in 37% yield.
MS m/z (%): 454 ([M+H]$^+$, 100)

Example 418

6-(4-(4-fluorobenzyl)piperazin-1-yl)-8-(4-fluorophenyl)-9H-purin-2-amine

This compound was obtained from 4-fluorobenzylpiperazine yielding the pure title compound in 36% yield.
MS m/z (%): 421 ([M+H]$^+$, 100)

Example 419

8-(4-fluorophenyl)-6-(4-(pyridin-4-yl)piperazin-1-yl)-9H-purin-2-amine

This compound was obtained from 1-(pyridin-4-yl)piperazine yielding the title compound in 70% yield.
MS m/z (%): 391 ([M+H]$^+$, 100)

Example 420

6-(1,4-diazepan-1-yl)-8-(4-fluorophenyl)-9H-purin-2-amine

This compound was obtained from homopiperazine, yielding the title compound in 92% yield.
MS m/z (%): 328 ([M+H]$^+$, 100)

Example 421

Synthesis of 1-(4-(2-amino-8-(4-fluorophenyl)-9H-purin-6-yl)-1,4-diazepan-1-yl)-2-(4-chlorophenoxy) ethanone To a solution of 2-amino-6-(homopiperazin-1-yl)-8-(4-fluorophenyl)-9H-purine (0.2 mmol) in dioxane/methanol (1:1; 5 ml) was added potassium carbonate (55 mg, 0.4 mmol) and a solution of 4-chlorophenoxyacetyl chloride (60 mg, 0.24 mmol) in dioxane (1 ml). The resulting mixture was stirred at room temperature for 1 hour. After concentration under reduced pressure, the residue was purified by flash chromatography on silica (methanol/dichloromethane 1:40), yielding the pure title compound (60 mg, 60%).

MS m/z (%): 496 ([M+H]$^+$, 100)

Example 422

Synthesis of 4-(2-amino-8-(4-fluorophenyl)-9H-purin-6-yl)-N-m-tolyl-1,4-diazepane-1-carboxamide To a solution of 2-amino-6-(N-homopiperazin-1-yl)-8-(4-fluorophenyl)-9H-purine (0.2 mmol) in dioxane/methanol (1:1; 5 ml) was added m-tolyl isocyanate (0.3 mmol). The resulting mixture was stirred at room temperature for 2 hours. After concentration under reduced pressure, the residue was purified by flash chromatography on silica (methanol/dichloromethane 1:40), yielding the pure title compound (60 mg, 65%).

MS m/z (%): 461 ([M+H]$^+$, 100)

Example 423

Synthesis of 1-(4-(2-amino-8-thioxo-8,9-dihydro-7H-purin-6-yl)piperazin-1-yl)-2-(4-chlorophenoxy)ethanone A mixture of 2,5,6-triamino-6-[4-(4-chlorophenoxyacetyl)piperazin-1-yl]-pyrimidine (1.3 g, 3.4 mmol), sodium bicarbonate (1.68 g, 20 mmol) and carbon disulfide (2.5 ml, 40 mmol) in ethanol/water (1:2; 30 ml) was heated under reflux for 8 hours. After cooling down to room temperature, the pH of the mixture was adjusted to 5-6. The precipitate was filtered off, washed with water, and dried over $P_2O_5$, yielding the title compound (1.0 g, 70%).

MS m/z (%): 420 ([M+H]$^+$, 100)

Examples 424-429

Synthesis of 2-amino-6-[4-(4-chlorophenoxyacetyl)piperazin-1-yl]-8-alkylthio-9H-purine analogues General Procedure To a solution of 2-amino-6-[4-(4-chlorophenoxyacetyl)piperazin-1-yl]-8-thiol-purine (0.24 mmol) and potassium carbonate (0.5 mmol) in DMF (5 ml), was added an appropriate alkyl halide (0.24 mmol). The resulting mixture was stirred at room temperature for 30 minutes. After concentration under reduced pressure, the residue was purified by flash chromatography on silica (methanol/dichloromethane 1:40), yielding the pure title compounds as a white solid.

The following compounds were synthesized according to this procedure:

Example 424

Synthesis of 1-(4-(2-amino-8-(methylthio)-9H-purin-6-yl)piperazin-1-yl)-2-(4-chlorophenoxy)ethanone This compound was synthesized using methyl iodide in 67% yield.

MS m/z (%): 434 ([M+H]$^+$, 100)

Example 425

Synthesis of 1-(4-(2-amino-8-(propylthio)-9H-purin-6-yl)piperazin-1-yl)-2-(4-chlorophenoxy)ethanone This compound was synthesized using propyl iodide yielding the title compound in 65% yield.

MS m/z (%): 462 ([M+H]$^+$, 100)

Example 426

Synthesis of 1-(4-(2-amino-8-(benzylthio)-9H-purin-6-yl)piperazin-1-yl)-2-(4-chlorophenoxy)ethanone This compound was synthesized using benzyl bromide yielding the title compound in 63% yield.

MS m/z (%): 510 ([M+H]$^+$, 100)

Example 427

Synthesis of 1-(4-(2-amino-8-(phenethylthio)-9H-purin-6-yl)piperazin-1-yl)-2-(4-chlorophenoxy)ethanone This compound was synthesized using phenethylbromide yielding the title compound in 67% yield.

MS m/z (%): 524 ([M+H]$^+$, 100)

Example 428

Synthesis of 1-(4-(2-amino-9-methyl-8-(methylthio)-9H-purin-6-yl)piperazin-1-yl)-2-(4-chlorophenoxy)ethanone This compound was synthesized from 2-amino-6-[4-(4-chlorophenoxyacetyl)piperazin-1-yl]-8-methylthio-9H-purine using methyl iodide, yielding the title compound in 97% yield.

MS m/z (%): 448 ([M+H]$^+$, 100)

Example 429

Synthesis of 1-(4-(2-amino-8-(cyclopentylthio)-9H-purin-6-yl)piperazin-1-yl)-2-(4-chlorophenoxy)ethanone This compound was prepared from 2-amino-6-[4-(4-chlorophenoxyacetyl)piperazin-1-yl]-8-thiol-9H-purine and cyclopentyl iodide yielding the title compound in 72% yield.

MS m/z (%): 488 ([M+H]$^+$, 100)

Example 430

Synthesis of 1-(4-(2-amino-8-(4-fluorophenyl)-9-methyl-9H-purin-6-yl)piperazin-1-yl)-2-(4-chlorophenoxy)ethanone To a solution of 2-amino-6-[4-(4-chlorophenoxyacetyl)piperazin-1-yl]-8-(4-fluorophenyl)-9H-purine (48 mg, 0.1 mmol) in DMF (2 ml) was added potassium carbonate (28 mg, 0.2 mmol) and methyl iodide (6 µl, 0.1 mmol). The reaction mixture was stirred at room temperature for 30 minutes. The reaction mixture was evaporated in vacuo and the crude residue was purified by flash chromatography on silica, the mobile phase being a mixture of methanol and dichloromethane (in a ratio of 1:50), yielding the pure title compound (40 mg, 80%).

MS m/z (%): 496 ([M+H]$^+$, 100)

Example 431

Synthesis of 1-(4-(2-amino-9-benzyl-8-(4-fluorophenyl)-9H-purin-6-yl)piperazin-1-yl)-2-(4-chlorophenoxy)ethanone This compound was synthesized according to the procedure mentioned for example 430, using benzylbromide instead of iodomethane, yielding the pure title compound in 68% yield.
MS m/z (%): 591 ([M+H]$^+$, 100)

Example 432

Synthesis of 2,6-diamino-4-thiomethyl-pyrimidine

To a solution of 2,6-diamino-4-mercaptopyrimidine sulfate salt (2 g, 10 mmol) in water (20 ml) was added potassium hydroxide (21 mmol, 1.17 g) and iodomethane (16 mmol, 977 µL). The reaction mixture was stirred for 1.5 hours at room temperature, after which a yellow precipitate was formed. The precipitate was filtered off, washed with water and dried. The product was used for further reactions without any further purification.
MS m/z (%): 157 ([M+H]$^+$, 100)

Example 433

Synthesis of 2,6-diamino-5-nitroso-4-thiomethyl-pyrimidine

To a suspension of 2,6-diamino-4-thiomethyl-pyrimidine (1.21 g, 7.75 mmol) in water (17 ml) was added acetic acid (15 mmol, 888 µl) and sodium nitrite (9.3 mmol, 641 mg). The reaction was stirred at room temperature for 1 hour, after which a pink precipitate was formed. The reaction mixture was put in the fridge for several hours and the precipitate was filtered off, yielding the title compound.

Example 434

Synthesis of 2-amino-6-(4-fluorobenzoylamino)-5-nitroso-4-thiomethyl-pyrimidine

To a solution of 2,6-diamino-5-nitroso-4-thiomethyl-pyrimidine (140 mg, 0.75 mmol) in THF (10 ml) was added triethylamine (0.98 mmol, 136 µl) and 4-fluorobenzoylchloride (0.83 mmol, 98 µl). The reaction was stirred at room temperature for 3 hours. The solvents were evaporated and the crude residue was used for further reaction, without any purification.

Example 435

Synthesis of 2-amino-6-thiomethyl-8-(4-fluorophenyl)-9H-purine

The crude residue, as obtained in Example 61, was redissolved in o-xylene (10 ml) and triphenylphosphine (1.5 mmol, 393 mg) was added. The reaction mixture was heated at 140° C. overnight. The solvents were evaporated in vacuo and the crude residue was purified by silica gel flash chromatography, the mobile phase being a mixture of methanol and dichloromethane (in a ratio gradually raising from 0.5% to 2% methanol), yielding the pure title compound (60 mg)
MS m/z (%): 276 ([M+H]$^+$, 100)

Example 436

Synthesis of a mixture of 2-amino-6-methylsulfoxide-8-(4-fluorophenyl)-9H-purine and 2-amino-6-methylsulfon-8-(4-fluorophenyl)-9H-purine To a solution of 2-amino-6-thiomethyl-8-(4-fluorophenyl)-9H-purine (60 mg, 0.22 mmol) in dichloromethane (10 ml) was added m-chloroperoxybenzoic acid (mCPBA, 0.66 mmol, 113 mg) at 0° C. The reaction temperature was gradually increased to room temperature over 3 hours. The solvents were evaporated in vacuo yielding a mixture of the corresponding sulfoxide and sulfon derivative, which were used as such in the following reaction.

Example 437

Synthesis of 2-amino-6-(piperazin-1-yl)-8-(4-fluorophenyl)-9H-purine

To a solution of the crude residue (as obtained in Example 63) in dioxane (10 ml) was added piperazine (1.1 mmol, 94 mg). The reaction was heated at 100° C. overnight. The solvents were evaporated in vacuo and the crude residue was further purified by flash chromatography on silica, with methanol and dichloromethane as the mobile phase (in a ratio gradually ranging from 5% to 6% methanol always with 0.5% aqueous ammonia solution), yielding the pure title compound (30 mg).
MS m/z (%): 314 ([M+H]$^+$, 100)

Example 438

Synthesis of 1-(4-(2-amino-8-(4-fluorophenyl)-9H-purin-6-yl)piperazin-1-yl)-3-phenylpropan-1-one To a solution of 2-amino-6-(N-piperazin-1-yl)-8-(4-fluorophenyl)-9H-purine (30 mg, 0.0958 mmol) in dioxane (10 ml) was added diisopropylethylamine (0.24 mmol, 40 µl) and hydrocinnamoyl chloride (0.12 mmol, 17 µl). The reaction was stirred overnight at room temperature. The solvents were evaporated in vacuo and the crude residue was purified by silica gel flash chromatography, the mobile phase being a mixture of methanol and dichloromethane (in a ratio gradually raising from 1% to 3% methanol) yielding the pure title compound (70%, 28 mg).
MS m/z (%): 446 ([M+H]$^+$, 100)

Example 439

Synthesis of 4-(5-amino-2-(pyridin-3-yl)thiazolo[5,4-d]pyrimidin-7-yl)-N-(4-(trifluoromethyl)phenyl)piperazine-1-carboxamide To a suspension of 7-(piperazin-1-yl)-2-(pyridin-3-yl)thiazolo[5,4-d]pyrimidin-5-amine (50 mg, 0.16 mmol) in dioxane (10 ml) was added 4-trifluorotolyl isocyanate (0.18 mmol). The resulting reaction mixture was stirred at room temperature for 30 minutes. The solvents were evaporated in vacuo and the crude residue was purified by flash chromatography, the mobile phase being a mixture of methanol and dichloromethane (in a ratio of 1:25), yielding the pure title compound as yellowish solid (50 mg, 63%).
MS m/z (%): 501 ([M+H]$^+$, 100)

¹H NMR (500 MHz, DMSO-d6, 25° C.): δ=9.13 (d, J=2.2 Hz, 1H, Ar—H), 8.98 (s, 1H, ArNH—), 8.66 (dd, J=4.7, 1.5 Hz, 1H, Ar—H), 8.27 (dt, J=8.0, 1.5 Hz, 1H, Ar—H), 7.72 (d, J=8.6 Hz, 2H, Ar—H), 7.61 (d, J=8.6 Hz, 2H, Ar—H), 7.55 (dd, J=8.0, 4.7 Hz, 1H, Ar—H), 6.56 (s, 2H, NH$_2$), 4.32 (br s, 4H, NCH$_2$), 3.67 (br s, 4H, NCH$_2$) ppm.

Example 440

Synthesis of 4-(5-amino-2-(pyridin-3-yl)thiazolo[5,4-d]pyrimidin-7-yl)-N-phenylpiperazine-1-carboxamide This compound was synthesized according to the procedure of example 439, using phenyl isocyanate, yielding the title compound in 67% yield.

MS m/z (%): 433 ([M+H]$^+$, 100)

¹H NMR (500 MHz, DMSO-d6, 25° C.): δ=9.12 (d, J=1.8 Hz, 1H, Ar—H), 8.66 (dd, J=4.8, 1.6 Hz, 1H, Ar—H), 8.58 (s, 1H, ArNH—), 8.27 (dt, J=7.9, 1.5 Hz, 1H, Ar—H), 7.54 (dd, J=7.9, 4.0 Hz, 1H, Ar—H), 7.49 (d, J=8.0 Hz, 2H, Ar—H), 7.25 (t, J=7.7 Hz, 2H, Ar—H), 6.95 (t, J=7.2 Hz, 1H, Ar—H), 6.55 (s, 2H, NH$_2$), 4.31 (br s, 4H, NCH$_2$), 3.64 (br s, 4H, NCH$_2$) ppm.

Example 441

Synthesis of 4-(5-amino-2-(pyridin-3-yl)thiazolo[5,4-d]pyrimidin-7-yl)-N-cyclohexylpiperazine-1-carboxamide This compound was synthesized according to the procedure of example 439, using cyclohexyl isocyanate, yielding the title compound in 63% yield.

MS m/z (%): 439 ([M+H]$^+$, 100)

¹H NMR (500 MHz, DMSO-d6, 25° C.): δ=9.09 (d, J=1.2 Hz, 1H, Ar—H), 8.65 (d, J=4.7 Hz, 1H, Ar—H), 8.25 (d, J=8.0 Hz, 1H, Ar—H), 7.53 (dd, J=8.0, 4.7 Hz, 1H, Ar—H), 6.52 (s, 2H, NH$_2$), 6.21 (d, J=7.6 Hz, —CONH), 4.21 (br s, 4H, NCH$_2$), 3.46 (br s, 5H, NCH— & NCH$_2$), 1.67 (m, 4H, CH$_2$), 1.20 (m, 6H, CH$_2$) ppm.

Example 442

Synthesis of 5-amino-7-[4-(N-4-fluorophenylcarboxamide)piperazin-1-yl]-2-(pyridine-3-yl)thiazolo[5,4-d]pyrimidine This compound was synthesized according to the procedure of example 439, using 4-fluorophenyl isocyanate, yielding the title compound in 72% yield.

MS m/z (%): 451 ([M+H]$^+$, 100)

¹H NMR (300 MHz, DMSO-d6, 25° C.): δ=9.12 (d, J=2.2 Hz, 1H, Ar—H), 8.66 (d, J=4.8 Hz, 1H, Ar—H), 8.63 (s, 1H, ArNH—), 8.27 (d, J=8.0 Hz, 1H, Ar—H), 7.54 (dd, J=8.0 Hz, 4.8 Hz, 1H, Ar—H), 7.51 (dd, J=8.9, 5.4 Hz, 2H, Ar—H), 7.09 (t, J=8.8 Hz, 2H, Ar—H), 6.56 (s, 2H, NH$_2$), 4.31 (br. s, 4H, NCH$_2$), 3.64 (br.s, 4H, NCH$_2$) ppm.

Example 443

Synthesis of 4-(5-amino-2-(pyridin-3-yl)thiazolo[5,4-d]pyrimidin-7-yl)-N-hexylpiperazine-1-carboxamide This compound was synthesized according to the procedure of example 439, using hexyl isocyanate, yielding the title compound in 72% yield.

MS m/z (%): 441 ([M+H]$^+$, 100)

¹H NMR (500 MHz, DMSO-d6, 25° C.): δ=9.09 (dd, J=2.2, 0.6 Hz, 1H, Ar—H), 8.65 (dd, J=4.8, 1.6 Hz, 1H, Ar—H), 8.24 (dt, J=8.0, 2.2 Hz, 1H, Ar—H), 7.54 (ddd, J=8.0, 4.8, 0.6 Hz, 1H, Ar—H), 6.51 (s, 3H, NH$_2$ & —CONH—), 4.22 (br s, 4H, NCH$_2$), 3.46 (br t, J=5.0 Hz, 4H, NCH$_2$), 3.03 (q, J=6.9 Hz, 2H, —NHCH$_2$—), 1.41 (m, 2H, CH$_2$), 1.25 (m, 6H, CH$_2$), 0.86 (t, J=7.0 Hz, CH$_3$) ppm.

Example 444

Synthesis of 4-(5-amino-2-(pyridin-3-yl)thiazolo[5,4-d]pyrimidin-7-yl)-N-p-tolylpiperazine-1-carbothioamide This compound was synthesized according to the procedure of example 439, using 4-tolyl isothiocyanate, yielding the title compound in 71% yield.

MS m/z (%): 463 ([M+H]$^+$, 100)

¹H NMR (500 MHz, DMSO-d6, 25° C.): δ=9.29 (s, 1H, CONH—), 9.12 (dd, J=2.2, 0.6 Hz, 1H, Ar—H), 8.65 (dd, J=4.8, 1.6 Hz, 1H, Ar—H), 8.27 (dt, J=8.0, 1.6 Hz, 1H, Ar—H), 7.53 (ddd, J=8.0 Hz, 4.8, 0.6 Hz, 1H, Ar—H), 7.20 (d, J=8.2 Hz, 2H, Ar—H), 7.11 (d, J=8.2 Hz, 2H, Ar—H), 6.56 (s, 2H, NH$_2$), 4.35 (br s, 4H, NCH$_2$), 4.10 (br s, 4H, NCH$_2$), 2.28 (s, 3H, ArCH$_3$) ppm.

Example 445

Synthesis of 4-(5-amino-2-(pyridin-3-yl)thiazolo[5,4-d]pyrimidin-7-yl)-N-methyl-N-p-tolylpiperazine-1-carboxamide To a suspension of 4-(5-amino-2-(pyridin-3-yl)thiazolo[5,4-d]pyrimidin-7-yl)-N-p-tolylpiperazine-1-carboxamide (90 mg, 0.2 mmol) in DMF (5 ml) was added NaH (60%, 12 mg, 0.31 mmol). The resulting mixture was stirred at room temperature for 10 minutes. Then, methyl iodide (0.3 mmol) was added to the mixture. After stirring at room temperature for 30 minutes, the solvents were evaporated in vacuo and the crude residue was purified by flash chromatography on silica, the mobile phase being a mixture of methanol and dichloromethane (in a ratio of 1/30), yielding the pure title compound as yellowish solid (40 mg, 43%).

MS m/z (%): 461 ([M+H]$^+$, 100)

¹H NMR (500 MHz, DMSO-d6, 25° C.): δ=9.07 (dd, J=2.2, 0.6 Hz, 1H, Ar—H), 8.65 (dd, J=4.8, 1.6 Hz, 1H, Ar—H), 8.23 (ddd, J=8.0, 2.2, 1.6 Hz, 1H, Ar—H), 7.53 (ddd, J=8.0, 4.8, 0.6 Hz, 1H, Ar—H), 7.17 (d, J=8.2 Hz, 2H, Ar—H), 7.06 (d, J=8.2 Hz, 2H, Ar—H), 6.49 (s, 2H, NH$_2$), 4.08 (br s, 4H, NCH$_2$), 3.28 (br.s, 4H, NCH$_2$), 3.10 (s, 3H, CONCH$_3$), 2.26 (s, 3H, ArCH$_3$) ppm.

Example 446

Synthesis of p-tolyl 4-(5-amino-2-(pyridin-3-yl)thiazolo[5,4-d]pyrimidin-7-yl)piperazine-1-carboxylate To a suspension of 7-(piperazin-1-yl)-2-(pyridin-3-yl)thiazolo[5,4-d]pyrimidin-5-amine (63 mg, 0.2 mmol) in dioxane (10 ml) was added diisopropylethylamine (33 μl, 0.2 mmol) and p-tolyl chloroformate (0.2 mmol). The resulting mixture was stirred at room temperature for 30 minutes. The mixture was evaporated in vacuo and the crude residue was purified by flash chromatography on silica, the mobile phase being a mixture of methanol and dichloromethane (in a ratio of 1/30), yielding the pure title compound as yellowish solid (60 mg, 67%).

MS m/z (%): 448 ([M+H]+, 100)

¹H NMR (500 MHz, DMSO-d6, 25° C.): δ=9.14 (dd, J=2.2, 0.6 Hz, 1H, Ar—H), 8.65 (dd, J=4.8, 1.6 Hz, 1H, Ar—H), 8.30 (ddd, J=8.0, 2.2, 1.6 Hz, 1H, Ar—H), 7.53 (ddd, J=8.0, 4.8, 0.6 Hz, 1H, Ar—H), 7.19 (d, J=8.2 Hz, 2H, Ar—H), 7.04 (d, J=8.2 Hz, 2H, Ar—H), 6.57 (s, 2H, NH₂), 4.35 (br s, 4H, NCH₂), 3.77-3.62 (br s, 4H, NCH₂), 2.30 (s, 3H, ArCH₃) ppm.

Thiazolo[5,4-d]pyrimidines and oxazolo[5,4-d]pyrimidines

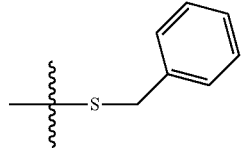

| Example | X | R² | R¹ | R³ |
|---|---|---|---|---|
| 28 | S | 4-fluorophenyl | NH₂ | 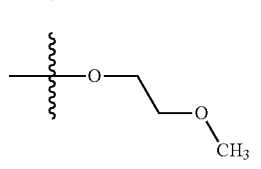 |
| 29 | S | 4-fluorophenyl | NH₂ | 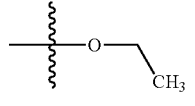 |
| 30 | S | 4-fluorophenyl | NH₂ | 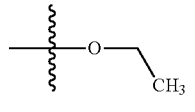 |
| 31 | S | 4-fluorobenzyl | NH₂ | 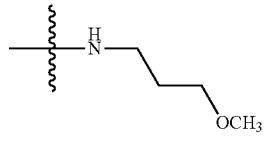 |
| 32 | S | 4-fluorophenyl | NH₂ | 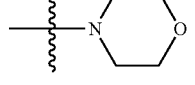 |
| 33 | S | 4-fluorophenyl | NH₂ | 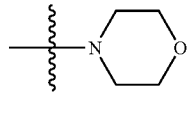 |
| 34 | S | 4-fluorobenzyl | NH₂ | 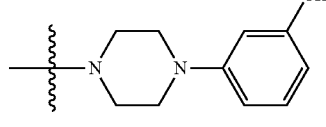 |
| 35 | S | 4-fluorophenyl | NH₂ | 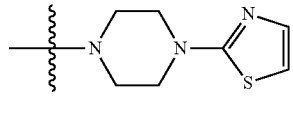 |
| 36 | S | 4-fluorophenyl | NH₂ | 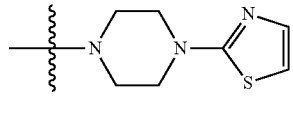 |

-continued

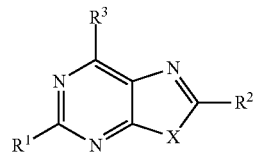

I

| Example | X | R² | R¹ | R³ |
|---|---|---|---|---|
| 37 | S | 4-fluorophenyl | NH₂ | piperazine-N-C₅H₁₁ |
| 38 | S | 4-fluorophenyl | NH₂ | piperazine-CH₂-C(O)-morpholine |
| 39 | S | 4-fluorophenyl | NH₂ | piperazine-CH₂-phenyl |
| 40 | S | 4-fluorophenyl | NH₂ | piperazine-C(O)O-CH₂-phenyl |
| 41 | S | 4-fluorophenyl | NH₂ | piperazine-SO₂-phenyl |
| 42 | S | 4-fluorophenyl | NH₂ | piperazine-C(O)NH-(4-methylphenyl) |
| 43 | S | 4-fluorophenyl | NH₂ | piperazine-C(O)NH-(3-methylphenyl) |
| 44 | S | 4-fluorobenzyl | NH₂ | piperazine-C(O)NH-(3-methylphenyl) |
| 45 | S | 4-fluorophenyl | NH₂ | piperazine-C(O)CH₂-O-(4-chlorophenyl) |

-continued

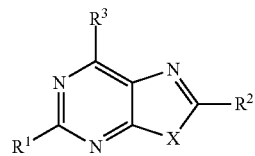

I

| Example | X | R² | R¹ | R³ |
|---|---|---|---|---|
| 46 | S | 4-fluorobenzyl | NH₂ | piperazine-C(O)CH₂-O-C₆H₄-4-Cl |
| 47 | S | 4-fluorophenyl | CH₃ | piperazine-C(O)CH₂-O-C₆H₄-4-Cl |
| 48 | S | -CH₂CH₂-O-C₆H₄-4-F | NH₂ | piperazine-C(O)CH₂-O-C₆H₄-4-Cl |
| 49 | S | -CH₂CH₂-C₆H₄-4-F | NH₂ | piperazine-C(O)CH₂-O-C₆H₄-4-Cl |
| 50 | S | -CH₂CH₂-C₆H₄-4-F | NH₂ | piperazine-C(O)CH₂-O-C₆H₄-4-OCH₃ |
| 51 | S | -CH₂CH₂-C₆H₄-4-F | NH₂ | piperazine-C(O)CH₂-O-C₆H₄-4-F |
| 52 | S | -CH₂CH₂-C₆H₄-4-F | NH₂ | piperazine-C(O)CH₂-O-C₆H₄-4-Br |
| 53 | S | -CH₂CH₂-C₆H₄-4-F | NH₂ | piperazine-C(O)CH₂-O-C₆H₄-3-CH₃ |
| 54 | S | -CH₂CH₂-C₆H₄-4-F | NH₂ | piperazine-C(O)CH₂-O-C₆H₃-2,4-Cl₂ |

-continued

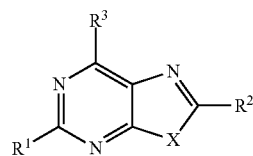

| Example | X | R² | R¹ | R³ |
|---|---|---|---|---|
| 55 | S | 4-fluorophenethyl | NH₂ | piperazine-N-C(O)-CH₂CH₂-O-(4-fluorophenyl) |
| 66 | S | 1-(4-fluorophenyl)ethyl | NH₂ | piperazine-N-C(O)-CH₂-O-(4-chlorophenyl) |
| 67 | S | 1-(4-fluorophenyl)-2-phenylethyl | NH₂ | piperazine-N-C(O)-CH₂-O-(4-chlorophenyl) |
| 68 | S | 1-(4-fluorophenyl)ethyl | NH₂ | piperazine-N-C(O)-NH-(3-methylphenyl) |
| 114 | S | 1-phenylcyclopropyl | NH₂ | piperazine-N-C(O)-CH₂-O-(4-chlorophenyl) |
| 115 | S | SCH₃ | NH₂ | piperazine-N-C(O)-CH₂-O-(4-chlorophenyl) |
| 116 | S | 3,4-dichlorophenyl | NH₂ | piperazine-N-C(O)-CH₂-O-(4-chlorophenyl) |

-continued

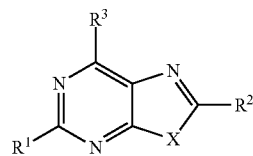

| Example | X | R² | R¹ | R³ |
|---|---|---|---|---|
| 117 | S | 1-(4-chlorophenyl)cyclopropyl | NH₂ | piperazine-N-C(O)-CH₂-O-(4-chlorophenyl) |
| 118 | S | -CH(CH₃)-CH₂-phenyl | NH₂ | piperazine-N-C(O)-CH₂-O-(4-chlorophenyl) |
| 119 | S | -CH(CH₃)-cyclopropyl | NH₂ | piperazine-N-C(O)-CH₂-O-(4-chlorophenyl) |
| 120 | S | -CH(CH₃)-cyclohexyl | NH₂ | piperazine-N-C(O)-CH₂-O-(4-chlorophenyl) |
| 121a | S | -CH(CH₃)-(3-pyridyl) | NH₂ | piperazine-N-C(O)-CH₂-O-(4-chlorophenyl) |
| 121b | S | -CH(CH₃)-(3-pyridyl N-oxide) | NH₂ | piperazine-N-C(O)-CH₂-O-(4-chlorophenyl) |
| 122 | S | -CH(CH₃)-CH₂-(4-chlorophenyl) | NH₂ | piperazine-N-C(O)-CH₂-O-(4-chlorophenyl) |
| 123 | S | -CH(CH₃)-(4-chlorophenyl) | NH₂ | piperazine-N-C(O)-CH₂-O-(4-chlorophenyl) |

-continued

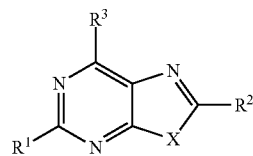

| Example | X | R² | R¹ | R³ |
|---|---|---|---|---|
| 124 | S | 3-methoxyphenyl | NH₂ | piperazine-N-CO-CH₂-O-(4-chlorophenyl) |
| 125 | S | 1-(4-chlorophenyl)ethyl | NH₂ | piperazine-N-CO-CH₂-O-(4-chlorophenyl) |
| 126 | S | S(O)CH₃ | NH₂ | piperazine-N-CO-CH₂-O-(4-chlorophenyl) |
| 127 | S | NH-(4-fluorophenyl) | NH₂ | piperazine-N-CO-CH₂-O-(4-chlorophenyl) |
| 128 | S | 4-fluorophenyl | NH₂ | piperazine-N-CO-CH₂-O-(4-bromophenyl) |
| 129 | S | 4-fluorophenyl | NH₂ | piperazine-N-CO-CH₂-O-(3-nitrophenyl) |
| 130 | S | 4-fluorophenyl | NH₂ | piperazine-N-CO-CH₂-O-phenyl |
| 131 | S | 2-(4-fluorophenyl)ethyl | NH₂ | piperazine-N-CO-CH₂-O-(3-nitrophenyl) |

-continued

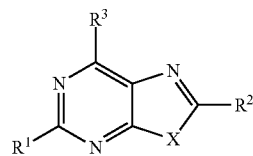

| Example | X | R² | R¹ | R³ |
|---|---|---|---|---|
| 132 | S | -CH₂CH₂-C₆H₄-F (4-F) | NH₂ | piperazine-C(O)CH₂-C₆H₄-Cl (4-Cl) |
| 133 | S | -CH₂CH₂-C₆H₄-F (4-F) | NH₂ | piperazine-C(O)NH-C₆H₄-CH₃ (3-CH₃) |
| 134 | S | -CH₂CH₂-C₆H₄-F (4-F) | NH₂ | piperazine-C(O)CH₂-O-C₆H₅ |
| 135 | S | -CH₂CH₂-C₆H₄-F (4-F) | NH₂ | piperazine-C(O)-C₆H₄-Cl (4-Cl) |
| 136 | S | -CH₂CH₂-C₆H₄-F (4-F) | NH₂ | piperazine-C(O)CH₂CH₂-C₆H₅ |
| 137 | S | -CH₂CH₂-C₆H₄-F (4-F) | NH₂ | piperazine-S(O)₂-CH₂-C₆H₅ |
| 138 | S | -CH₂CH₂-C₆H₄-F (4-F) | NH₂ | homopiperazine-C(O)CH₂-O-C₆H₄-Cl (4-Cl) |
| 139 | S | -CH₂CH₂-C₆H₄-F (4-F) | NH₂ | piperazine-CH₂C(O)N(CH₃)-C₆H₅ |

-continued

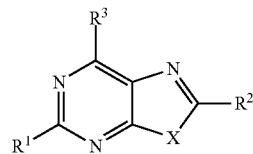

| Example | X | R² | R¹ | R³ |
|---|---|---|---|---|
| 140 | S | ⸹-CH(-)-CH₂-C₆H₄-F(4) | NH₂ | piperazinyl-thiazole |
| 141 | S | ⸹-CH(-)-CH₂-C₆H₄-F(4) | NH₂ | piperazinyl-CH₂-C(O)NH-CH₂CH₂-phenyl |
| 142 | S | ⸹-CH(-)-CH₂-C₆H₄-F(4) | NH₂ | (3-NHBoc)-1-methyl-pyrrolidinyl |
| 143 | S | ⸹-CH(-)-CH₂-C₆H₄-F(4) | NH₂ | pyrrolidin-3-yl-NH-C(O)-CH₂-O-C₆H₄-Cl(4) |
| 144 | S | ⸹-CH(-)-CH₂-C₆H₄-F(4) | NH₂ | pyrrolidin-3-yl-NH-C(O)-C₆H₄-Cl(4) |
| 145 | S | ⸹-CH(-)-CH₂-C₆H₄-F(4) | NH₂ | piperidin-3-yl-NH-, N-Cbz |
| 146 | S | ⸹-CH(-)-CH₂-C₆H₄-F(4) | NH₂ | (3R)-1-Boc-pyrrolidin-3-yl-NH- |
| 147 | S | ⸹-CH(-)-CH₂-C₆H₄-F(4) | NH₂ | 1-[2-(4-chlorophenoxy)acetyl]-pyrrolidin-3-yl-NH- |
| 148 | S | ⸹-CH(-)-CH₂-C₆H₄-F(4) | NH₂ | 4-benzoyl-piperidin-1-yl |

-continued

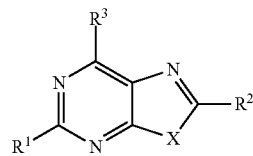

| Example | X | R² | R¹ | R³ |
|---|---|---|---|---|
| 149 | S | 2-(4-fluorophenyl)ethyl | NH₂ | 4-(2-phenoxyethyl)piperazin-1-yl |
| 150 | S | 1-(4-fluorophenyl)propyl | NH₂ | 4-[2-(4-chlorophenoxy)acetyl]piperazin-1-yl |
| 151 | S | cyclopentyl(4-fluorophenyl)methyl | NH₂ | 4-[2-(4-chlorophenoxy)acetyl]piperazin-1-yl |
| 154 | S | 2-(thiophen-2-yl)ethyl | NH₂ | 4-[2-(4-chlorophenoxy)acetyl]piperazin-1-yl |
| 155 | S | 2-(thiophen-2-yl)ethyl | NH₂ | 4-[2-(4-chlorophenyl)acetyl]piperazin-1-yl |
| 156 | S | 2-(thiophen-2-yl)ethyl | NH₂ | 4-(4-chlorobenzoyl)piperazin-1-yl |
| 157 | S | 2-(thiophen-2-yl)ethyl | NH₂ | 4-[(3-methylphenyl)carbamoyl]piperazin-1-yl |
| 167 | O | 4-fluorophenyl | H | 4-[2-(4-chlorophenoxy)acetyl]piperazin-1-yl |

-continued

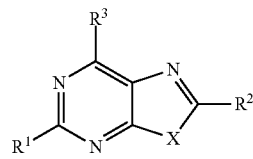

I

| Example | X | R² | R¹ | R³ |
|---|---|---|---|---|
| 168 | O | 4-fluorophenyl | CH₃ | piperazine-N-C(O)-CH₂-O-(4-chlorophenyl) |
| 169 | O | 4-fluorophenyl | NH₂ | piperazine-N-C(O)-CH₂-O-(4-chlorophenyl) |
| 170 | O | 4-fluorobenzyl | H | piperazine-N-C(O)-CH₂-O-(4-chlorophenyl) |
| 171 | O | 4-fluorobenzyl | CH₃ | piperazine-N-C(O)-CH₂-O-(4-chlorophenyl) |
| 172 | O | -CH₂-(4-fluorophenyl) | NH₂ | piperazine-N-C(O)-CH₂-O-(4-chlorophenyl) |
| 173 | O | 4-fluorophenyl | H | -NH-(3-chloro-4-fluorophenyl) |
| 174 | O | 4-fluorophenyl | NH₂ | -NH-(3-chloro-4-fluorophenyl) |
| 185 | O | cyclopropyl | NH₂ | piperazine-N-C(O)-CH₂-O-(4-chlorophenyl) |
| 186 | O | -CH₂OCH₃ | NH₂ | piperazine-N-C(O)-CH₂-O-(4-chlorophenyl) |

-continued

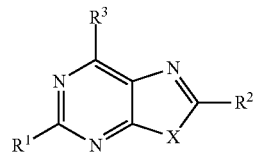

| Example | X | R² | R¹ | R³ |
|---|---|---|---|---|
| 187 | O | cyclohexylmethyl | NH₂ | piperazine-N-C(O)-CH₂-O-(4-chlorophenyl) |
| 188 | O | C₅H₁₁ | NH₂ | piperazine-N-C(O)-CH₂-O-(4-chlorophenyl) |
| 189 | O | 2-phenylethyl | NH₂ | piperazine-N-C(O)-CH₂-O-(4-chlorophenyl) |
| 190 | O | 4-fluorophenyl | NH₂ | piperazine-N-CH₂-CH(CH₃)₂ |
| 191 | O | 4-fluorophenyl | NH₂ | piperazine-N-C(O)-CH₃ |
| 192 | O | 4-fluorophenyl | NH₂ | piperazine-N-CH₂CH₂-O-CH₃ |
| 193 | O | 2-(4-fluorophenyl)ethyl | NH₂ | piperazine-N-C(O)-CH₂-O-(3-nitrophenyl) |
| 194 | O | 2-(4-fluorophenyl)ethyl | NH₂ | piperazine-N-C(O)-CH₂-(4-chlorophenyl) |
| 195 | O | 2-(4-fluorophenyl)ethyl | NH₂ | piperazine-N-C(O)-(4-chlorophenyl) |

-continued

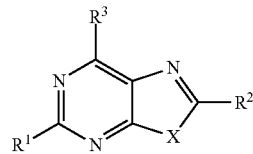

| Example | X | R² | R¹ | R³ |
|---|---|---|---|---|
| 196 | O | -CH₂-C₆H₄-F (4-F) | NH₂ | piperazine-C(O)NH-(3-methylphenyl) |
| 197 | O | -CH₂-C₆H₄-F (4-F) | NH₂ | piperazine-CH₂CH₂-O-phenyl |
| 198 | O | -CH₂-C₆H₄-F (4-F) | NH₂ | piperazine-CH₂-C(O)-N(CH₃)-phenyl |
| 208 | S | phenyl | NH₂ | piperazine-C(O)-CH₂-O-(4-OCH₃-phenyl) |
| 209 | S | 2-furyl | NH₂ | piperazine-C(O)-CH₂-O-(4-F-phenyl) |
| 210 | S | 2-furyl | NH₂ | piperazine-C(O)-CH₂-O-(3-methylphenyl) |
| 211 | S | 4-fluorophenyl | NH₂ | piperazine-C(O)-CH₂-O-(3-methylphenyl) |
| 212 | S | 4-fluorophenyl | NH₂ | piperazine-C(O)-CH₂-O-(2,4-dichlorophenyl) |
| 213 | S | 4-fluorophenyl | NH₂ | piperazine-C(O)-CH₂-O-(4-chloro-2-methylphenyl) |

-continued
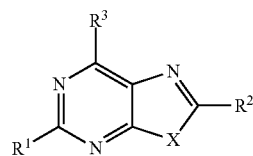
I
| Example | X | R² | R¹ | R³ |
|---|---|---|---|---|
| 214 | S | 4-fluorophenyl | NH₂ | 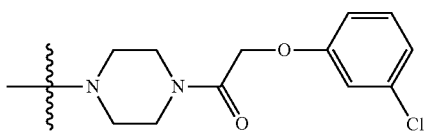 [SMILES: *N1CCN(C(=O)COc2cccc(Cl)c2)CC1] |
| 215 | S | phenyl | NH₂ | 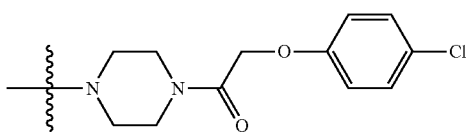 |
| 216 | S | 4-fluorophenyl | NH₂ | 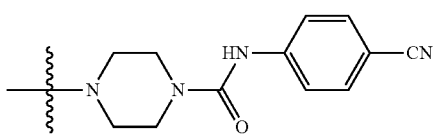 [SMILES: *N1CCN(C(=O)Nc2ccc(C#N)cc2)CC1] |
| 217 | S | 4-fluorophenyl | NH₂ | 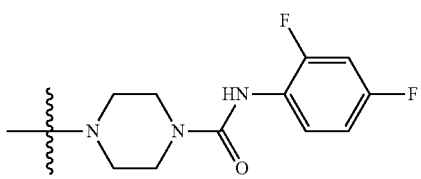 [SMILES: *N1CCN(C(=O)Nc2ccc(F)cc2F)CC1] |
| 218 | S | 4-fluorophenyl | NH₂ | 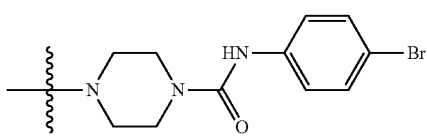 [SMILES: *N1CCN(C(=O)Nc2ccc(Br)cc2)CC1] |
| 219 | S | 4-fluorophenyl | NH₂ | 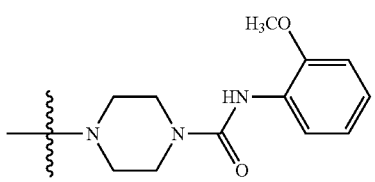 [SMILES: *N1CCN(C(=O)Nc2ccccc2OC)CC1] |
| 220 | S | phenyl | NH₂ | 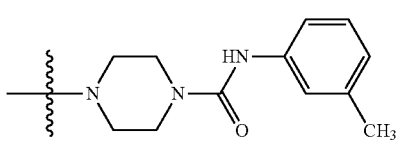 |
| 222 | S | 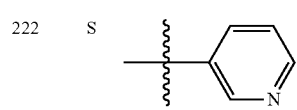 | NH₂ | 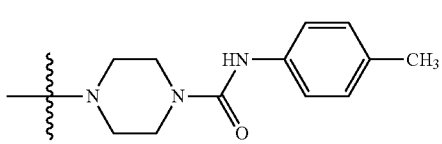 [SMILES: *N1CCN(C(=O)Nc2ccc(C)cc2)CC1] |

-continued

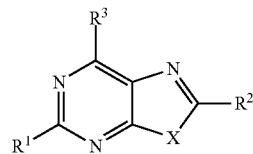

| Example | X | R² | R¹ | R³ |
|---|---|---|---|---|
| 223 | S | 2-(4-fluorophenyl)ethyl | NH₂ | piperazine-N-C(O)-CH₂CH₂-(4-bromophenyl) |
| 224 | S | 2-(4-fluorophenyl)ethyl | NH₂ | piperazine-N-C(O)-CH₂-O-(4-hydroxyphenyl) |
| 225 | S | 2-(4-fluorophenyl)ethyl | NH₂ | piperazine-N-C(O)-CH₂-O-(4-COOCH₃-phenyl) |
| 226 | S | 2-(4-fluorophenyl)ethyl | NH₂ | piperazine-N-C(O)-CH₂-O-(4-OCF₃-phenyl) |
| 227 | S | 2-(4-fluorophenyl)ethyl | NH₂ | piperazine-N-C(O)-CH₂-O-(4-acetylphenyl) |
| 228 | S | 2-(4-fluorophenyl)ethyl | NH₂ | piperazine-N-C(O)-CH₂-O-(3-chlorophenyl) |
| 229 | S | 2-(4-fluorophenyl)ethyl | NH₂ | piperazine-N-C(O)-NH-(4-cyanophenyl) |
| 230 | S | 4-fluorobenzyl | NH₂ | piperazine-N-C(O)-CH₂-O-(4-methoxyphenyl) |
| 231 | S | 4-fluorobenzyl | NH₂ | piperazine-N-C(O)-CH₂-O-(4-bromophenyl) |

-continued

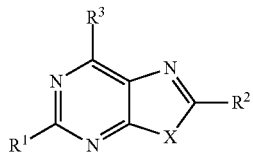

| Example | X | R² | R¹ | R³ |
|---|---|---|---|---|
| 232 | S | 4-fluorobenzyl | NH₂ | piperazine-C(O)NH-(4-cyanophenyl) |
| 233 | S | 4-fluorophenyl | NH₂ | piperazine-C(O)CH₂-O-(4-fluorophenyl) |
| 234 | S | 4-fluorophenyl | NH₂ | piperazine-C(O)CH₂-O-(4-methoxyphenyl) |
| 235 | S | 4-fluorophenyl | NH₂ | piperazine-C(O)CH₂-O-(4-bromophenyl) |
| 236 | S | 4-fluorophenyl | NH₂ | piperazine-C(O)CH₂CH₂-(4-fluorophenyl) |
| 237 | S | 4-fluorophenyl | NH₂ | piperazine-C(O)-C(CH₃)₂-O-(4-chlorophenyl) |
| 253 | S | -CH₂-(3-methoxyphenyl) | NH₂ | piperazine-C(O)CH₂-O-(4-methoxyphenyl) |
| 254 | S | -CH₂-(3-methoxyphenyl) | NH₂ | piperazine-C(O)CH₂-O-(4-bromophenyl) |

-continued

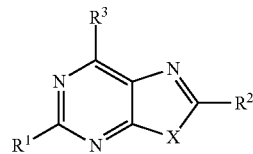

| Example | X | R² | R¹ | R³ |
|---|---|---|---|---|
| 255 | S | 3-methoxyphenethyl | NH₂ | piperazine-N-C(O)-CH₂-O-(4-chlorophenyl) |
| 256 | S | 3,4-dimethoxyphenethyl | NH₂ | piperazine-N-C(O)-CH₂-O-(4-bromophenyl) |
| 257 | S | 3,4-dimethoxyphenethyl | NH₂ | piperazine-N-C(O)-CH₂-O-(4-methoxyphenyl) |
| 258 | S | 4-methylphenethyl | NH₂ | piperazine-N-C(O)-CH₂-O-(4-bromophenyl) |
| 259 | S | 4-methylphenethyl | NH₂ | piperazine-N-C(O)-CH₂-O-(4-methoxyphenyl) |
| 260 | S | 4-methylphenethyl | NH₂ | piperazine-N-C(O)-CH₂-O-(4-chlorophenyl) |
| 270 | S | 4-chlorophenyl | NH₂ | piperazine-N-C(O)-CH₂-O-(4-methoxyphenyl) |
| 271 | S | pyridin-3-yl | NH₂ | piperazine-N-C(O)-CH₂-O-(4-methoxyphenyl) |

-continued
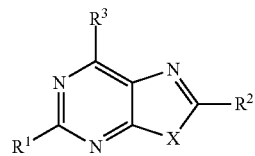
I
| Example | X | R² | R¹ | R³ |
|---|---|---|---|---|
| 272 | S | 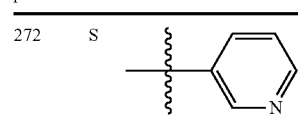 | NH₂ | 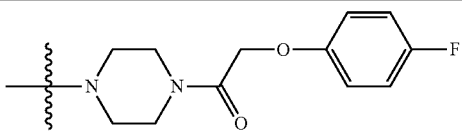 [SMILES: *N1CCN(C(=O)COc2ccc(F)cc2)CC1] |
| 273 | S | 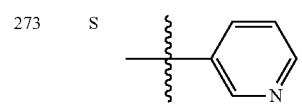 | NH₂ | 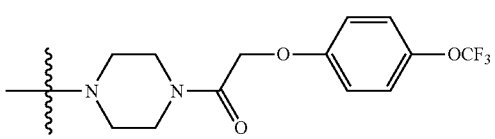 [SMILES: *N1CCN(C(=O)COc2ccc(OC(F)(F)F)cc2)CC1] |
| 274 | S | 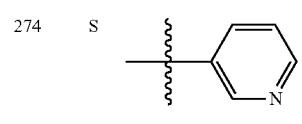 | NH₂ | 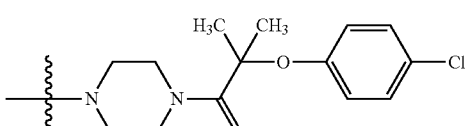 |
| 275 | S | 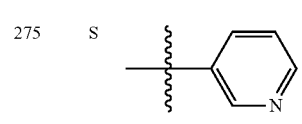 | NH₂ | 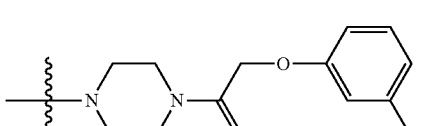 |
| 276 | S | 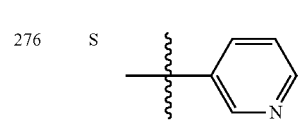 | NH₂ | 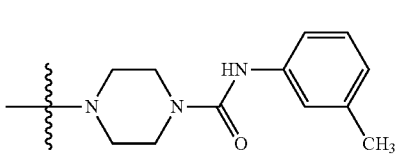 |
| 277 | S | 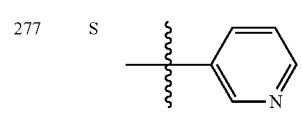 | NH₂ | 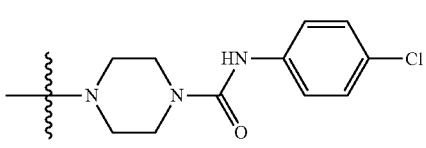 |
| 278 | S | 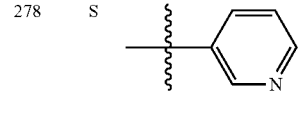 | NH₂ | 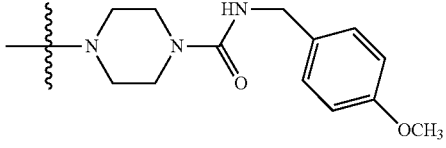 |
| 279 | S | 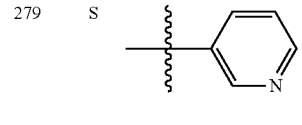 | NH₂ | 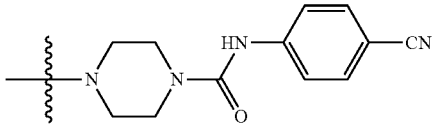 |
| 280 | S | 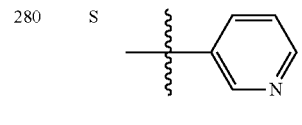 | NH₂ | 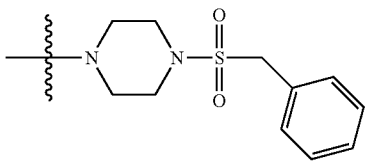 [SMILES: *N1CCN(S(=O)(=O)Cc2ccccc2)CC1] |

-continued

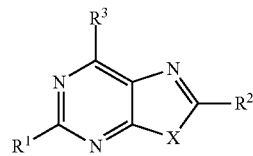

| Example | X | R² | R¹ | R³ |
|---|---|---|---|---|
| 281 | S | 4-pyridyl | NH₂ | piperazine-C(O)CH₂O-(4-Cl-phenyl) |
| 282 | S | 2-pyridyl | NH₂ | piperazine-C(O)CH₂O-(4-Cl-phenyl) |
| 290 | S | -CH₂CH₂-(4-F-phenyl) | NH₂ | piperazine-C(O)CH₂O-(4-Cl-phenyl) |
| 291 | S | -CH₂CH₂-(4-F-phenyl) | NH₂ | piperazine-C(O)CH₂O-(4-OCH₃-phenyl) |
| 292 | S | -CH₂CH₂CH₂-(4-F-phenyl) | NH₂ | piperazine-C(O)CH₂O-(4-Cl-phenyl) |
| 293 | S | -CH₂CH₂CH₂-(4-F-phenyl) | NH₂ | piperazine-C(O)CH₂O-(4-OCH₃-phenyl) |
| 294 | S | 4-CH₃-phenyl | NH₂ | piperazine-C(O)CH₂O-(4-OCH₃-phenyl) |
| 295 | S | 5-CH₃-pyridyl | NH₂ | piperazine-C(O)CH₂O-(4-Cl-phenyl) |

-continued

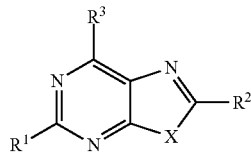

| Example | X | R² | R¹ | R³ |
|---|---|---|---|---|
| 296 | S | C₅H₁₁ | NH₂ | piperazine-C(O)-CH₂-O-C₆H₄-OCH₃ |
| 297 | S | C₅H₁₁ | NH₂ | piperazine-C(O)-CH₂-O-C₆H₄-Cl |
| 298 | S | -CH₂-C₆H₄-Br | NH₂ | piperazine-C(O)-CH₂-O-C₆H₄-OCH₃ |
| 299 | S | -CH₂-C₆H₄-Br | NH₂ | piperazine-C(O)-CH₂-O-C₆H₄-Cl |
| 300 | S | 4-fluorophenyl | H | piperazine-C(O)-CH₂-O-C₆H₄-OCH₃ |
| 301 | S | 4-fluorophenyl | H | piperazine-C(O)-CH₂-O-C₆H₄-Cl |
| 302 | S | -CH₂-C₆H₄-F | H | piperazine-C(O)-CH₂-O-C₆H₄-OCH₃ |
| 303 | S | -CH₂-C₆H₄-F | H | piperazine-C(O)-CH₂-O-C₆H₄-Cl |
| 439 | S | 3-pyridyl | NH₂ | piperazine-C(O)-NH-C₆H₄-CF₃ |

-continued
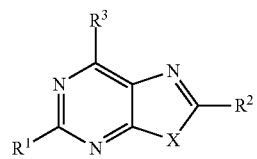
| Example | X | R² | R¹ | R³ |
|---|---|---|---|---|
| 440 | S | 3-pyridyl | NH₂ | piperazine-C(O)NH-phenyl |
| 441 | S | 3-pyridyl | NH₂ | piperazine-C(O)NH-cyclohexyl |
| 442 | S | 3-pyridyl | NH₂ | piperazine-C(O)NH-(4-F-phenyl) |
| 443 | S | 3-pyridyl | NH₂ | piperazine-C(O)NH-hexyl |
| 444 | S | 3-pyridyl | NH₂ | piperazine-C(S)NH-(4-CH₃-phenyl) |
| 445 | S | 3-pyridyl | NH₂ | piperazine-C(O)N(CH₃)-(4-CH₃-phenyl) |
| 446 | S | 3-pyridyl | NH₂ | piperazine-C(O)O-(4-CH₃-phenyl) |

Thieno[2,3-d]pyrimidines
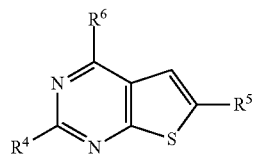
| Example | R⁵ | R⁴ | R⁶ |
|---|---|---|---|
| 312 | 4-fluorophenyl | H | 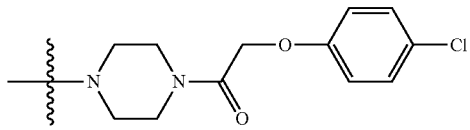 |
| 313 | 4-fluorophenyl | n-butyl | 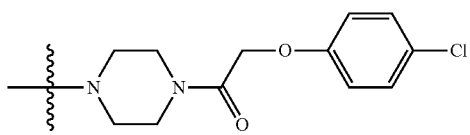 |
| 314 | 4-fluorophenyl | H | 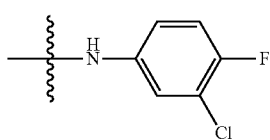 [SMILES: *Nc1ccc(F)c(Cl)c1] |
| 315 | 4-fluorophenyl | n-butyl | 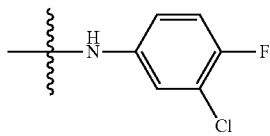 [SMILES: *Nc1ccc(F)c(Cl)c1] |
| 325 | 4-fluorophenyl | CH₃ | 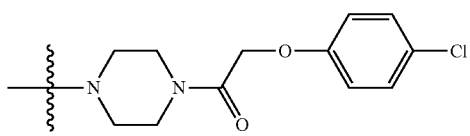 |
| 326 | 4-fluorophenyl | NH₂ | 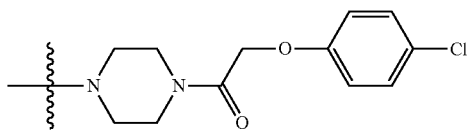 [SMILES: *N1CCN(C(=O)COc2ccc(Cl)cc2)CC1] |
| 327 | 4-fluorophenyl | NH₂ | 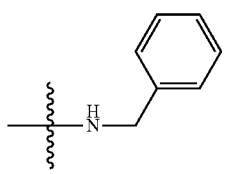 [SMILES: *NCc1ccccc1] |
| 329 | phenyl | NH₂ | 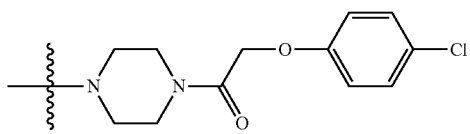 |
| 330 | phenyl | NH₂ | 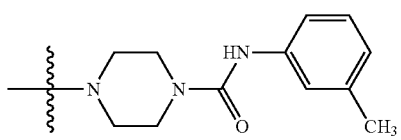 |

-continued
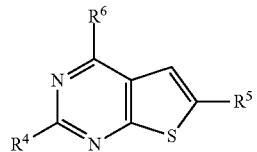
II
| Example | R⁵ | R⁴ | R⁶ |
|---|---|---|---|
| 331 | phenyl | NH₂ | 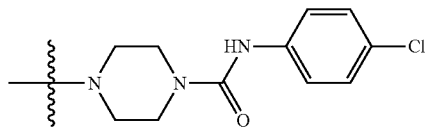 [SMILES: *N1CCN(C(=O)Nc2ccc(Cl)cc2)CC1] |
| 332 | phenyl | NH₂ | 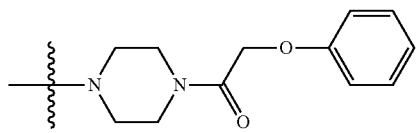 [SMILES: *N1CCN(C(=O)COc2ccccc2)CC1] |
| 334 | phenyl | NH₂ | 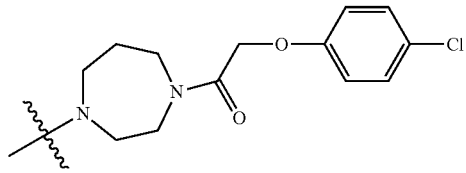 [SMILES: *N1CCCN(C(=O)COc2ccc(Cl)cc2)CC1] |
| 335 | phenyl | NH₂ | 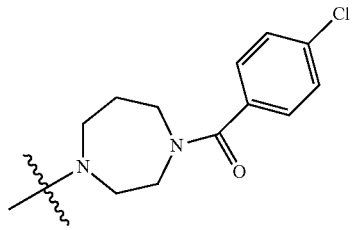 [SMILES: *N1CCCN(C(=O)c2ccc(Cl)cc2)CC1] |
| 336 | phenyl | NH₂ | 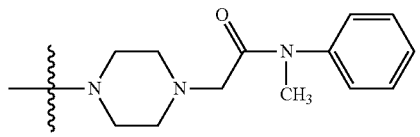 [SMILES: *N1CCN(CC(=O)N(C)c2ccccc2)CC1] |
| 337 | phenyl | NH₂ | 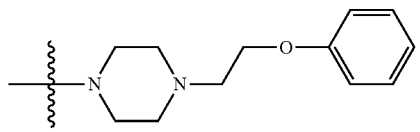 |
| 338 | 4-fluorophenyl | NH₂ | 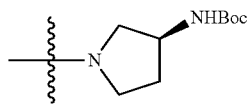 [SMILES: *N1CC[C@H](NC(=O)OC(C)(C)C)C1] |
| 339 | 4-fluorophenyl | NH₂ | 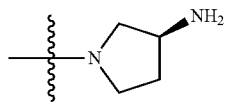 [SMILES: *N1CC[C@H](N)C1] |
| 340 | 4-fluorophenyl | NH₂ | 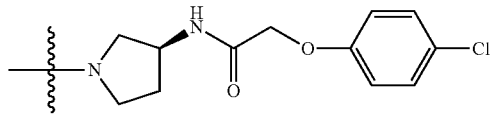 [SMILES: *N1CC[C@H](NC(=O)COc2ccc(Cl)cc2)C1] |

-continued
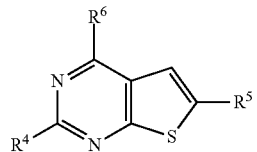
II
| Example | R⁵ | R⁴ | R⁶ |
|---|---|---|---|
| 341 | 4-fluorophenyl | NH₂ | 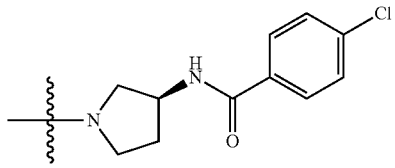 [SMILES: *N1CC[C@H](NC(=O)c2ccc(Cl)cc2)C1] |
| 343 | 4-fluorophenyl | NH₂ | 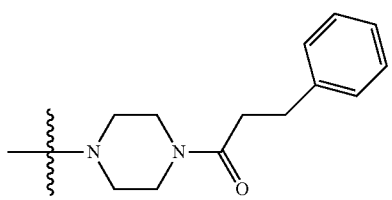 [SMILES: *N1CCN(C(=O)CCc2ccccc2)CC1] |
| 344 | 4-fluorophenyl | NH₂ | 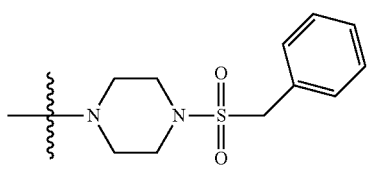 [SMILES: *N1CCN(S(=O)(=O)Cc2ccccc2)CC1] |
| 345 | 4-fluorophenyl | NH₂ | 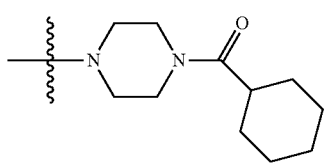 [SMILES: *N1CCN(C(=O)C2CCCCC2)CC1] |
| 346 | 4-fluorophenyl | NH₂ | 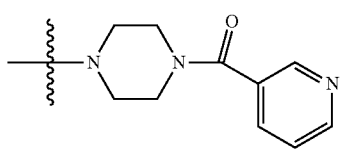 [SMILES: *N1CCN(C(=O)c2cccnc2)CC1] |
| 347 | 4-fluorophenyl | NH₂ | 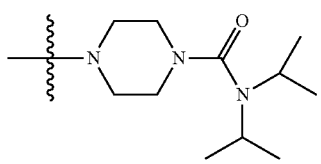 [SMILES: *N1CCN(C(=O)N(C(C)C)C(C)C)CC1] |
| 348 | 4-fluorophenyl | NH₂ | 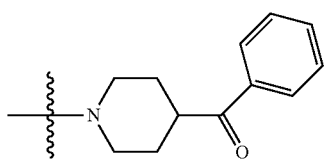 [SMILES: *N1CCC(C(=O)c2ccccc2)CC1] |
| 351 | H | NH₂ | 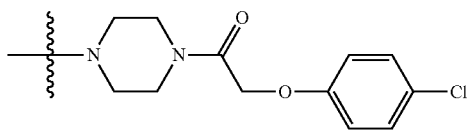 |

-continued
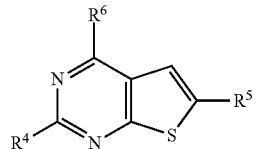
II
| Example | R⁵ | R⁴ | R⁶ |
|---|---|---|---|
| 352 | 4-fluorophenyl | phenyl | 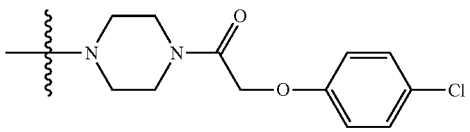 [SMILES: *N1CCN(C(=O)COc2ccc(Cl)cc2)CC1] |
| 353 | 4-fluorophenyl | 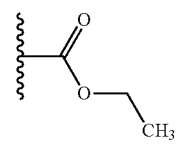 | 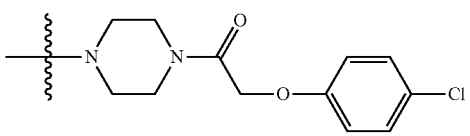 [SMILES: *N1CCN(C(=O)COc2ccc(Cl)cc2)CC1] |
| 354 | 4-fluorophenyl | 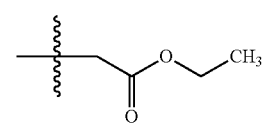 [SMILES: *CC(=O)OCC] | 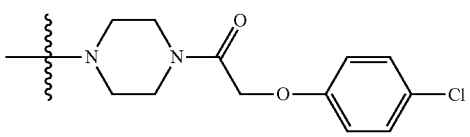 |
| 355 | 4-fluorophenyl | 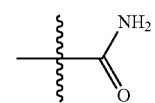 | 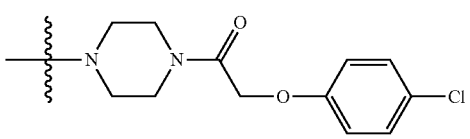 |
| 356 | 4-fluorophenyl | 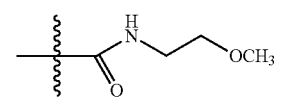 [SMILES: *C(=O)NCCOC] | 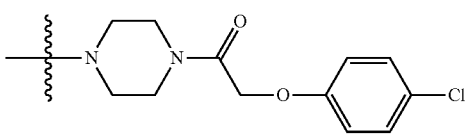 [SMILES: *N1CCN(C(=O)COc2ccc(Cl)cc2)CC1] |
| 357 | 4-fluorophenyl | COOH | 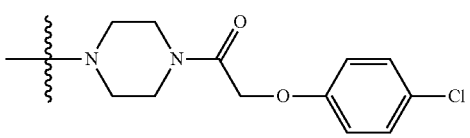 [SMILES: *N1CCN(C(=O)COc2ccc(Cl)cc2)CC1] |
| 358 | 4-fluorophenyl | 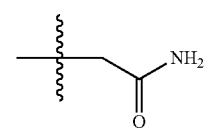 [SMILES: *CC(N)=O] | 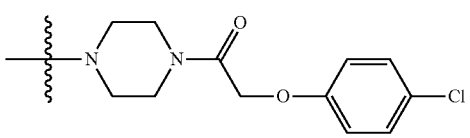 |
| 359 | 4-fluorophenyl | NH₂ | 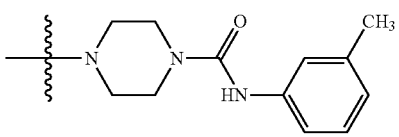 [SMILES: *N1CCN(C(=O)Nc2cccc(C)c2)CC1] |
| 360 | 4-fluorophenyl | phenyl | 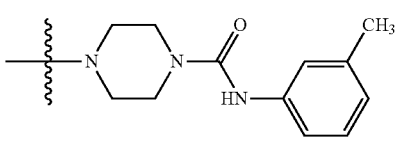 [SMILES: *N1CCN(C(=O)Nc2cccc(C)c2)CC1] |

-continued
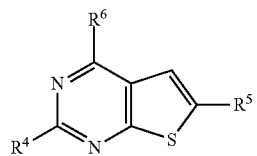
| Example | R⁵ | R⁴ | R⁶ |
|---|---|---|---|
| 361 | 4-fluorophenyl | COOEt | 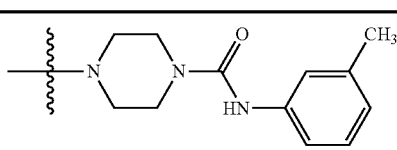 |
| 362 | 4-fluorophenyl | CONH₂ | 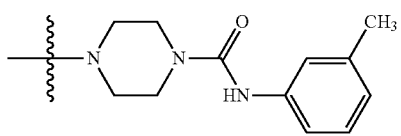 |
| 363 | 4-fluorophenyl | NH₂ | ethoxy |
| 364 | 4-fluorophenyl | NH₂ | 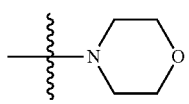 |
| 367 | 4-fluorophenyl | CH₃ | 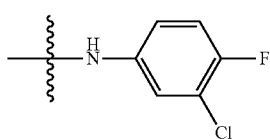 [SMILES: *Nc1ccc(F)c(Cl)c1] |
| 368 | 4-fluorophenyl | COOEt | 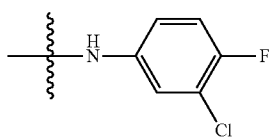 [SMILES: *Nc1ccc(F)c(Cl)c1] |
| 369 | phenyl | NH₂ | 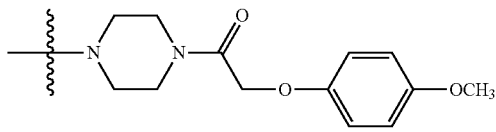 |
| 370 | phenyl | NH₂ | 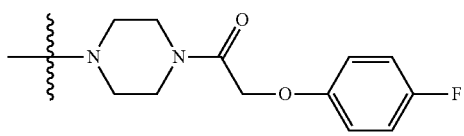 [SMILES: *N1CCN(C(=O)COc2ccc(F)cc2)CC1] |
| 371 | phenyl | NH₂ | 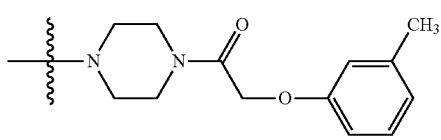 [SMILES: *N1CCN(C(=O)COc2cccc(C)c2)CC1] |
| 372 | phenyl | NH₂ | 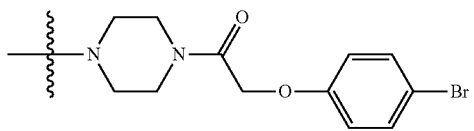 |

-continued
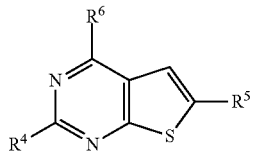
II
| Example | R⁵ | R⁴ | R⁶ |
|---|---|---|---|
| 373 | phenyl | NH₂ | 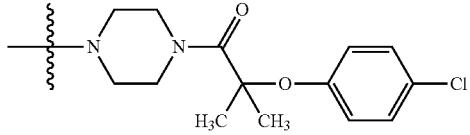 |
Purines
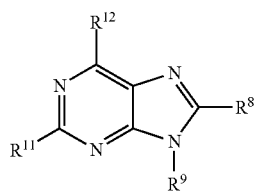
III
| Example | R⁹ | R¹¹ | R⁸ | R¹² |
|---|---|---|---|---|
| 389 | H | NH₂ | 4-fluorophenyl | 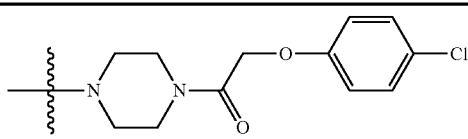 |
| 390 | H | NH₂ | 3,4-dimethoxyphenyl | 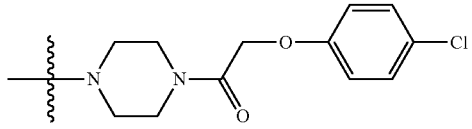 |
| 391 | H | NH₂ | 4-bromophenyl | 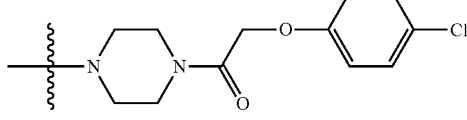 |
| 392 | H | NH₂ | 4-chlorophenyl | 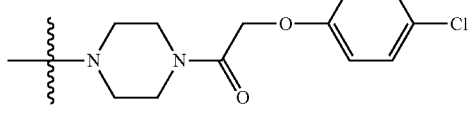 |
| 393 | H | NH₂ | 3-chlorophenyl | 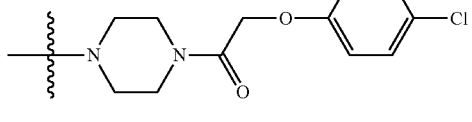 |
| 394 | H | NH₂ | 4-trifluoromethylphenyl | 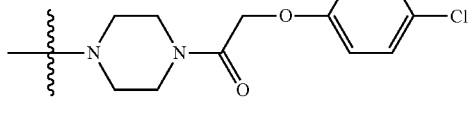 |

-continued

III

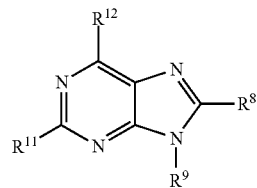

| Example | R⁹ | R¹¹ | R⁸ | R¹² |
|---|---|---|---|---|
| 395 | H | NH₂ | 4-trifluoromethoxyphenyl | piperazine-C(O)CH₂-O-(4-chlorophenyl) |
| 396 | H | NH₂ | 4-methylphenyl | piperazine-C(O)CH₂-O-(4-chlorophenyl) |
| 397 | H | NH₂ | propyl | piperazine-C(O)CH₂-O-(4-chlorophenyl) |
| 398 | H | NH₂ | cyclopropyl | piperazine-C(O)CH₂-O-(4-chlorophenyl) |
| 399 | H | NH₂ | tert-butyl | piperazine-C(O)CH₂-O-(4-chlorophenyl) |
| 400 | H | NH₂ | methyl | piperazine-C(O)CH₂-O-(4-chlorophenyl) |
| 401 | H | NH₂ | 4-fluorophenyl | piperazine-C(O)CH₂-O-phenyl |
| 402 | H | NH₂ | 4-fluorophenyl | piperazine-C(O)-(3-methoxyphenyl) |
| 403 | H | NH₂ | 4-fluorophenyl | piperazine-C(O)CH₂-(2-thienyl) |

-continued
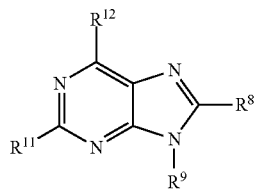
III
| Example | R⁹ | R¹¹ | R⁸ | R¹² |
|---|---|---|---|---|
| 404 | H | NH₂ | 4-fluorophenyl | 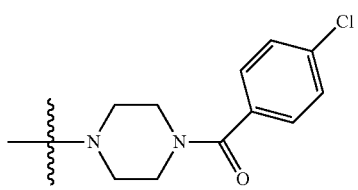 [SMILES: *N1CCN(C(=O)c2ccc(Cl)cc2)CC1] |
| 405 | H | NH₂ | 4-fluorophenyl | 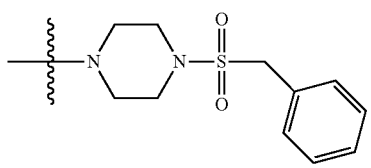 [SMILES: *N1CCN(S(=O)(=O)Cc2ccccc2)CC1] |
| 406 | H | NH₂ | 4-fluorophenyl | 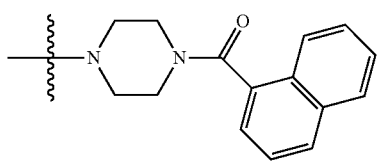 [SMILES: *N1CCN(C(=O)c2cccc3ccccc23)CC1] |
| 408 | H | NH₂ | 4-fluorophenyl | 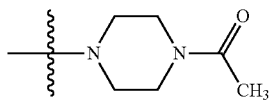 |
| 409 | H | NH₂ | 4-fluorophenyl | 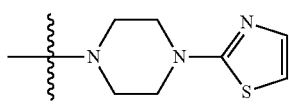 |
| 410 | H | NH₂ | 4-fluorophenyl | 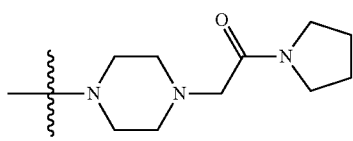 [SMILES: *N1CCN(CC(=O)N2CCCC2)CC1] |
| 411 | H | NH₂ | 4-fluorophenyl | 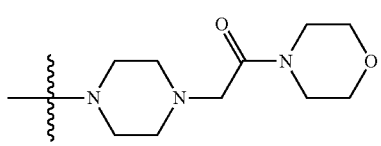 [SMILES: *N1CCN(CC(=O)N2CCOCC2)CC1] |
| 412 | H | NH₂ | 4-fluorophenyl | 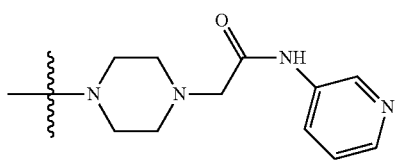 [SMILES: *N1CCN(CC(=O)Nc2cccnc2)CC1] |

-continued

III

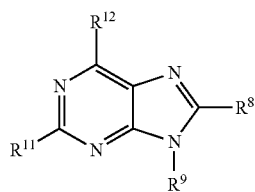

| Example | R⁹ | R¹¹ | R⁸ | R¹² |
|---|---|---|---|---|
| 413 | H | NH₂ | 4-fluorophenyl | piperazine-CH₂-C(=O)-N(CH₃)-phenyl |
| 414 | H | NH₂ | 4-fluorophenyl | piperazine-(4-chlorophenyl) |
| 415 | H | NH₂ | 4-fluorophenyl | piperazine-(4-fluorophenyl) |
| 416 | H | NH₂ | 4-fluorophenyl | piperazine-CH₂-C(=O)-NH-(pyridin-2-yl) |
| 417 | H | NH₂ | 4-fluorophenyl | piperazine-CH₂-C(=O)-NH-(thiazol-2-yl) |
| 418 | H | NH₂ | 4-fluorophenyl | piperazine-CH₂-(4-fluorophenyl) |
| 419 | H | NH₂ | 4-fluorophenyl | piperazine-(pyridin-4-yl) |
| 421 | H | NH₂ | 4-fluorophenyl | homopiperazine-C(=O)-CH₂-O-(4-chlorophenyl) |

-continued
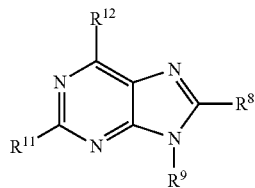
| Example | R⁹ | R¹¹ | R⁸ | R¹² |
|---|---|---|---|---|
| 422 | H | NH₂ | 4-fluorophenyl | |
| 423 | H | NH₂ | SH | |
| 424 | H | NH₂ | SCH₃ | |
| 425 | H | NH₂ | SC₃H₇ | |
| 426 | H | NH₂ | SCH₂C₆H₅ | |
| 427 | H | NH₂ | SCH₂CH₂C₆H₅ | |
| 428 | CH₃ | NH₂ | SCH₃ | |
| 429 | H | NH₂ | -S-cyclopentyl | |
| 430 | CH₃ | NH₂ | 4-fluorophenyl | |

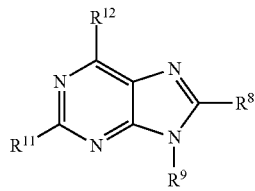

| Example | $R^9$ | $R^{11}$ | $R^8$ | $R^{12}$ |
|---|---|---|---|---|
| 431 | benzyl | $NH_2$ | 4-fluorophenyl | piperazine-C(O)CH$_2$-O-(4-Cl-phenyl) |
| 438 | H | $NH_2$ | 4-fluorophenyl | piperazine-C(O)CH$_2$-phenyl |

Example 447

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, N° CCL-156) cells were treated with mitomycin C (Kyowa, Nycomed, Brussel, Belgium) and used as "Stimulator" cells. Responder cells ($0.12 \times 10^6$), Stimulator cells ($0.045 \times 10^6$) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 µCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The IC$_{50}$ was determined from a graph with at least four points, each derived from the mean of 2 experiments. The IC$_{50}$ value represents the lowest concentration of the thiazolo[5,4-d]pyrimidine, oxazolo[5,4-d]pyrimidine, thieno[2,3-d]pyrimidine or purine derivative (expressed in µM) that resulted in a 50% inhibition of the MLR. The results are shown in Table 1 for a number of compounds, using the following symbols:

TABLE 1

MLR data of selected examples

| Example | IC$_{50}$ (µM) |
|---|---|
| 28 | >10 |
| 29 | >10 |
| 30 | >10 |
| 31 | 9.7 |
| 32 | >10 |
| 33 | >10 |
| 34 | >10 |
| 35 | >10 |
| 36 | >10 |
| 37 | >10 |
| 38 | 4.8 |
| 39 | >10 |
| 40 | 4.9 |
| 42 | 0.7 |
| 43 | 0.3 |
| 44 | 0.4 |
| 45 | 0.3 |
| 46 | 0.7 |
| 48 | 3.54 |
| 49 | 4.4 |
| 52 | >10 |
| 66 | 4.38 |
| 101 | 0.4 |
| 114 | 1.56 |
| 115 | >10 |
| 116 | 5.29 |
| 117 | 2.51 |
| 118 | 0.86 |
| 119 | 0.6 |
| 120 | 0.83 |
| 121a | 0.05 |
| 121b | 0.83 |
| 122 | >10 |
| 123 | 0.26 |
| 124 | 0.12 |
| 126 | 2.65 |
| 127 | 6.77 |
| 128 | 0.38 |
| 129 | 0.29 |
| 130 | 0.35 |

TABLE 1-continued

MLR data of selected examples

| Example | IC$_{50}$ (μM) |
|---|---|
| 131 | 3.25 |
| 132 | 0.44 |
| 133 | >10 |
| 134 | 4.92 |
| 135 | >10 |
| 136 | >10 |
| 137 | 6.68 |
| 138 | 2.1 |
| 139 | 3.29 |
| 140 | 8.82 |
| 141 | 1.41 |
| 143 | >10 |
| 144 | 5.13 |
| 145 | 4.35 |
| 147 | 4.52 |
| 148 | 2.61 |
| 149 | 5.76 |
| 150 | 5.39 |
| 151 | >10 |
| 154 | 0.79 |
| 155 | >10 |
| 156 | >10 |
| 157 | 0.63 |
| 169 | 3 |
| 172 | 0.8 |
| 185 | 1.76 |
| 186 | 1.83 |
| 187 | >10 |
| 188 | 4.43 |
| 189 | 5.53 |
| 191 | >10 |
| 192 | >10 |
| 193 | 0.7 |
| 194 | 9.04 |
| 195 | >10 |
| 196 | 3.97 |
| 197 | 1.95 |
| 198 | >10 |
| 208 | 0.042 |
| 209 | 0.055 |
| 210 | 0.072 |
| 211 | 0.052 |
| 212 | 0.375 |
| 213 | 0.219 |
| 214 | 0.121 |
| 215 | 0.116 |
| 216 | 0.019 |
| 217 | 0.345 |
| 218 | 0.177 |
| 219 | 0.323 |
| 220 | 0.17 |
| 223 | >10 |
| 224 | 1.1 |
| 225 | >10 |
| 226 | 7.12 |
| 227 | 0.61 |
| 228 | 1.72 |
| 229 | 2.66 |
| 230 | 0.27 |
| 231 | 0.55 |
| 232 | 0.86 |
| 233 | 0.074 |
| 234 | 0.037 |
| 235 | 0.46 |
| 236 | 0.89 |
| 237 | >10 |
| 253 | 0.71 |
| 254 | 1.22 |
| 255 | 0.71 |
| 256 | 0.74 |
| 257 | 1.14 |
| 258 | 0.93 |
| 259 | 0.96 |
| 260 | 0.82 |
| 270 | 0.15 |
| 271 | 0.012 |

TABLE 1-continued

MLR data of selected examples

| Example | IC$_{50}$ (μM) |
|---|---|
| 272 | 0.012 |
| 273 | 0.045 |
| 274 | >10 |
| 275 | 0.003 |
| 276 | 0.001 |
| 277 | 0.024 |
| 278 | 0.08 |
| 279 | 0.1 |
| 280 | >10 |
| 281 | 0.041 |
| 282 | 0.229 |
| 290 | 0.96 |
| 291 | 1.11 |
| 292 | 0.92 |
| 293 | 0.93 |
| 294 | 0.75 |
| 295 | 0.35 |
| 296 | 7.59 |
| 297 | 0.69 |
| 298 | 1.19 |
| 299 | 3.11 |
| 300 | 5.53 |
| 301 | 0.67 |
| 303 | 5.59 |
| 312 | 6.35 |
| 313 | 1.33 |
| 325 | 3.39 |
| 326 | 0.7 |
| 327 | 6.8 |
| 329 | 0.33 |
| 330 | 0.93 |
| 331 | 6.7 |
| 332 | 0.78 |
| 334 | 8.83 |
| 335 | >10 |
| 337 | 9.64 |
| 341 | 7.23 |
| 343 | 6.99 |
| 344 | >10 |
| 345 | >10 |
| 346 | >10 |
| 347 | 8.2 |
| 348 | 8.27 |
| 351 | 1.23 |
| 352 | >10 |
| 353 | >10 |
| 355 | >10 |
| 357 | >10 |
| 359 | 2.8 |
| 369 | 0.072 |
| 370 | 0.066 |
| 371 | 0.21 |
| 372 | 0.32 |
| 373 | 6.92 |
| 389 | 0.81 |
| 390 | 0.53 |
| 391 | 0.26 |
| 392 | 0.54 |
| 393 | 0.66 |
| 394 | 0.63 |
| 395 | >10 |
| 396 | 0.47 |
| 397 | 0.94 |
| 398 | 0.43 |
| 399 | 6.31 |
| 400 | 0.45 |
| 401 | 1.09 |
| 402 | >10 |
| 403 | 7.08 |
| 404 | >10 |
| 405 | >10 |
| 406 | 6.4 |
| 408 | >10 |
| 409 | 7.47 |
| 410 | >10 |
| 411 | >10 |

TABLE 1-continued

MLR data of selected examples

| Example | IC$_{50}$ (µM) |
|---|---|
| 412 | 8.61 |
| 413 | >10 |
| 414 | 3.87 |
| 415 | 4.16 |
| 416 | 5.76 |
| 417 | >10 |
| 418 | 9.86 |
| 419 | >10 |
| 421 | 3.71 |
| 422 | 1.18 |
| 424 | 0.61 |
| 425 | 1.02 |
| 426 | 3.28 |
| 427 | >10 |
| 428 | 0.3 |
| 429 | 0.51 |
| 430 | 0.36 |
| 431 | >10 |
| 438 | 2.58 |

Example 448

In Vivo Efficacy of 5-amino-7-[4-(4-chlorophenoxyacetyl)piperazin-1-yl]-2-(pyridine-3-yl)thiazolo[5,4-d]pyrimidine Graft Survival The in vivo efficacy of the compound of example 121a was studied in a mouse model of cardiac allograft transplantation. Drug vehicle (n=6) or compound 121a (n=4) was given by oral gavage daily, beginning one day prior to transplantation, until day 30 post transplantation. Cyclosporine A, the major immunosuppressive drug used in organ transplantation, was used as a reference and was also administered by daily gavage (n=4). Animals treated with vehicle alone rejected their allograft within 6-9 days post transplantation. CsA at the given dose achieved all 4 grafts survival as long as the treatment continuing. However, rejection occurred to all 4 grafts within 2 weeks after withdrawal of the treatment. Oral administration of compound 121a (at a dose of 40 mg/kg) resulted in continuous graft survival in 3 out of 4 grafts. The grafts continued beating after withdrawal of the treatment (up to 60 days), indicating the induction of certain type of graft tolerance. The data are shown in Table 2. These data indicate that compound 121a can suppress a robust in vivo allogeneic response.

TABLE 2

| Compd | Dose[a] (mg/kg/d) | Surviving days | p value[b] |
|---|---|---|---|
| Vehicle |  | 6, 7, 8, 8, 9, 9 |  |
| CsA | 40 | 39, 40, 42, 43 | <0.001 |
| 121a | 40 | 17, >60, >60, >60 | <0.03 |

[a]by daily gavage.
[b]student t test: vs. vehicle.

Materials and Methods

Inbreed C57BL/6 H-2[b] and Balb/c H-2[d] female mice, 8-10 weeks old, 20-25 g, were used as donor and recipient, respectively. Heterotopic heart transplantation was performed by implanting the donor heart on the neck of recipients using conventional microsurgery techniques. Graft beating was checked daily by inspection and palpation. Cessation of beating indicated graft rejection, which was confirmed by histological examination. Housing and all experimental animal procedures were approved by the Institutional Animal Care and Research Advisory Committee of the KU Leuven.

Animals were randomly divided into 3 groups: (i) Vehicle group: vehicle ((30% 2-hydroxypropyl-β-cyclodextrin) only by daily gavage, n=6; (ii) Reference drug group: CsA 40 mg per kg by daily gavage, n=4; (iii) compound 121a group: 40 mg per kg by daily gavage, n=4. Treatment started one day prior to transplantation (day −1) until day 30 post transplantation.

Example 449

In Vivo Efficacy of 4-(5-amino-2-(pyridin-3-yl)thiazolo[5,4-d]pyrimidin-7-yl)-N-p-tolylpiperazine-1-carboxamide The in vivo efficacy of the compound of example 222 was studied in a mouse model of cardiac allograft transplantation as described in Example 448. Animal treated with vehicle rejected the graft within 6-8 days post-transplantation. CsA at 40 mg/kg per day prevented rejection as long as treatment continued in 3 of the 4 grafts. However, all grafts were rejected within 20 days after withdrawal of the treatment on day 30 post-transplantation. 222 at a dose of 20 mg/kg per day slightly prolonged graft survival up to 13 days. 222 at 40 mg/kg per day resulted continuous graft survival of 4/6 grafts. The grafts (3/4 cases) continuously functioned after stopping the treatment on day 30, suggesting a kind of immune tolerance. The results are shown in Table 3. These results supported that the compound of example 222 effectively suppressed allograft rejection in a dose dependent manner.

TABLE 3

| Compound | Dose[#] (mg/kg/d) | Surviving days | p value[§] |
|---|---|---|---|
| Vehicle |  | 6, 7, 7, 8 |  |
| CsA | 40 | 10, 40, 41, 50 (n = 3) | <0.01 |
| Example 222 | 20 | 6, 7, 8, 9, 11, 13 | >0.05 |
| Example 222 | 40 | 9, 11, 50, >60 (n = 3) | <0.01 |

[#]by daily gavage.
[§]student t test: vs. vehicle.

Materials and method are identical to the ones mentioned in Example 448.

The invention claimed is:
1. A compound having the general formula I, or II,

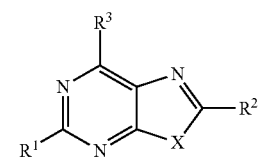

I

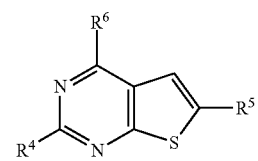

II wherein
- X is S or O;
- $R^1$ is selected from the group consisting of amino, halogen, cyano, carboxylic acid, acyl, thioacyl, alkoxycarbonyl, acyloxy, carbonate, carbamate, aryl, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, and $C_{1-7}$ alkyloxy;
- $R^2$ is selected from the group consisting of heteroaryl and aryl groups; halogen; $C_{1-7}$ alkyl; $C_{2-7}$ alkenyl; $C_{2-7}$ alkynyl; halo $C_{1-7}$ alkyl; $C_{3-10}$ cycloalkyl; carboxy $C_{1-7}$ alkyl; carboxyaryl; $C_{1-7}$ alkoxy; $C_{3-10}$ cycloalkoxy; aryloxy; arylalkyloxy; oxyheterocyclic; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; thio-acylamino; alkoxyamino; thioalkyl-amino; acetal; thio-acetal; carboxylic acid; carboxylic acid esters, thiocarboxylic acid; thiocarboxylic acid esters, thioesters, halides, anhydrides, amides and thioamides; hydroxyl; sulfhydryl; nitro; cyano; carbamoyl; thiocarbamoyl; ureido; thioureido; amino; alkylamino; cycloalkylamino; alkenylamino; cyclo-alkenylamino; alkynylamino; arylamino; arylalkylamino; hydroxyalkylamino; mercaptoalkylamino; heterocyclic amino; heterocyclic substituted arylamino; heterocyclic-substituted alkyl-amino; oximino; alkyloximino; hydrazino; alkylhydrazino; phenylhydrazino; esters, thioesters, halides, anhydrides, amides and thioamides thereof; and aromatic or heterocyclic substituents substituted with an aliphatic spacer between the thiazolo(5,4-d)pyrimidine or oxazolo(5,4-d)pyrimidine ring and the aromatic or heterocyclic substituent, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, and heterocyclic amino; wherein said aliphatic spacer is a branched or straight, saturated or unsaturated aliphatic chains of 1 to 7 carbon atoms optionally containing one or more functions, atoms or radicals independently selected from the group consisting of halogen, carbonyl, thiocarbonyl, hydroxyl, thiol, ether, thio-ether, acetal, thio-acetal, amino, imino, oximino, alkyloximino, aminoacid, cyano, acylamino, thioacylamino, carbamoyl, thiocarbamoyl, ureido, thio-ureido, carboxylic acid ester or halide or anhydride or amide, thiocarboxylic acid or ester or thioester or halide or anhydride or amide, nitro, thio $C_{1-7}$ alkyl, thio $C_{3-10}$ cycloalkyl, hydroxylamino, mercaptoamino, alkyl-amino, cycloalkylamino, alkenylamino, cycloalkenylamino, alkynylamino, arylamino, arylalkyl-amino, hydroxyalkylamino, mercaptoalkylamino, heterocyclic-substituted alkylamino, hetero-cyclic amino, heterocyclic-substituted arylamino, hydrazino, alkylhydrazino, phenylhydrazino, sulfonyl, sulfinyl and sulfonamido;
- $R^3$ is selected from the group consisting of piperazinyl, homopiperazinyl, (mono- or di-) $C_{1-12}$ alkylamino; monoarylamino; diarylamino; (mono- or di-) $C_{3-10}$ cycloalkylamino; (mono- or di-) hydroxy $C_{1-7}$ alkylamino; (mono- or di-) $C_{1-4}$ alkylarylamino; (mono- or di-) aryl$C_{1-4}$ alkylamino; morpholinyl; mercapto $C_{1-7}$ alkyl; $C_{1-7}$ alkoxy, aralkylthio, piperidinyl, and pyrrolidinyl, and, wherein said piperidinyl, pyrrolidinyl, homopiperazinyl or piperazinyl is optionally N-substituted with a substituent $R^{20}$ selected from the group consisting of formyl, acyl, thioacyl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioacyl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl, wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioaklamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino;
- $R^4$ is selected from the group consisting of halogen, cyano, carboxylic acid, acyl, thioacyl, alkoxycarbonyl, acyloxy, carbonate, carbamate, aryl, amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, (mono- or di) $C_{1-4}$ alkyl-arylamino, mercapto $C_{1-7}$ alkyl, and $C_{1-7}$ alkyloxy;
- $R^5$ is selected from the group consisting of heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, and heterocyclic amino;

$R^6$ is selected from the group consisting of (mono- or di-) $C_{1-12}$ alkylamino, monoarylamino, diarylamino, (mono- or di-) $C_{3-10}$ cycloalkylamino, (mono- or di-) hydroxy $C_{1-7}$ alkylamino, (mono- or di-) $C_{1-4}$ alkylarylamino, (mono- or di-) aryl$C_{1-4}$ alkylamino, morpholinyl, mercapto $C_{1-7}$ alkyl, $C_{1-7}$ alkoxy, homopiperazinyl and piperazinyl, wherein said homopiperazinyl or piperazinyl is optionally N-substituted with a substituent $R^{21}$ selected from the group consisting of formyl, acyl, thioaryl, amide, thioamide, sulfonyl, sulfinyl, carboxylate, thiocarboxylate, amino-substituted acyl, alkoxyalkyl, $C_{3-10}$ cycloalkyl-alkyl, $C_{3-10}$ cycloalkyl, dialkylaminoalkyl, heterocyclic-substituted alkyl, acyl-substituted alkyl, thioaryl-substituted alkyl, amido-substituted alkyl, thioamido-substituted alkyl, carboxylato-substituted alkyl, thiocarboxylato-substituted alkyl, (amino-substituted acyl)alkyl, heterocyclic, carboxylic acid ester, ω-cyanoalkyl, ω-carboxylic ester-alkyl, halo $C_{1-7}$ alkyl, $C_{2-7}$ alkenyl, $C_{2-7}$ alkynyl, arylalkenyl, aryloxyalkyl, arylalkyl and aryl; wherein the aryl moiety of each of said arylalkenyl, aryloxyalkyl, arylalkyl and aryl radicals is optionally substituted with one or more substituents independently selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cyclo-alkenylamino, alkynylamino, arylamino, arylalkylamino, hydroxyalkylamino, mercaptoalkylamino, heterocyclic amino, hydrazino, alkylhydrazino and phenylhydrazino; wherein acyl group refers to a carbonyl group adjacent to a $C_{1-7}$ alkyl, a $C_{3-10}$ cycloalkyl, an aryl, an arylalkyl or a heterocyclic group, or is selected from the group consisting of alkanoyl, cycloalkanoyl, cycloalkyl-alkanoyl, alkenoyl, alkylthioalkanoyl, alkanesulfonyl, alkoxycarbonyl, alkylcarbamoyl, alkylcarbamidoyl, alkoxalyl, aroyl, aralkanoyl, aralkenoyl, aryloxyalkanoyl, arylthioalkanoyl, arylaminoalkanoyl, aryloxycarbonyl, aralkoxycarbonyl, arylcarbamoyl, arylglyoxyloyl, arylthiocarbamoyl, arylcarbamidoyl, heterocyclic-carbonyl, and heterocyclic-alkanoyl, wherein said heterocyclic group is an aromatic or non-aromatic 5- to 7-membered heterocyclic ring with one or more heteroatoms selected from the group consisting of nitrogen, oxygen and sulfur in said ring;

and/or a pharmaceutical acceptable addition salt thereof and/or a stereoisomer thereof.

2. The compound according to claim 1, wherein $R^1$ and $R^4$ are each independently selected from the group consisting of amino, acetamido, N-protected amino, (mono- or di) $C_{1-7}$ alkylamino, (mono- or di) arylamino, (mono- or di) $C_{3-10}$ cycloalkylamino, (mono- or di) hydroxy $C_{1-7}$ alkylamino, and (mono- or di) $C_{1-4}$ alkyl-arylamino.

3. The compound according to claim 1, wherein X is S.

4. The compound according to claim 1, wherein X is O.

5. The compound according to claim 1, wherein $R^3$ is selected from the group consisting of monoarylamino; diarylamino; (mono- or di-) aryl$C_{1-4}$ alkylamino; morpholinyl; $C_{1-7}$ alkoxy, aralkylthio, piperidinyl, pyrrolidinyl, homopiperazinyl and piperazinyl, wherein said piperidinyl, pyrrolidinyl, homopiperazinyl and piperazinyl is optionally N-substituted with a substituent $R^{20}$, wherein $R^{20}$ has the same meaning as defined in claim 1.

6. The compound according to claim 1, wherein $R^6$ is selected from the group consisting of (mono- or di-) $C_{1-12}$ alkylamino, monoarylamino, diarylamino, (mono- or di-) $C_{3-10}$ cycloalkylamino, (mono- or di-) aryl$C_{1-4}$ alkylamino, morpholinyl, $C_{1-7}$ alkoxy, homopiperazinyl and piperazinyl, wherein said homopiperazinyl and piperazinyl is optionally N-substituted with a substituent $R^{21}$, wherein $R^{21}$ has the same meaning as that defined in claim 1.

7. The compound according to claim 1, wherein $R^2$ is selected from the group consisting of heteroaryl and aryl groups; $C_{1-7}$ alkyl; $C_{3-10}$ cycloalkyl; halo $C_{1-7}$ alkyl; carboxy $C_{1-7}$ alkyl; carboxyaryl; $C_{1-7}$ alkoxy; $C_{3-10}$ cycloalkoxy; aryloxy; arylalkyloxy; heterocyclic-substituted alkyloxy; thio $C_{1-7}$ alkyl; thio $C_{3-10}$ cycloalkyl; thioaryl; thioheterocyclic; arylalkylthio; heterocyclic-substituted alkylthio; hydroxylamino; acylamino; thio-acylamino; alkoxyamino; carbamoyl; thiocarbamoyl; and aromatic or heterocyclic substituents substituted with an aliphatic spacer between the thiazolo(5,4-d)pyrimidine or oxazolo(5,4-d)pyrimidine ring and the aromatic or heterocyclic substituent, wherein said heteroaryl or aryl groups are optionally substituted with one or more substituents selected from the group consisting of halogen, $C_{1-7}$ alkyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, thio $C_{1-7}$ alkyl, thio $C_{3-10}$ cycloalkyl, thioaryl, thio-heterocyclic, arylalkylthio, heterocyclic-substituted alkylthio, carbamoyl, thiocarbamoyl, sulfonamido, hydroxylamino, alkoxy-amino, acylamino, thioacylamino, and cyano, wherein said aliphatic spacer is a branched or straight, saturated or unsaturated aliphatic chains of 1 to 7 carbon atoms optionally containing one or more functions, atoms or radicals independently selected from the group consisting of halogen, thiol, ether, thio-ether, amino, cyano, acylamino, nitro, and thio $C_{1-7}$ alkyl.

8. The compound according to claim 1, wherein $R^5$ is an aryl group, wherein said aryl group is optionally substituted with one or more substituents selected from the group consisting of halogen, $C_{1-7}$ alkyl, halo $C_{1-7}$ alkyl, nitro, hydroxyl, sulfhydryl, $C_{1-7}$ alkoxy, thio $C_{1-7}$ alkyl, and cyano.

9. The compound according to claim 1, wherein $R^3$ and $R^6$ are each independently homopiperazinyl or piperazinyl, wherein said homopiperazinyl or piperazinyl is each respectively optionally N-substituted with a substituent $R^{20}$, $R^{21}$, wherein $R^{20}$ and $R^{21}$ have the same meaning as that defined in claim 1.

10. The compound according to claim 1, wherein $R^1$ and $R^4$ are each independently amino.

11. The compound according to claim 1, wherein $R^2$ is selected from the group consisting of phenyl; pyridin-3-yl; pyridin-2-yl; pyridin-4-yl; 4-fluorophenethyl; 4-fluorophenyl; 4-bromophenethyl; pentyl; tolyl; (4-fluorophenyl)butyl; (4-fluorophenyl)propyl; 4-chlorophenyl; 4-methylphenethyl; 3,4-dimethoxyphenethyl; 3-methoxyphenethyl; furan-2-yl; 2-phenylethyl; cyclohexyl; methoxylmethyl; cyclopropyl; 2-thiophen-2-ylethyl; cyclopentyl-(4-fluorophenyl)methyl;

1-(4-fluorophenyl)propyl; 4-fluorophenylamino; methylsulfinyl; 1-(4-chlorophenyl)ethyl; 3-methoxyphenyl; 4-chlorophenyl; 4-chlorophenylmethyl; N-oxopyridine-3-yl; 1-(4-chlorophenyl)cyclopropyl; 3,4-dichlorophenyl; methylthio; 1-phenylcyclopropyl; 1-(4-fluorophenyl)ethyl; 1-(4-fluorophenyl)-2-phenylethyl; 2-(4-fluorophenoxy)ethyl; and morpholino.

12. The compound according to claim 1, wherein $R^3$ is selected from the group consisting of p-tolylpiperazinyl-1-carboxylate; N-methyl-N-p-tolylpiperazinyl-1-carboxamide; N-p-tolylpiperazinyl-1-carbothioamide; —N-hexylpiperazinyl-1-carboxamide; 4-(N-4-fluorophenylcarboxamide) piperazin-1-yl; N-cyclohexylpiperazinyl-1-carboxamide; N-phenylpiperazinyl-1-carboxamide; N-(4-(trifluoromethyl) phenyl)piperazinyl-1-carboxamide, piperazin-1-yl-2-(4-chlorophenoxy)ethanone; piperazin-1-yl-2-(4-methoxyphenoxy)ethanone; benzylsulfonylpiperazin-1-yl; N-(4-cyanophenyl)piperazinyl-1-carboxamide; N-(4-methoxybenzyl)piperazinyl-1-carboxamide; N-(4-chlorophenyl)piperazinyl-1-carboxamide; N-m-tolylpiperazinyl-1-carboxamide; piperazin-1-yl-2-(m-tolyloxy)ethanone; piperazin-1-yl-2-(4-chlorophenoxy)-2-methylpropan-1-one; piperazin-1-yl-2-(4-trifluoromethoxyphenoxy)ethanone; piperazin-1-yl-2-(4-fluorophenoxy)ethanone; piperazin-1-yl-2-(4-bromophenoxy)ethanone; piperazin-1-yl-3-(4-fluorophenyl) propan-1-one; piperazin-1-yl-2-(3-chlorophenoxy) ethanone; 4-acetylphenoxy-piperazin-1-yl-ethanone; piperazin-1-yl-2-oxoethoxy)benzoate; piperazin-1-yl-2-(4-hydroxyphenoxy)ethanone; piperazin-1-yl-3-(4-bromophenyl)propan-1-one; N-(2-methoxyphenyl)piperazinyl-carboxamide; N-(4-bromophenyl)piperazinyl-carboxamide; N-(2,4-difluorophenyl)piperazinyl-carboxamide; piperazin-1-yl-2-(4-chloro-2-methylphenoxy)ethanone; piperazin-1-yl-2-(2,4-dichlorophenoxy)ethanone; (methylphenyl-carbamoyl)methyl]piperazin-1-yl; phenoxyethyl)piperazin-1-yl; (4-chlorophenyl)acetyl]-piperazin-1-yl; (4-chlorophenyl) acetyl]-piperazin-1-yl; [2-(3-nitrophenoxy)acetyl]-piperazin-1-yl; 4-(2-methoxyethyl)-piperazin-1-yl; 4-acetylpiperazin-1-yl; 4-isobutylpiperazin-1-yl; 3-chloro-4-fluorophenyl-amino; 4-(2-phenoxyethyl)piperazin-1-yl; 4-benzoylpiperidine-1-yl; 4-chlorophenoxyacetyl)pyrrolidin-3-(S)-ylamino; 1-tert-butoxycarbonylpyrrolidin-3-(S)-ylamino; 1-benzyloxycarbonylpiperidin-3-ylamino; 3-(R)-(4-chlorobenzoylamino)-pyrrolidin-1-yl; 3-(R)-[2-(4-chlorophenoxy)-acetylamino]pyrrolidin-1-yl; 3-(R)-tert-butoxycarbonylamino; 4-(phenethylcarbamoyl-methyl) piperazin-1-yl; 4-thiazol-2-yl-piperazine-1-yl; 4-[(methylphenylcarbamoyl)-methyl]piperazin-1-yl; 4-chlorophenoxy)acetyl]homopiperazin-1-yl; 4-phenylmethanesulfonylpiperazin-1-yl; 4-(3-phenylpropionyl)piperazin-1-yl; 4-[2-phenoxyacetyl]piperazin-1-yl; 4-[2-(4-chlorophenyl)acetyl]piperazin-1-yl; 4-[2-(3-nitrophenoxy) acetyl]piperazin-1-yl; 4-(phenylsulfonyl)piperazin-1-yl; pyrimidin-7-yl-piperazinyl-1-carboxylate; 4-benzylpiperazin-1-yl; piperazin-1-yl-1-morpholinoethanone; 4-pentylpiperazin-1-yl; 4-(thiazol-2-yl)piperazin-1-yl; 4-m-tolylpiperazin-1-yl; 3-methoxypropylamino; ethoxy; 2-methoxyethoxy; benzylthio; and benzyl amino.

13. A compound according to claim 1 selected from the group consisting of:
2-(4-fluorophenyl)-7-(piperazin-1-yl)-thiazolo[5,4-d]pyrimidin-5-amine;
2-(4-fluorobenzyl)-7-(piperazin-1-yl)-thiazolo[5,4-d]pyrimidin-5-amine;
2-(4-fluorophenethyl)-7-(piperazin-1-yl)thiazolo[5,4-d]pyrimidin-5-amine;
2-(4-fluorophenyl)-7-(2-methoxyethoxy)-thiazolo[5,4-d]pyrimidin-5-amine;
7-ethoxy-2-(4-fluorophenyl)thiazolo[5,4-d]pyrimidin-5-amine;
7-ethoxy-2-(4-fluorobenzyl)thiazolo[5,4-d]pyrimidin-5-amine;
2-(4-fluorophenyl)-N-7-(3-methoxypropyl)thiazolo[5,4-d]pyrimidine-5,7-diamine;
2-(4-fluorophenyl)-7-morpholino-thiazolo[5,4-d]pyrimidin-5-amine;
2-(4-fluorobenzyl)-7-morpholino-thiazolo[5,4-d]pyrimidin-5-amine;
2-(4-fluorophenyl)-7-(4-m-tolylpiperazin-1-yl)-thiazolo[5,4-d]pyrimidin-5-amine;
2-(4-fluorophenyl)-7-(4-(thiazol-2-yl)piperazin-1-yl)thiazolo[5,4-d]pyrimidin-5-amine;
2-(4-fluorophenyl)-7-(4-pentylpiperazin-1-yl)thiazolo[5,4-d]pyrimidin-5-amine;
2-(4-(5-amino-2-(4-fluorophenyl)thiazolo[5,4-d]pyrimidin-7-yl)piperazin-1-yl)-1-morpholinoethanone;
7-(4-benzylpiperazin-1-yl)-2-(4-fluorophenyl)thiazolo[5,4-d]pyrimidin-5-amine;
benzyl-4-(5-amino-2-(4-fluorophenyl)thiazolo[5,4-d]pyrimidin-7-yl)piperazine-1-carboxylate;
2-(4-fluorophenyl)-7-(4-(phenylsulfonyl)piperazin-1-yl) thiazolo[5,4-d]pyrimidin-5-amine;
4-(5-amino-2-(4-fluorophenyl)-thiazolo[5,4-d]pyrimidin-7-yl)-N-p-tolylpiperazine-1-carboxamide;
4-(5-amino-2-(4-fluorophenyl)thiazolo[5,4-d]pyrimidin-7-yl)-N-m-tolylpiperazine-1-carboxamide;
4-(5-amino-2-(4-fluorobenzyl)thiazolo[5,4-d]pyrimidin-7-yl)-N-m-tolylpiperazine-1-carboxamide;
1-(4-(5-amino-2-(4-fluorophenyl)thiazolo[5,4-d]pyrimidin-7-yl)piperazin-1-yl)-2-(4-chlorophenoxy)ethanone;
1-(4-(5-amino-2-(4-fluorobenzyl)thiazolo[5,4-d]pyrimidin-7-yl)piperazin-1-yl)-2-(4-chlorophenoxy)ethanone;
2-(4-chlorophenoxy)-1-(4-(2-(4-fluorophenyl)-5-methylthiazolo[5,4-d]pyrimidin-7-yl)piperazin-1-yl)ethanone;
1-(4-(5-amino-2-(2-(4-fluorophenoxy)ethyl)thiazolo[5,4-d]pyrimidin-7-yl)piperazin-1-yl)-2-(4-chlorophenoxy) ethanone;
1-(4-(5-amino-2-(4-fluorophenethyl)-thiazolo[5,4-d]pyrimidin-7-yl)piperazin-1-yl)-2-(4-chlorophenoxy)ethanone;
1-(4-(5-amino-2-(4-fluorophenethyl)thiazolo[5,4-d]pyrimidin-7-yl)piperazin-1-yl)-2-(4-methoxyphenoxy) ethanone;
1-(4-(5-amino-2-(4-fluorophenethyl)thiazolo[5,4-d]pyrimidin-7-yl)piperazin-1-yl)-2-(4-fluorophenoxy)ethanone;
1-(4-(5-amino-2-(4-fluorophenethyl)thiazolo[5,4-d]pyrimidin-7-yl)piperazin-1-yl)-2-(4-bromophenoxy)ethanone;
1-(4-(5-amino-2-(4-fluorophenethyl)thiazolo[5,4-d]pyrimidin-7-yl)piperazin-1-yl)-2-(m-tolyloxy)ethanone;
1-(4-(5-amino-2-(4-fluorophenethyl)thiazolo[5,4-d]pyrimidin-7-yl)piperazin-1-yl)-2-(2,4-dichlorophenoxy) ethanone;
1-(4-(5-amino-2-(4-fluorophenethyl)thiazolo[5,4-d]pyrimidin-7-yl)piperazin-1-yl)-3-(4-fluorophenoxy)propan-1-one;
1-(4-(5-amino-2-(1-(4-fluorophenyl)ethyl)thiazolo[5,4-d] pyrimidin-7-yl)piperazin-1-yl)-2-(4-chlorophenoxy) ethanone;

1-(4-(5-amino-2-(1-(4-fluorophenyl)-2-phenylethyl)thiazolo[5,4-d]pyrimidin-7-yl)piperazin-1-yl)-2-(4-chlorophenoxy)ethanone;
4-(5-amino-2-(1-(4-fluorophenyl)ethyl)thiazolo[5,4-d]pyrimidin-7-yl)-N-m-tolylpiperazine-1-carboxamide;
5-amino-2-cyclopropyl-7-methoxythiazolo[5,4-d]pyrimidine;
5-amino-2-cyclopropyl-7-N-piperazino-thiazolo[5,4-d]pyrimidine;
5-amino-2-(3,4-dichlorophenyl)-7-(N-piperazino)thiazolo[5,4-d]pyrimidine;
5-amino-2-(1-phenylcyclopropyl)-7-(N-piperazino)thiazolo[5,4-d]pyrimidine;
5-amino-2-(1-(4-chlorophenyl)cyclopropyl)-7-(N-piperazino)thiazolo[5,4-d]pyrimidine;
5-amino-7-N-piperazino-2-methylthio-thiazolo[5,4-d]pyrimidine;
5-amino-7-[4-(4-chlorophenoxyacetyl)piperazin-1-yl]-2-(1-phenylcyclopropyl)thiazolo[5,4-d]pyrimidine;
5-amino-7-[4-(4-chlorophenoxyacetyl)piperazin-1-yl]-2-methylthio-thiazolo[5,4-d]pyrimidine;
5-amino-7-[4-(4-chlorophenoxyacetyl)piperazin-1-yl]-2-(3,4-dichlorophenyl)thiazolo[5,4-d]pyrimidine;
5-amino-7-[4-(4-chlorophenoxyacetyl)piperazin-1-yl]-2-(1-(4-chlorophenyl)cyclopropyl)thiazolo[5,4-d]pyrimidine;
5-amino-7-[4-(4-chlorophenoxyacetyl)piperazin-1-yl]-2-(2-phenylethyl)thiazolo[5,4-d]pyrimidine;
5-amino-2-cyclopropyl-7-[4-(4-chlorophenoxyacetyl)piperazin-1-yl]-thiazolo[5,4-d]pyrimidine;
5-amino-7-[4-(4-chlorophenoxyacetyl)piperazin-1-yl]-2-cyclohexylthiazolo[5,4-d]pyrimidine;
5-amino-7-[4-(4-chlorophenoxyacetyl)piperazin-1-yl]-2-(pyridine-3-yl)thiazolo[5,4-d]pyrimidine;
5-amino-7-[4-(4-chlorophenoxyacetyl)piperazin-1-yl]-2-(N-oxopyridine-3-yl)thiazolo[5,4-d]pyrimidine;
5-amino-7-[4-(4-chlorophenoxyacetyl)piperazin-1-yl]-2-(4-chlorophenylmethyl)thiazolo[5,4-d]pyrimidine;
5-amino-7-[4-(4-chlorophenoxyacetyl)piperazin-1-yl]-2-(4-chlorophenyl)thiazolo[5,4-d]pyrimidine;
5-amino-7-[4-(4-chlorophenoxyacetyl)piperazin-1-yl]-2-(3-methoxyphenyl)thiazolo[5,4-d]pyrimidine;
5-amino-7-[4-(4-chlorophenoxyacetyl)piperazin-1-yl]-2-(1-(4-chlorophenyl)ethyl)thiazolo[5,4-d]pyrimidine;
5-amino-7-[4-(4-chlorophenoxyacetyl)piperazin-1-yl]-2-(4-fluorophenylamino)-thiazolo[5,4-d]pyrimidine;
5-amino-2-(4-fluorophenyl)-7-(4-[2-(4-bromophenoxy)acetyl]-piperazin-1-yl)-thiazolo[5,4-d]pyrimidine;
5-amino-2-(4-fluorophenyl)-7-(4-[2-(3-nitrophenoxy)acetyl]-piperazin-1-yl)-thiazolo[5,4-d]pyrimidine;
5-amino-2-(4-fluorophenyl)-7-(4-(2-phenoxyacetyl)-piperazin-1-yl)-thiazolo[5,4-d]pyrimidine;
5-amino-2-[2-(4-fluorophenyl)ethyl]-7-(4-[2-(3-nitrophenoxy)acetyl]piperazin-1-yl)-thiazolo[5,4-d]pyrimidine;
5-amino-2-[2-(4-fluorophenyl)ethyl]-7-(4-[2-(4-chlorophenyl)acetyl]piperazin-1-yl)-thiazolo[5,4-d]pyrimidine;
5-amino-2-[2-(4-fluorophenyl)ethyl]-7-(4-m-tolylcarbamoylpiperazin-1-yl)-thiazolo[5,4-d]pyrimidine;
5-amino-2-[2-(4-fluorophenyl)ethyl]-7-(4-[2-phenoxyacetyl]piperazin-1-yl)-thiazolo[5,4-d]pyrimidine;
5-amino-2-[2-(4-fluorophenyl)ethyl]-7-[4-(4-chlorobenzoyl)piperazin-1-yl]-thiazolo[5,4-d]pyrimidine;
5-amino-2-[2-(4-fluorophenyl)ethyl]-7-[4-(3-phenylpropionyl)piperazin-1-yl]-thiazolo[5,4-d]pyrimidine;
5-amino-2-[2-(4-fluorophenyl)ethyl]-7-[4-phenylmethanesulfonylpiperazin-1-yl]-thiazolo[5,4-d]pyrimidine;
5-amino-2-[2-(4-fluorophenyl)ethyl]-7-(4-[2-(4-chlorophenoxy)acetyl]homopiperazin-1-yl)-thiazolo[5,4-d]pyrimidine;
5-amino-2-[2-(4-fluorophenyl)ethyl]-7-(4-[(methylphenylcarbamoyl)-methyl]piperazin-1-yl)-thiazolo[5,4-d]pyrimidine;
5-amino-2-[2-(4-fluorophenyl)ethyl]-7-(4-thiazol-2-yl-piperazine-1-yl)-thiazolo[5,4-d]pyrimidine;
5-amino-2-[2-(4-fluorophenyl)ethyl]-7-(4-(phenethylcarbamoyl-methyl)piperazin-1-yl)-thiazolo[5,4-d]pyrimidine;
5-amino-2-[2-(4-fluorophenyl)ethyl]-7-((3-(R)-tert-butoxycarbonylamino)pyrrolidin-1-yl)-thiazolo[5,4-d]pyrimidine;
5-amino-2-[2-(4-fluorophenyl)ethyl]-7-(3-(R)-[2-(4-chlorophenoxy)-acetylamino]pyrrolidin-1-yl)-thiazolo[5,4-d]pyrimidine;
5-amino-2-[2-(4-fluorophenyl)ethyl]-7-(3-(R)-(4-chlorobenzoylamino)-pyrrolidin-1-yl)-thiazolo[5,4-d]pyrimidine;
5-amino-2-[2-(4-fluorophenyl)ethyl]-7-(1-benzyloxycarbonylpiperidin-3-ylamino)-thiazolo[5,4-d]pyrimidine;
5-amino-2-[2-(4-fluorophenyl)ethyl]-7-(1-tert-butoxycarbonylpyrrolidin-3-(S)-ylamino)-thiazolo[5,4-d]pyrimidine;
5-amino-2-[2-(4-fluorophenyl)ethyl]-7-(1-(4-chlorophenoxyacetyl)pyrrolidin-3-(S)-ylamino)-thiazolo[5,4-d]pyrimidine;
5-amino-2-[2-(4-fluorophenyl)ethyl]-7-(4-benzoylpiperidine-1-yl)-thiazolo[5,4-d]pyrimidine;
5-amino-2-[2-(4-fluorophenyl)ethyl]-7-(4-(2-phenoxyethyl)piperazin-1-yl)-thiazolo[5,4-d]pyrimidine;
5-amino-2-[1-(4-fluorophenyl)propyl]-7-(4-[2-(4-chlorophenoxy)acetyl]piperazin-1-yl)thiazolo[5,4-d]pyrimidine;
5-amino-2-[cyclopentyl-(4-fluorophenyl)methyl]-7-(4-[2-(4-chlorophenoxy)acetyl]piperazin-1-yl)thiazolo[5,4-d]pyrimidine;
5-amino-7-piperazin-1-yl-2-(2-thiophen-2-yl-ethyl)-thiazolo[5,4-d]pyrimidine;
5-amino-2-(2-thiophen-2-ylethyl)-7-(4-[2-(4-chloro-phenoxy)acetyl]piperazin-1-yl)thiazolo[5,4-d]pyrimidine;
5-amino-2-(2-thiophen-2-ylethyl)-7-(4-[2-(4-chloro-phenyl)acetyl]piperazin-1-yl)thiazolo[5,4-d]pyrimidine;
5-amino-2-(2-thiophen-2-ylethyl)-7-(4-(4-chloro-benzoyl)piperazin-1-yl)thiazolo[5,4-d]pyrimidine;
5-amino-2-(2-thiophen-2-ylethyl)-7-(4-m-tolylcarbamoylpiperazin-1-yl)thiazolo[5,4-d]pyrimidine;
2-(4-chlorophenoxy)-1-(4-(2-(4-fluorophenyl)oxazolo[5,4-d]pyrimidin-7-yl)piperazin-1-yl)ethanone;
2-(4-chlorophenoxy)-1-(4-(2-(4-fluorophenyl)-5-methyloxazolo[5,4-d]pyrimidin-7-yl)piperazin-1-yl)ethanone;
1-(4-(5-amino-2-(4-fluorophenyl)oxazolo[5,4-d]pyrimidin-7-yl)piperazin-1-yl)-2-(4-chlorophenoxy)ethanone;
2-(4-chlorophenoxy)-1-(4-(2-(4-fluorobenzyl)oxazolo[5,4-d]pyrimidin-7-yl)piperazin-1-yl)ethanone;
2-(4-chlorophenoxy)-1-(4-(2-(4-fluorobenzyl)-5-methyloxazolo[5,4-d]pyrimidin-7-yl)piperazin-1-yl)ethanone;
1-(4-(5-amino-2-(4-fluorophenethyl)oxazolo[5,4-d]pyrimidin-7-yl)piperazin-1-yl)-2-(4-chlorophenoxy)ethanone;

N-(3-chloro-4-fluorophenyl)-2-(4-fluorophenyl)-oxazolo[5,4-d]pyrimidin-7-amine;
N-7-(3-chloro-4-fluorophenyl)-2-(4-fluorophenyl)-oxazolo[5,4-d]pyrimidine-5,7-diamine;
5-amino-2-cyclopropyl-7-N-piperazino-oxazolo[5,4-d]pyrimidine;
5-amino-2-methoxymethyl-7-N-piperazino-oxazolo[5,4-d]pyrimidine;
5-amino-2-cyclohexyl-7-N-piperazino-oxazolo[5,4-d]pyrimidine;
5-amino-2-pentyl-7-N-piperazino-oxazolo[5,4-d]pyrimidine;
5-amino-2-(2-phenylethyl)-7-N-piperazino-oxazolo[5,4-d]pyrimidine;
5-amino-2-cyclopropyl-7-[4-(4-chlorophenoxyacetyl)piperazin-1-yl]-oxazolo[5,4-d]pyrimidine;
5-amino-7-[4-(4-chlorophenoxyacetyl)piperazin-1-yl]-2-methoxymethyloxazolo[5,4-d]pyrimidine;
5-amino-2-cyclohexyl-7-[4-(4-chlorophenoxyacetyl)piperazin-1-yl]oxazolo[5,4-d]pyrimidine;
5-amino-7-[4-(4-chlorophenoxyacetyl)piperazin-1-yl]-2-pentyloxazolo[5,4-d]pyrimidine;
5-amino-2-(2-phenylethyl)-7-[4-(4-chlorophenoxyacetyl)piperazin-1-yl]oxazolo[5,4-d]pyrimidine;
5-amino-2-(4-fluorophenyl)-7-(4-isobutylpiperazin-1-yl)-oxazolo[5,4-d]pyrimidine;
5-amino-2-(4-fluorophenyl)-7-(4-acetylpiperazin-1-yl)-oxazolo[5,4-d]pyrimidine;
5-amino-2-(4-fluorophenyl)-7-[4-(2-methoxyethyl)-piperazin-1-yl]-oxazolo[5,4-d]pyrimidine;
5-amino-2-(4-fluorophenyl)-7-(4-[2-(3-nitrophenoxy)acetyl]-piperazin-1-yl)-oxazolo[5,4-d]pyrimidine;
5-amino-2-[2-(4-fluorophenyl)ethyl]-7-(4-[2-(4-chlorophenyl)acetyl]-piperazin-1-yl)-oxazolo[5,4-d]pyrimidine;
5-amino-2-[2-(4-fluorophenyl)ethyl]-7-(4-[4-chlorobenzoyl]piperazin-1-yl)-oxazolo[5,4-d]pyrimidine;
5-amino-2-[2-(4-fluorophenyl)ethyl]-7-(4-m-tolylcarbamoylpiperazin-1-yl)-oxazolo[5,4-d]pyrimidine;
5-amino-2-[2-(4-fluorophenyl)ethyl]-7-(4-(2-phenoxyethyl)piperazin-1-yl)-oxazolo[5,4-d]pyrimidine;
5-amino-2-[2-(4-fluorophenyl)ethyl]-7-(4-[(methylphenyl-carbamoyl)methyl]piperazin-1-yl)-oxazolo[5,4-d]pyrimidine;
5-amino-2-phenyl-7-N-piperazinyl-thiazolo[5,4-d]pyrimidine;
5-amino-2-(2-furyl)-7-N-piperazinyl-thiazolo[5,4-d]pyrimidine;
5-amino-2-(4-fluoro-phenyl)-7-N-piperazinyl-thiazolo[5,4-d]pyrimidine;
1-(4-(5-amino-2-phenylthiazolo[5,4-d]pyrimidin-7-yl)piperazin-1-yl)-2-(4-methoxyphenoxy)ethanone;
1-(4-(5-amino-2-(furan-2-yl)thiazolo[5,4-d]pyrimidin-7-yl)piperazin-1-yl)-2-(4-fluorophenoxy)ethanone;
1-(4-(5-amino-2-(furan-2-yl)thiazolo[5,4-d]pyrimidin-7-yl)piperazin-1-yl)-2-(m-tolyloxy)ethanone;
1-(4-(5-amino-2-(4-fluorophenyl)thiazolo[5,4-d]pyrimidin-7-yl)piperazin-1-yl)-2-(m-tolyloxy)ethanone;
1-(4-(5-amino-2-(4-fluorophenyl)thiazolo[5,4-d]pyrimidin-7-yl)piperazin-1-yl)-2-(2,4-dichlorophenoxy)ethanone;
1-(4-(5-amino-2-(4-fluorophenyl)thiazolo[5,4-d]pyrimidin-7-yl)piperazin-1-yl)-2-(4-chloro-2-methylphenoxy)ethanone;
1-(4-(5-amino-2-(4-fluorophenyl)thiazolo[5,4-d]pyrimidin-7-yl)piperazin-1-yl)-2-(3-chlorophenoxy)ethanone;
1-(4-(5-amino-2-phenylthiazolo[5,4-d]pyrimidin-7-yl)piperazin-1-yl)-2-(4-chlorophenoxy)ethanone;
4-(5-amino-2-(4-fluorophenyl)thiazolo[5,4-d]pyrimidin-7-yl)-N-(4-cyanophenyl)piperazine-1-carboxamide;
4-(5-amino-2-(4-fluorophenyl)thiazolo[5,4-d]pyrimidin-7-yl)-N-(2,4-difluorophenyl)piperazine-1-carboxamide;
4-(5-amino-2-(4-fluorophenyl)thiazolo[5,4-d]pyrimidin-7-yl)-N-(4-bromophenyl)piperazine-1-carboxamide;
4-(5-amino-2-(4-fluorophenyl)thiazolo[5,4-d]pyrimidin-7-yl)-N-(2-methoxyphenyl)piperazine-1-carboxamide;
4-(5-amino-2-phenylthiazolo[5,4-d]pyrimidin-7-yl)-N-m-tolylpiperazine-1-carboxamide;
5-amino-7-(N-piperazin-1-yl)-2-(pyridin-3-yl)thiazolo[5,4-d]pyrimidine;
4-(5-amino-2-(pyridin-3-yl)thiazolo[5,4-d]pyrimidin-7-yl)-N-p-tolylpiperazine-1-carboxamide;
1-(4-(5-amino-2-(4-fluorophenethyl)thiazolo[5,4-d]pyrimidin-7-yl)piperazin-1-yl)-3-(4-bromophenyl)propan-1-one;
1-(4-(5-amino-2-(4-fluorophenethyl)thiazolo[5,4-d]pyrimidin-7-yl)piperazin-1-yl)-2-(4-hydroxyphenoxy)ethanone;
methyl 4-(2-(4-(5-amino-2-(4-fluorophenethyl)thiazolo[5,4-d]pyrimidin-7-yl)piperazin-1-yl)-2-oxoethoxy)benzoate;
1-(4-(5-amino-2-(4-fluorophenethyl)thiazolo[5,4-d]pyrimidin-7-yl)piperazin-1-yl)-2-(4-(trifluoromethoxy)phenoxy)ethanone;
2-(4-acetylphenoxy)-1-(4-(5-amino-2-(4-fluorophenethyl)thiazolo[5,4-d]pyrimidin-7-yl)piperazin-1-yl)ethanone;
1-(4-(5-amino-2-(4-fluorophenethyl)thiazolo[5,4-d]pyrimidin-7-yl)piperazin-1-yl)-2-(3-chlorophenoxy)ethanone;
4-(5-amino-2-(4-fluorophenethyl)thiazolo[5,4-d]pyrimidin-7-yl)-N-(4-cyanophenyl)piperazine-1-carboxamide;
1-(4-(5-amino-2-(4-fluorobenzyl)thiazolo[5,4-d]pyrimidin-7-yl)piperazin-1-yl)-2-(4-methoxyphenoxy)ethanone;
1-(4-(5-amino-2-(4-fluorobenzyl)thiazolo[5,4-d]pyrimidin-7-yl)piperazin-1-yl)-2-(4-bromophenoxy)ethanone;
4-(5-amino-2-(4-fluorobenzyl)thiazolo[5,4-d]pyrimidin-7-yl)-N-(4-cyanophenyl)piperazine-1-carboxamide;
1-(4-(5-amino-2-(4-fluorophenyl)thiazolo[5,4-d]pyrimidin-7-yl)piperazin-1-yl)-2-(4-fluorophenoxy)ethanone;
1-(4-(5-amino-2-(4-fluorophenyl)thiazolo[5,4-d]pyrimidin-7-yl)piperazin-1-yl)-2-(4-methoxyphenoxy)ethanone;
1-(4-(5-amino-2-(4-fluorophenyl)thiazolo[5,4-d]pyrimidin-7-yl)piperazin-1-yl)-2-(4-bromophenoxy)ethanone;
1-(4-(5-amino-2-(4-fluorophenyl)thiazolo[5,4-d]pyrimidin-7-yl)piperazin-1-yl)-3-(4-fluorophenyl)propan-1-one;
1-(4-(5-amino-2-(4-fluorophenyl)thiazolo[5,4-d]pyrimidin-7-yl)piperazin-1-yl)-2-(4-chlorophenoxy)-2-methylpropan-1-one;
2-(3-methoxyphenethyl)-7-(piperazin-1-yl)thiazolo[5,4-d]pyrimidin-5-amine;
2-(3,4-dimethoxyphenethyl)-7-(piperazin-1-yl)thiazolo[5,4-d]pyrimidin-5-amine;
2-(4-methylphenethyl)-7-(piperazin-1-yl)thiazolo[5,4-d]pyrimidin-5-amine;

1-(4-(5-amino-2-(3-methoxyphenethyl)thiazolo[5,4-d]pyrimidin-7-yl)piperazin-1-yl)-2-(4-methoxyphenoxy)ethanone;
1-(4-(5-amino-2-(3-methoxyphenethyl)thiazolo[5,4-d]pyrimidin-7-yl)piperazin-1-yl)-2-(4-bromophenoxy)ethanone;
1-(4-(5-amino-2-(3-methoxyphenethyl)thiazolo[5,4-d]pyrimidin-7-yl)piperazin-1-yl)-2-(4-chlorophenoxy)ethanone;
1-(4-(5-amino-2-(3,4-dimethoxyphenethyl)thiazolo[5,4-d]pyrimidin-7-yl)piperazin-1-yl)-2-(4-bromophenoxy)ethanone;
1-(4-(5-amino-2-(3,4-dimethoxyphenethyl)thiazolo[5,4-d]pyrimidin-7-yl)piperazin-1-yl)-2-(4-methoxyphenoxy)ethanone;
1-(4-(5-amino-2-(4-methylphenethyl)thiazolo[5,4-d]pyrimidin-7-yl)piperazin-1-yl)-2-(4-bromophenoxy)ethanone;
1-(4-(5-amino-2-(4-methylphenethyl)thiazolo[5,4-d]pyrimidin-7-yl)piperazin-1-yl)-2-(4-methoxyphenoxy)ethanone;
1-(4-(5-amino-2-(4-methylphenethyl)thiazolo[5,4-d]pyrimidin-7-yl)piperazin-1-yl)-2-(4-chlorophenoxy)ethanone;
7-(piperazin-1-yl)-2-(pyridin-3-yl)thiazolo[5,4-d]pyrimidin-5-amine;
7-(piperazin-1-yl)-2-(pyridin-2-yl)thiazolo[5,4-d]pyrimidin-5-amine;
7-(piperazin-1-yl)-2-(pyridin-4-yl)thiazolo[5,4-d]pyrimidin-5-amine;
2-(4-chlorophenyl)-7-(piperazin-1-yl)thiazolo[5,4-d]pyrimidin-5-amine;
1-(4-(5-amino-2-(4-chlorophenyl)thiazolo[5,4-d]pyrimidin-7-yl)piperazin-1-yl)-2-(4-methoxyphenoxy)ethanone;
1-(4-(5-amino-2-(pyridin-3-yl)thiazolo[5,4-d]pyrimidin-7-yl)piperazin-1-yl)-2-(4-methoxyphenoxy)ethanone;
1-(4-(5-amino-2-(pyridin-3-yl)thiazolo[5,4-d]pyrimidin-7-yl)piperazin-1-yl)-2-(4-fluorophenoxy)ethanone;
1-(4-(5-amino-2-(pyridin-3-yl)thiazolo[5,4-d]pyrimidin-7-yl)piperazin-1-yl)-2-(4-trifluoromethoxyphenoxy)ethanone;
1-(4-(5-amino-2-(pyridin-3-yl)thiazolo[5,4-d]pyrimidin-7-yl)piperazin-1-yl)-2-(4-chlorophenoxy)-2-methylpropan-1-one;
1-(4-(5-amino-2-(pyridin-3-yl)thiazolo[5,4-d]pyrimidin-7-yl)piperazin-1-yl)-2-(m-tolyloxy)ethanone;
4-(5-amino-2-(pyridin-3-yl)thiazolo[5,4-d]pyrimidin-7-yl)-N-m-tolylpiperazine-1-carboxamide;
4-(5-amino-2-(pyridin-3-yl)thiazolo[5,4-d]pyrimidin-7-yl)-N-(4-chlorophenyl)piperazine-1-carboxamide;
4-(5-amino-2-(pyridin-3-yl)thiazolo[5,4-d]pyrimidin-7-yl)-N-(4-methoxybenzyl)piperazine-1-carboxamide;
4-(5-amino-2-(pyridin-3-yl)thiazolo[5,4-d]pyrimidin-7-yl)-N-(4-cyanophenyl)piperazine-1-carboxamide;
1-(4-(5-amino-2-(4-chlorophenyl)thiazolo[5,4-d]pyrimidin-7-yl)piperazin-1-yl)-2-(4-methoxyphenoxy)ethanone;
1-(4-(5-amino-2-(pyridin-4-yl)thiazolo[5,4-d]pyrimidin-7-yl)piperazin-1-yl)-2-(4-chlorophenoxy)ethanone;
1-(4-(5-amino-2-(pyridin-2-yl)thiazolo[5,4-d]pyrimidin-7-yl)piperazin-1-yl)-2-(4-chlorophenoxy)ethanone;
2-(4-fluorophenethyl)-7-(piperazin-1-yl)thiazolo[5,4-d]pyrimidine;
2-(4-fluorophenyl)-7-(piperazin-1-yl)thiazolo[5,4-d]pyrimidine;
2-(3-(4-fluorophenyl)propyl)-7-(piperazin-1-yl)thiazolo[5,4-d]pyrimidin-5-amine;
2-(4-(4-fluorophenyl)butyl)-7-(piperazin-1-yl)thiazolo[5,4-d]pyrimidin-5-amine;
2-(4-bromophenethyl)-7-(piperazin-1-yl)thiazolo[5,4-d]pyrimidin-5-amine;
2-pentyl-7-(piperazin-1-yl)thiazolo[5,4-d]pyrimidin-5-amine;
7-(piperazin-1-yl)-2-p-tolylthiazolo[5,4-d]pyrimidin-5-amine;
1-(4-(5-amino-2-(3-(4-fluorophenyl)propyl)thiazolo[5,4-d]pyrimidin-7-yl)piperazin-1-yl)-2-(4-chlorophenoxy)ethanone;
1-(4-(5-amino-2-(3-(4-fluorophenyl)propyl)thiazolo[5,4-d]pyrimidin-7-yl)piperazin-1-yl)-2-(4-methoxyphenoxy)ethanone;
1-(4-(5-amino-2-(4-(4-fluorophenyl)butyl)thiazolo[5,4-d]pyrimidin-7-yl)piperazin-1-yl)-2-(4-chlorophenoxy)ethanone;
1-(4-(5-amino-2-(4-(4-fluorophenyl)butyl)thiazolo[5,4-d]pyrimidin-7-yl)piperazin-1-yl)-2-(4-methoxyphenoxy)ethanone;
1-(4-(5-amino-2-p-tolylthiazolo[5,4-d]pyrimidin-7-yl)piperazin-1-yl)-2-(4-methoxyphenoxy)ethanone;
1-(4-(5-amino-2-p-tolylthiazolo[5,4-d]pyrimidin-7-yl)piperazin-1-yl)-2-(4-chlorophenoxy)ethanone;
1-(4-(5-amino-2-pentylthiazolo[5,4-d]pyrimidin-7-yl)piperazin-1-yl)-2-(4-methoxyphenoxy)ethanone;
1-(4-(5-amino-2-pentylthiazolo[5,4-d]pyrimidin-7-yl)piperazin-1-yl)-2-(4-chlorophenoxy)ethanone;
1-(4-(5-amino-2-(4-bromophenethyl)thiazolo[5,4-d]pyrimidin-7-yl)piperazin-1-yl)-2-(4-methoxyphenoxy)ethanone;
1-(4-(5-amino-2-(4-bromophenethyl)thiazolo[5,4-d]pyrimidin-7-yl)piperazin-1-yl)-2-(4-chlorophenoxy)ethanone;
1-(4-(2-(4-fluorophenyl)thiazolo[5,4-d]pyrimidin-7-yl)piperazin-1-yl)-2-(4-methoxyphenoxy)ethanone;
1-(4-(2-(4-fluorophenyl)thiazolo[5,4-d]pyrimidin-7-yl)piperazin-1-yl)-2-(4-chlorophenoxy)ethanone;
1-(4-(2-(4-fluorophenethyl)thiazolo[5,4-d]pyrimidin-7-yl)piperazin-1-yl)-2-(4-methoxyphenoxy)ethanone;
1-(4-(2-(4-fluorophenethyl)thiazolo[5,4-d]pyrimidin-7-yl)piperazin-1-yl)-2-(4-chlorophenoxy)ethanone;
2-(4-chlorophenoxy)-1-(4-(6-(4-fluorophenyl)thieno[2,3-d]pyrimidin-4-yl)piperazin-1-yl)ethanone;
1-(4-(2-butyl-6-(4-fluorophenyl)thieno[2,3-d]pyrimidin-4-yl)piperazin-1-yl)-2-(4-chlorophenoxy)ethanone;
N-(3-chloro-4-fluorophenyl)-6-(4-fluorophenyl)thieno[2,3-d]pyrimidin-4-amine;
2-butyl-N-(3-chloro-4-fluorophenyl)-6-(4-fluorophenyl)thieno[2,3-d]pyrimidin-4-amine;
2-(4-chlorophenoxy)-1-(4-(6-(4-fluorophenyl)-2-methylthieno[2,3-d]pyrimidin-4-yl)piperazin-1-yl)ethanone;
1-(4-(2-amino-6-(4-fluorophenyl)thieno[2,3-d]pyrimidin-4-yl)piperazin-1-yl)-2-(4-chlorophenoxy)ethanone;
2-amino-4-N-benzylamino-6-(4-fluorophenyl)-thieno[2,3-d]pyrimidine;
2-amino-4-N-piperazinyl-6-phenyl-thieno[2,3-d]pyrimidine;
1-(4-(2-amino-6-phenylthieno[2,3-d]pyrimidin-4-yl)piperazin-1-yl)-2-(4-chlorophenoxy)ethanone;
4-(2-amino-6-phenylthieno[2,3-d]pyrimidin-4-yl)-N-m-tolylpiperazine-1-carboxamide;
4-(2-amino-6-phenylthieno[2,3-d]pyrimidin-4-yl)-N-(4-chlorophenyl)piperazine-1-carboxamide;

1-(4-(2-amino-6-phenylthieno[2,3-d]pyrimidin-4-yl)piperazin-1-yl)-2-phenoxyethanone;
2-amino-4-N-homopiperazinyl-6-phenyl-thieno[2,3-d]pyrimidine;
1-(4-(2-amino-6-phenylthieno[2,3-d]pyrimidin-4-yl)-1,4-diazepan-1-yl)-2-(4-chlorophenoxy)ethanone;
1-(4-(2-amino-6-phenylthieno[2,3-d]pyrimidin-4-yl)-1,4-diazepan-1-yl)(4-chlorophenyl)methanone;
2-(4-(2-amino-6-phenylthieno[2,3-d]pyrimidin-4-yl)piperazin-1-yl)-N-methyl-N-phenylacetamide;
4-(4-(2-phenoxyethyl)piperazin-1-yl)-6-phenylthieno[2,3-d]pyrimidin-2-amine;
(R)-tert-butyl 1-(2-amino-6-(4-fluorophenyl)thieno[2,3-d]pyrimidin-4-yl)pyrrolidin-3-ylcarbamate;
(R)-4-(3-aminopyrrolidin-1-yl)-6-(4-fluorophenyl)thieno[2,3-d]pyrimidin-2-amine;
(R)—N-(1-(2-amino-6-(4-fluorophenyl)thieno[2,3-d]pyrimidin-4-yl)pyrrolidin-3-yl)-2-(4-chlorophenoxy)acetamide;
(R)—N-(1-(2-amino-6-(4-fluorophenyl)thieno[2,3-d]pyrimidin-4-yl)pyrrolidin-3-yl)-4-chlorobenzamide;
2-amino-4-N-piperazinyl-6-(4-fluorophenyl)-thieno[2,3-d]pyrimidine;
1-(4-(2-amino-6-(4-fluorophenyl)thieno[2,3-d]pyrimidin-4-yl)piperazin-1-yl)-3-phenylpropan-1-one;
4-(4-(benzylsulfonyl)piperazin-1-yl)-6-(4-fluorophenyl)thieno[2,3-d]pyrimidin-2-amine;
(4-(2-amino-6-(4-fluorophenyl)thieno[2,3-d]pyrimidin-4-yl)piperazin-1-yl)(cyclohexyl)methanone;
4-(2-amino-6-(4-fluorophenyl)thieno[2,3-d]pyrimidin-4-yl)piperazin-1-yl)(pyridin-3-yl)methanone;
4-(2-amino-6-(4-fluorophenyl)thieno[2,3-d]pyrimidin-4-yl)-N,N-diisopropylpiperazine-1-carboxamide;
(1-(2-amino-6-(4-fluorophenyl)thieno[2,3-d]pyrimidin-4-yl)piperidin-4-yl)(phenyl)methanone;
2-amino-4-N-piperazino-thieno[2,3-d]pyrimidine;
1-(4-(2-aminothieno[2,3-d]pyrimidin-4-yl)piperazin-1-yl)-2-(4-chlorophenoxy)ethanone;
2-(4-chlorophenoxy)-1-(4-(6-(4-fluorophenyl)-2-phenylthieno[2,3-d]pyrimidin-4-yl)piperazin-1-yl)ethanone;
ethyl 4-(4-(2-(4-chlorophenoxy)acetyl)piperazin-1-yl)-6-(4-fluorophenyl)thieno[2,3-d]pyrimidine-2-carboxylate;
ethyl 2-(4-(4-(2-(4-chlorophenoxy)acetyl)piperazin-1-yl)-6-(4-fluorophenyl)thieno[2,3-d]pyrimidin-2-yl)acetate;
4-(4-(2-(4-chlorophenoxy)acetyl)piperazin-1-yl)-6-(4-fluorophenyl)thieno[2,3-d]pyrimidine-2-carboxamide;
4-(4-(2-(4-chlorophenoxy)acetyl)piperazin-1-yl)-6-(4-fluorophenyl)-N-(2-methoxyethyl)thieno[2,3-d]pyrimidine-2-carboxamide;
4-(4-(2-(4-chlorophenoxy)acetyl)piperazin-1-yl)-6-(4-fluorophenyl)thieno[2,3-d]pyrimidine-2-carboxylic acid;
2-(4-(4-(2-(4-chlorophenoxy)acetyl)piperazin-1-yl)-6-(4-fluorophenyl)thieno[2,3-d]pyrimidin-2-yl)acetamide;
4-(2-amino-6-(4-fluorophenyl)thieno[2,3-d]pyrimidin-4-yl)-N-m-tolylpiperazine-1-carboxamide;
4-(6-(4-fluorophenyl)-2-phenylthieno[2,3-d]pyrimidin-4-yl)-N-m-tolylpiperazine-1-carboxamide;
ethyl 6-(4-fluorophenyl)-4-(4-(m-tolylcarbamoyl)piperazin-1-yl)thieno[2,3-d]pyrimidine-2-carboxylate;
6-(4-fluorophenyl)-4-(4-(m-tolylcarbamoyl)piperazin-1-yl)thieno[2,3-d]pyrimidine-2-carboxamide;
4-ethoxy-6-(4-fluorophenyl)thieno[2,3-d]pyrimidin-2-amine; 6-(4-fluorophenyl)-4-morpholinothieno[2,3-d]pyrimidin-2-amine;
N-(3-chloro-4-fluorophenyl)-6-(4-fluorophenyl)-2-methylthieno[2,3-d]pyrimidin-4-amine;
ethyl 4-(3-chloro-4-fluorophenylamino)-6-(4-fluorophenyl)thieno[2,3-d]pyrimidine-2-carboxylate;
1-(4-(2-amino-6-phenylthieno[2,3-d]pyrimidin-4-yl)piperazin-1-yl)-2-(4-methoxyphenoxy)ethanone;
1-(4-(2-amino-6-phenylthieno[2,3-d]pyrimidin-4-yl)piperazin-1-yl)-2-(4-fluorophenoxy)ethanone;
1-(4-(2-amino-6-phenylthieno[2,3-d]pyrimidin-4-yl)piperazin-1-yl)-2-(m-tolyloxy)ethanone;
1-(4-(2-amino-6-phenylthieno[2,3-d]pyrimidin-4-yl)piperazin-1-yl)-2-(4-bromophenoxy)ethanone;
1-(4-(2-amino-6-phenylthieno[2,3-d]pyrimidin-4-yl)piperazin-1-yl)-2-(4-chlorophenoxy)-2-methylpropan-1-one;
1-(4-(2-amino-8-(4-fluorophenyl)-9H-purin-6-yl)piperazin-1-yl)-2-(4-chlorophenoxy)ethanone;
4-(5-amino-2-(pyridin-3-yl)thiazolo[5,4-d]pyrimidin-7-yl)-N-(4-(trifluoromethyl)phenyl)piperazine-1-carboxamide;
4-(5-amino-2-(pyridin-3-yl)thiazolo[5,4-d]pyrimidin-7-yl)-N-phenylpiperazine-1-carboxamide;
4-(5-amino-2-(pyridin-3-yl)thiazolo[5,4-d]pyrimidin-7-yl)-N-cyclohexylpiperazine-1-carboxamide;
5-amino-7-[4-(N-4-fluorophenylcarboxamide)piperazin-1-yl]-2-(pyridine-3-yl)thiazolo[5,4-d]pyrimidine;
4-(5-amino-2-(pyridin-3-yl)thiazolo[5,4-d]pyrimidin-7-yl)-N-hexylpiperazine-1-carboxamide;
4-(5-amino-2-(pyridin-3-yl)thiazolo[5,4-d]pyrimidin-7-yl)-N-p-tolylpiperazine-1-carbothioamide;
4-(5-amino-2-(pyridin-3-yl)thiazolo[5,4-d]pyrimidin-7-yl)-N-methyl-N-p-tolylpiperazine-1-carboxamide; and
p-tolyl 4-(5-amino-2-(pyridin-3-yl)thiazolo[5,4-d]pyrimidin-7-yl)piperazine-1-carboxylate.

14. A pharmaceutical composition comprising a compound according to claim 1.

15. A pharmaceutical composition comprising a therapeutically effective amount of a compound according to claim 1 and one or more pharmaceutically acceptable excipients.

16. The pharmaceutical composition according to claim 15, further comprising one or more biologically active drugs being selected from the group consisting of immunosuppressant and/or immunomodulator drugs, and antineoplastic drugs.

* * * * *